(12) United States Patent
Pinzon

(10) Patent No.: US 12,045,897 B2
(45) Date of Patent: Jul. 23, 2024

(54) CLOUD-BASED ENTERPRISE PLATFORM FOR EVENT HANDLING

(71) Applicant: HSC Acquisition, LLC, Mahwah, NJ (US)

(72) Inventor: Marlon Pinzon, Cresskill, NJ (US)

(73) Assignee: HSC Acquisition, LLC, Mahwah, NJ (US)

(*) Notice: Subject to any disclaimer, the term of this patent is extended or adjusted under 35 U.S.C. 154(b) by 258 days.

(21) Appl. No.: 17/089,342

(22) Filed: Nov. 4, 2020

(65) Prior Publication Data

US 2021/0133898 A1 May 6, 2021

Related U.S. Application Data

(60) Provisional application No. 62/930,501, filed on Nov. 4, 2019.

(51) Int. Cl.
*G06Q 30/00* (2023.01)
*G06F 3/0482* (2013.01)
(Continued)

(52) U.S. Cl.
CPC ........... *G06Q 50/01* (2013.01); *G06F 3/0482* (2013.01); *G06Q 10/101* (2013.01);
(Continued)

(58) Field of Classification Search
CPC .............. G06Q 50/01; G06Q 30/0185; G06Q 30/0205; G06Q 10/101; G06Q 10/103;
(Continued)

(56) References Cited

U.S. PATENT DOCUMENTS

| 5,509,112 A | 4/1996 | Doi et al. |
| 5,781,190 A | 7/1998 | Gorbet et al. |

(Continued)

FOREIGN PATENT DOCUMENTS

| JP | H08249385 A | 9/1996 |
| JP | 2000149045 A | 5/2000 |

(Continued)

OTHER PUBLICATIONS

Free C, Phillips G, Watson L, Galli L, Felix L, Edwards P, et al. (2013) The Effectiveness of Mobile-Health Technologies to Improve Health Care Service Delivery Processes: a Systematic Review and Meta-Analysis. PLoS Med 10(1): e1001363. https://doi.org/10.1371/journal.pmed.1001363 (Year: 2013).*

(Continued)

*Primary Examiner* — Sun M Li
(74) *Attorney, Agent, or Firm* — Taft Stettinius & Hollister LLP

(57) ABSTRACT

A system according to one embodiment includes an enterprise system configured to provide an enterprise-wide integrated solution for pharmaceutical companies including data integration, template-driven communication, and event planning with end-to-end legal compliance and validation, wherein the enterprise-wide integrated solution includes at least a representative portal and a speaker portal, a representative device of a pharmaceutical company representative configured to communicate with the enterprise system to interact with the representative portal, and a speaker device of a key opinion leader configured to communicate with the enterprise system to interaction with the speaker portal, wherein the representative portal includes at least a programs section that allows the representative to plan a program and a speakers section that allows the representative to view profiles of a plurality of healthcare providers (Continued)

identified as key opinion leaders, and the speaker portal allows the key opinion leader to interact with presentation materials and upcoming program data.

12 Claims, 186 Drawing Sheets

(51) Int. Cl.
| | |
|---|---|
| G06Q 10/10 | (2023.01) |
| G06Q 10/101 | (2023.01) |
| G06Q 10/105 | (2023.01) |
| G06Q 30/018 | (2023.01) |
| G06Q 30/0204 | (2023.01) |
| G06Q 50/00 | (2012.01) |
| G16H 40/20 | (2018.01) |
| G16H 70/20 | (2018.01) |

(52) U.S. Cl.
CPC ......... *G06Q 10/103* (2013.01); *G06Q 10/105* (2013.01); *G06Q 30/0185* (2013.01); *G06Q 30/0205* (2013.01); *G16H 40/20* (2018.01); *G16H 70/20* (2018.01)

(58) Field of Classification Search
CPC ...... G06Q 10/105; G16H 40/20; G16H 70/20; G06F 3/0482
See application file for complete search history.

(56) References Cited

U.S. PATENT DOCUMENTS

| | | | |
|---|---|---|---|
| 7,493,561 B2 | 2/2009 | Sareen et al. | |
| 7,703,003 B2 | 4/2010 | Payne et al. | |
| 7,743,323 B1 | 6/2010 | Rodriguez | |
| 7,814,404 B2 | 10/2010 | Shenfield | |
| 7,836,110 B1 | 11/2010 | Schoenbach et al. | |
| 7,996,767 B2 | 8/2011 | Lee et al. | |
| 8,214,518 B1 | 7/2012 | Bertz | |
| 8,341,528 B2 | 12/2012 | Chaudhary et al. | |
| 8,434,002 B1 | 4/2013 | Shah et al. | |
| 8,856,659 B2 | 10/2014 | Mindrum | |
| 9,058,396 B2 | 6/2015 | Kim et al. | |
| 9,436,685 B2 | 9/2016 | Roth et al. | |
| 9,699,629 B2 | 7/2017 | Chang et al. | |
| 9,715,485 B2 | 7/2017 | Roth et al. | |
| 10,049,084 B2 | 8/2018 | Mahafzah | |
| 10,380,224 B2 | 8/2019 | Mahafzah | |
| 10,706,964 B2 * | 7/2020 | Perlroth | G16H 50/20 |
| 11,087,886 B1 * | 8/2021 | Brown | G16H 50/80 |
| 11,126,696 B1 * | 9/2021 | Srivastava | G16H 40/20 |
| 2001/0025274 A1 | 9/2001 | Zehr et al. | |
| 2002/0077902 A1 | 6/2002 | Marcus | |
| 2002/0103737 A1 | 8/2002 | Briere | |
| 2002/0178093 A1 | 11/2002 | Dean et al. | |
| 2003/0036683 A1 | 2/2003 | Kehr et al. | |
| 2003/0066028 A1 | 4/2003 | Payne et al. | |
| 2003/0149618 A1 | 8/2003 | Sender et al. | |
| 2004/0015783 A1 | 1/2004 | Lennon et al. | |
| 2004/0115608 A1 | 6/2004 | Meyer et al. | |
| 2004/0205479 A1 | 10/2004 | Seaman et al. | |
| 2004/0259068 A1 | 12/2004 | Philipp et al. | |
| 2005/0119957 A1 | 6/2005 | Faber et al. | |
| 2005/0119990 A1 | 6/2005 | Lee et al. | |
| 2005/0138198 A1 | 6/2005 | May | |
| 2005/0188402 A1 | 8/2005 | de Andrade et al. | |
| 2005/0237931 A1 | 10/2005 | Punj et al. | |
| 2006/0037052 A1 | 2/2006 | McDowell et al. | |
| 2006/0057550 A1 | 3/2006 | Sahashi | |
| 2006/0085369 A1 | 4/2006 | Bauer et al. | |
| 2006/0095320 A1 | 5/2006 | Jones | |
| 2006/0122861 A1 * | 6/2006 | Scott | G06Q 10/00 705/7.19 |
| 2006/0136971 A1 | 6/2006 | Uchida et al. | |
| 2006/0188859 A1 | 8/2006 | Yakobi | |
| 2006/0247968 A1 | 11/2006 | Kadry | |
| 2006/0253213 A1 | 11/2006 | Ocke et al. | |
| 2007/0118801 A1 | 5/2007 | Harshbarger et al. | |
| 2007/0124172 A1 | 5/2007 | Moura et al. | |
| 2007/0130177 A1 | 6/2007 | Schneider et al. | |
| 2008/0147484 A1 | 6/2008 | Davis | |
| 2008/0215426 A1 | 9/2008 | Guldimann et al. | |
| 2008/0215437 A1 | 9/2008 | Levy et al. | |
| 2008/0275726 A1 | 11/2008 | Yannicelli | |
| 2009/0198542 A1 | 8/2009 | D'Amore et al. | |
| 2010/0005142 A1 | 1/2010 | Xiao et al. | |
| 2010/0049562 A1 | 2/2010 | White et al. | |
| 2010/0083358 A1 | 4/2010 | Govindarajan et al. | |
| 2010/0088605 A1 | 4/2010 | Livshin et al. | |
| 2010/0121709 A1 | 5/2010 | Berezin et al. | |
| 2010/0122220 A1 | 5/2010 | Ainsworth et al. | |
| 2010/0136509 A1 | 6/2010 | Mejer et al. | |
| 2010/0149307 A1 | 6/2010 | Iyer et al. | |
| 2010/0178902 A1 | 7/2010 | Boctor | |
| 2010/0191554 A1 | 7/2010 | Singh et al. | |
| 2010/0217613 A1 | 8/2010 | Kelly | |
| 2011/0077956 A1 | 3/2011 | Kapu et al. | |
| 2011/0078560 A1 | 3/2011 | Weeldreyer et al. | |
| 2011/0093328 A1 | 4/2011 | Woolcott | |
| 2011/0164822 A1 | 7/2011 | Jegou et al. | |
| 2011/0178854 A1 | 7/2011 | Sofer et al. | |
| 2011/0179344 A1 | 7/2011 | Paxson | |
| 2011/0180441 A1 | 7/2011 | Bach | |
| 2011/0182415 A1 | 7/2011 | Jacobstein et al. | |
| 2011/0246219 A1 | 10/2011 | Smith et al. | |
| 2011/0252031 A1 | 10/2011 | Blumenthal et al. | |
| 2011/0314053 A1 | 12/2011 | Morikawa et al. | |
| 2012/0095817 A1 | 4/2012 | Kamil et al. | |
| 2012/0110196 A1 | 5/2012 | Balasaygun et al. | |
| 2012/0110443 A1 | 5/2012 | Lemonik et al. | |
| 2012/0136804 A1 | 5/2012 | Lucia, Sr. et al. | |
| 2012/0192086 A1 | 7/2012 | Ghods et al. | |
| 2012/0215737 A1 | 8/2012 | Jennings | |
| 2012/0243848 A1 | 9/2012 | Martin | |
| 2012/0246105 A1 | 9/2012 | James | |
| 2012/0284605 A1 | 11/2012 | Sitrick et al. | |
| 2013/0073449 A1 | 3/2013 | Voynow et al. | |
| 2013/0144714 A1 | 6/2013 | Yuan et al. | |
| 2014/0088980 A1 | 3/2014 | Mahafzah | |
| 2014/0095254 A1 | 4/2014 | Chauhan et al. | |
| 2014/0122595 A1 | 5/2014 | Murdoch et al. | |
| 2014/0136237 A1 * | 5/2014 | Anderson | G16H 10/60 705/3 |
| 2014/0180970 A1 | 6/2014 | Hettenkofer et al. | |
| 2014/0207870 A1 | 7/2014 | Vaya | |
| 2014/0222474 A1 | 8/2014 | Mahafzah | |
| 2014/0250056 A1 | 9/2014 | Kuspa | |
| 2014/0380171 A1 | 12/2014 | Maloney et al. | |
| 2015/0010894 A1 | 1/2015 | Morisset | |
| 2015/0143243 A1 | 5/2015 | Balfe | |
| 2015/0170303 A1 | 6/2015 | Geritz et al. | |
| 2015/0177964 A1 | 6/2015 | Spirer | |
| 2015/0212982 A1 | 7/2015 | Berger et al. | |
| 2015/0243177 A1 | 8/2015 | Heikkila et al. | |
| 2015/0278222 A1 * | 10/2015 | Claussenelias | G06F 16/24578 707/723 |
| 2015/0332397 A1 | 11/2015 | Clarke et al. | |
| 2016/0012027 A9 | 1/2016 | Rebstock et al. | |
| 2016/0246936 A1 * | 8/2016 | Kahn | H04L 65/4025 |
| 2016/0253741 A1 | 9/2016 | Otto et al. | |
| 2017/0000450 A1 | 1/2017 | Ferro, Jr. | |
| 2017/0046317 A1 | 2/2017 | Geva et al. | |
| 2017/0090854 A1 | 3/2017 | Richardson et al. | |
| 2017/0092331 A1 | 3/2017 | Eppolito et al. | |
| 2017/0177553 A1 | 6/2017 | Bruner et al. | |
| 2018/0181717 A1 * | 6/2018 | Kendall | G16H 70/20 |
| 2018/0247717 A1 | 8/2018 | Mahafzah | |
| 2018/0349892 A1 | 12/2018 | Lattanzio et al. | |

(56) References Cited

U.S. PATENT DOCUMENTS

2019/0027257 A1* 1/2019 Ghogawala ............ G16H 30/40
2019/0199724 A1* 6/2019 Kallman ............. G06F 21/6218

FOREIGN PATENT DOCUMENTS

| JP | 2006126881 A | 5/2006 |
| JP | 2007128400 A | 5/2007 |
| JP | 2007272563 A | 10/2007 |
| WO | 0139485 A2 | 5/2001 |
| WO | 2010076562 A1 | 7/2010 |

OTHER PUBLICATIONS

M. Azarm and L. Peyton, "An Ontology for a Patient-Centric Healthcare Interoperability Framework," 2018 IEEE/ACM International Workshop on Software Engineering in Healthcare Systems (SEHS), Gothenburg, Sweden, 2018, pp. 34-41. (Year: 2018).*
Franklin et al., Plan-based Interfaces: Keeping Track of User Tasks and Acting to Cooperate, ACM 2002, pp. 79-86.
Bergman et al., Outline Wizard: Presentation Composition and Search, ACM 2010, pp. 209-218.

* cited by examiner

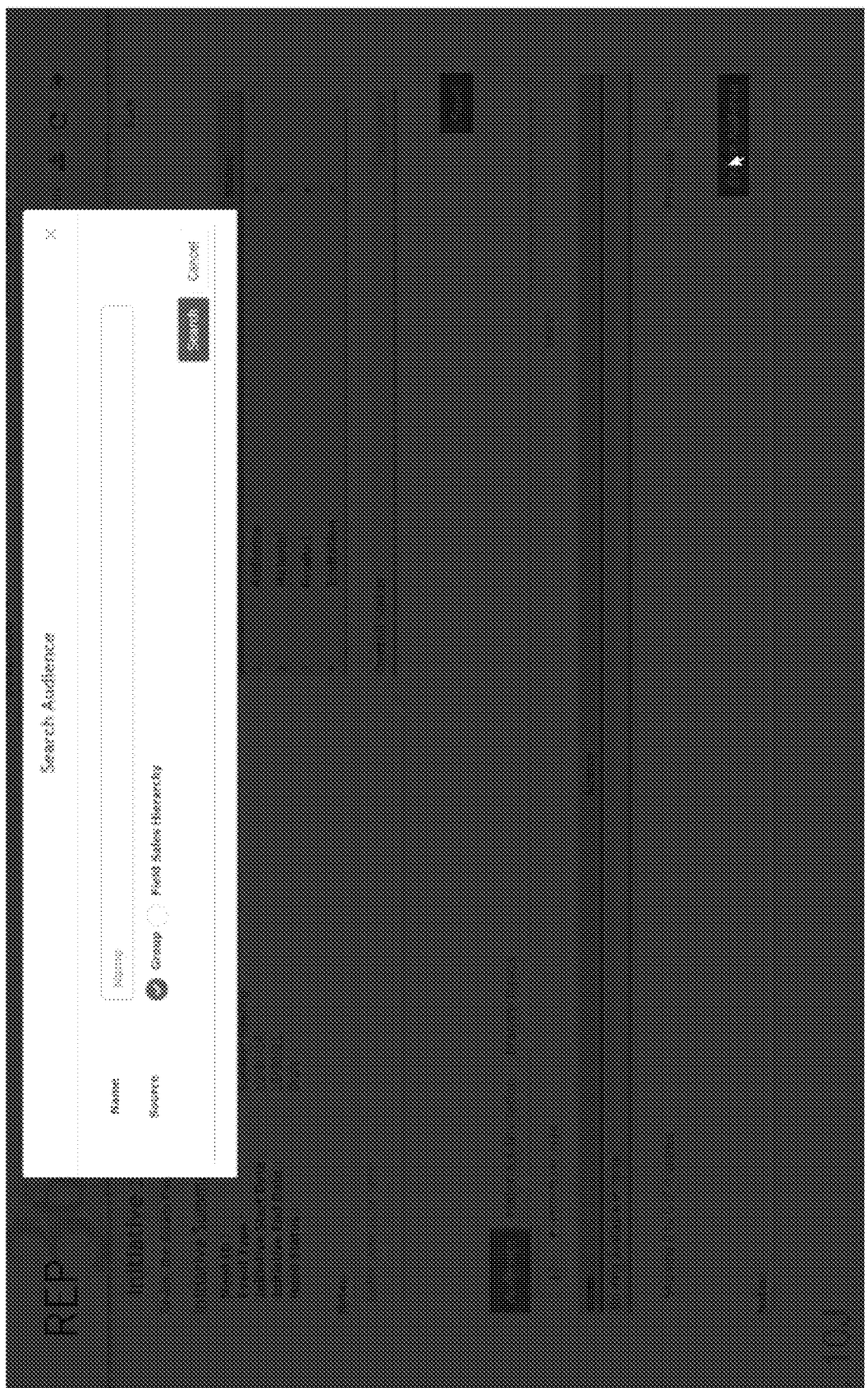

Speaker Bureau Summary

Year: 2021  Brand: Redacted  Min of Desired Events Per Speaker: 3

Alliance Brand: No  Max Size: 2  Concierge Max: 0

Alliance Partner: N/A  Current Size: 21  Concierge Count: 1

Notes

Aligned Users

| First Name | Last Name | Group | Max Allocation |
|---|---|---|---|
| Redacted | | Nominator | 25 |
| | | Nominator | |
| | | Approver | |
| | | Approver | |
| | | Approver | |
| | | Approver | |

Showing 1 to 6 of 6 entries

Previous | Next

Speaker Profile

Name: Redacted
Specialty:
Affiliation:
CM ID:
HSE ID:
Office City:
Office State:
Office Zip:
Cell Phone:
Email:
Concierge: No The information displayed in this tile is used by default when displayed on marketing approved invitations

Nomination History

| Year | BrandID | Brand | Nomination Date | Nomination Type | Nomination Status | Nominated By |
|------|---------|-------|-----------------|-----------------|-------------------|--------------|
| 2020 | 22 | Redacted | 7/8/2020 12:00:00 AM | Renew | Processed | HSE System Administrator |
| 2021 | 22 | Redacted | 7/28/2020 12:00:00 AM | New | Pending | Redacted |

Showing 1 to 2 of 2 entries

Previous 1 Next

CLOUD-BASED ENTERPRISE PLATFORM FOR EVENT HANDLING

CROSS-REFERENCE TO RELATED PATENT APPLICATIONS

This application claims the benefit of U.S. Provisional Application No. 62/930,501 filed on Nov. 4, 2019, the contents of which are incorporated herein by reference in their entirety.

BACKGROUND

Industry opinion leaders are individuals considered to be effective at influencing others within an industry to make certain choices and to conform their opinions to coincide with those of the opinion leader. More specifically, in the healthcare industry, a key opinion leader is a physician or other healthcare provider who is capable of influencing other healthcare providers to prescribe a certain therapy (e.g., a certain drug manufactured by a certain pharmaceutical manufacturer). However, the pharmaceutical and healthcare industries are highly regulated with respect to the opinions given by those key opinion leaders, for example, with respect to certain disclosure and certification requirements.

As technology advances, the ability for healthcare providers and others to interact with one another continues to become more efficient and seamless irrespective of the location of the relevant persons. For example, key opinion leaders can present remotely regarding the efficacy of a particular drug using appropriate web conferencing or remote collaboration software (e.g., Adobe Connect). However, while the injection of technology allows for efficient communication, it also introduces additional risk associated with governmental compliance and other technical challenges.

SUMMARY

One embodiment is directed to a unique system, components, and methods for a cloud-based enterprise platform for event handling. Other embodiments are directed to apparatuses, systems, devices, hardware, methods, and combinations thereof for enterprise platforms for event handling.

According to an embodiment, a cloud-based enterprise platform for event handling may include at least one processor and at least one memory comprising a plurality of instructions stored thereon that, in response to execution by the at least one processor, causes the cloud-based enterprise platform to communicate with a representative device of a pharmaceutical company representative to provide a representative portal to the representative device, wherein the representative portal includes at least a programs section that allows the representative to plan a program and a speakers section that allows the representative to view profiles of a plurality of healthcare providers identified as key opinion leaders, wherein the representative interacts with the representative portal via a graphical user interface corresponding with the representative portal displayed on the representative device, and communicate with a speaker device of a key opinion leader to provide a speaker portal to the speaker device, wherein the speaker portal allows the key opinion leader to interact with presentation materials and upcoming program data, wherein the key opinion leader interacts with the speaker portal via a graphical user interface corresponding with the speaker portal displayed on the speaker device.

In some embodiments, the programs section may allow the representative to target healthcare providers as prospective attendees to the program based on one or more criteria associated with the healthcare providers.

In some embodiments, a particular healthcare provider may be identified as a prospective attendee based on a determination that the particular healthcare provider's medical practice includes at least a threshold number of healthcare providers.

In some embodiments, the particular healthcare provider may be identified as a prospective attendee based further on a determination that the particular healthcare provider's medical practice has at least a threshold patient volume.

In some embodiments, the particular healthcare provider may be identified as a prospective attendee based further on a determination that the particular healthcare provider's practice is of a particular specialty.

In some embodiments, the particular healthcare provider may be identified as a prospective attendee based further on a determination that the particular healthcare provider is associated with an academic hospital.

In some embodiments, the targeted healthcare providers may be identified on a geographical heat map that displays indicia corresponding with respective locations of the targeted healthcare providers.

In some embodiments, the representative portal may include an online registration module configurable by the representative to support online customizable online event registration websites.

In some embodiments, the online registration module may include site templates for layout and presentation, content areas, and merged fields for customizable generation of online event registration websites.

In some embodiments, the plurality of instructions may further cause the cloud-based enterprise platform to communicate with an administrative device of an administrator of the cloud-based enterprise platform to provide an admin portal to the administrative device.

In some embodiments, the programs section may include a programs tab and the speakers section comprises a speakers tab of the graphical user interface corresponding with the representative portal.

According to another embodiment, a system may include an enterprise system configured to provide an enterprise-wide integrated solution for pharmaceutical companies including data integration, template-driven communication, and event planning with end-to-end legal compliance and validation, wherein the enterprise-wide integrated solution includes at least a representative portal and a speaker portal, a representative device of a pharmaceutical company representative configured to communicate with the enterprise system to interact with the representative portal, and a speaker device of a key opinion leader configured to communicate with the enterprise system to interaction with the speaker portal, wherein the representative portal includes at least a programs section that allows the representative to plan a program and a speakers section that allows the representative to view profiles of a plurality of healthcare providers identified as key opinion leaders, and wherein the speaker portal allows the key opinion leader to interact with presentation materials and upcoming program data.

In some embodiments, the programs section may allow the representative to target healthcare providers as prospective attendees to the program based on one or more criteria associated with the healthcare providers.

In some embodiments, a particular healthcare provider may be identified as a prospective attendee based on a determination that the particular healthcare provider's medical practice includes at least a threshold number of healthcare providers.

In some embodiments, the particular healthcare provider may be identified as a prospective attendee based further on a determination that the particular healthcare provider's medical practice has at least a threshold patient volume.

In some embodiments, the particular healthcare provider may be identified as a prospective attendee based further on a determination that the particular healthcare provider's practice is of a particular specialty.

In some embodiments, the particular healthcare provider may be identified as a prospective attendee based further on a determination that the particular healthcare provider is associated with an academic hospital.

In some embodiments, the targeted healthcare providers may be identified on a geographical heat map that displays indicia corresponding with respective locations of the targeted healthcare providers.

In some embodiments, the representative portal may include an online registration module configurable by the representative to support online customizable online event registration websites.

In some embodiments, the online registration module may include site templates for layout and presentation, content areas, and merged fields for customizable generation of online event registration websites.

This summary is not intended to identify key or essential features of the claimed subject matter, nor is it intended to be used as an aid in limiting the scope of the claimed subject matter. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
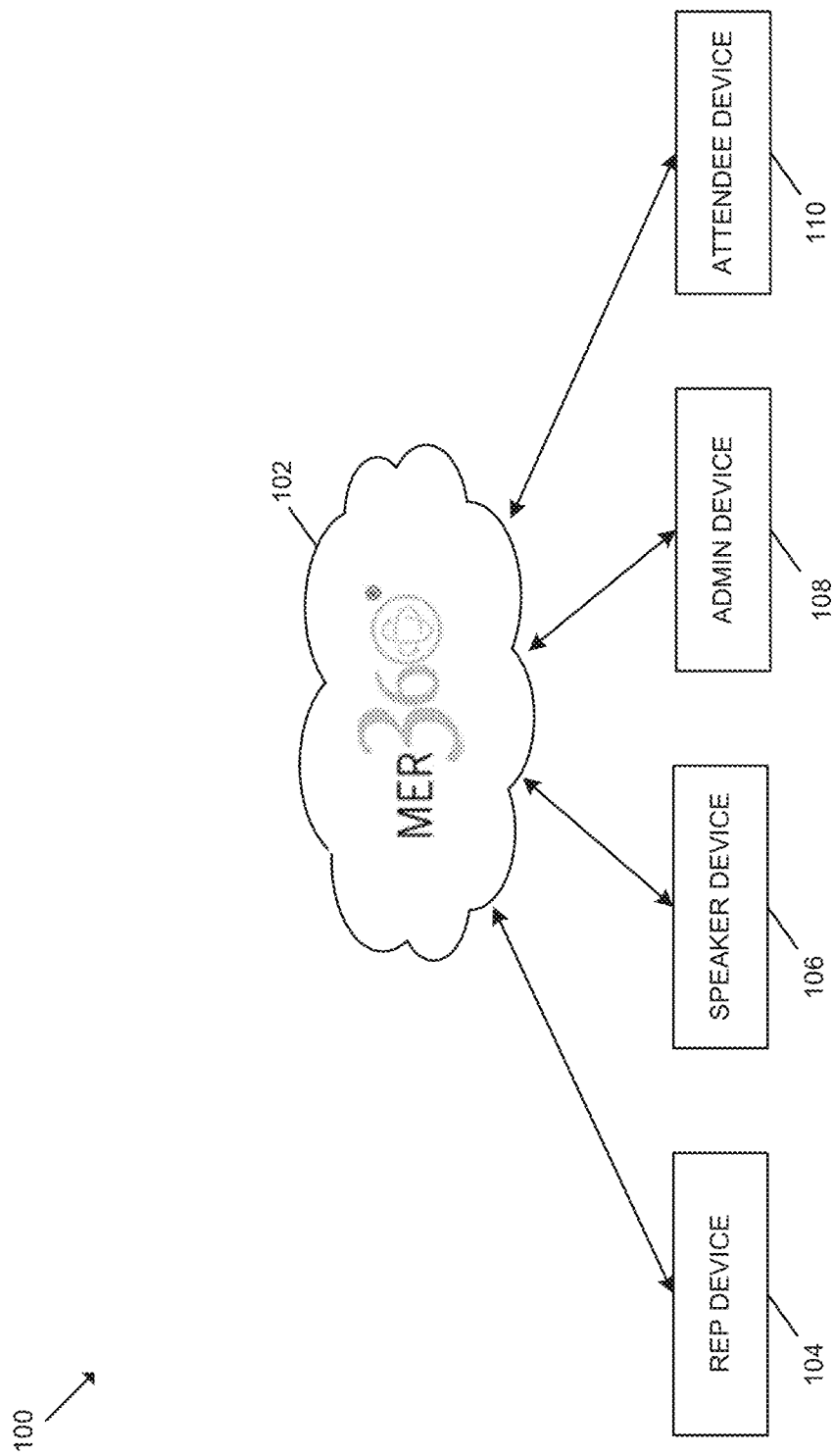
FIG. 1 is a simplified block diagram of at least one embodiment of a system for event handling using a cloud-based enterprise platform.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

Referring now to FIG. 1, in the illustrative embodiment, a system 100 for event handling includes an enterprise platform 102 (e.g., MER360) and one or more devices configured to communicate with the enterprise platform 102. For example, in the illustrative embodiment, the system 100 includes a representative device 104 configured to be used by a pharmaceutical company representative, a speaker device 106 configured to be used to a speaker engaged by the pharmaceutical company to discuss a particular topic (e.g., a particular drug or treatment), an admin device 108 configured to be used by a system administrator of the enterprise platform 102, and an attendee device 110 configured to be used by a healthcare provider/professional (HCP) attending (or targeted to attend) a particular healthcare event. Although the devices 104-110 are described as separate devices, it should be appreciated that a particular user may use the same device in different roles depending on the particular circumstances (e.g., as a representative, speaker, admin, and/or attendee).

As described in greater detail below, the enterprise platform 102 may function as an enterprise-wide integrated solution for pharmaceutical companies, providing various technical features for data integration, template-driven communication, and event planning while ensuring end-to-end statutory/regulatory (legal) compliance and validation. In some embodiments, the enterprise platform 102 provides real-time (or near real-time) integration of various databases for event handling/management and service delivery as described below. Although the enterprise platform 102 is described herein primarily as being a cloud-based solution or system, it should be appreciated that the enterprise platform 102 may be situated "outside" of a cloud computing environment in other embodiments. It should be further appreciated that the enterprise platform 102 may include one or more computing devices, systems, databases, and/or other systems depending on the particular system architecture. In some embodiments, the enterprise platform 102 leverage cloud storage, which may be embodied as one or more databases, data structures, and/or data storage devices capable of storing data in a cloud-based system or otherwise facilitating the storage of such data for the enterprise platform 102.

Each of the representative device 104, the speaker device 106, the admin device 108, and the attendee device 110 may be embodied as any type of device capable of executing an application and otherwise performing the functions described herein. It should be appreciated that each of the applications executed by the respective devices may be embodied as any type of application suitable for performing the functions described herein. In particular, in some embodiments, one or more of the applications may be embodied as a mobile application (e.g., a smartphone application), a cloud-based application, a web application, a thin-client application, and/or another type of application. For example, in some embodiments, one or more of the applications may serve as a client-side interface (e.g., via a web browser) for a web-based application or service (e.g., of a web server associated with the enterprise platform 102). As such, in some embodiments, it should be appreciated that the enterprise platform 102 may include one or more web servers configured to serve web pages that form and/or interact with the applications of the various devices 104, 106, 108, 110. In the illustrative embodiment, it should be appreciated that the enterprise platform 102 is configured to communicate various data with the representative device 104, the speaker device 106, the admin device 108, and/or the attendee device 110, which results in various graphical user interfaces being displayed on the respective device(s) via the application as described herein. Each graphical user interface page, tab, or screen includes various graphical elements/components as depicted in the figures, some of which may not be explicitly identified or referenced in the written description for brevity of the description. Further, although the graphical user interface may describe various portions as "tabs," it should be appreciated that such data may otherwise be represented in different sections of the graphical user interface (i.e., not necessarily in a tabular format).

In some embodiments, the enterprise platform 102 (or devices thereof) may be embodied as or include a virtual computing environment residing "on" a computing system (e.g., a distributed network of devices) in which various virtual functions (e.g., Lambda functions, Azure functions, Amazon Web Services cloud functions, Google cloud functions, and/or other suitable virtual functions) may be executed corresponding with the functions of the enterprise platform 102 described herein. For example, when an event occurs (e.g., data is transferred to the enterprise platform 102 for handling), the virtual computing environment may be communicated with (e.g., via a request to an API of the virtual computing environment), whereby the API may route the request to the correct virtual function (e.g., a particular server-ambiguous computing resource) based on a set of rules. As such, when a request for the transmission of particular data is made (e.g., via an appropriate interface to the enterprise platform 102), the appropriate virtual function(s) may be executed to perform the actions before eliminating the instance of the virtual function(s). Although the enterprise platform 102 is described herein as including one or more cloud-based devices, it should be appreciated that the enterprise platform 102 may be embodied as, or include, one or more servers located "outside" of a cloud computing environment in other embodiments.

It should be appreciated that the various devices of the system 100 may communicate with one another via one or more networks (not shown for clarity). In such embodiments, the network(s) may be embodied as any type of communication network(s) capable of facilitating communication between the various devices of the system 100 depending on the particular embodiment. As such, the network(s) may include one or more networks, routers, switches, computers, and/or other intervening devices. For example, the network(s) may be embodied as or otherwise include one or more cellular networks, telephone networks, local or wide area networks, publicly available global networks (e.g., the Internet), ad hoc networks, short-range wireless communication networks, long-range wireless communication networks, other networks, or a combination thereof.

It should be further appreciated that the representative device 104, the speaker device 106, the admin device 108, the attendee device 110, and/or devices of the enterprise platform 102 may be embodied as (or include) one or more computing devices similar to the computing device 200 described below in reference to FIG. 2. For example, in the illustrative embodiment, each of the representative device 104, the speaker device 106, the admin device 108, the attendee device 110, and the devices of the enterprise platform 102 may include a processing device 202 and a memory 206 having stored thereon operating logic 208 (e.g., a plurality of instructions) for execution by the processing device 202 for operation of the corresponding device.

Figure 2:
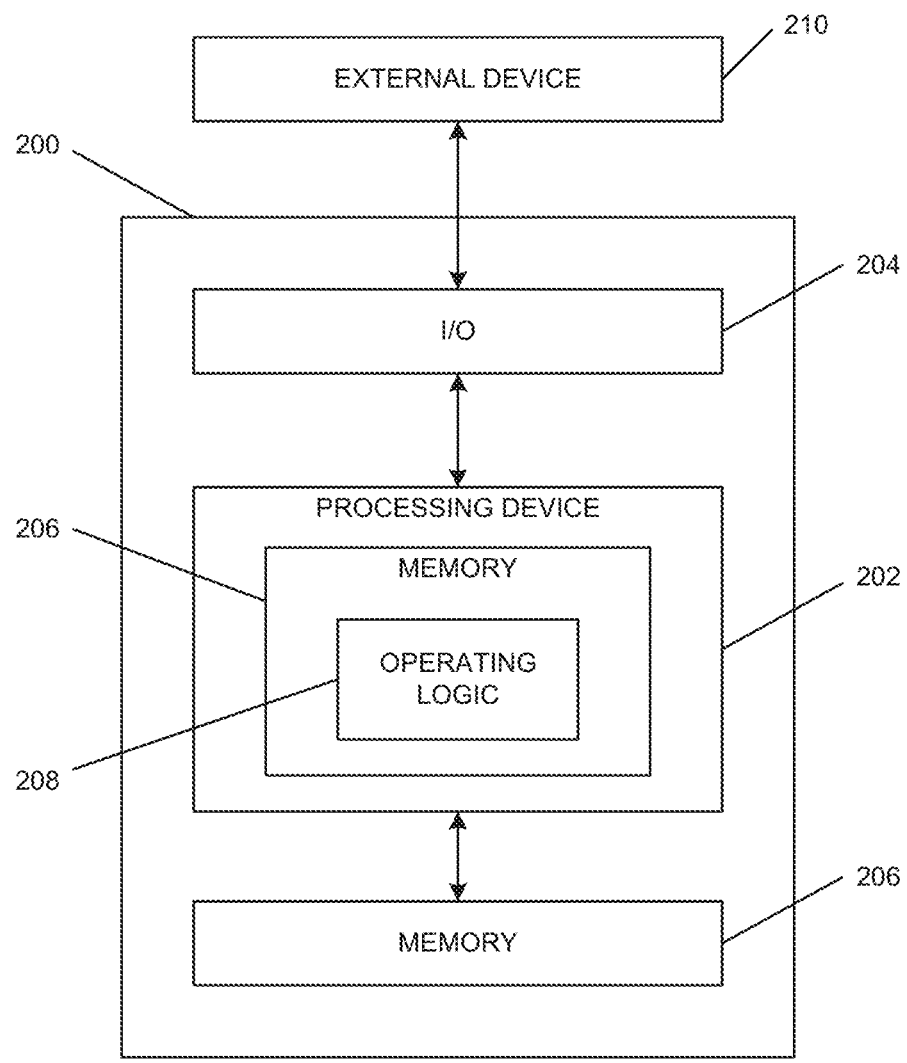
FIG. 2 is a simplified block diagram of at least one embodiment of a computing device.

Referring now to FIG. 2, a simplified block diagram of at least one embodiment of a computing device 200 is shown. The illustrative computing device 200 depicts at least one embodiment of a computing device, cloud-based system, server, client device, and/or other device that may be utilized in connection with the representative device 104, the speaker device 106, the admin device 108, the attendee device 110, and/or devices of the enterprise platform 102 illustrated in FIG. 1. Depending on the particular embodiment, the computing device 200 may be embodied as a server, desktop computer, laptop computer, tablet computer, notebook, netbook, Ultrabook™, cellular phone, mobile computing device, smartphone, wearable computing device, personal digital assistant, Internet of Things (IoT) device, processing system, wireless access point, router, gateway, and/or any other computing, processing, and/or communication device capable of performing the functions described herein.

The computing device 200 includes a processing device 202 that executes algorithms and/or processes data in accordance with operating logic 208, an input/output device 204 that enables communication between the computing device 200 and one or more external devices 210, and memory 206 which stores, for example, data received from the external device 210 via the input/output device 204.

The input/output device 204 allows the computing device 200 to communicate with the external device 210. For example, the input/output device 204 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 200 may be configured to use any one or more communication technologies (e.g., wireless or wired communications) and associated protocols (e.g., Ethernet, Bluetooth®, Wi-Fi®, WiMAX, etc.) to effect such communication depending on the particular computing device 200. The input/output device 204 may include hardware, software, and/or firmware suitable for performing the techniques described herein.

The external device 210 may be any type of device that allows data to be inputted or outputted from the computing device 200. For example, in various embodiments, the external device 210 may be embodied as the representative device 104, the speaker device 106, the admin device 108, the attendee device 110, and/or devices of the enterprise platform 102. Further, in some embodiments, the external device 210 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 210 may be integrated into the computing device 200.

The processing device 202 may be embodied as any type of processor(s) capable of performing the functions described herein. In particular, the processing device 202 may be embodied as one or more single or multi-core processors, microcontrollers, or other processor or processing/controlling circuits. For example, in some embodiments, the processing device 202 may include or be embodied as an arithmetic logic unit (ALU), central processing unit (CPU), digital signal processor (DSP), and/or another suitable processor(s). The processing device 202 may be a programmable type, a dedicated hardwired state machine, or a combination thereof. Processing devices 202 with multiple processing units may utilize distributed, pipelined, and/or parallel processing in various embodiments. Further, the processing device 202 may be dedicated to performance of just the operations described herein, or may be utilized in one or more additional applications. In the illustrative embodiment, the processing device 202 is programmable and executes algorithms and/or processes data in accordance with operating logic 208 as defined by programming instructions (such as software or firmware) stored in memory 206.

Additionally or alternatively, the operating logic 208 for processing device 202 may be at least partially defined by hardwired logic or other hardware. Further, the processing device 202 may include one or more components of any type suitable to process the signals received from input/output device 204 or from other components or devices and to provide desired output signals. Such components may include digital circuitry, analog circuitry, or a combination thereof.

The memory 206 may be of one or more types of non-transitory computer-readable media, such as a solid-state memory, electromagnetic memory, optical memory, or a combination thereof. Furthermore, the memory 206 may be volatile and/or nonvolatile and, in some embodiments, some or all of the memory 206 may be of a portable type, such as a disk, tape, memory stick, cartridge, and/or other suitable portable memory. In operation, the memory 206 may store various data and software used during operation of the computing device 200 such as operating systems, applications, programs, libraries, and drivers. It should be appreciated that the memory 206 may store data that is manipulated by the operating logic 208 of processing device 202, such as, for example, data representative of signals received from and/or sent to the input/output device 204 in addition to or in lieu of storing programming instructions defining operating logic 208. As shown in FIG. 2, the memory 206 may be included with the processing device 202 and/or coupled to the processing device 202 depending on the particular embodiment. For example, in some embodiments, the processing device 202, the memory 206, and/or other components of the computing device 200 may form a portion of a system-on-a-chip (SoC) and be incorporated on a single integrated circuit chip.

In some embodiments, various components of the computing device 200 (e.g., the processing device 202 and the memory 206) may be communicatively coupled via an input/output subsystem, which may be embodied as circuitry and/or components to facilitate input/output operations with the processing device 202, the memory 206, and other components of the computing device 200. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 200 may include other or additional components, such as those commonly found in a typical computing device (e.g., various input/output devices and/or other components), in other embodiments. It should be further appreciated that one or more of the components of the computing device 200 described herein may be distributed across multiple computing devices. In other words, the techniques described herein may be employed by a computing system that includes one or more computing devices. Additionally, although only a single processing device 202, I/O device 204, and memory 206 are illustratively shown in FIG. 2, it should be appreciated that a particular computing device 200 may include multiple processing devices 202, I/O devices 204, and/or memories 206 in other embodiments. Further, in some embodiments, more than one external device 210 may be in communication with the computing device 200.

Figure 3:
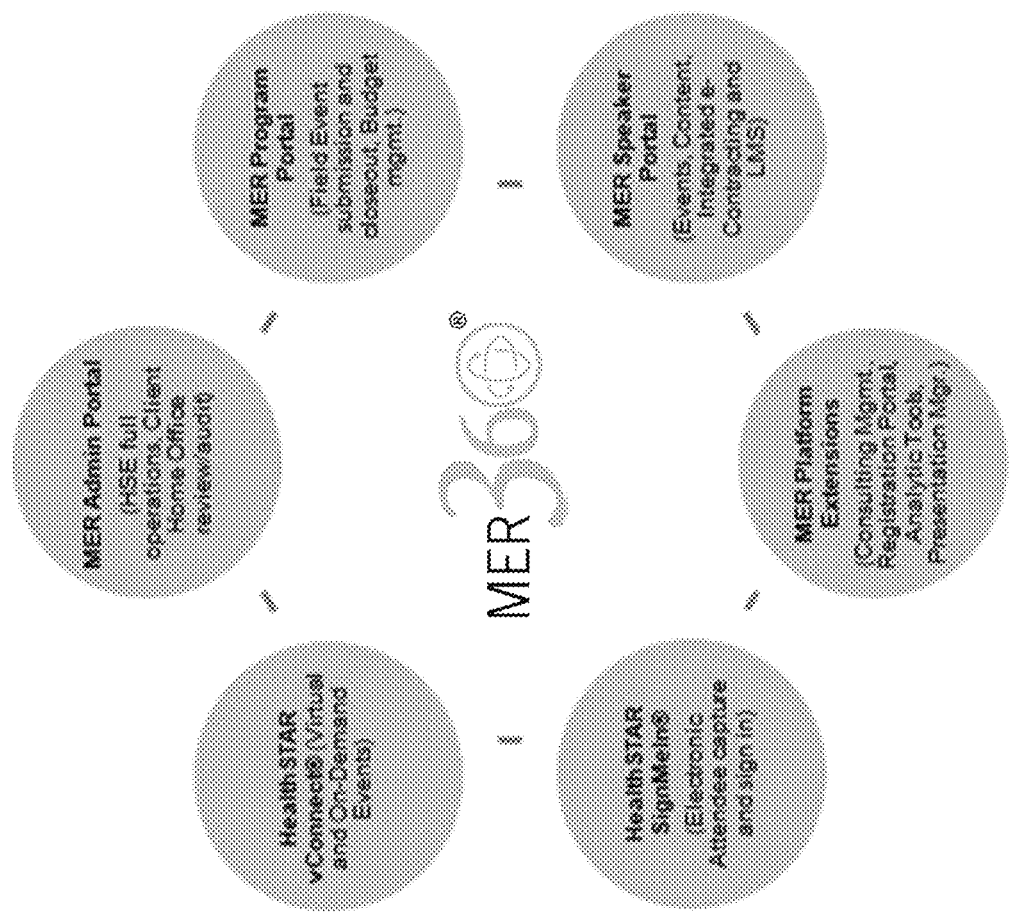
FIG. 3 is a simplified diagram of at least one embodiment of the systems of the enterprise platform.
Figure 8:
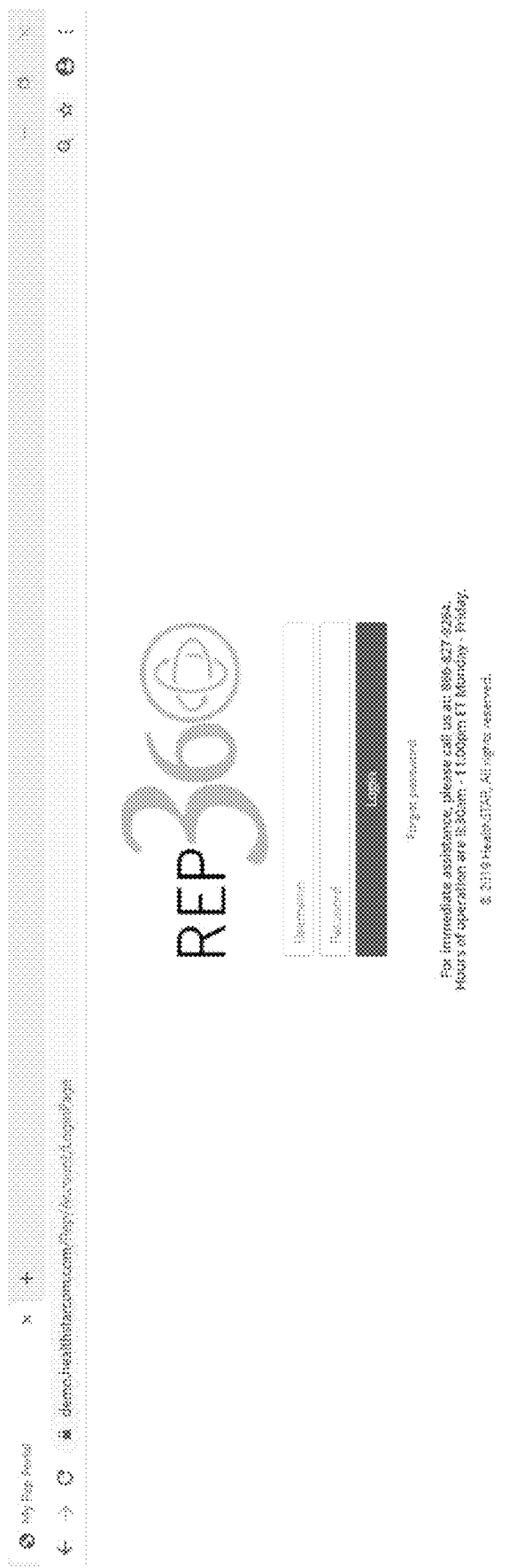
Figure 82:
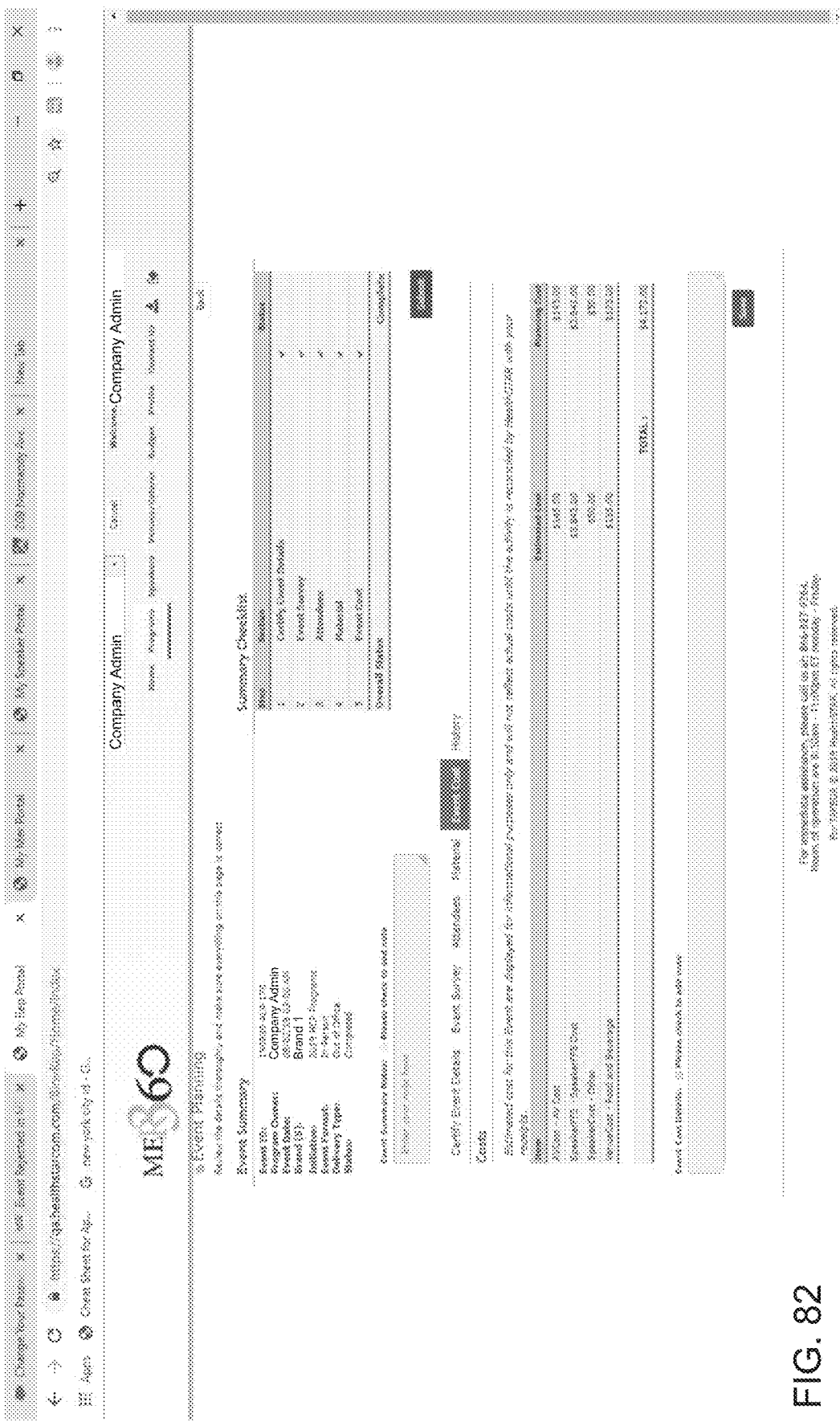
Figure 83:
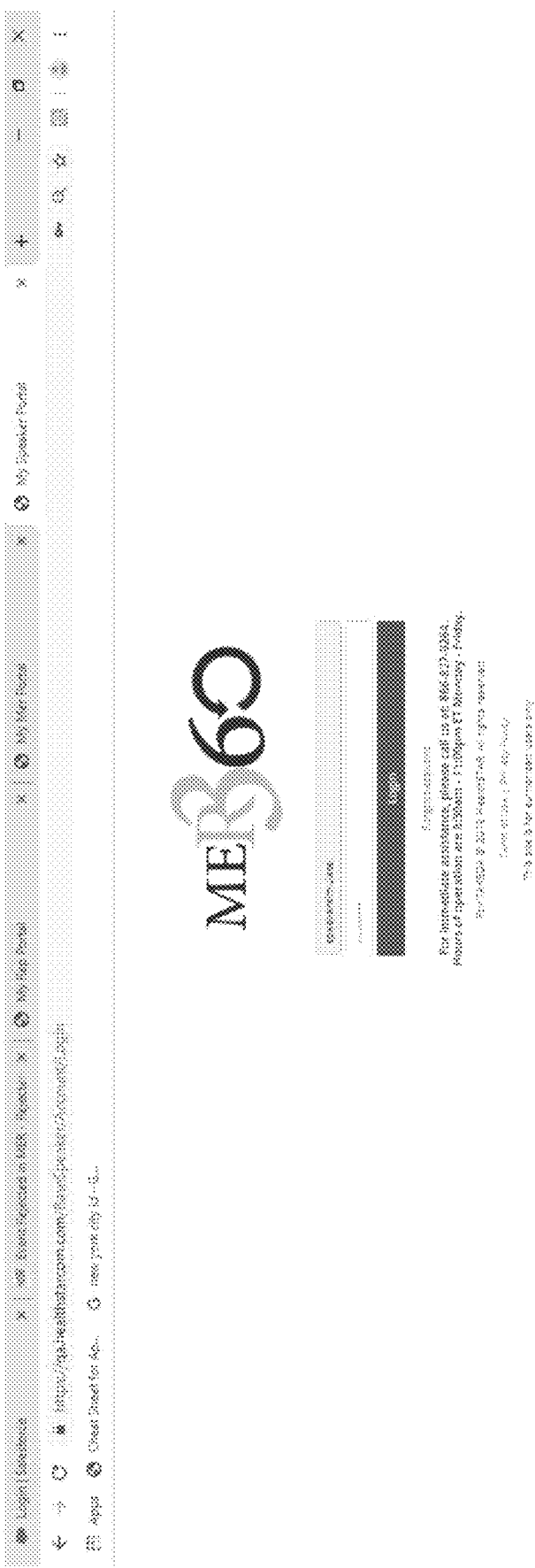

Referring now to FIG. 3, various systems of at least one embodiment of the enterprise platform are shown. For example, in the illustrative embodiment of FIG. 3, the enterprise platform may include an admin portal, a program/ representative portal, a speaker portal, platform extensions, electronic attendee capture and sign-in system, and a virtual and on-demand event system. The program/representative portal may be used by client home office users and field representatives. At least one embodiment of a graphical user interface associated with the program/representative portal is depicted in FIGS. 8-82. The speaker portal may be used by HCPs. At least one embodiment of a graphical user interface associated with the speaker portal is depicted in FIGS. 83-100. The admin portal may be used by administrators of the enterprise platform. At least one embodiment of a graphical user interface associated with the admin portal is depicted in FIGS. 101-105. The platform extensions/modules may include consulting management, attendee online registration (see FIGS. 65A-E), mobile applications, and/or other extensions/modules. The electronic attendee capture and sign-in system may be embodied as the system described in U.S. patent application Ser. No. 13/758,545 filed on Feb. 4, 2013, the entirety of which is incorporated herein by reference in its entirety. The virtual and on-demand event system may be embodied as the system described in U.S. patent application Ser. No. 13/624,412 filed on Sep. 21, 2012, the entirety of which is incorporated herein by reference in its entirety. In some embodiments, other platform extensions may include attendee survey module (e.g., attendee polling and survey data collection), presentation manager (e.g., integrated capabilities with other systems that allow speakers to modify existing presentation materials within approved client rules (e.g., drag and drop functionality)), invitation and communications engine (e.g., invitation generator that merges event details into regulatory-approved PDF formats), learning management system module (e.g., system for presenting and tracking completion of video content, including Q&A/testing functionality), needs assessment module (e.g., client platform for submission, routing, and internal approval of business justifications for promotional and clinical activities), consultant management portal (e.g., consulting engagement (e.g., advisory boards, research/publication reviews) management tool, including nomination, vetting, contracting, proof-of-performance, and payment functions), my attendee resource (e.g., electronic registration for activities that maintains event attendee engagement through confirmations, activity updates, and reminders), and other platform modules configured to seamlessly integrate with a client's native system architecture.

Figure 4:
FIG. 4 is a simplified diagram of at least one embodiment of one or more databases of the enterprise platform.

Referring now to FIG. 4, one or more potential databases of the enterprise platform are shown. In particular, in some embodiments, the databases may include databases associated with medical systems (e.g., speaker training, educational programs, product training), finance (e.g., budget tracking, accruals/invoicing, accounts payable), brand teams (e.g., analytics/dashboards, budget management, national programs), customer data (e.g., customer master, call plans, zip-to-territory), SAP (e.g., sales roster, accounts payable (check requests, payment status, vendor records), T&E), data warehouse (e.g., state and federal compliance and reporting, program data, document management), field sales (e.g., budget tracking, promotional programs (speaker, remote, D&E), closeout), sales management (e.g., budget management program approvals, speaker nominations, analytics/dashboards), home office (e.g., promotional policy, application admin, reporting), speakers (contracting and training, slide and content library, calendar and financials, profile maintenance), customers (multimedia pre-work, post-program evaluations, content library), and vendors (e.g., service orders, speaker contracting and training, program initiation). In other embodiments, it should be appreciated that the enterprise platform may leverage data from additional, or different databases. Further, in some embodiments, one or more of the databases depicted in FIG. 4 may be omitted from the enterprise platform. In some embodiments, two or more of the databases described in reference to FIG. 4 may be combined and/or the content may overlap.

Figure 5:
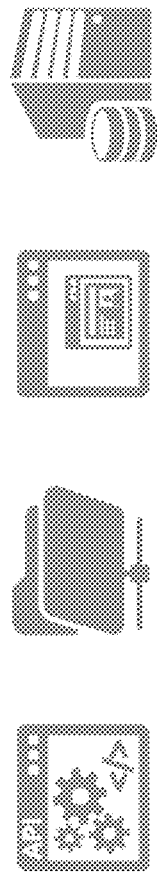
FIG. 5 is a simplified diagram of at least one embodiment of an integration approach for the enterprise platform.
Figure 5:
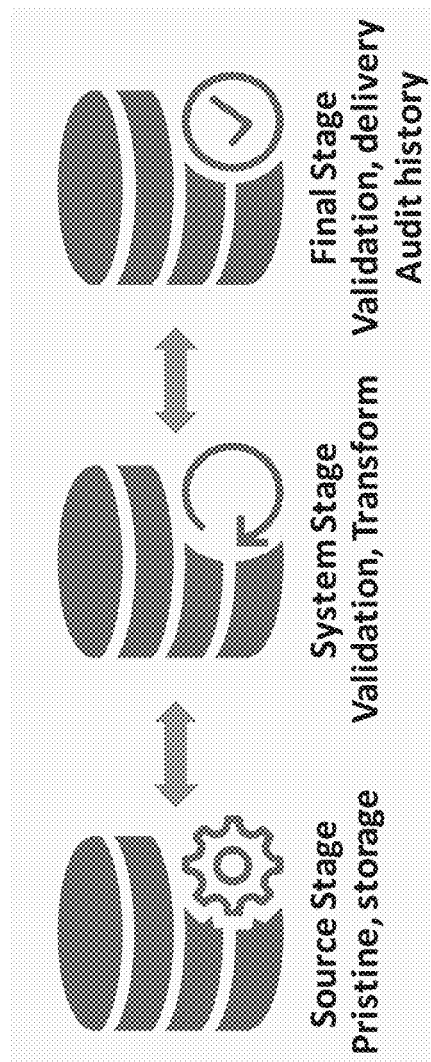
Figure 5:
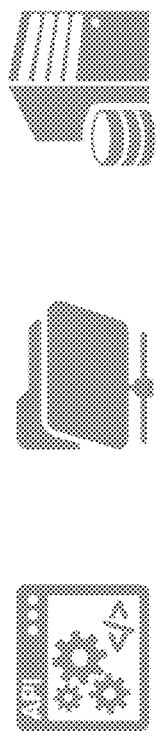

FIG. 5 illustrates at least one integration approach for the enterprise platform. In some embodiments, the layout, formatting, mapping/transform, differencing, and/or validation rules for the source and destination systems/interfaces may be stored as configuration data. The loosely coupled design allows for source/destination systems to change over time, and staging tables store original raw data, processed/intermediate/mapped data, final instructions, and transaction results. Workflow orchestration includes automated archival and delivery, including full control over every transaction type, format, delivery, and schedule. Further, the enterprise platform may provide a full audit history of every integration transaction.

Figure 6:
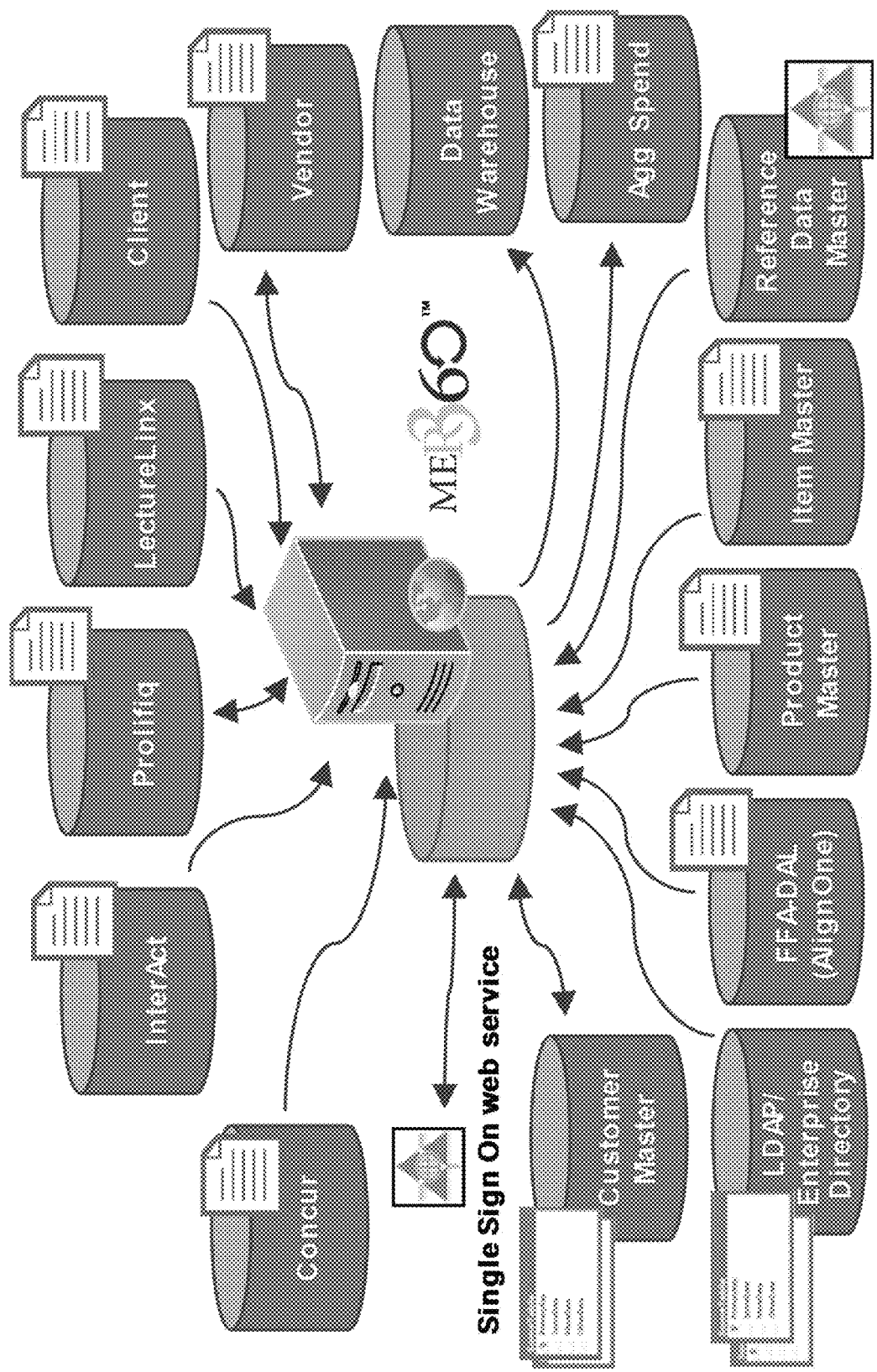
FIG. 6 is a simplified diagram of at least one embodiment of an integration architecture of the enterprise platform.

Referring now to FIG. 6, at least one embodiment of an integration architecture of the enterprise platform is shown. As shown, the integration may include various databases and systems. For example, in some embodiments, the integration may include Concur (e.g., non-speaker spend (raw expenses), non-speaker spend budget consumptions), InterAct (e.g., inbound: MSL-led speaker trainings, outbound: topic master data), Prolifiq (e.g., invitees/RSVPs, topic mapping report), LectureLinx (e.g., speaker contract data, speaker documents (contract, CV, CIF, W-9, photo), speaker fee for service, speaker training data, speaker rating web service), client databases/systems (e.g., meetings, speakers, and payments (speaker portal), operational and field manager reports), vendor databases/systems (e.g., peer perspective meetings, registrants, web/teleconference details), data warehouse (e.g., business data feed for reporting, C-SCAN, CIH), agg spend (e.g., transfer of value and aggregate spend reporting, exception reporting, top-down audit report), reference data master (e.g., geographic reference lists), item master (e.g., promotional item IDs and descriptions), product master (e.g., product/brand names, IDs, and statuses), FFA-DAL (AlignOne) (e.g., roster and territory assignment, customer target alignment, MSL and IOCL speakers, product alignment, target level values, ONC targets), LDAP/Enterprise directory (e.g., core user profiles for SSO), customer master (e.g., customer profiles and addresses (HCP, HCO), add a customer lifecycle, add an org lifecycle, updates, merges, purges, data stewardship, last update date, regression testing), and sign sign-on web service (e.g., web authentication).

Figure 7:
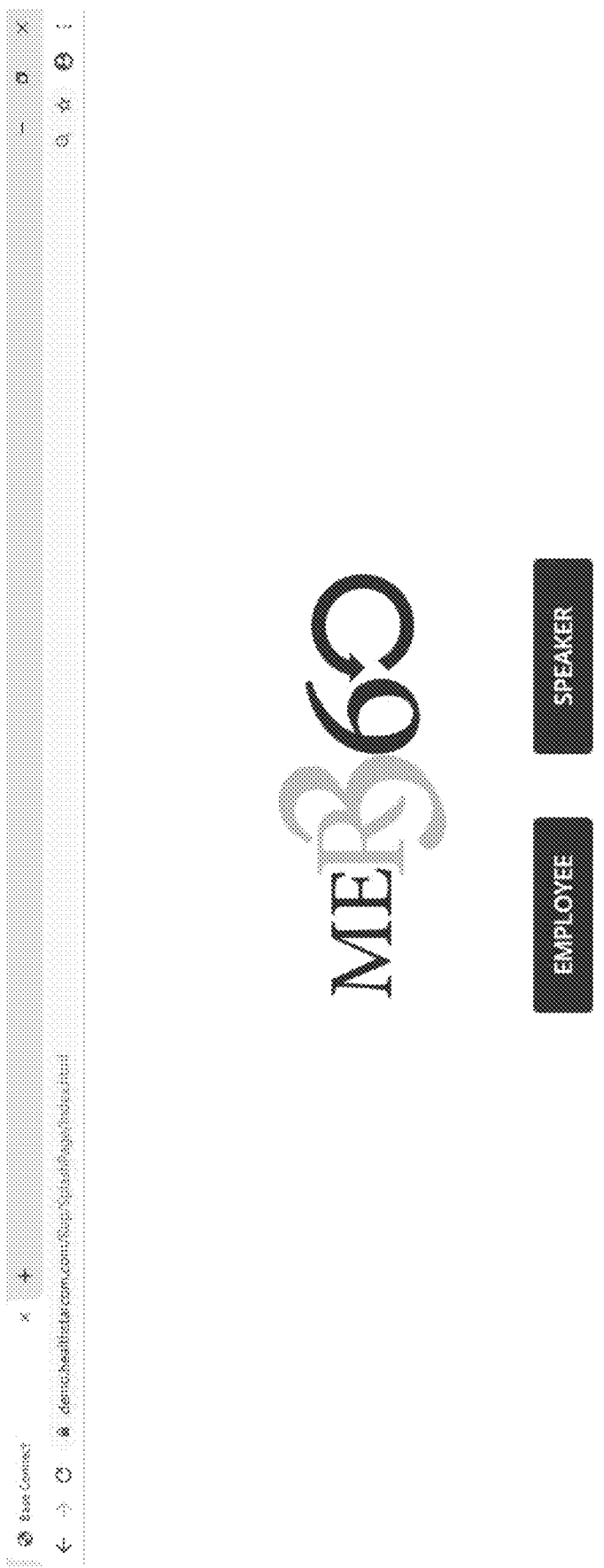
FIGS. 7-160 illustrate various states of at least one graphical user interface of the various portals of the enterprise platform.
Figure 160:
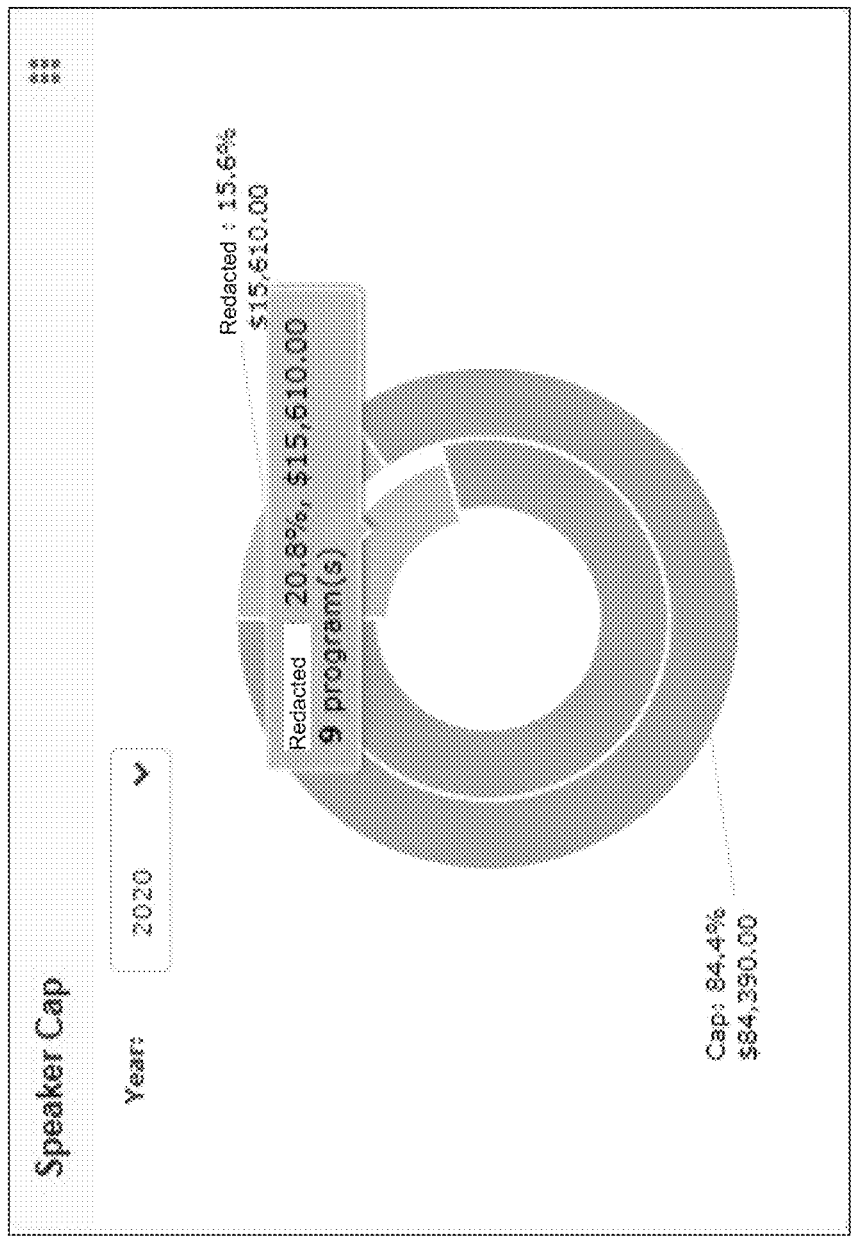

Referring now to FIGS. 7-160, various graphical user interfaces (or states thereof) of the enterprise platform according to at least one embodiment are shown. FIG. 7 depicts a splash screen in which the user may select "employee" to login to the representative portal or "speaker" to login to the speaker portal. FIG. 8 depicts the representative portal, which is launched upon the user's selection of that portal. In some embodiments, users (Field Team) will be authenticated via username and password functionality. SSO configuration may be available in the system if the client desires to implement SSO as a separate level of effort. FIGS. 8-82 depict various configurations of the graphical user interface associated with the representative portal.

Figure 32:
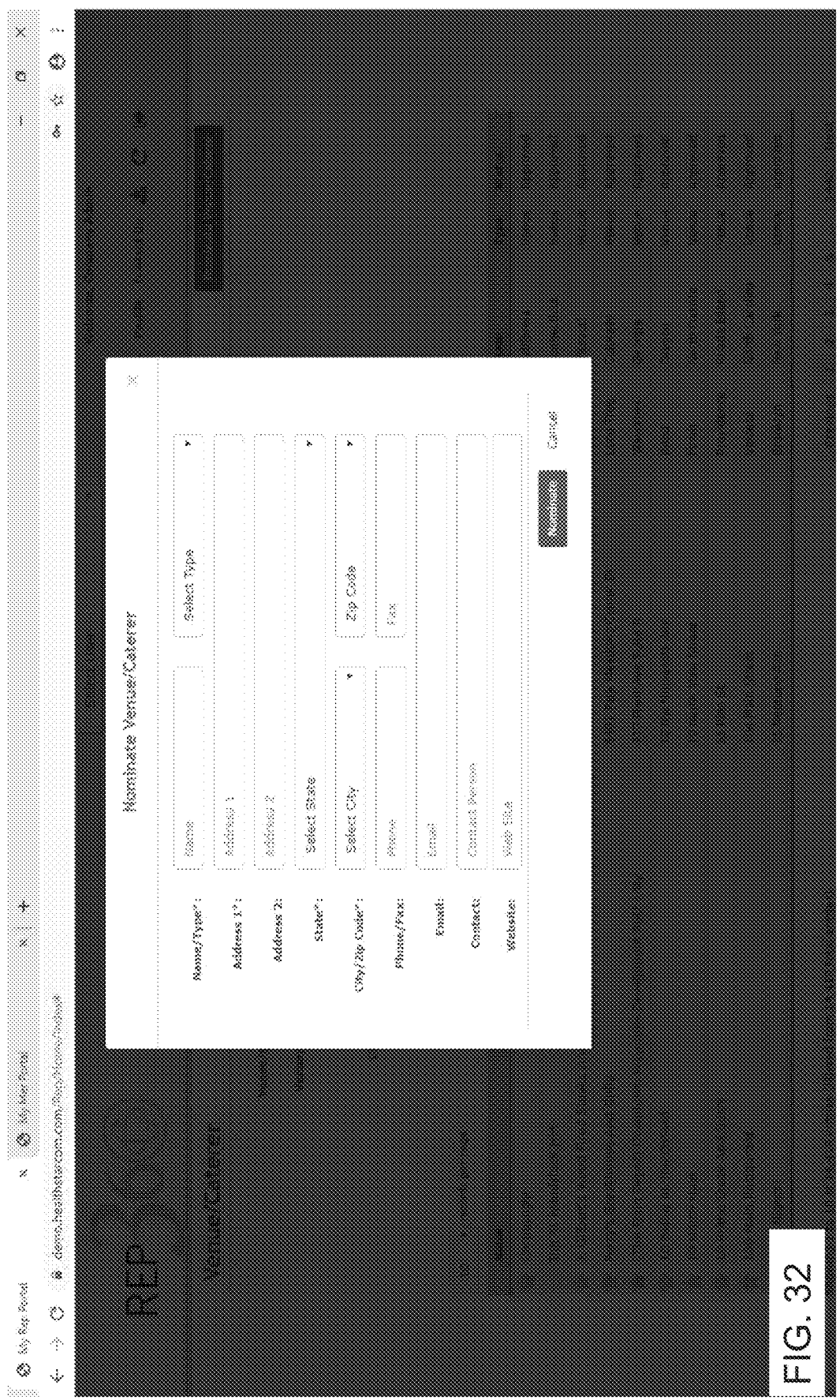
Figure 33:
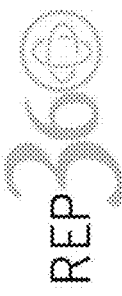
Figure 34:
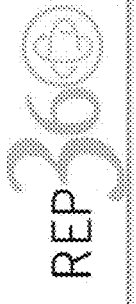
Figure 35:
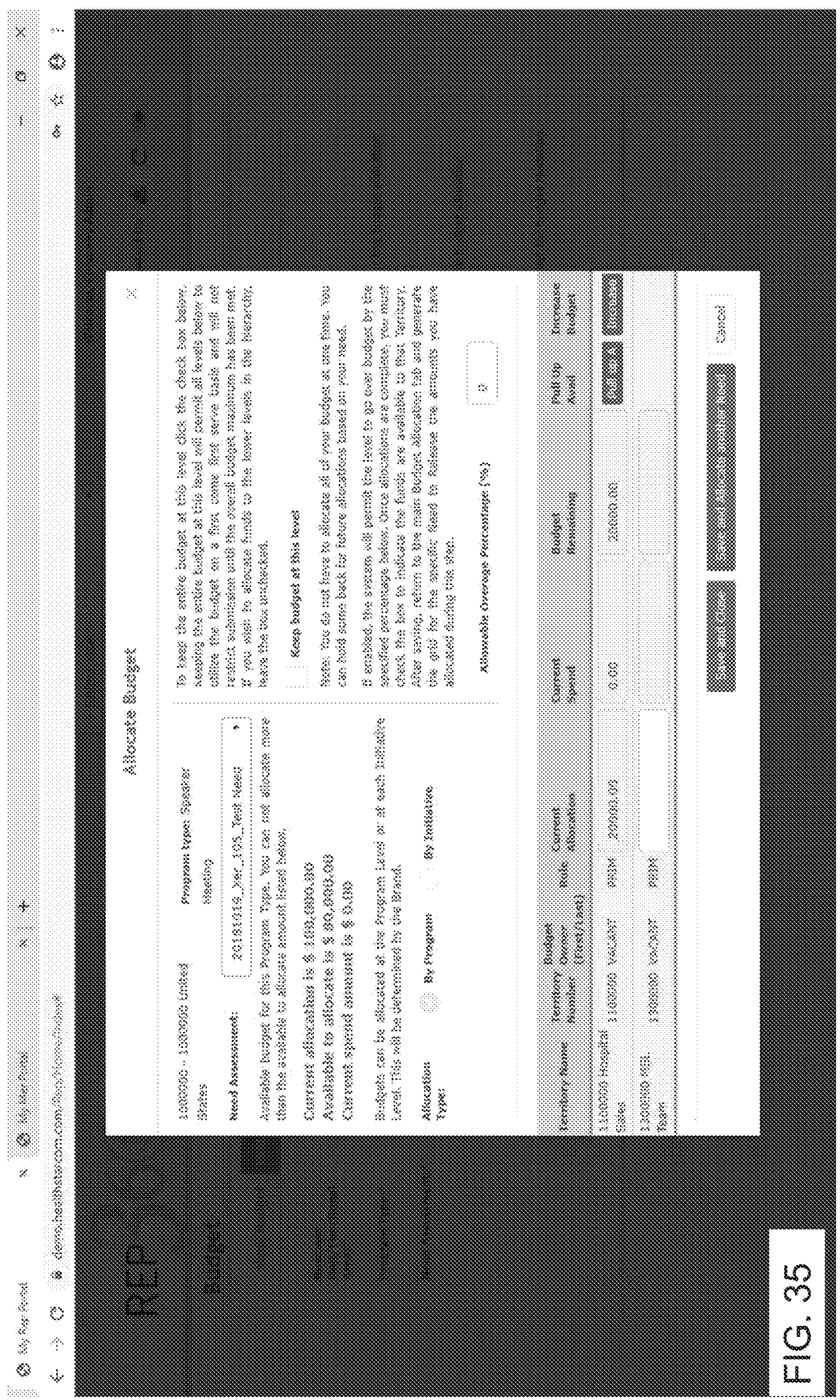
Figure 37:
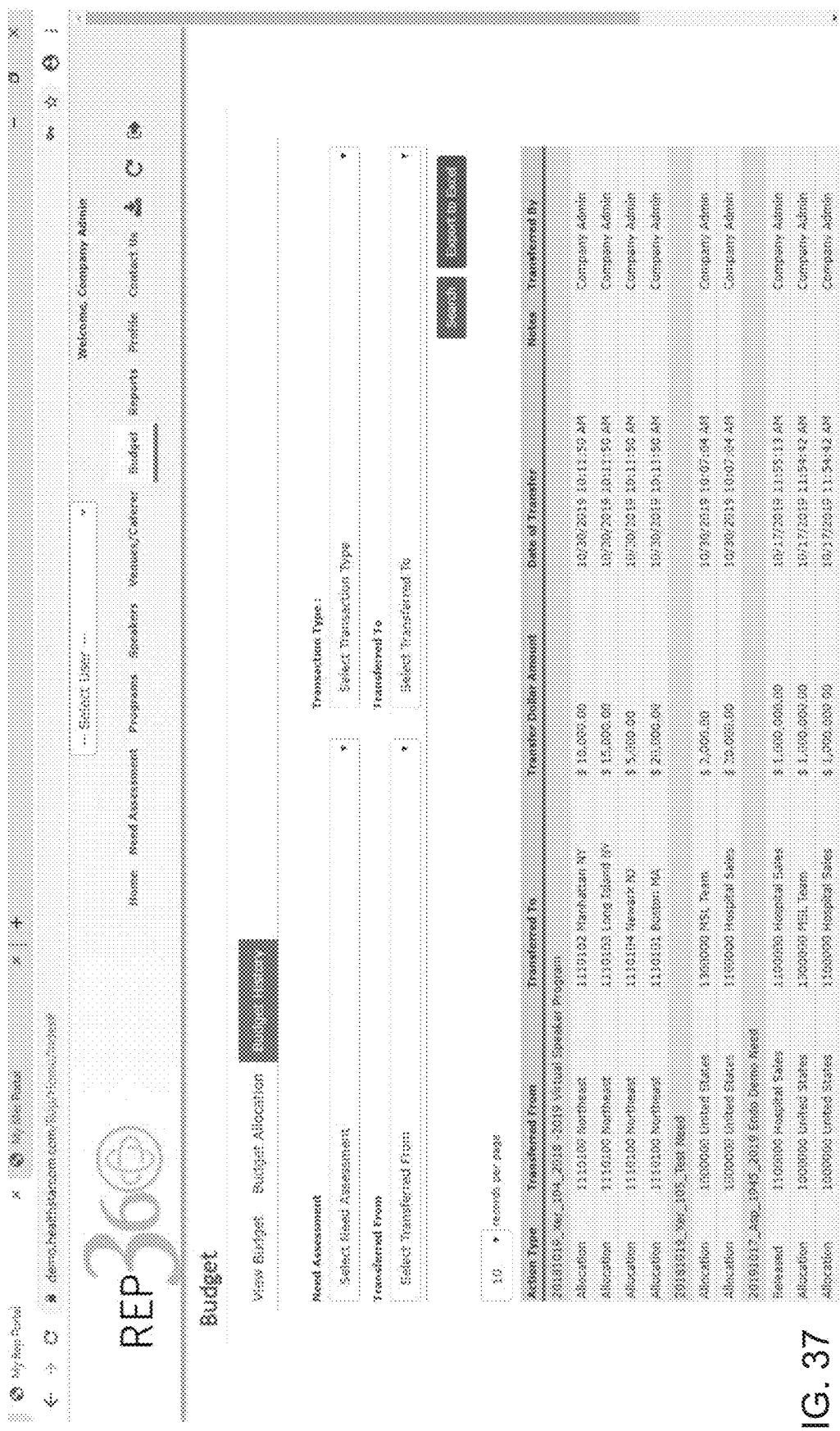
Figure 38:
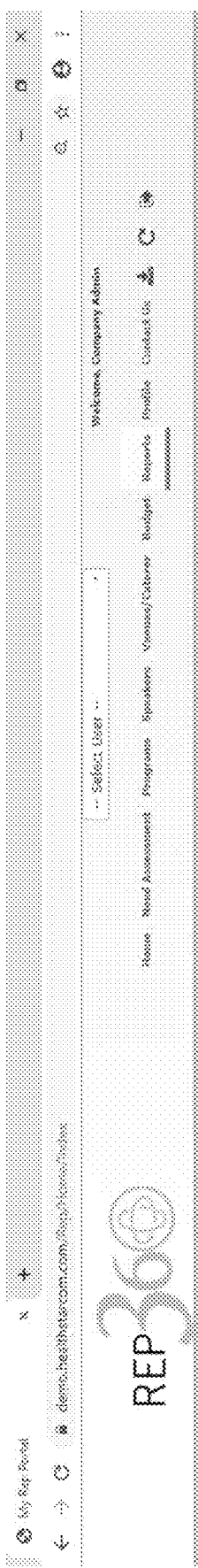
Figure 43:
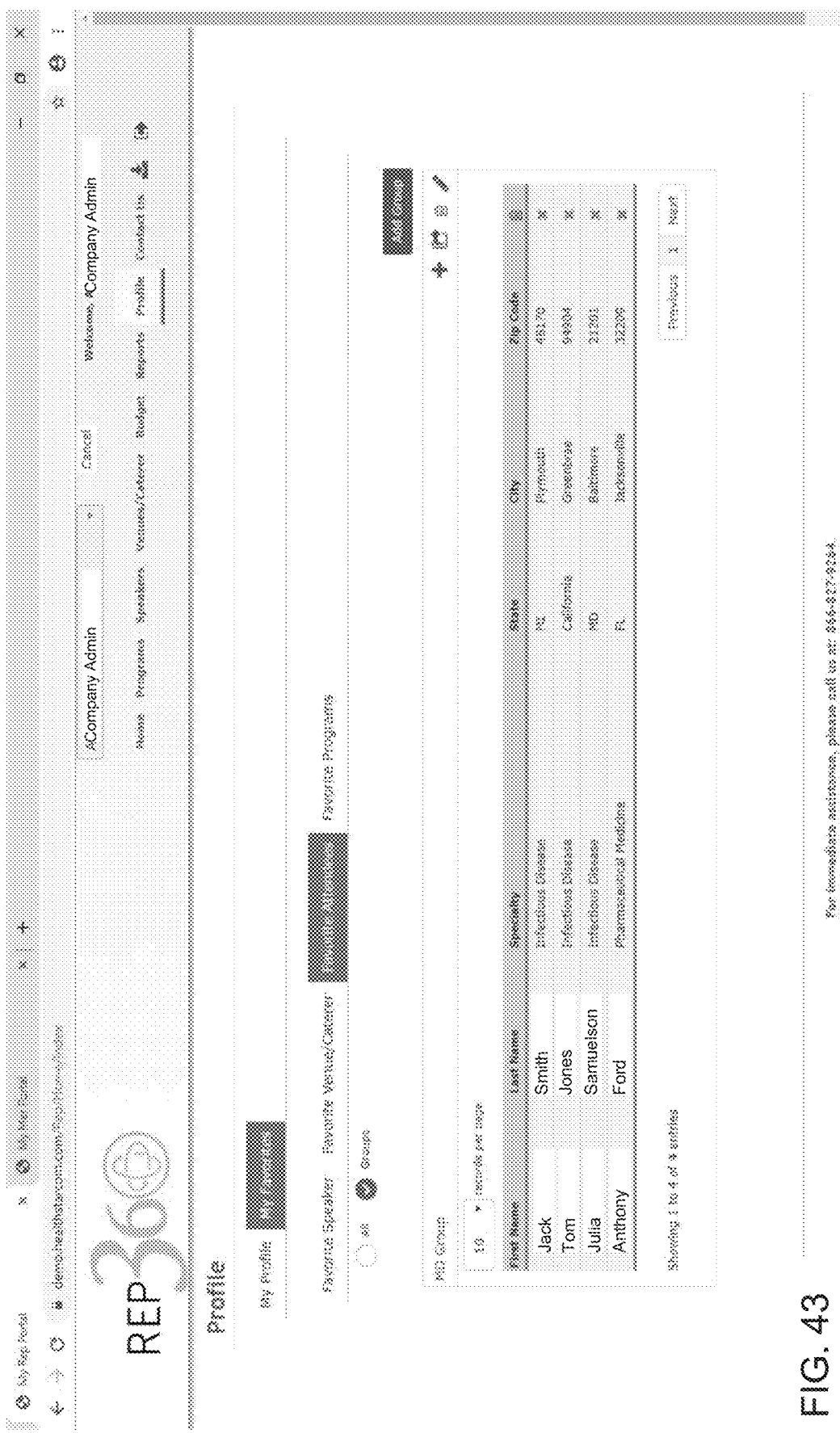
Figure 45:
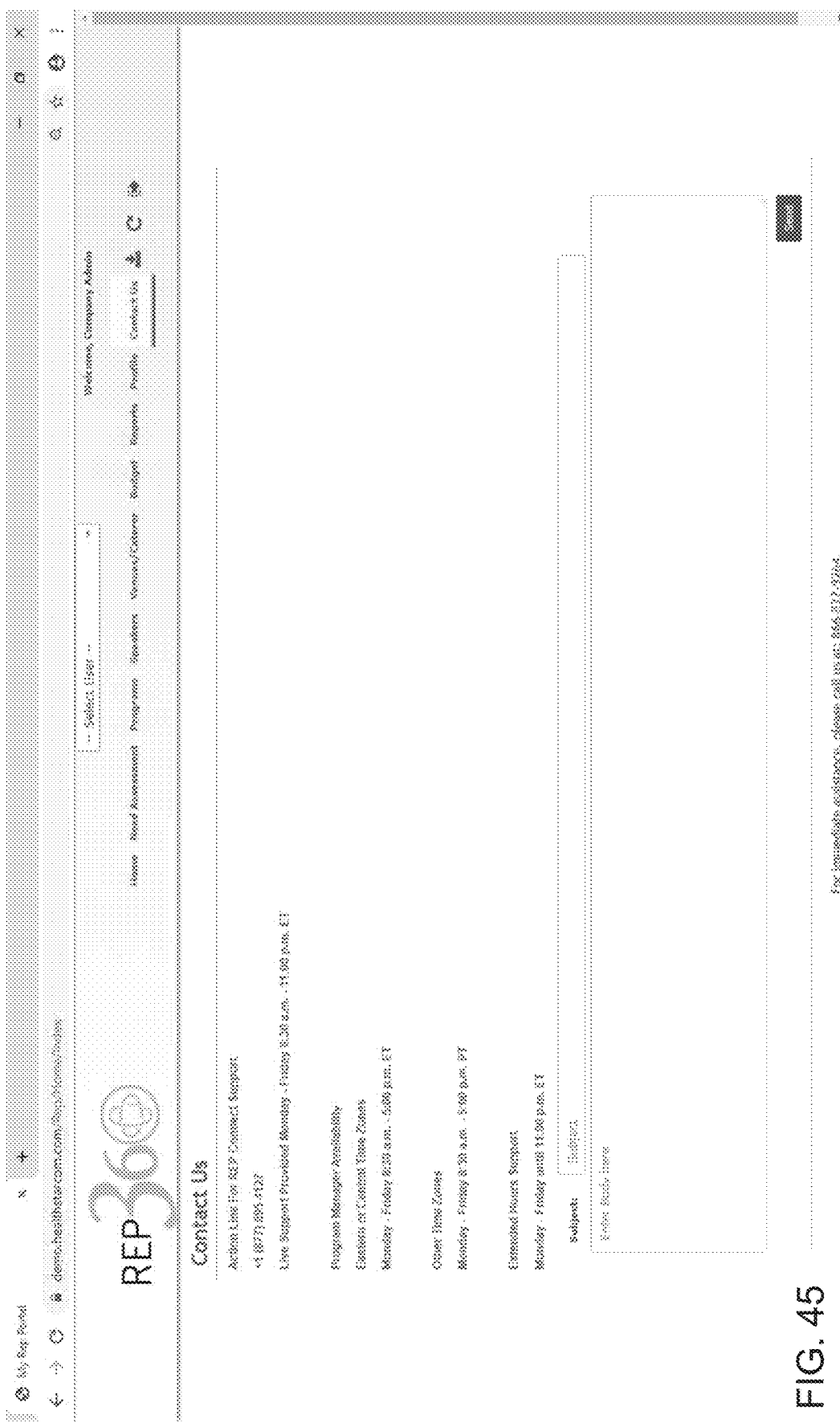
Figure 46:
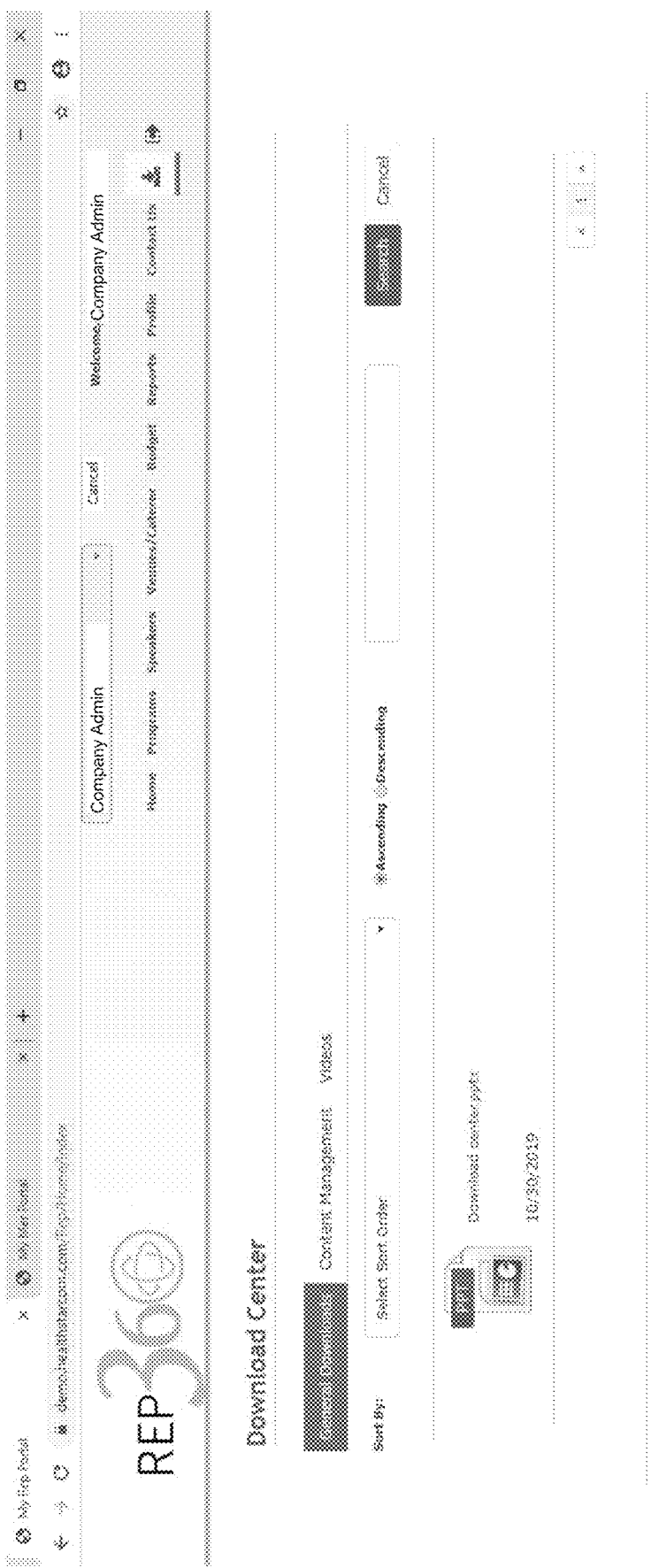
Figure 50:
Figure 51:
Figure 52:
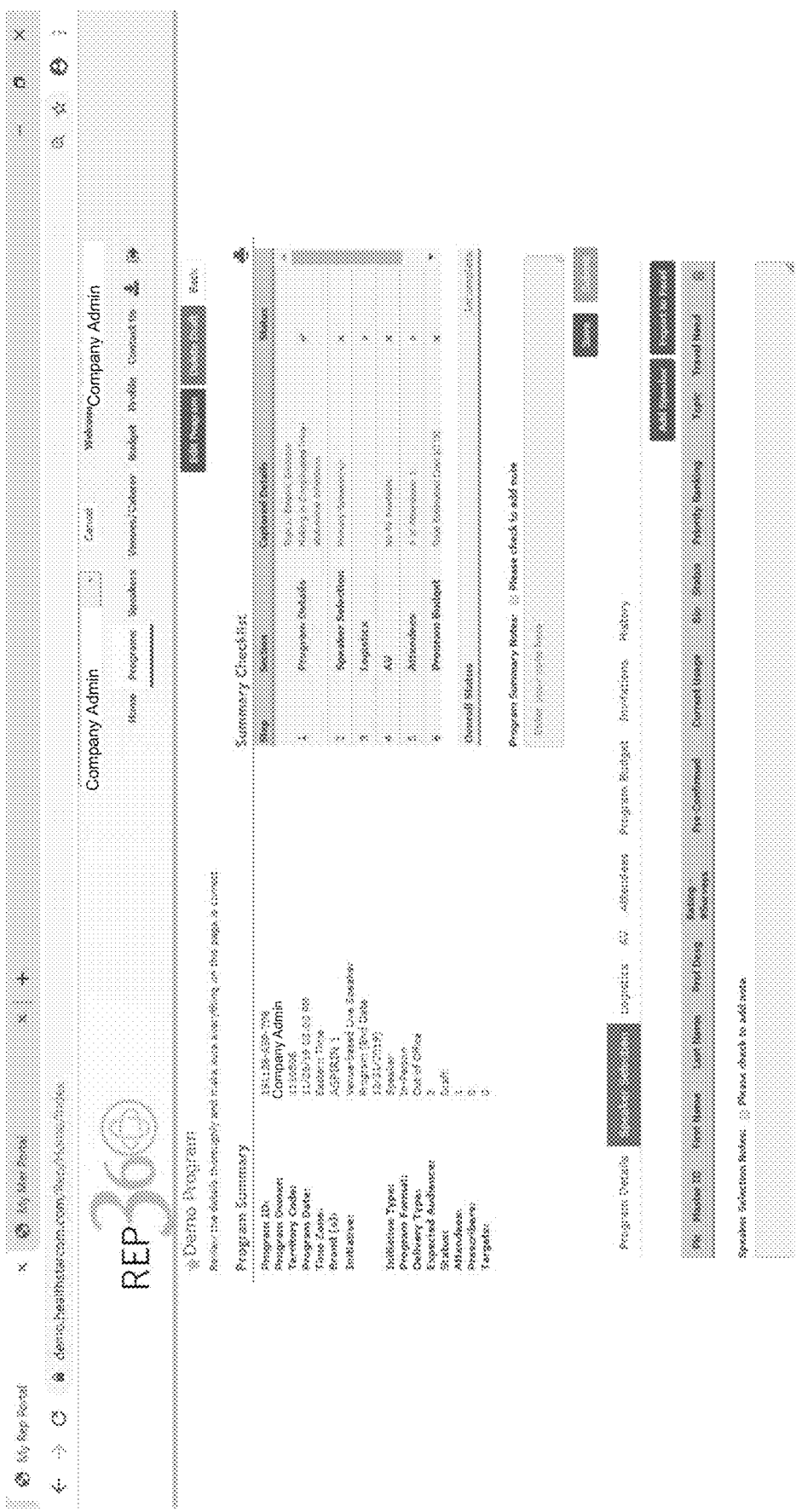
Figure 53:
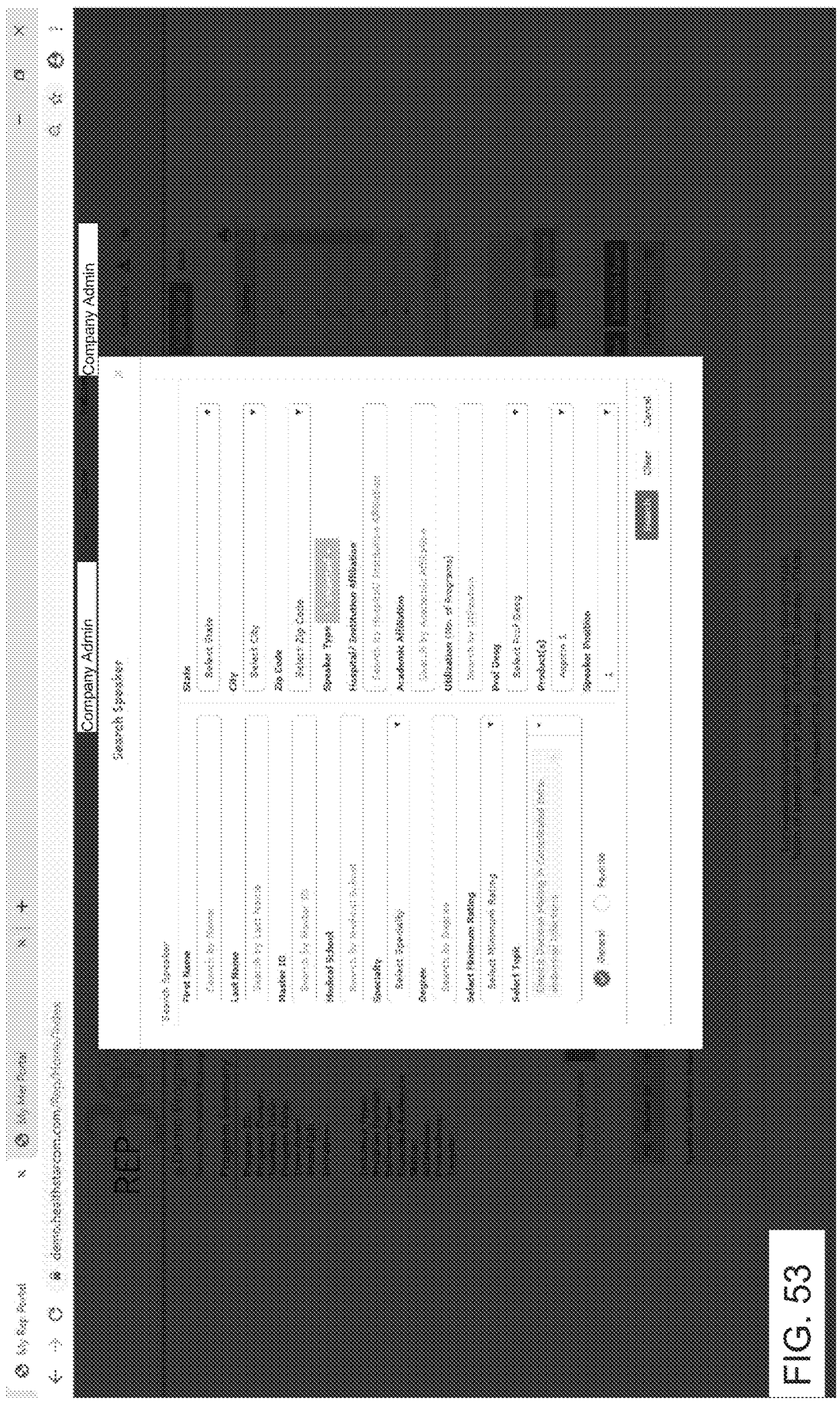
Figure 54:
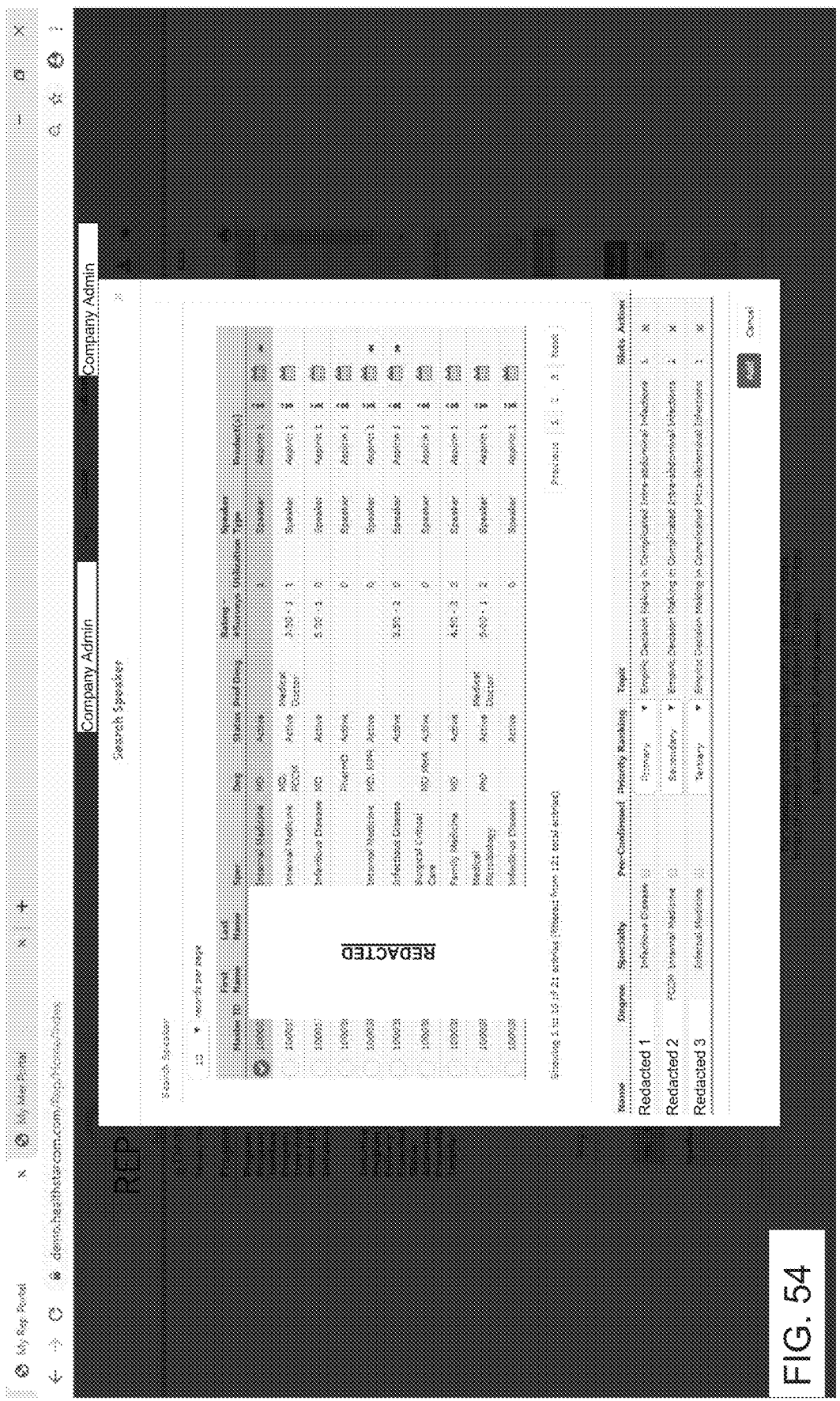
Figure 55:
Figure 56:
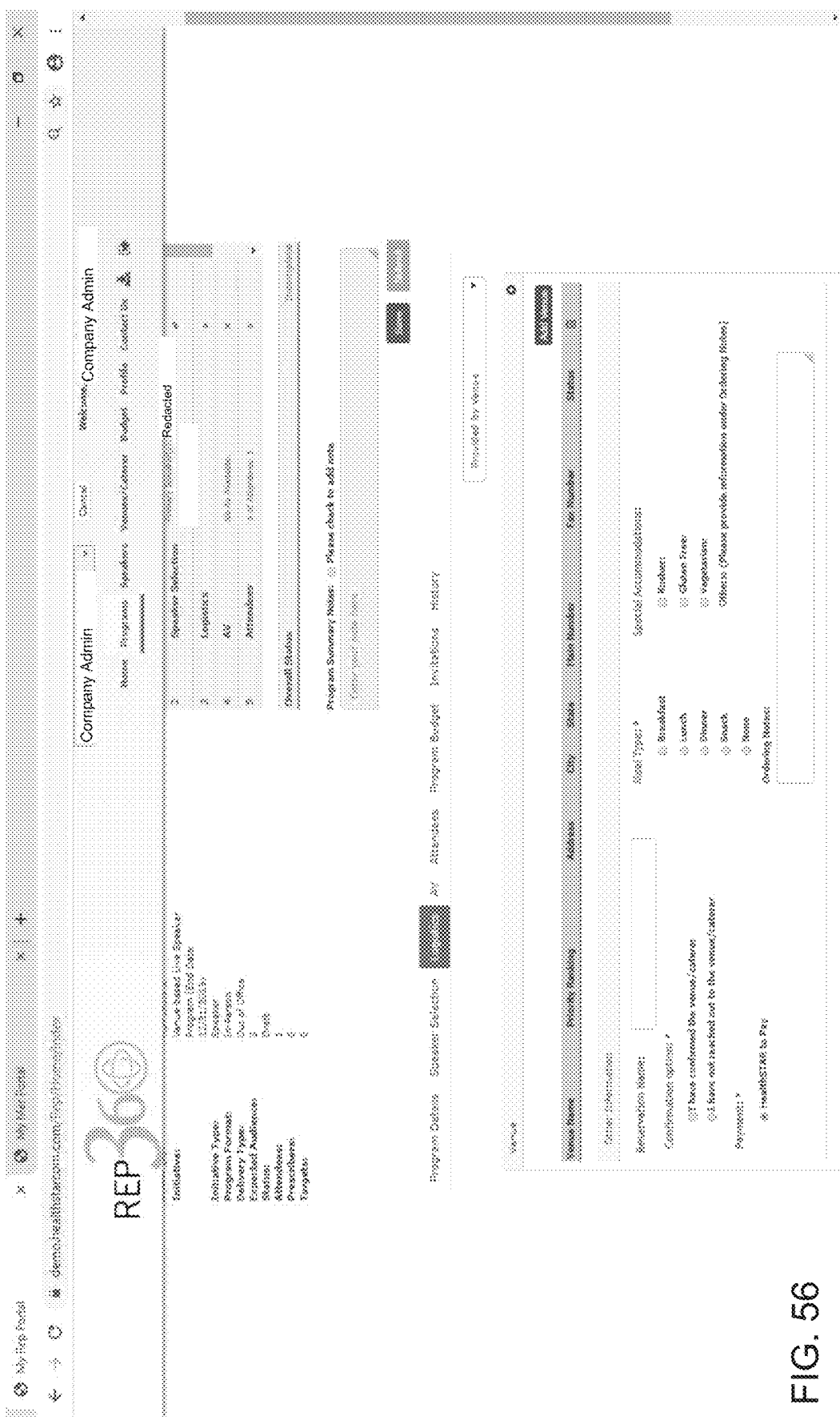
Figure 57:
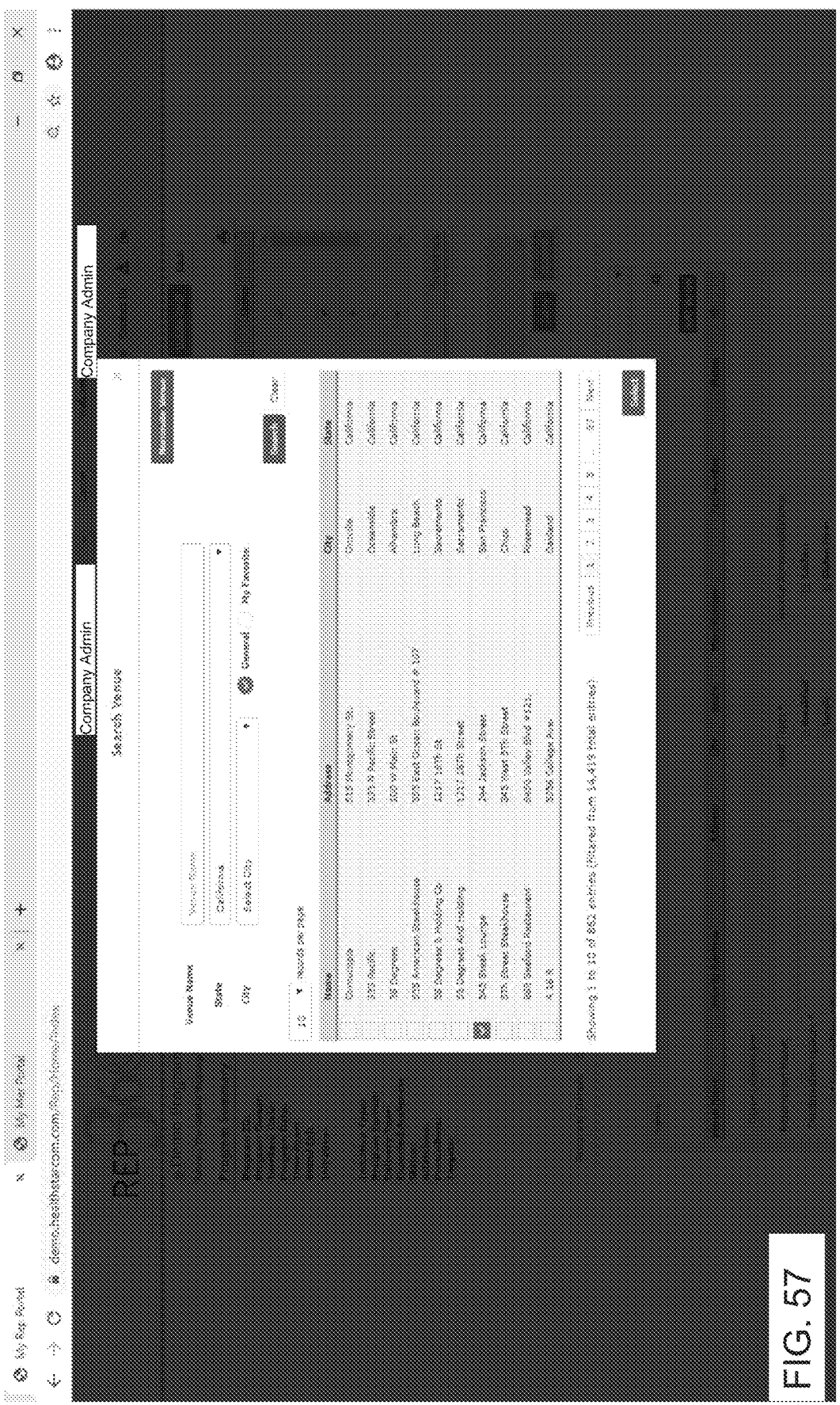
Figure 58:
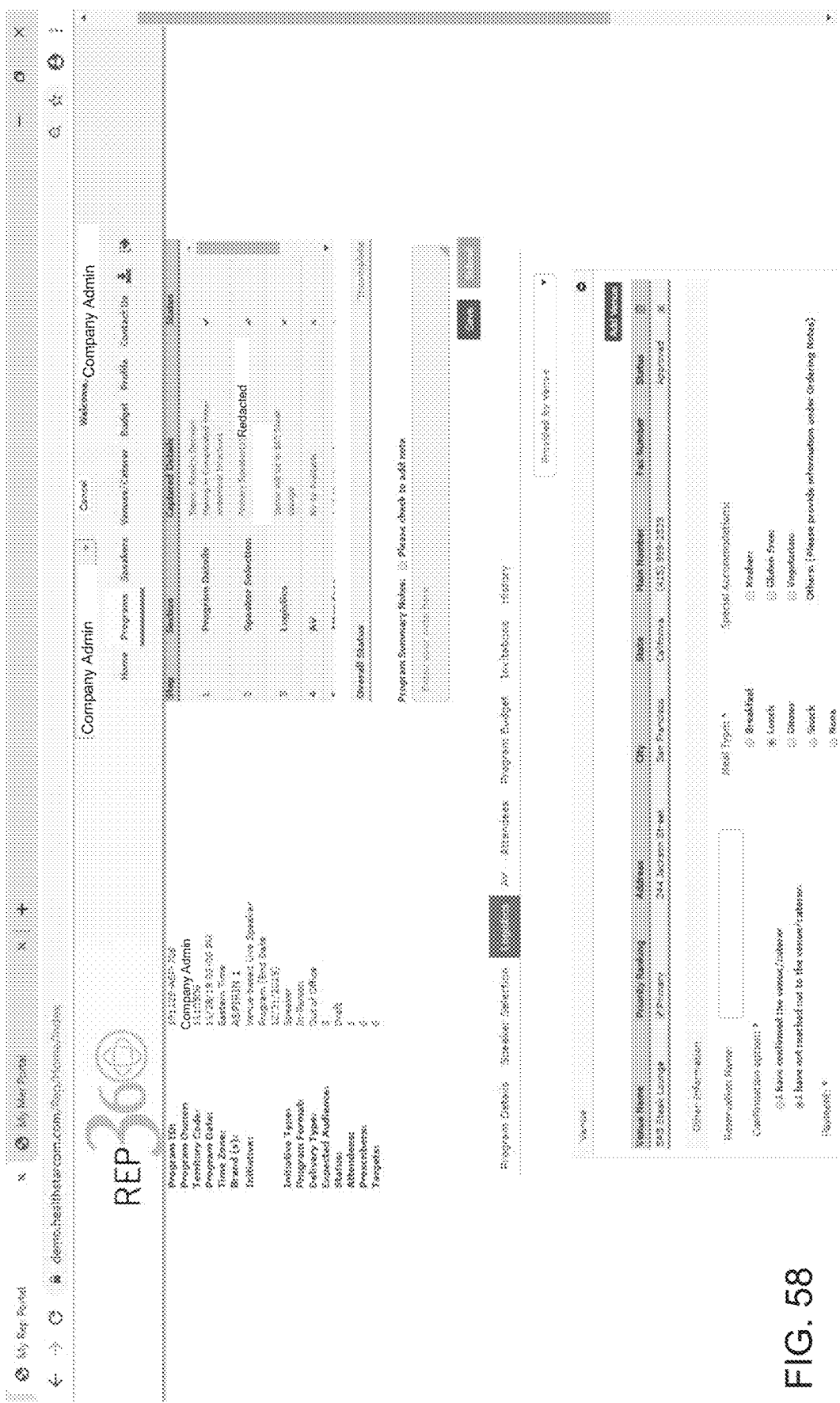
Figure 59:
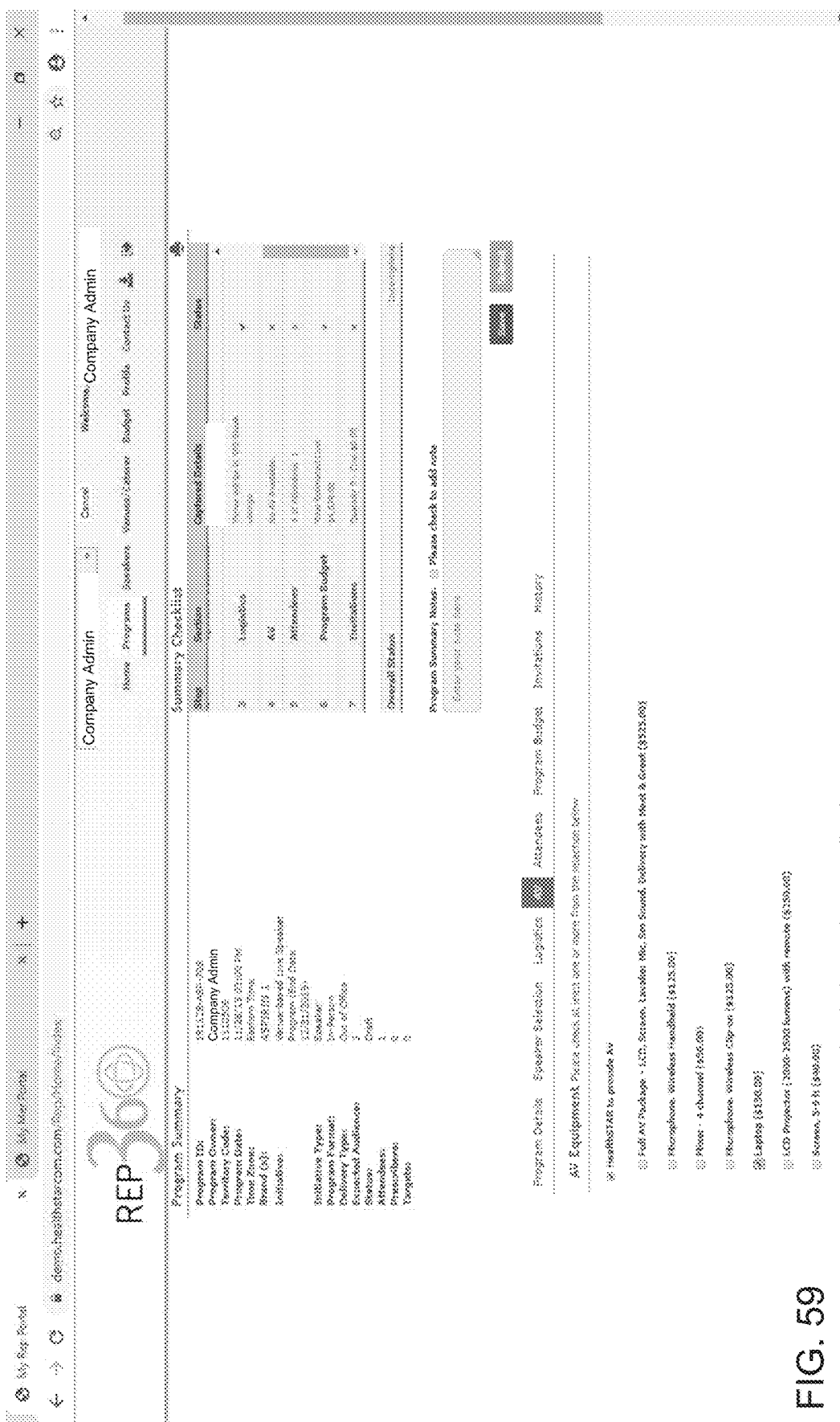
Figure 60:
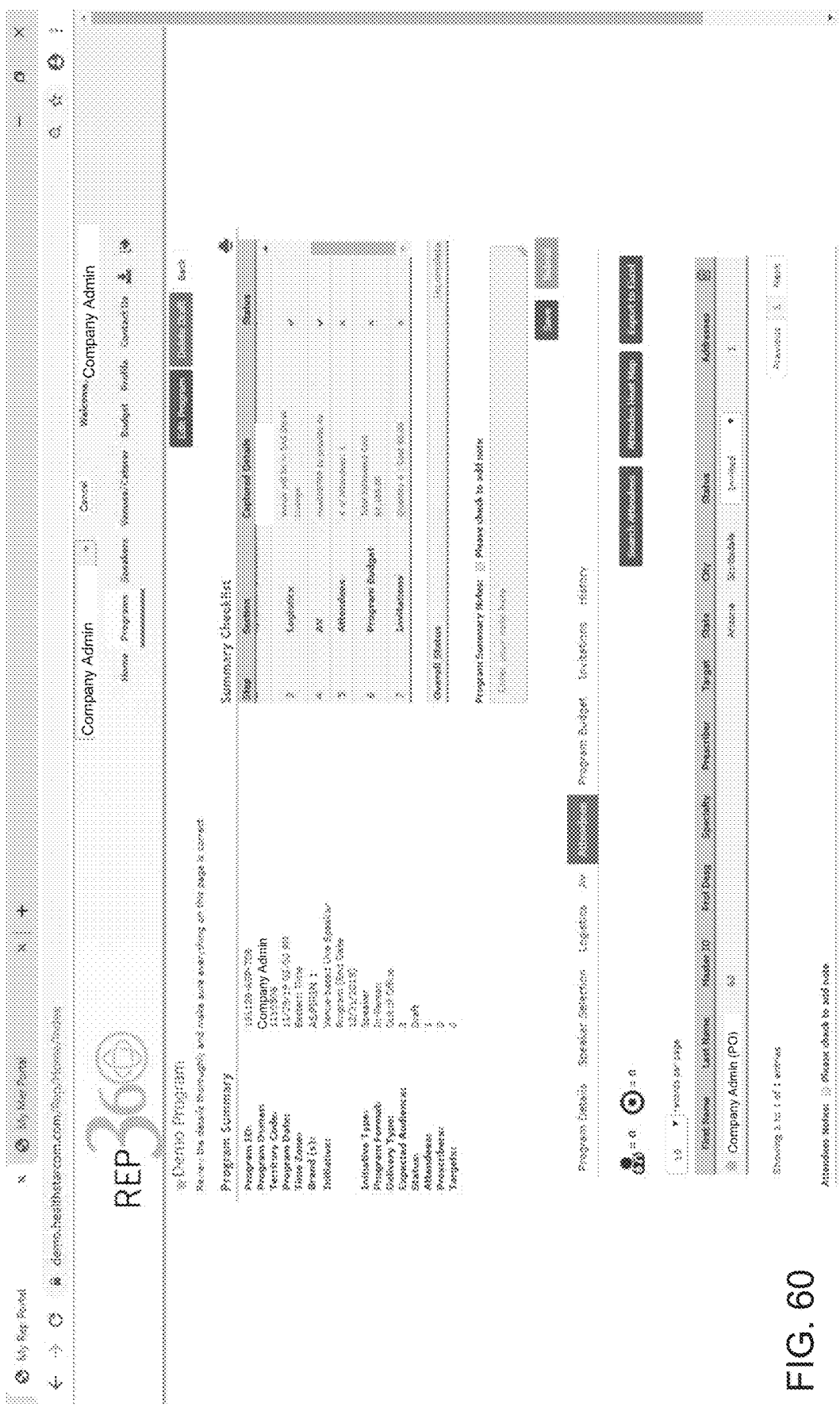
Figure 61:
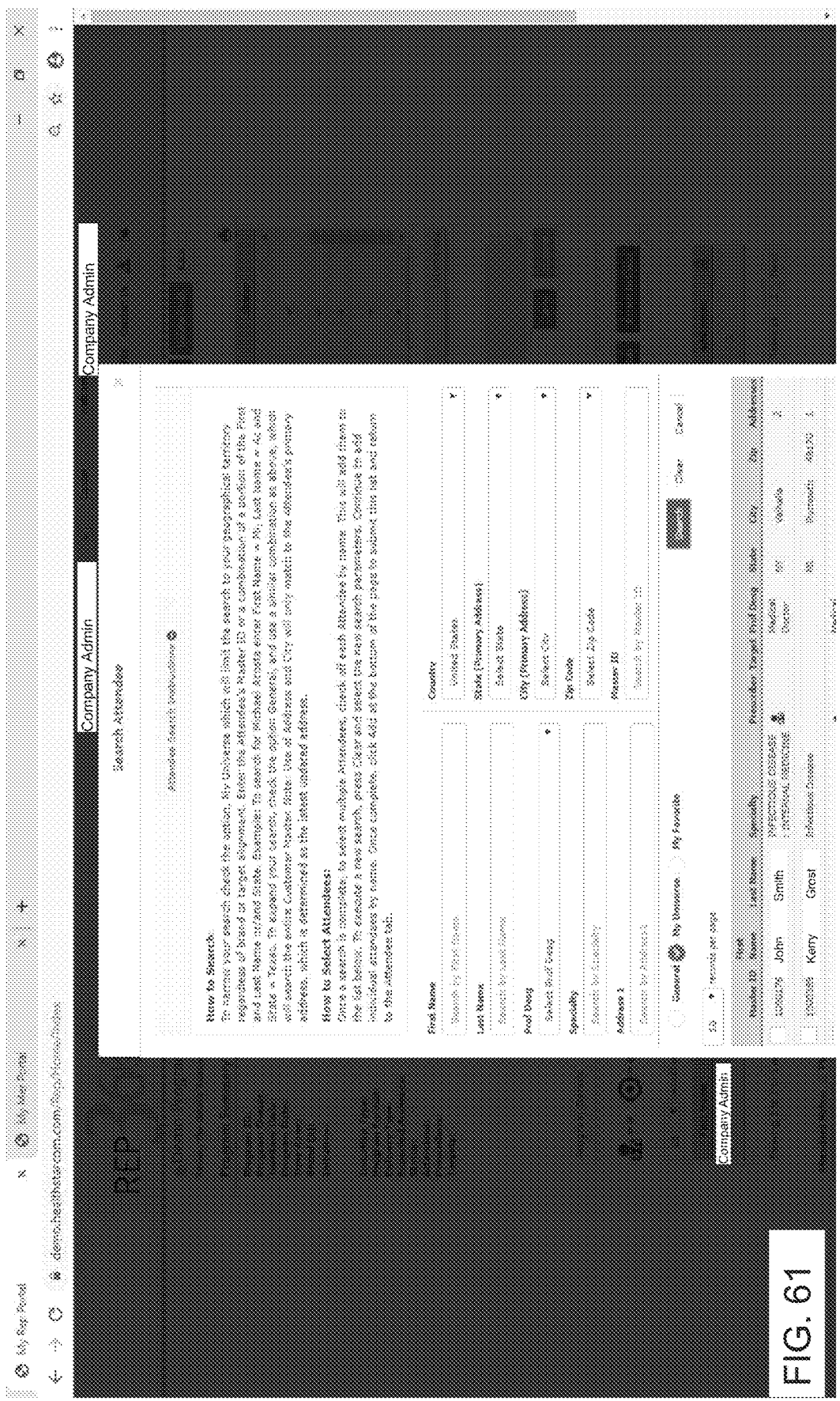
Figure 62:
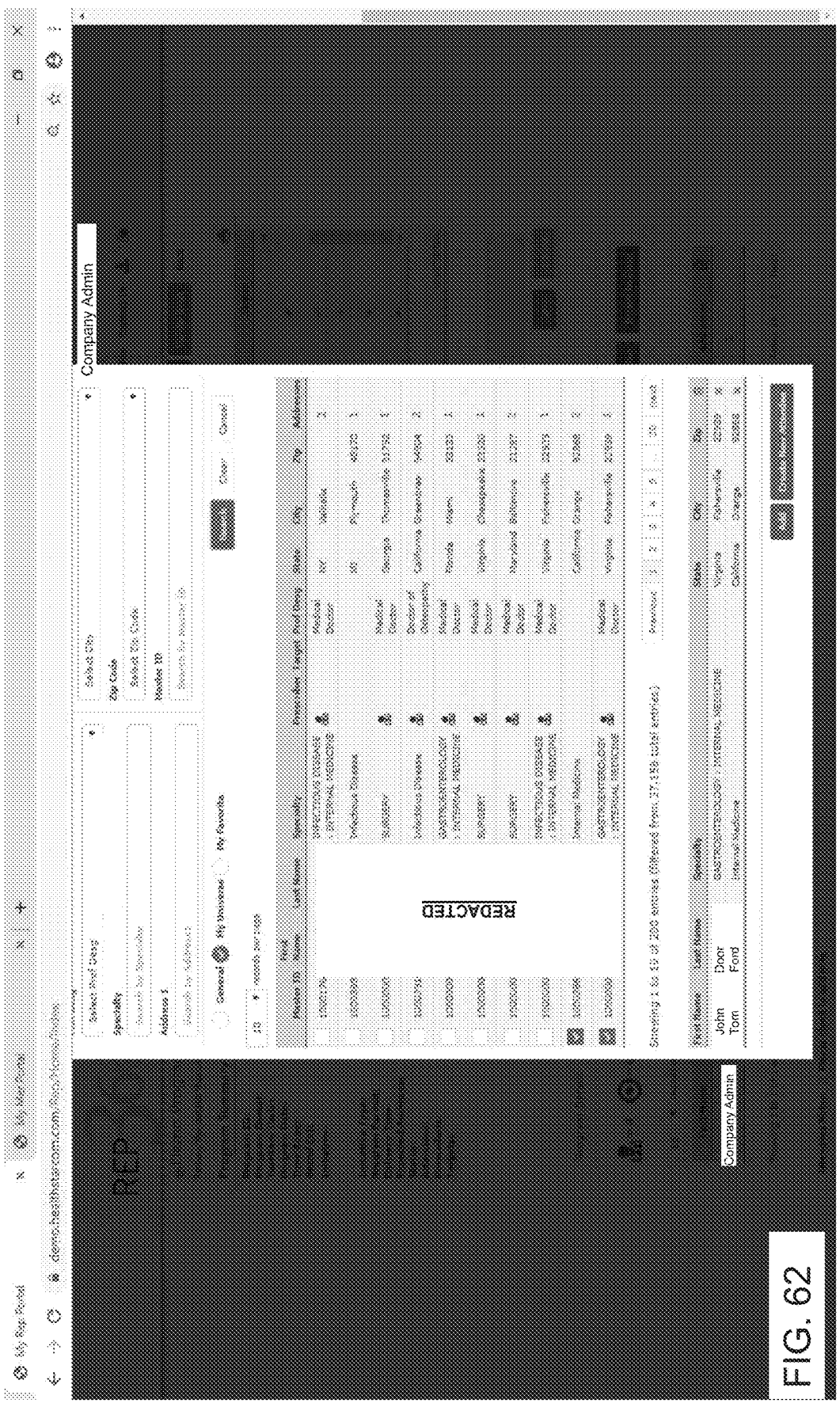
Figure 63:
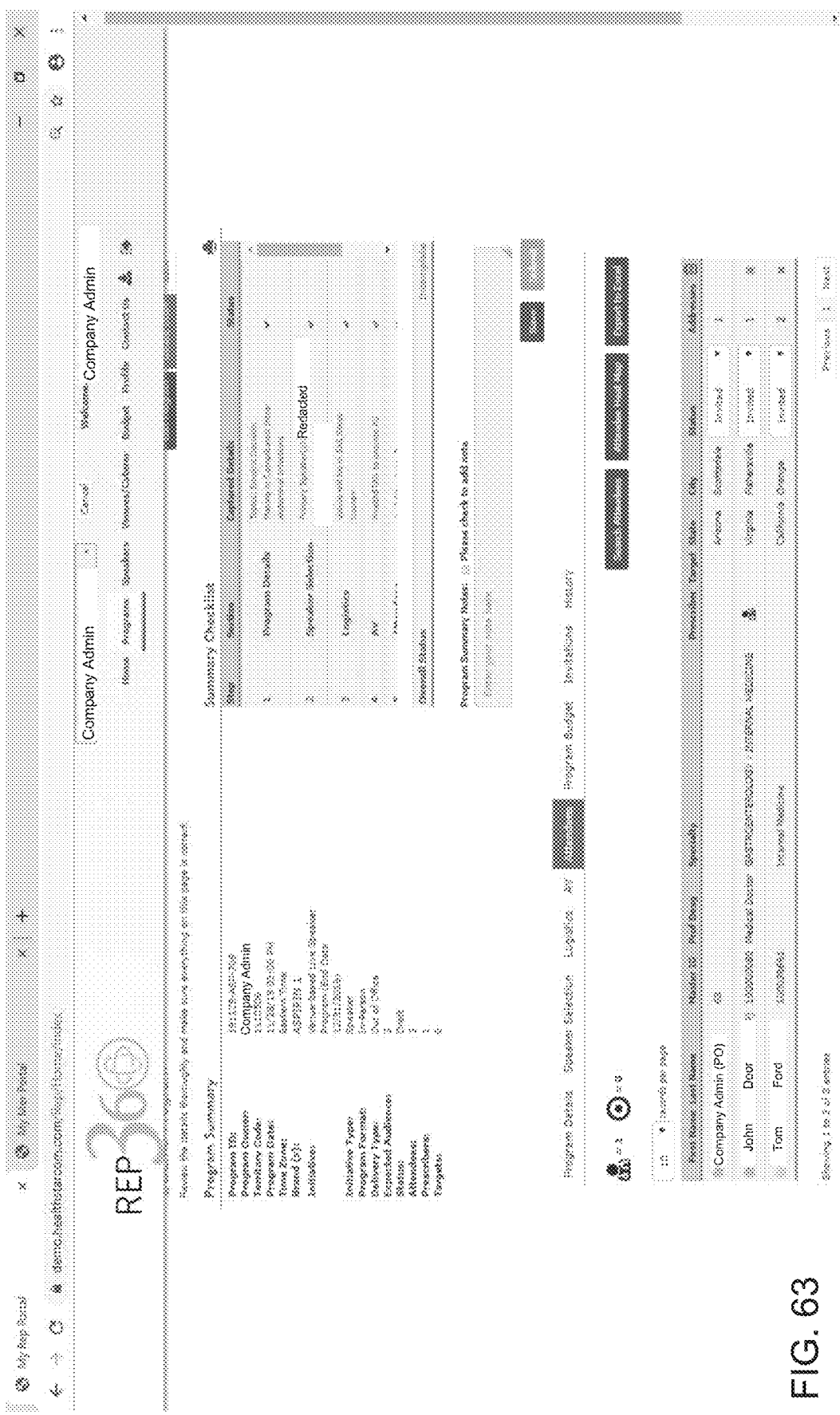
Figure 64:
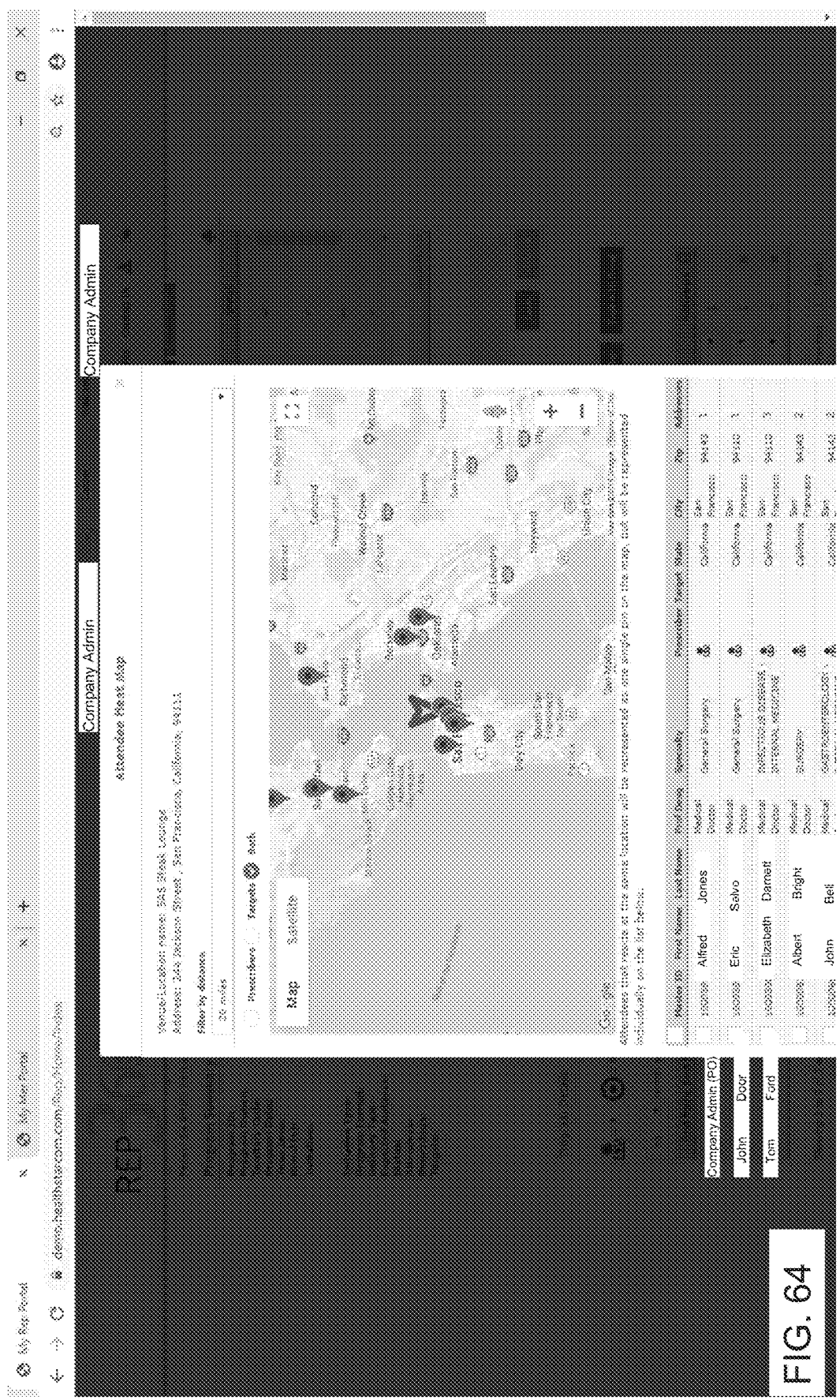
Figure 65:
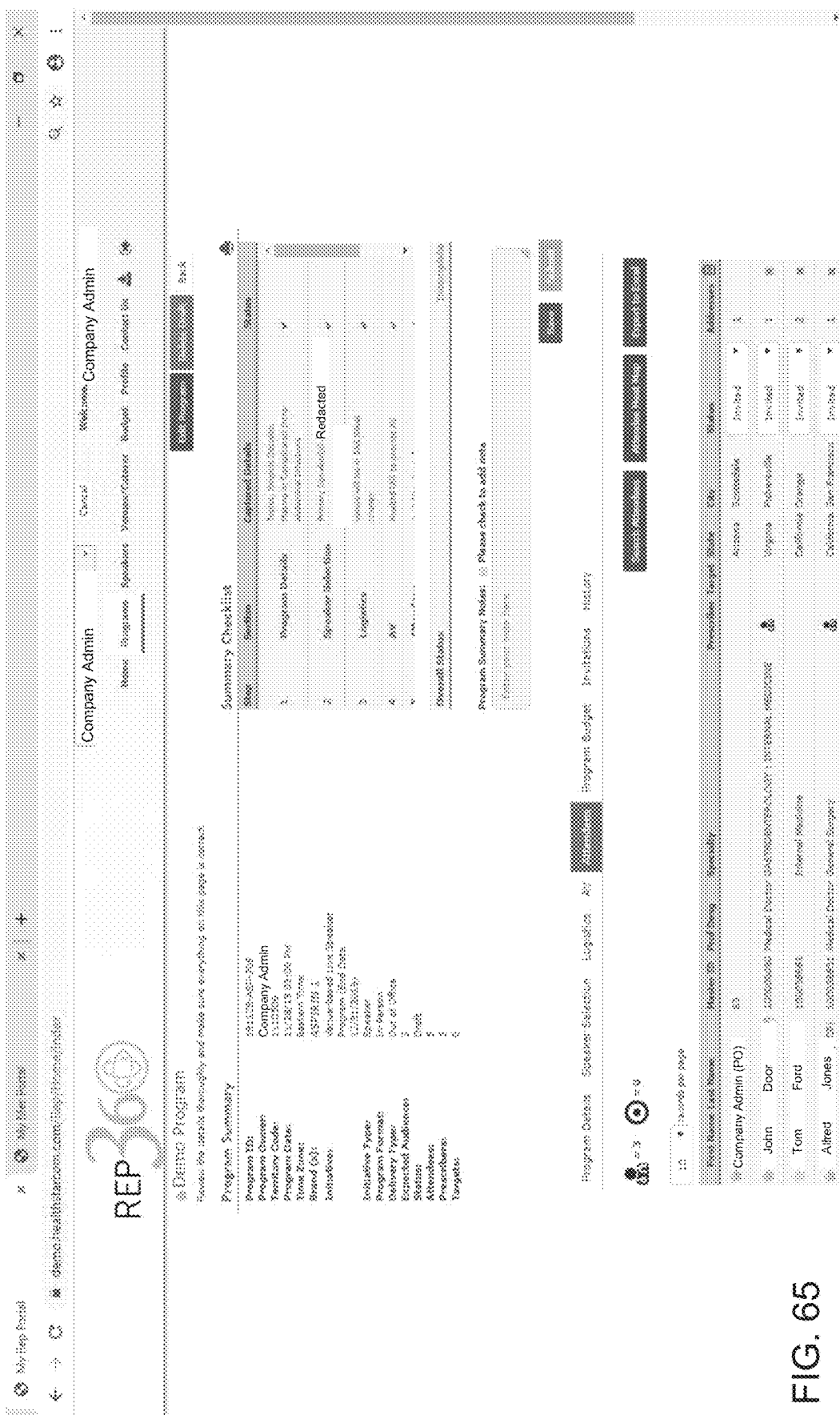
Figure 65A:
Figure 65B:
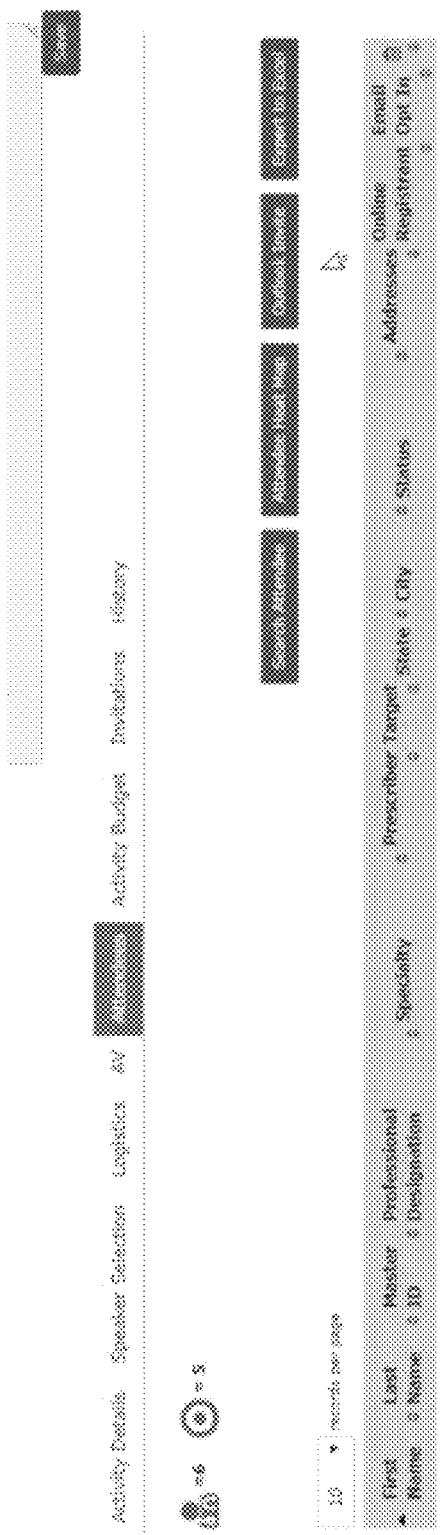
Figure 65C:
Figure 65D:
Figure 67:
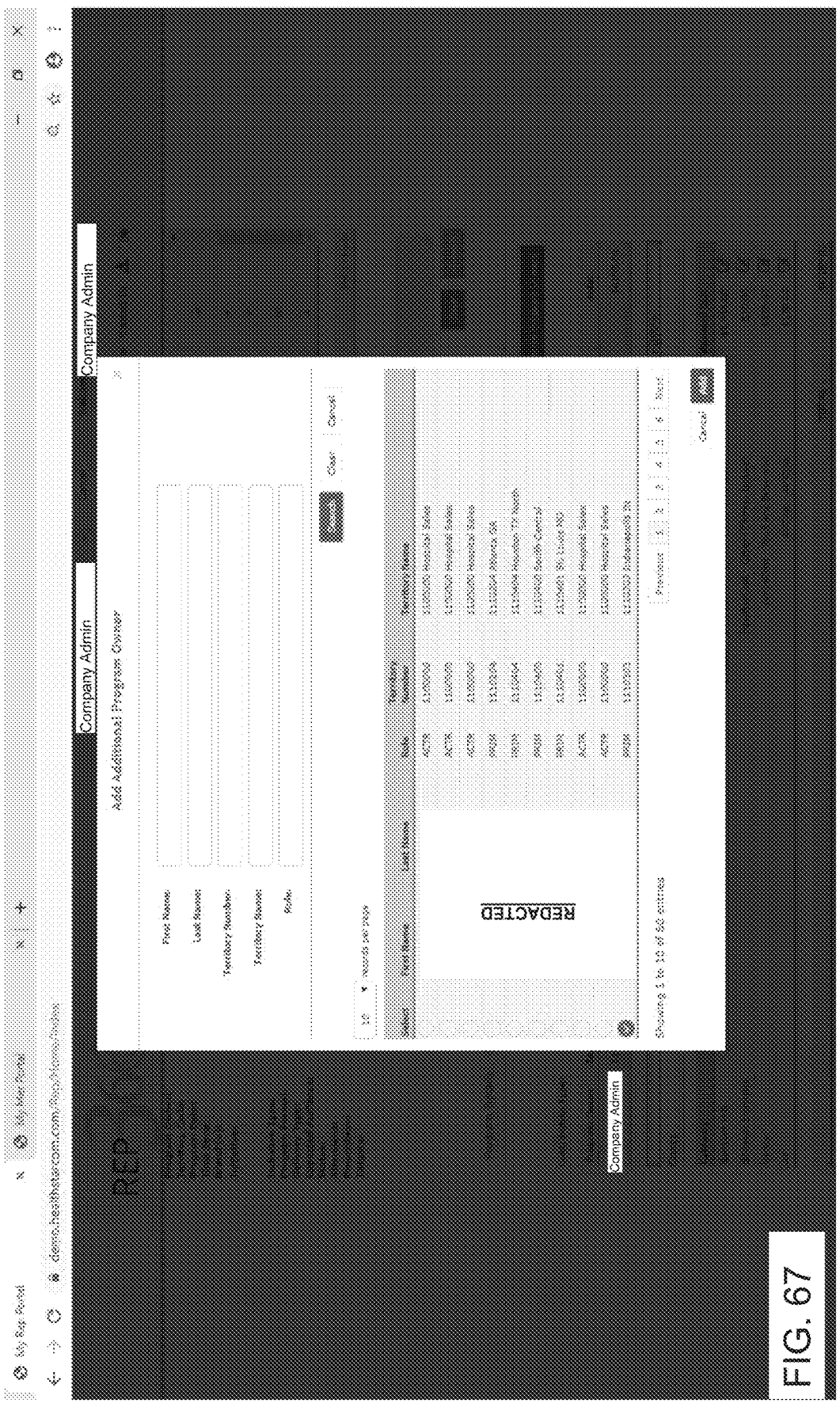
Figure 68:
Figure 69:
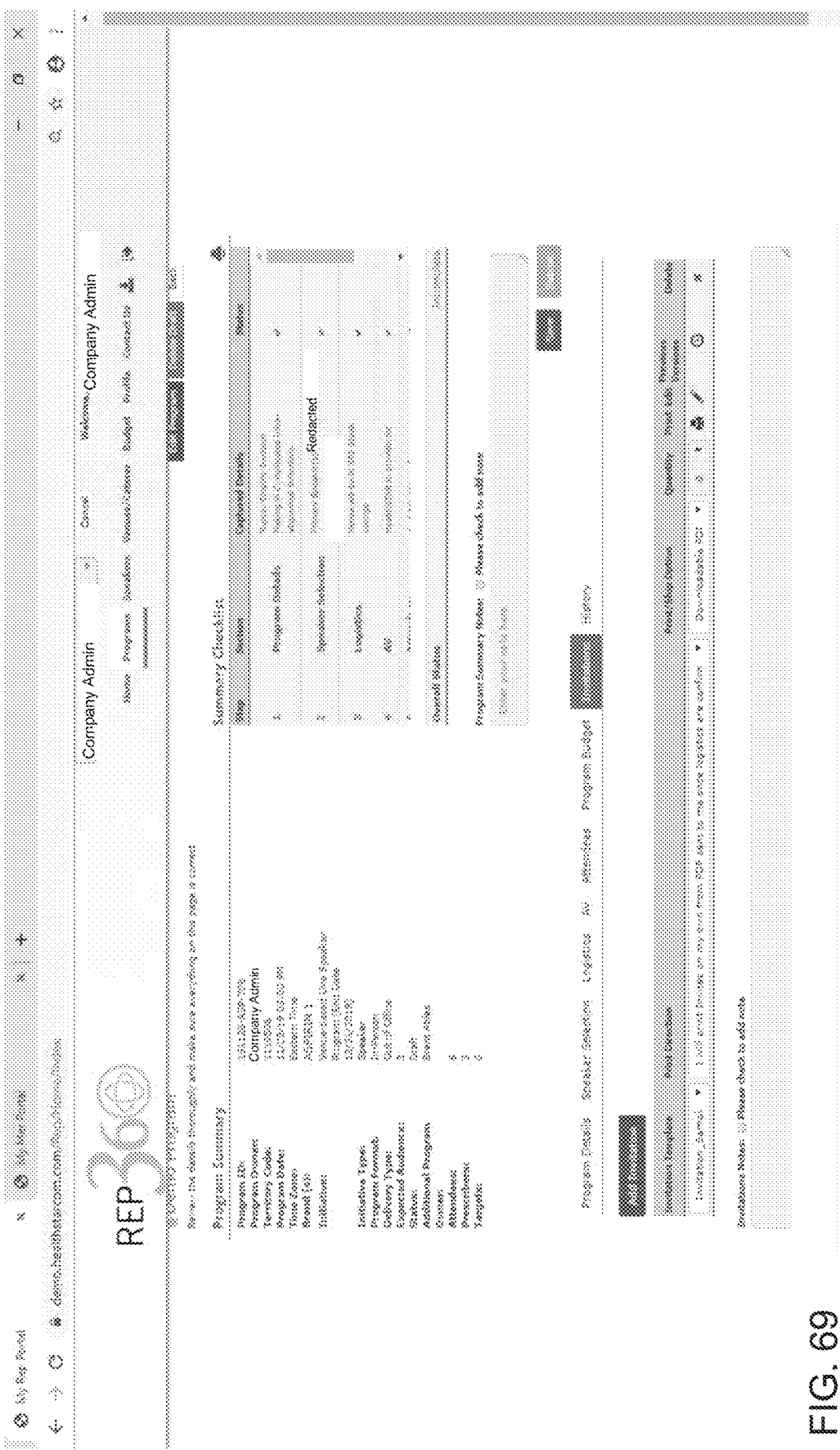

In the illustrative embodiment, the representative portal includes the user home page (FIGS. 9-10), a need assessment tab (FIGS. 10A-S and FIGS. 11-23), a programs tab (FIGS. 49-82), a speakers tab (FIGS. 24-30), a venue/ caterers tab (FIGS. 31-32), a budget tab (FIGS. 33-37), a reports tab (FIG. 38), a profile tab (FIGS. 39-44), a contact us tab (FIG. 45), a download center (FIGS. 46-49), and a logout icon. However, in some embodiments, it should be appreciated that the tabs visible may vary depending on the particular user's level and role within the system. Further, in some embodiments, the representative portal may include a speaker bureau tab (FIGS. 132-160).

It should be appreciated that the representative portal essentially allows a representative to plan a meeting through the interface of the portal in which a KOL/speaker is invited to attend. A speaker is an individual that has been contracted, topic trained on the product, and compliance trained as well. This contract will identify how much a speaker is going to get paid for attending this meeting and for talking to other doctors or HCPs about the pharmaceutical product (e.g., for regulatory compliance). The speakers/KOLs are the people that have the knowledge and have been trained for that product. The representative portal and the enterprise platform generally essentially allows the pharmaceutical company to use the system to ensure an end-to-end compliance and validation solution from scheduling a meeting, picking the venue, speaker training, vetting the speakers, and other features associated with healthcare event scheduling and coordination.

Figure 9:
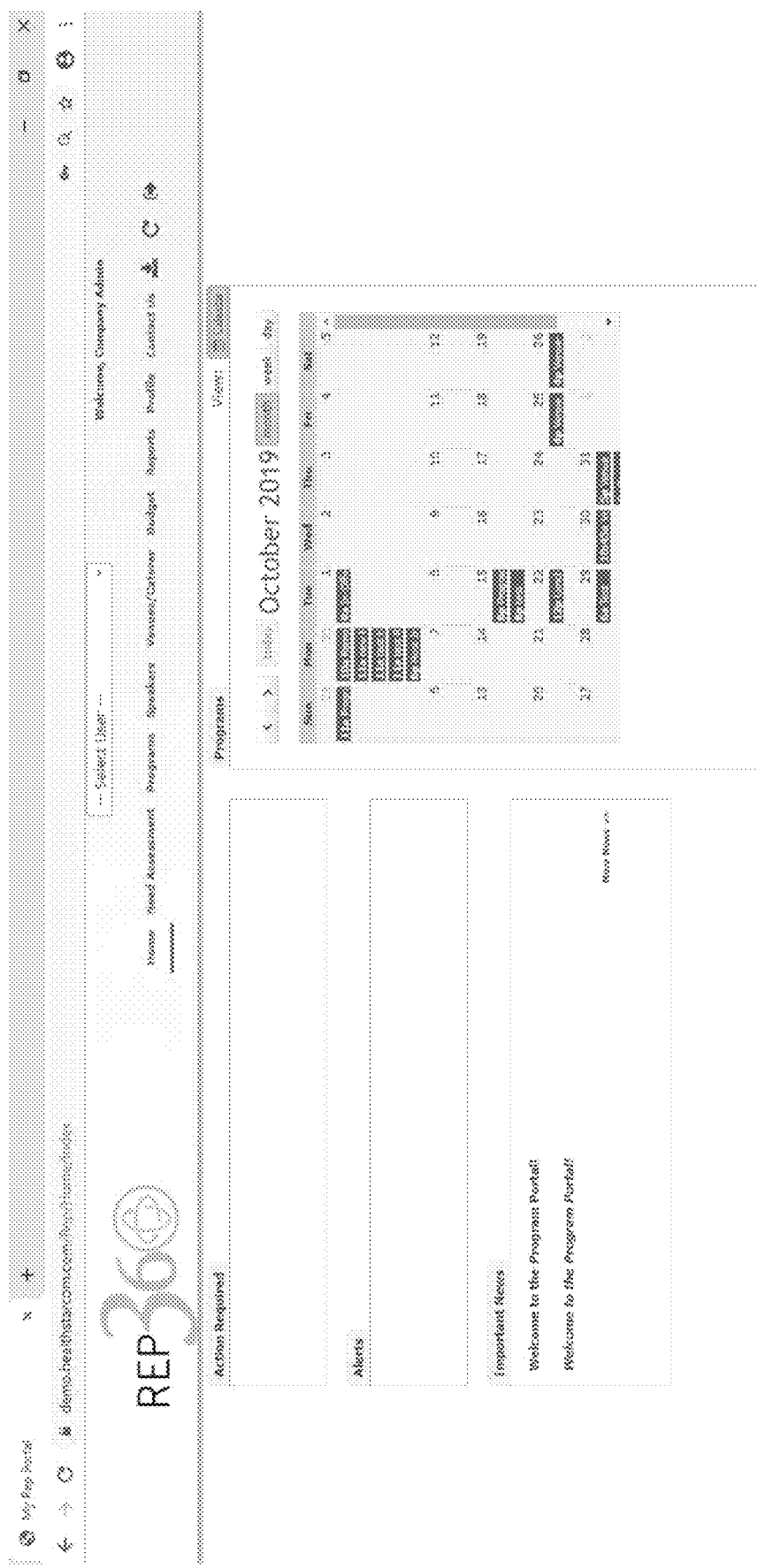
Figure 10:
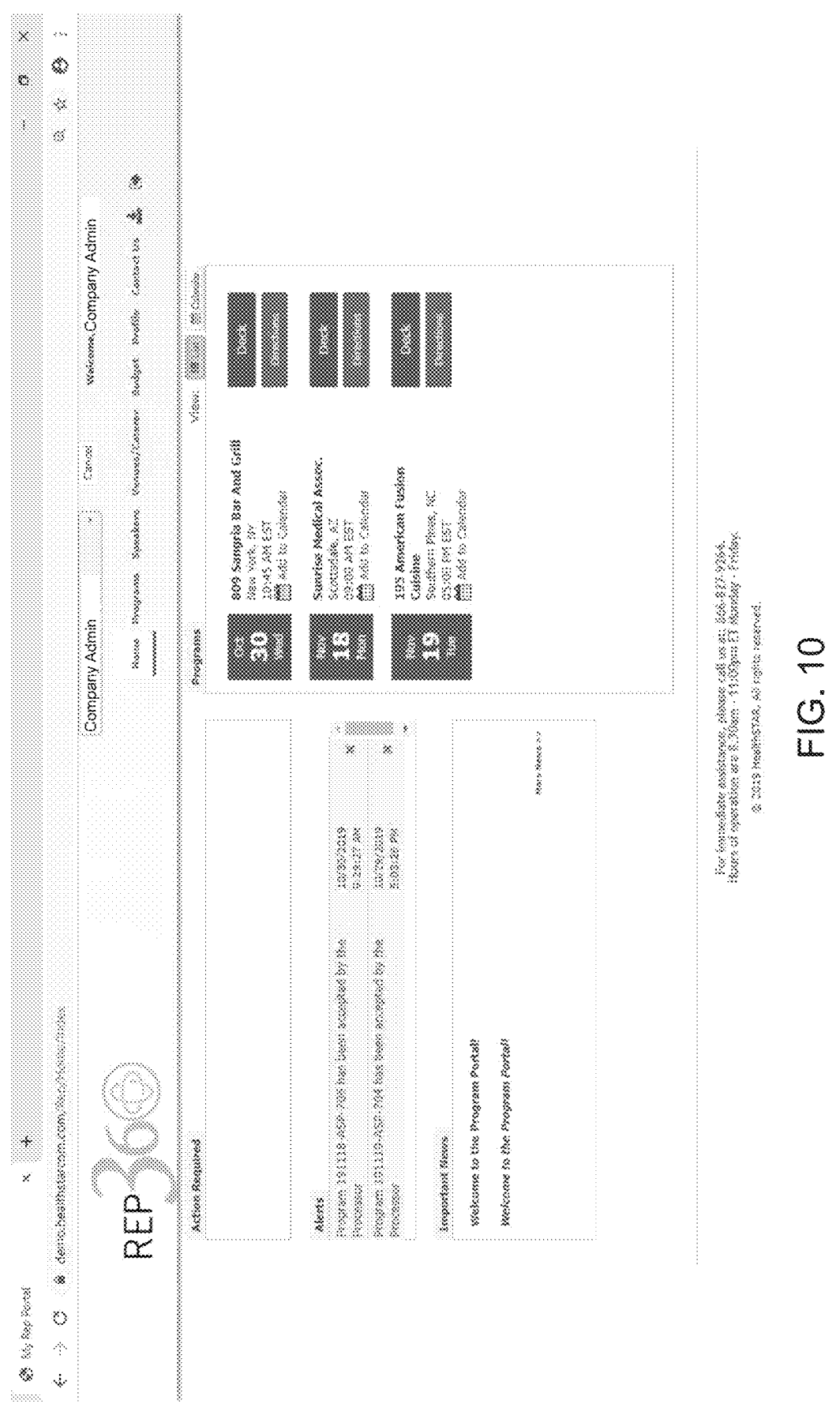

In general, upon logging in to the representative (rep) portal, the user is brought to the user portal home page (FIGS. 9-10). As shown, users will see an Action Required, Alerts, and Important News sections on left side of the graphical user interface. Users will see a calendar on the right that will display upcoming and past meetings based on the user's level and role. It should be appreciated that the user may select the 'Deck' button for a particular event on the calendar to retrieve the relevant slide deck for that presentation (FIG. 10). Likewise, the user may selected the 'Directions' button to obtain directions (e.g., via GPS mapping) to the event location (FIG. 10).

Figure 10A:
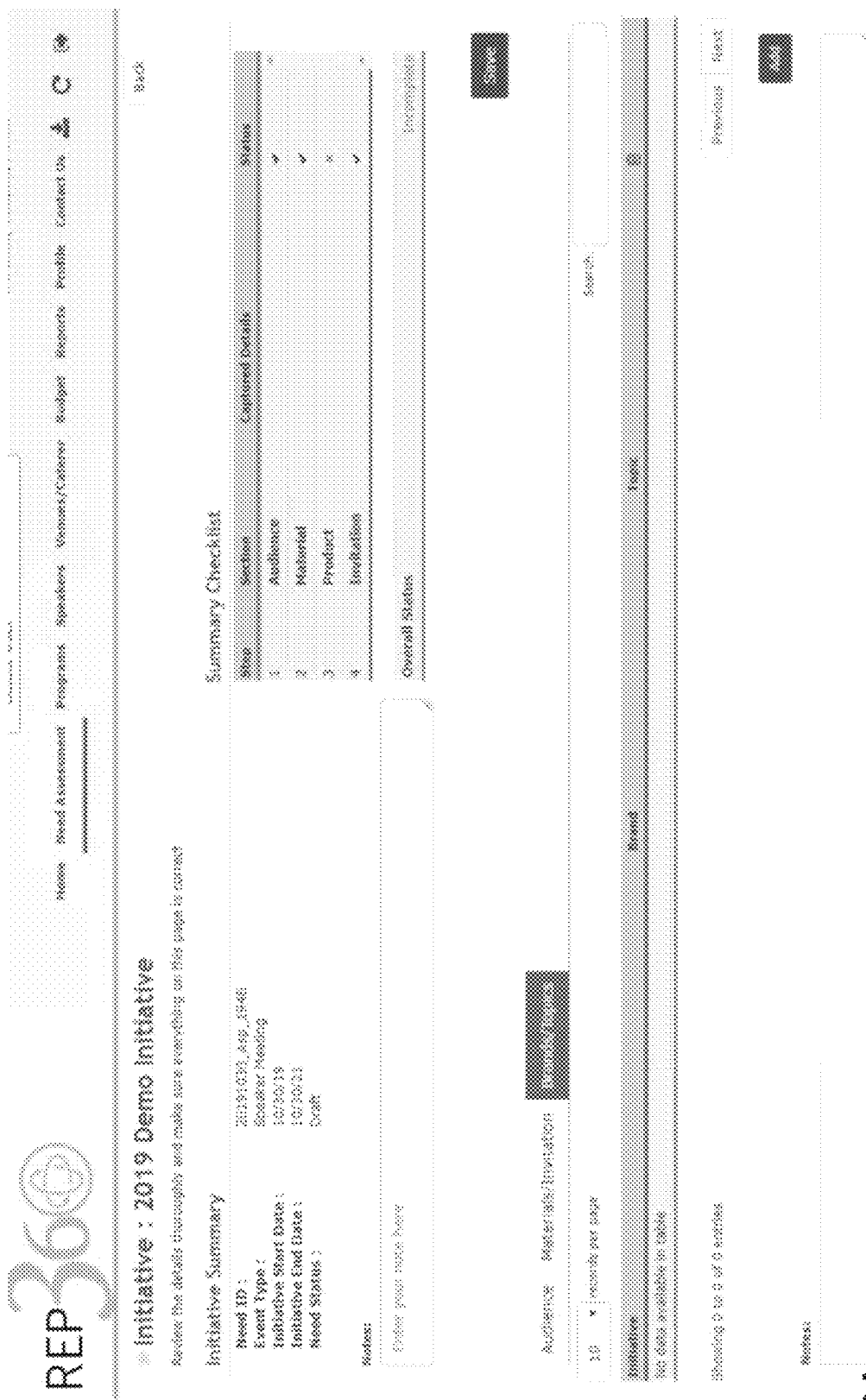
Figure 10B:
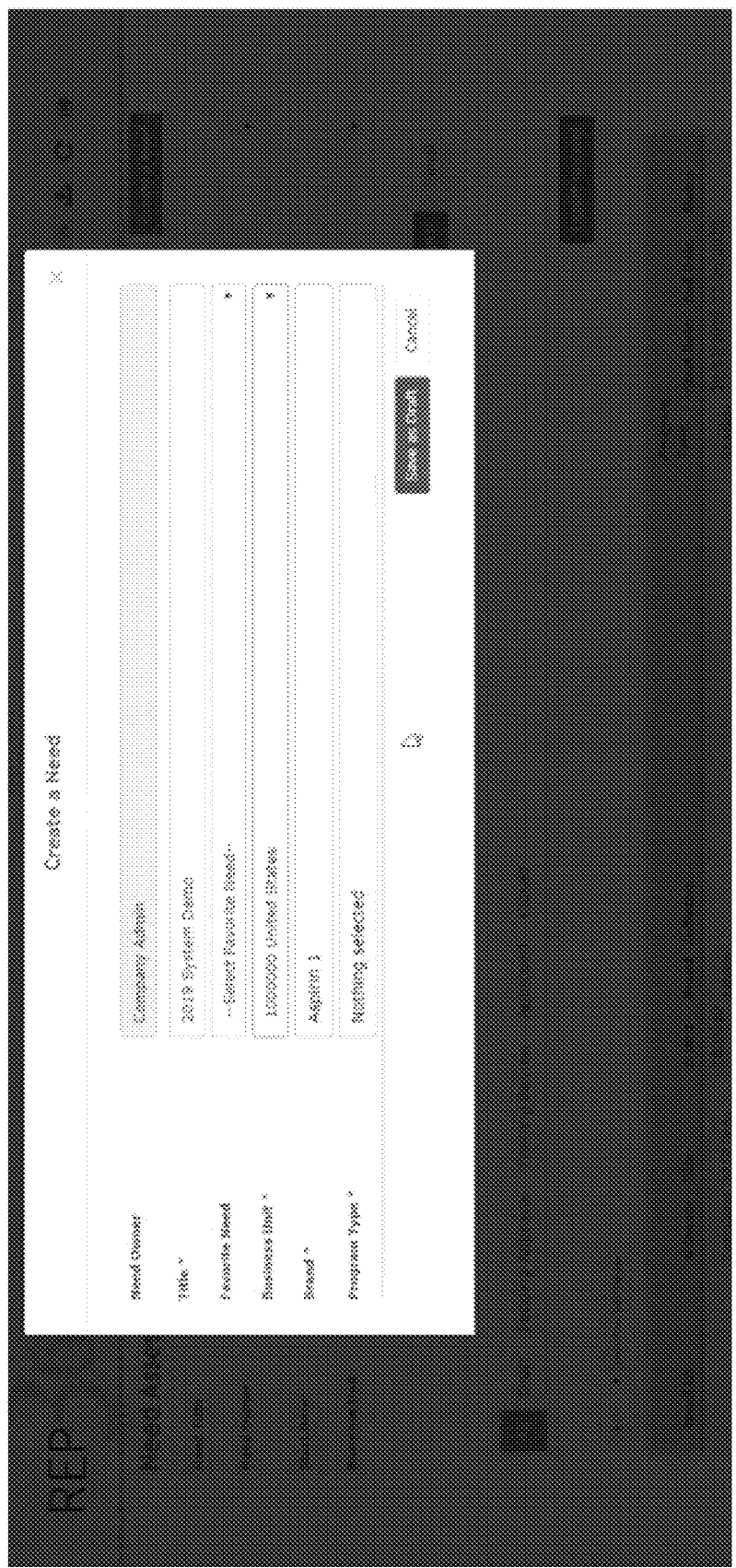
Figure 10C:
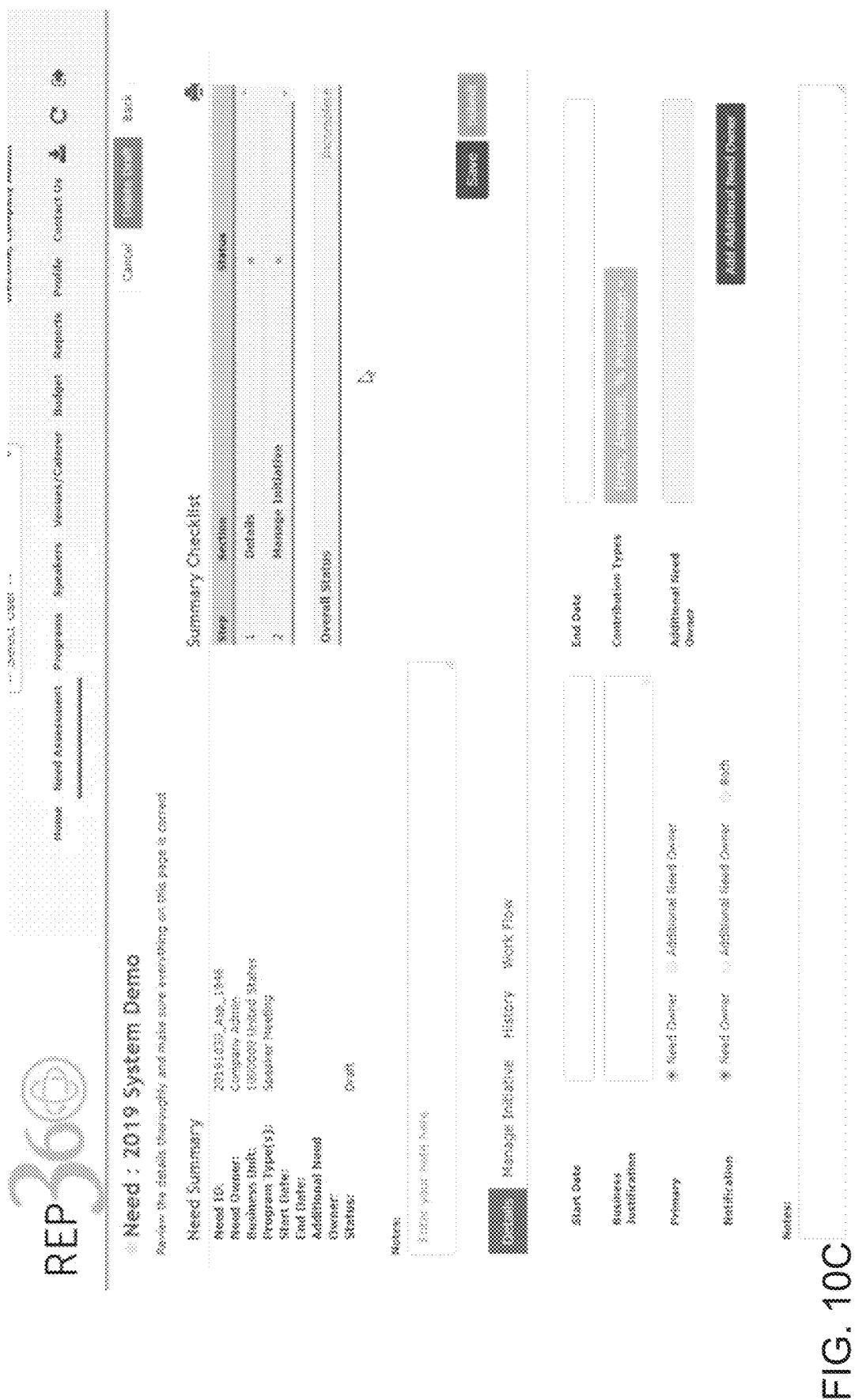
Figure 10E:
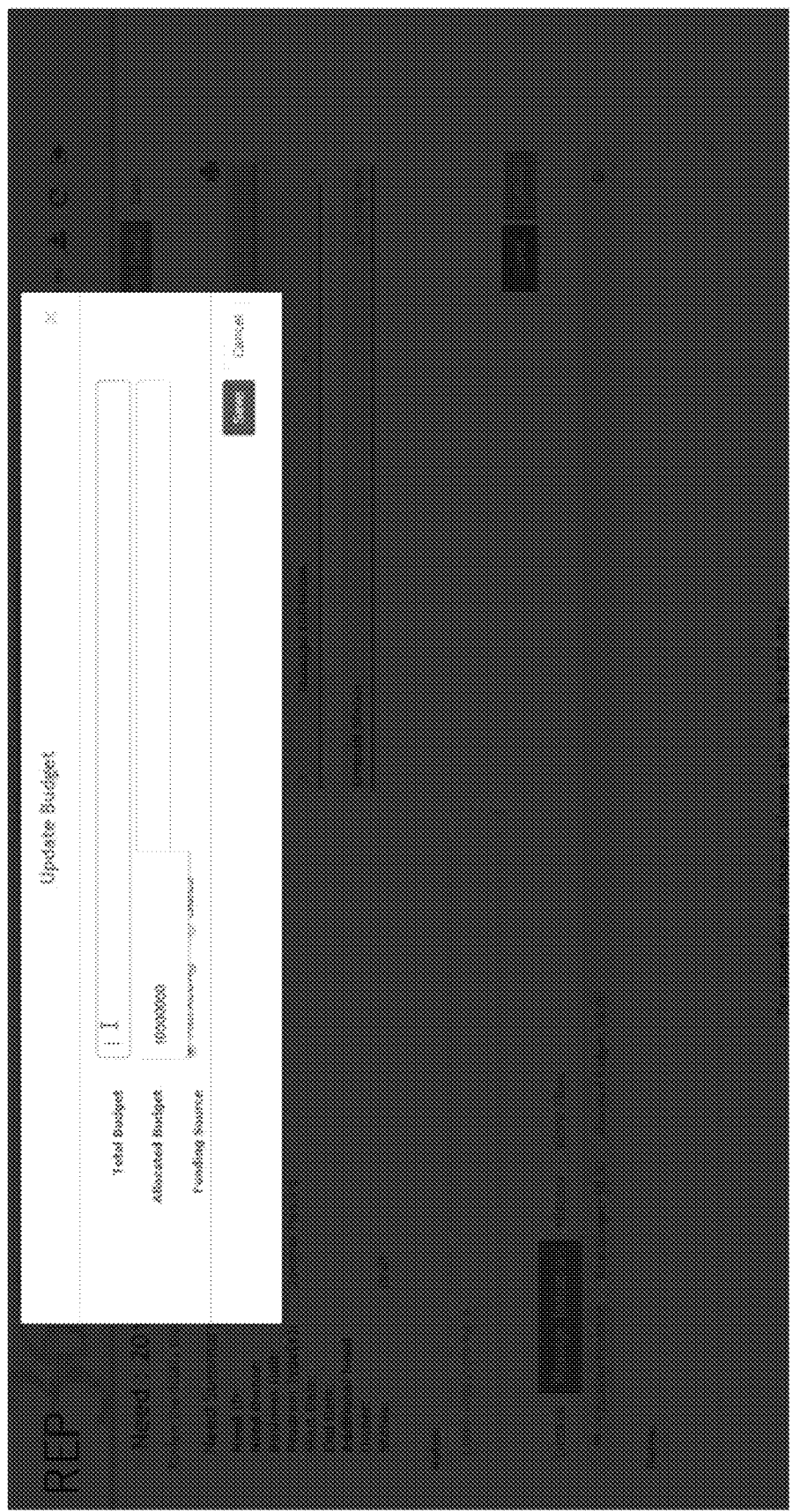
Figure 10F:
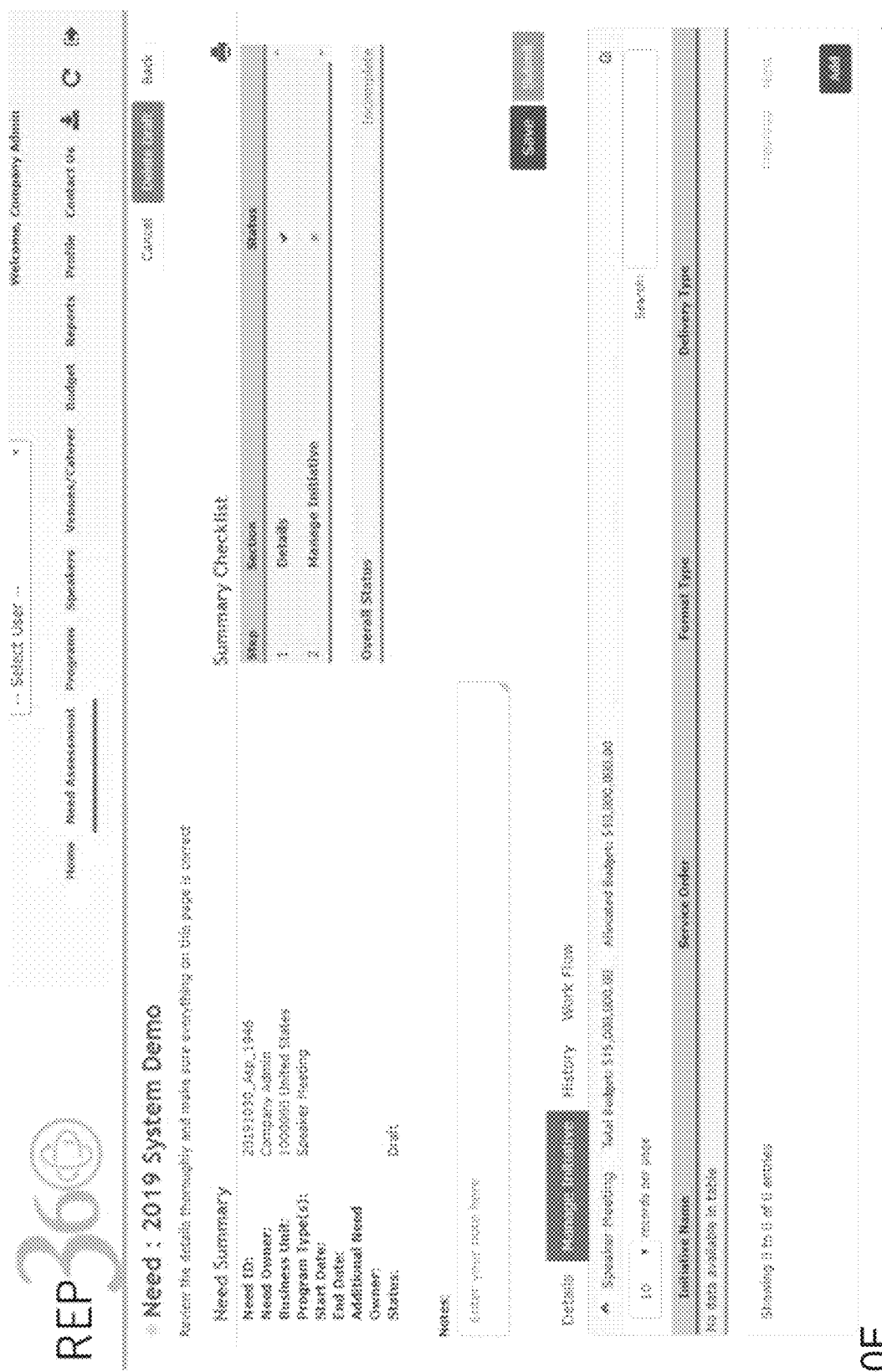
Figure 10G:
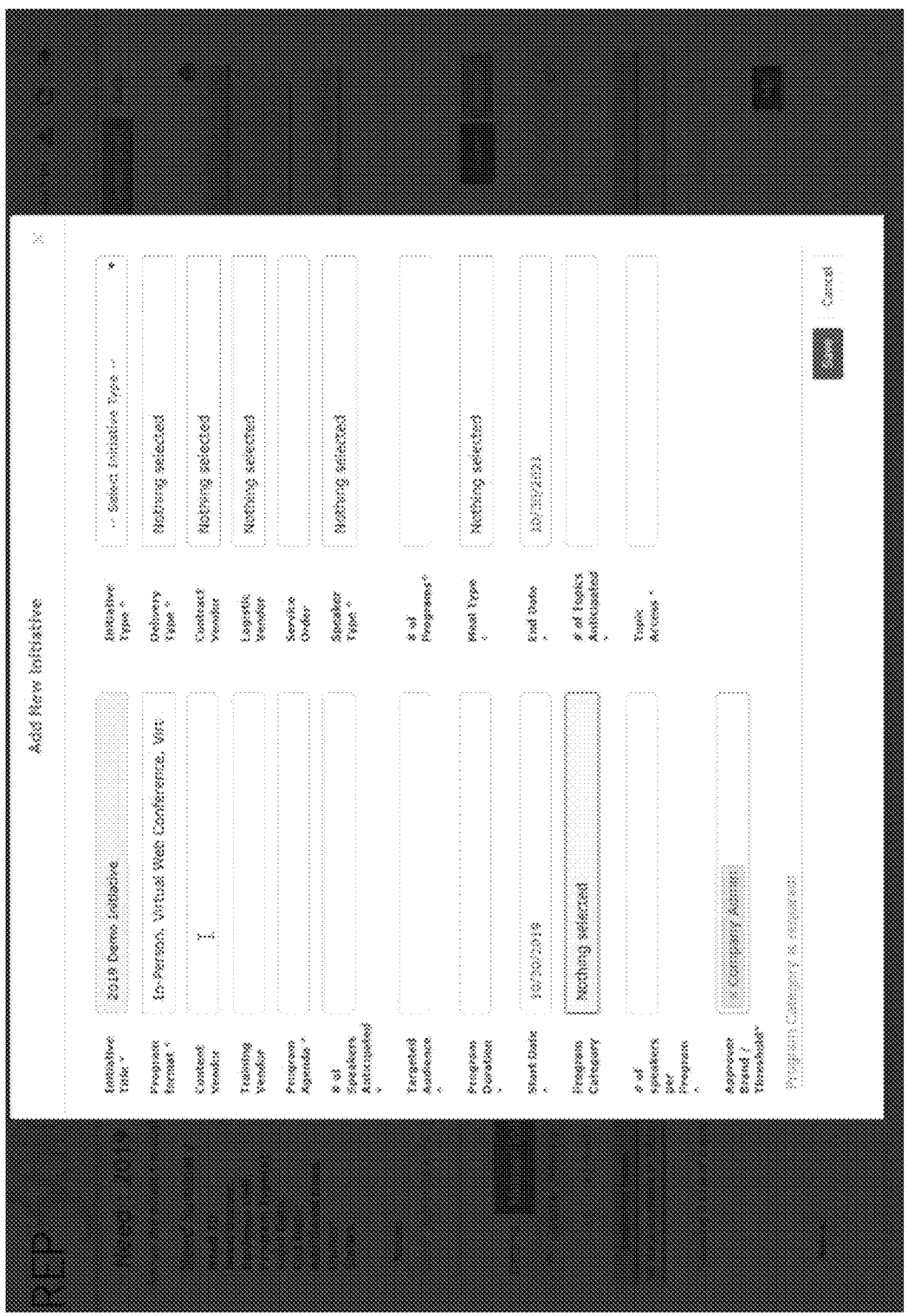
Figure 10H:
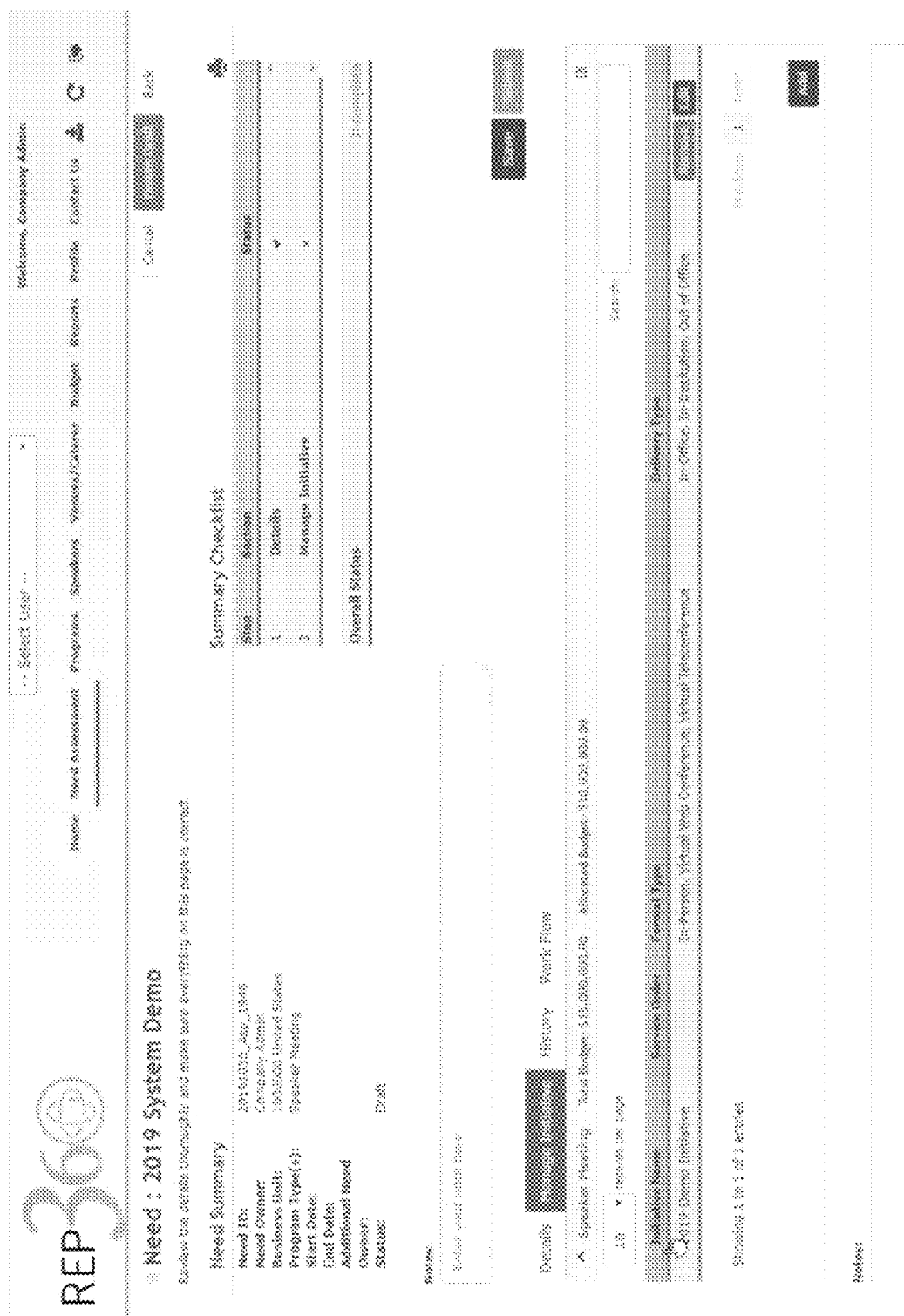
Figure 10K:
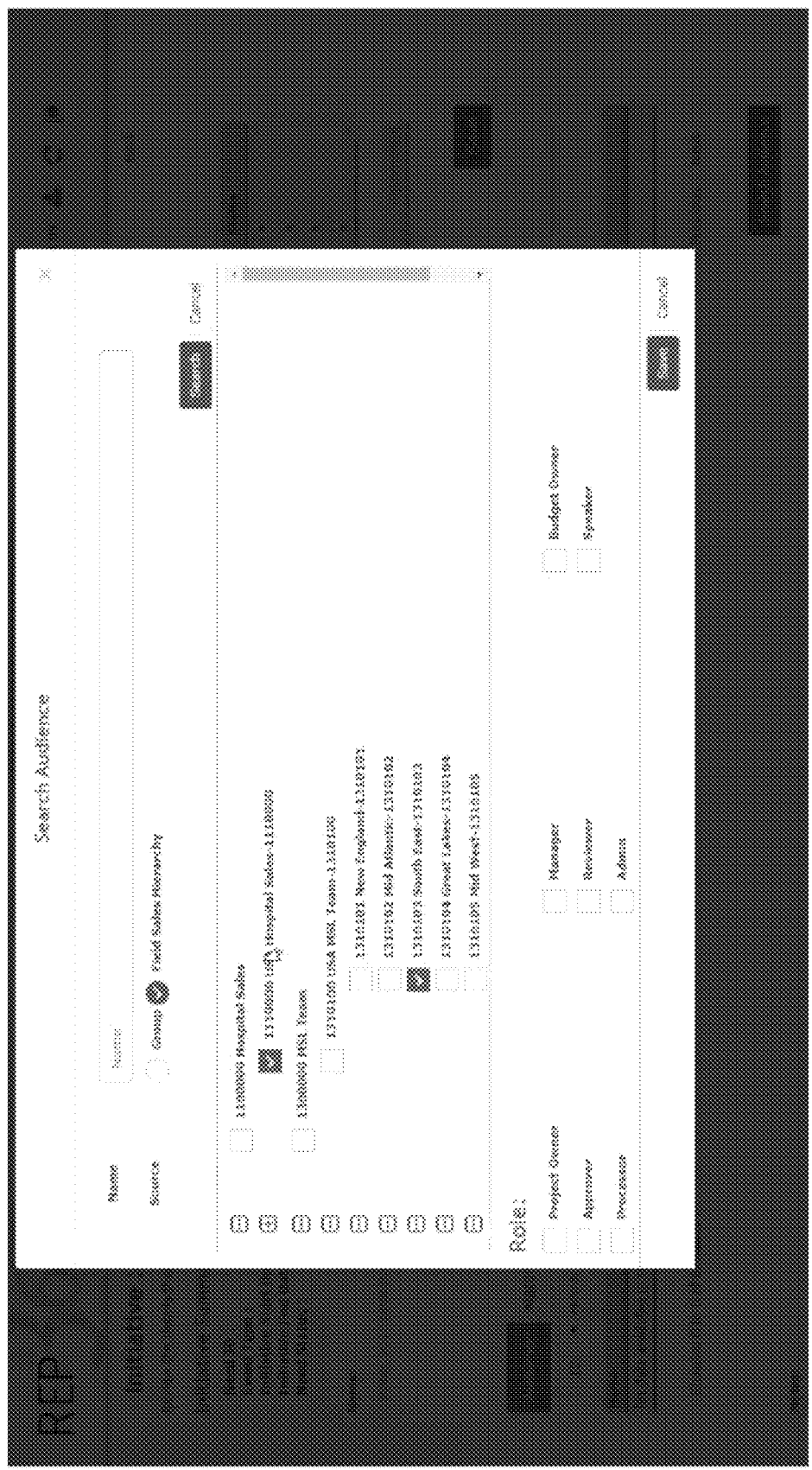
Figure 10L:
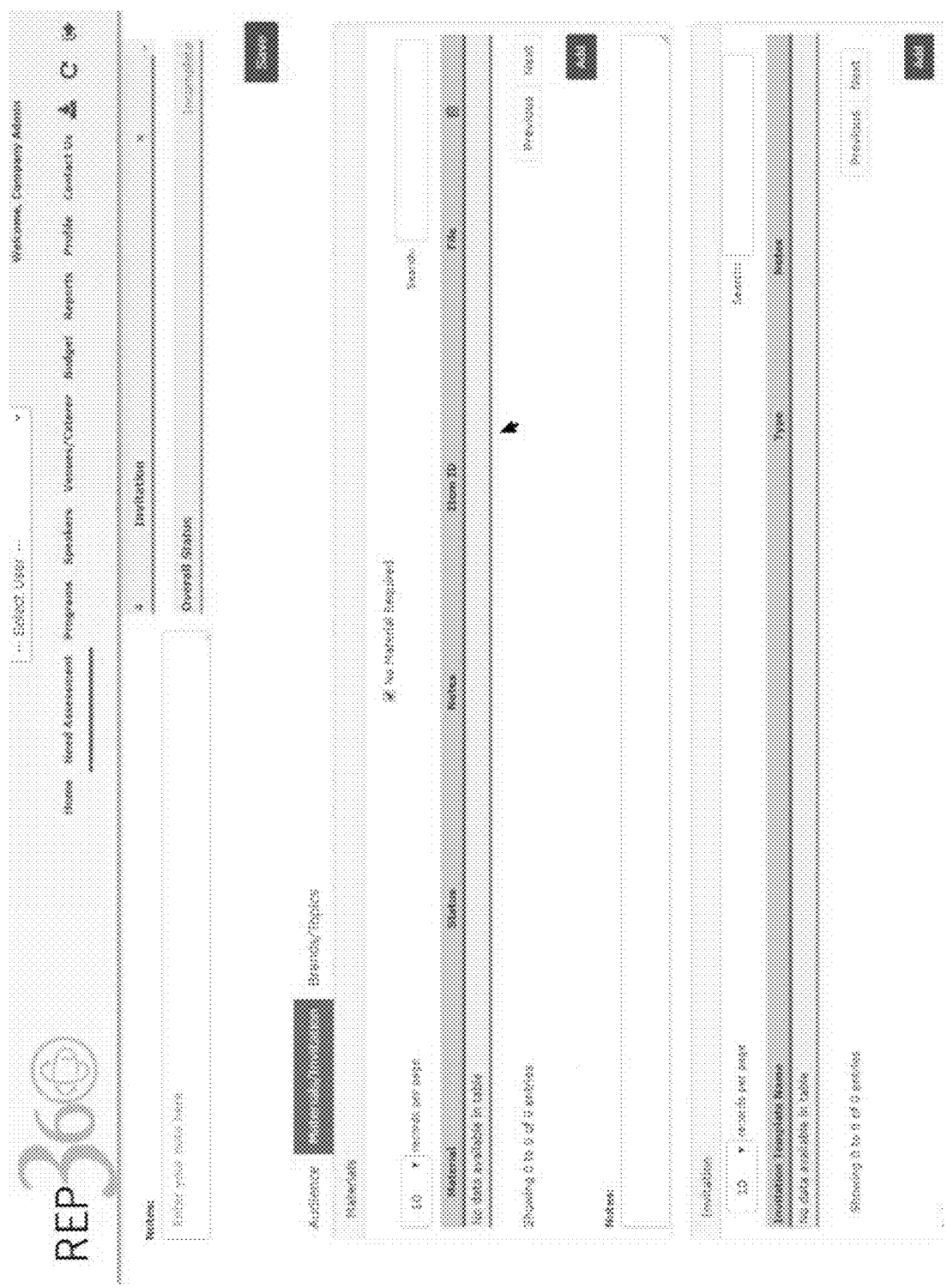
Figure 10M:
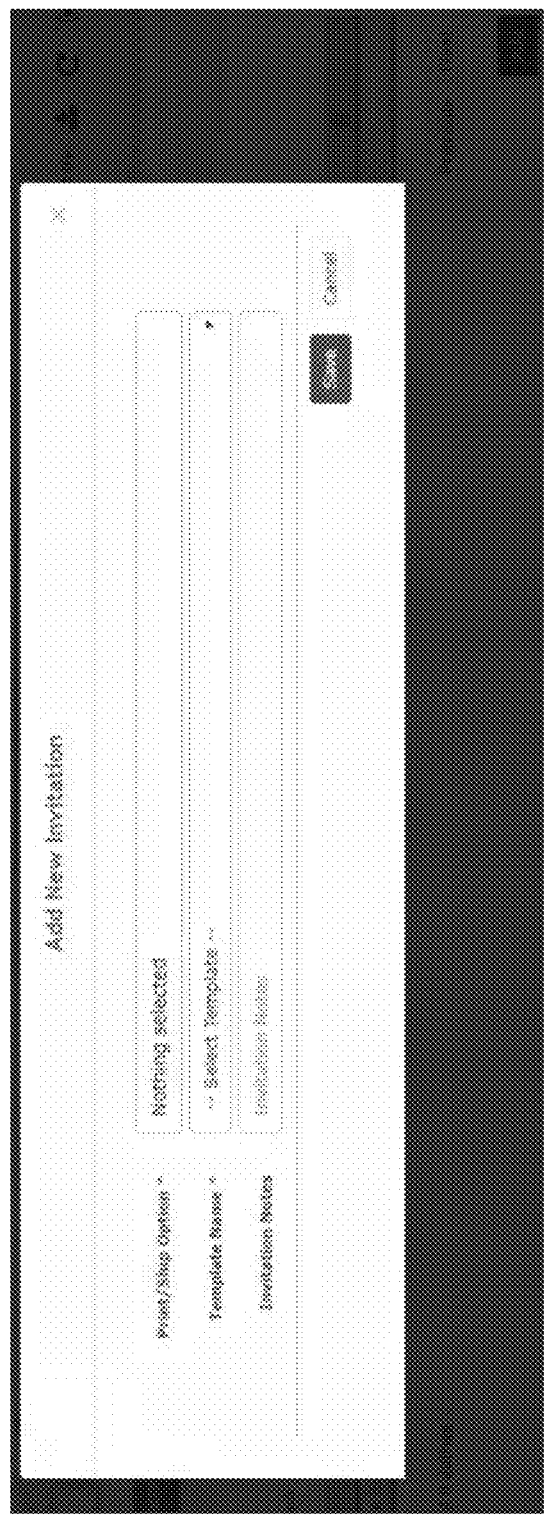
Figure 10N:
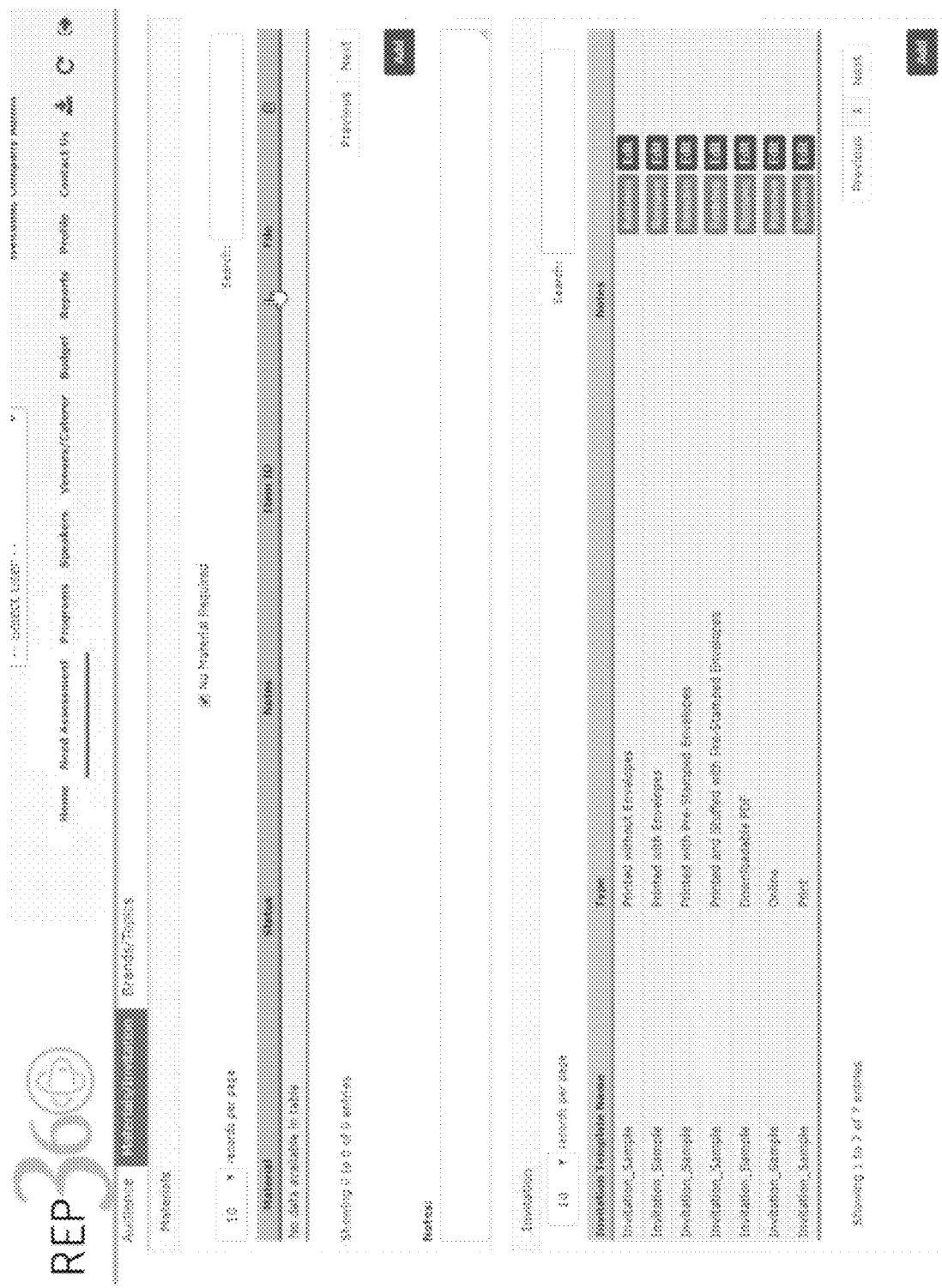
Figure 10P:
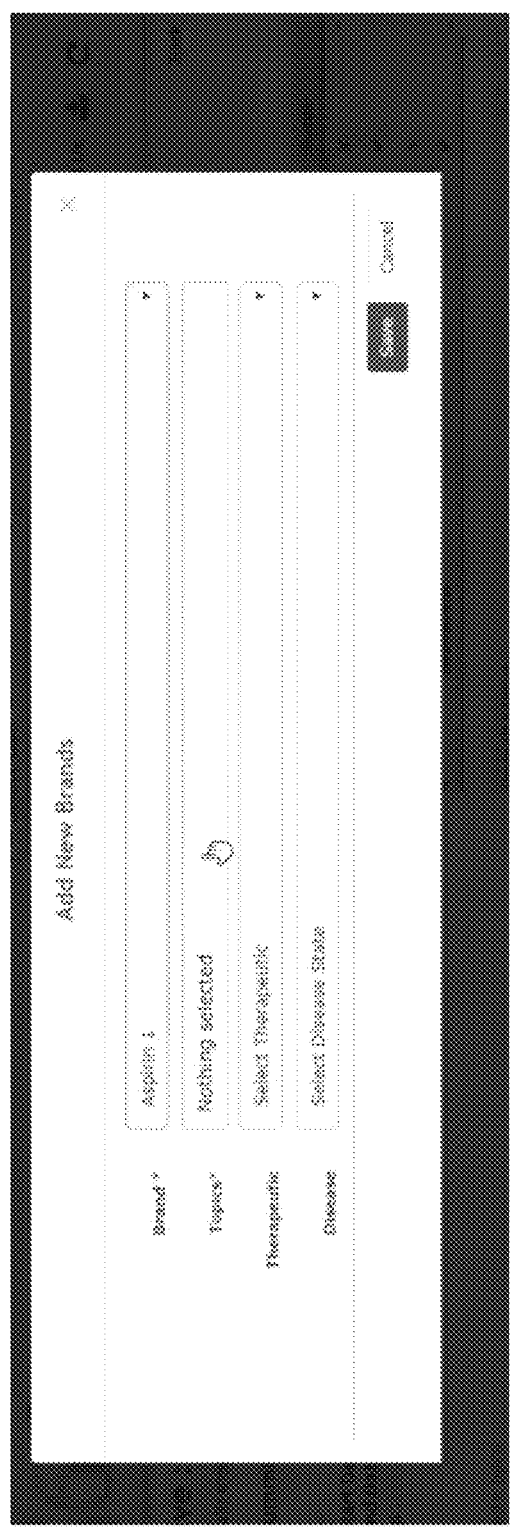
Figure 10Q:
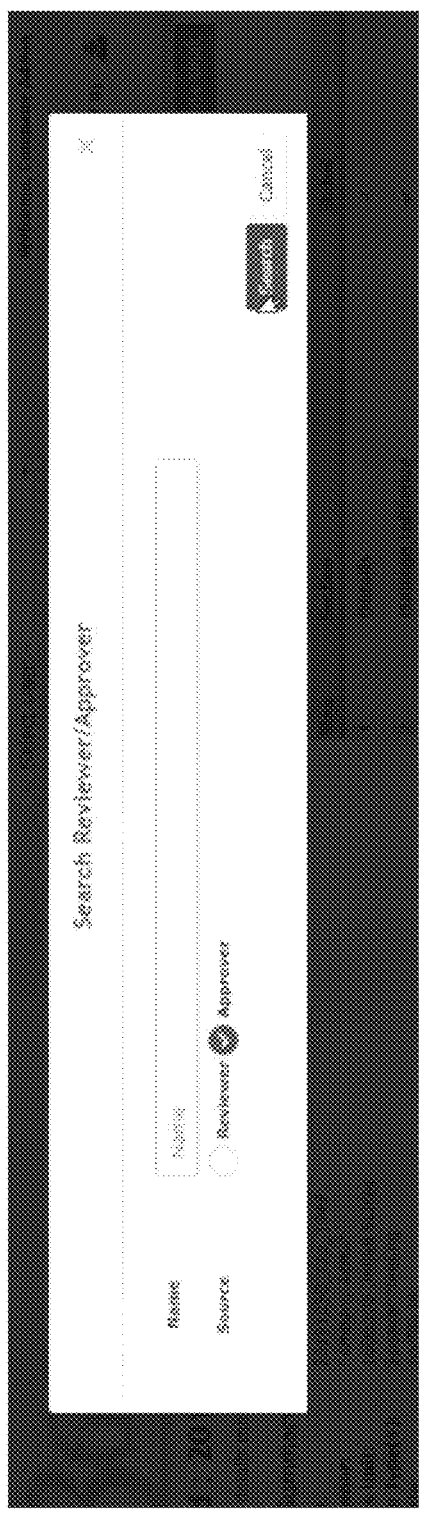
Figure 10S:
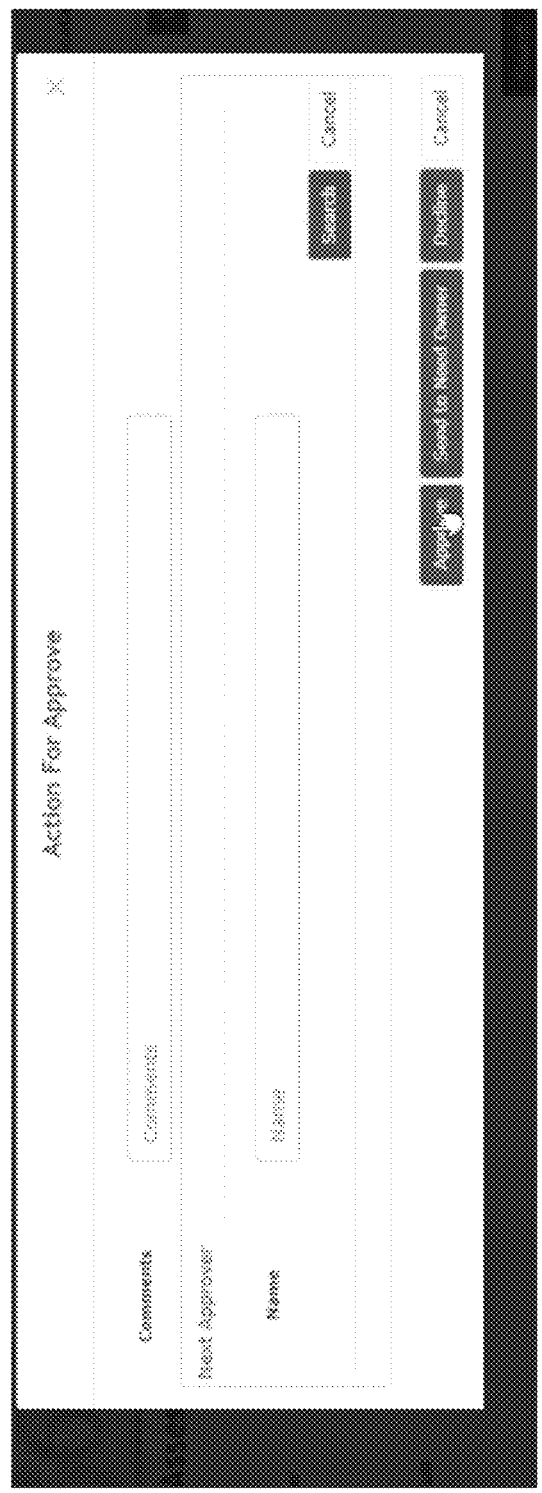
Figure 10T:
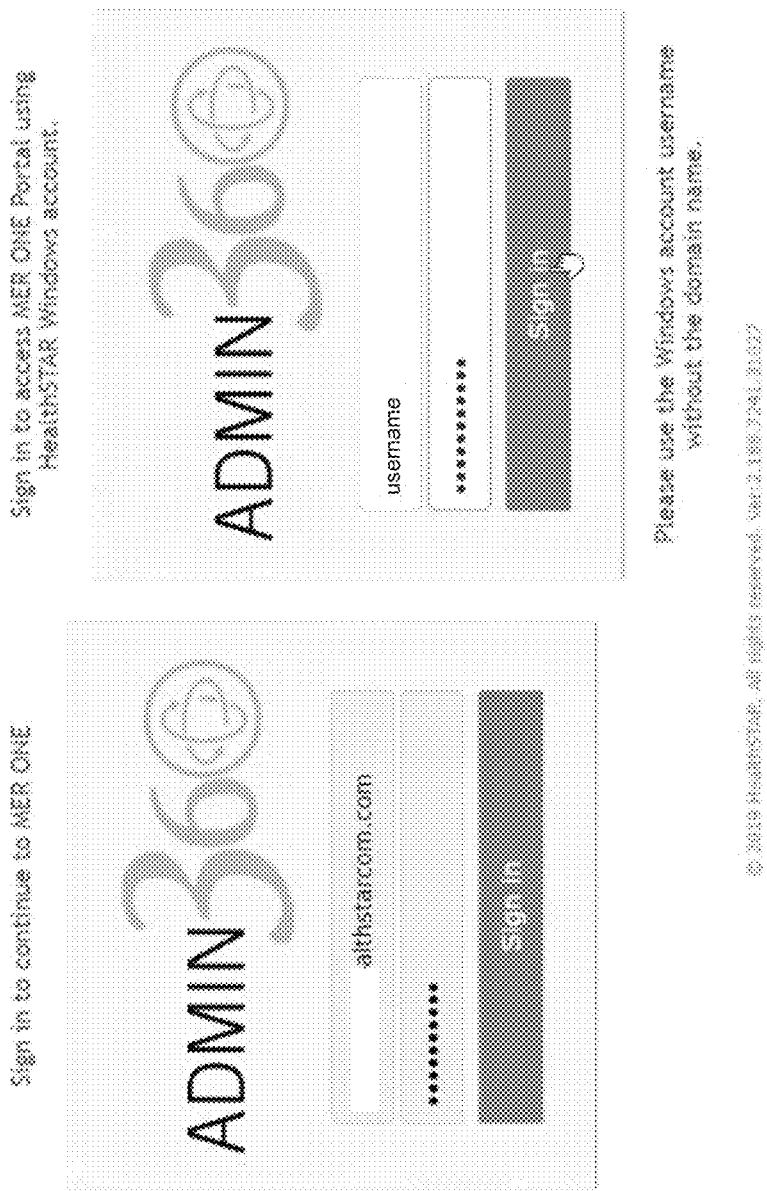
Figure 10U:
Figure 11:
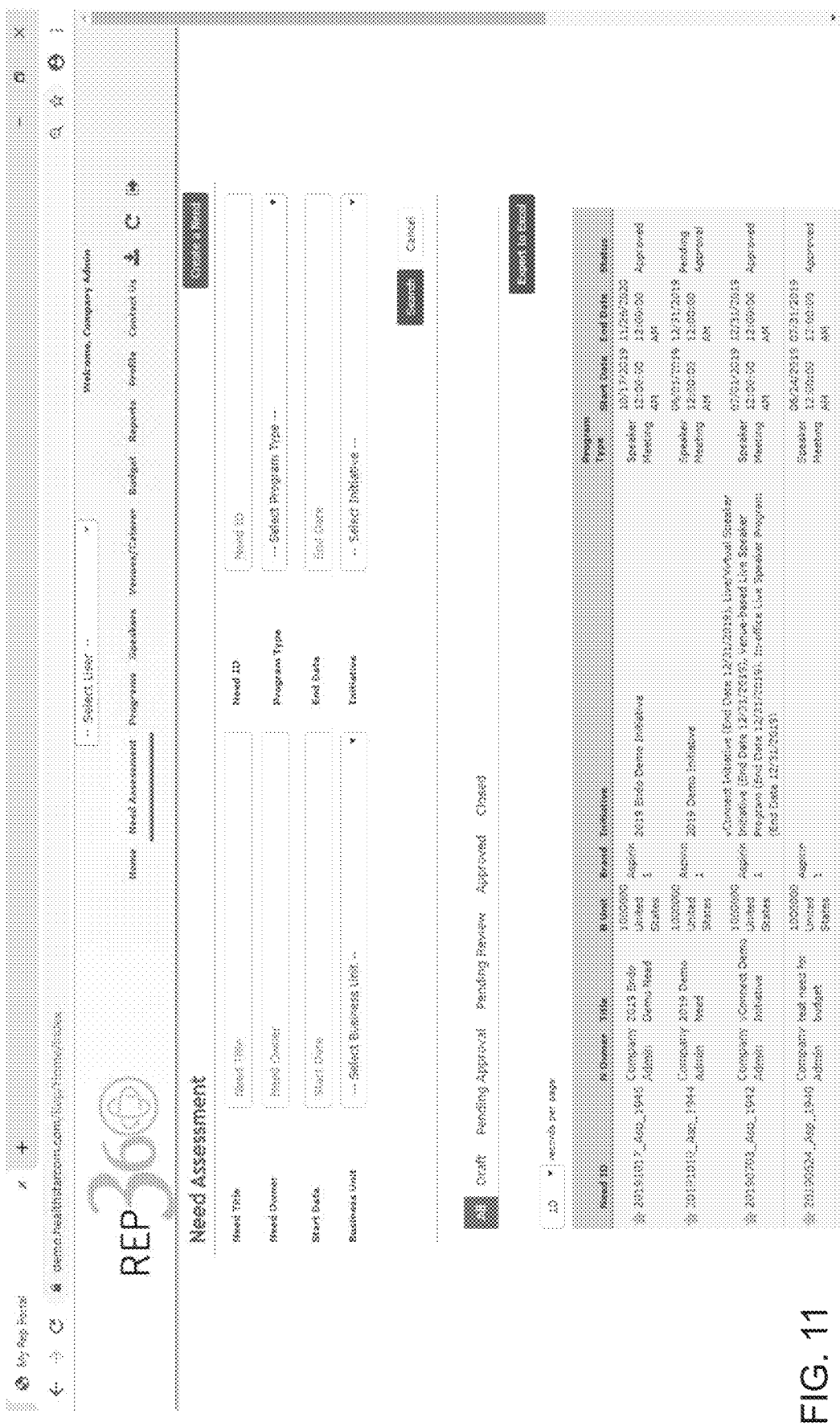
Figure 12:
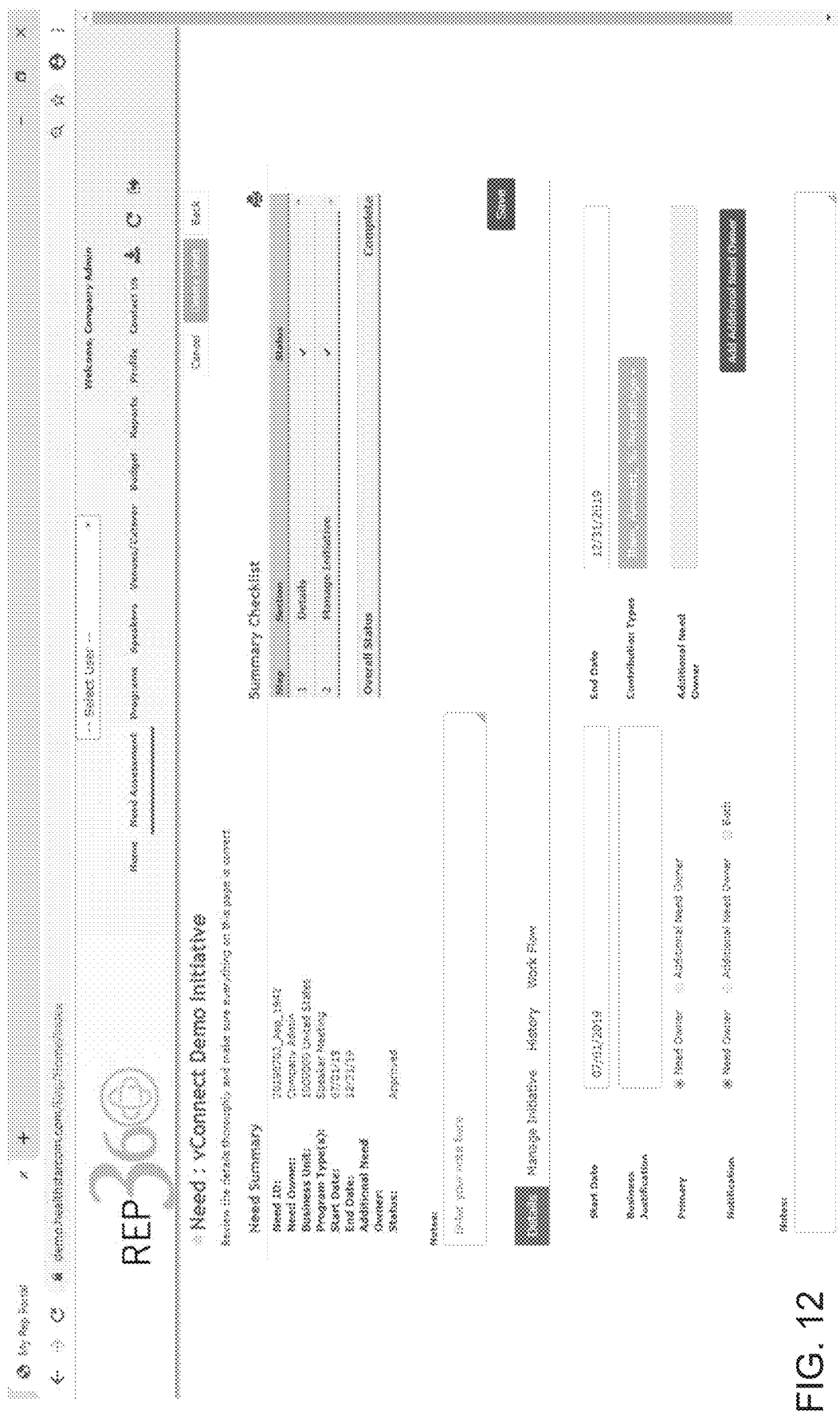
Figure 13:
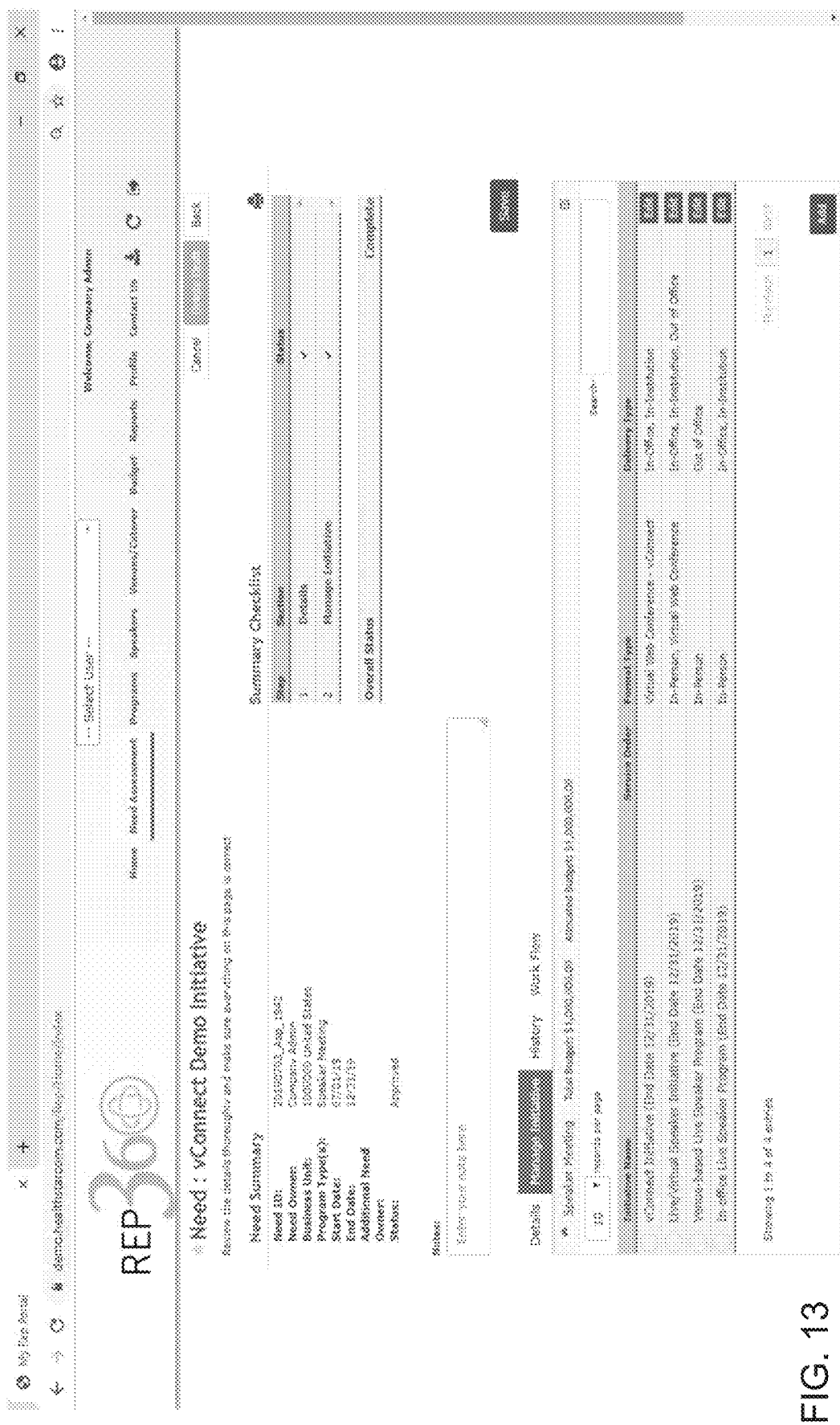
Figure 14:
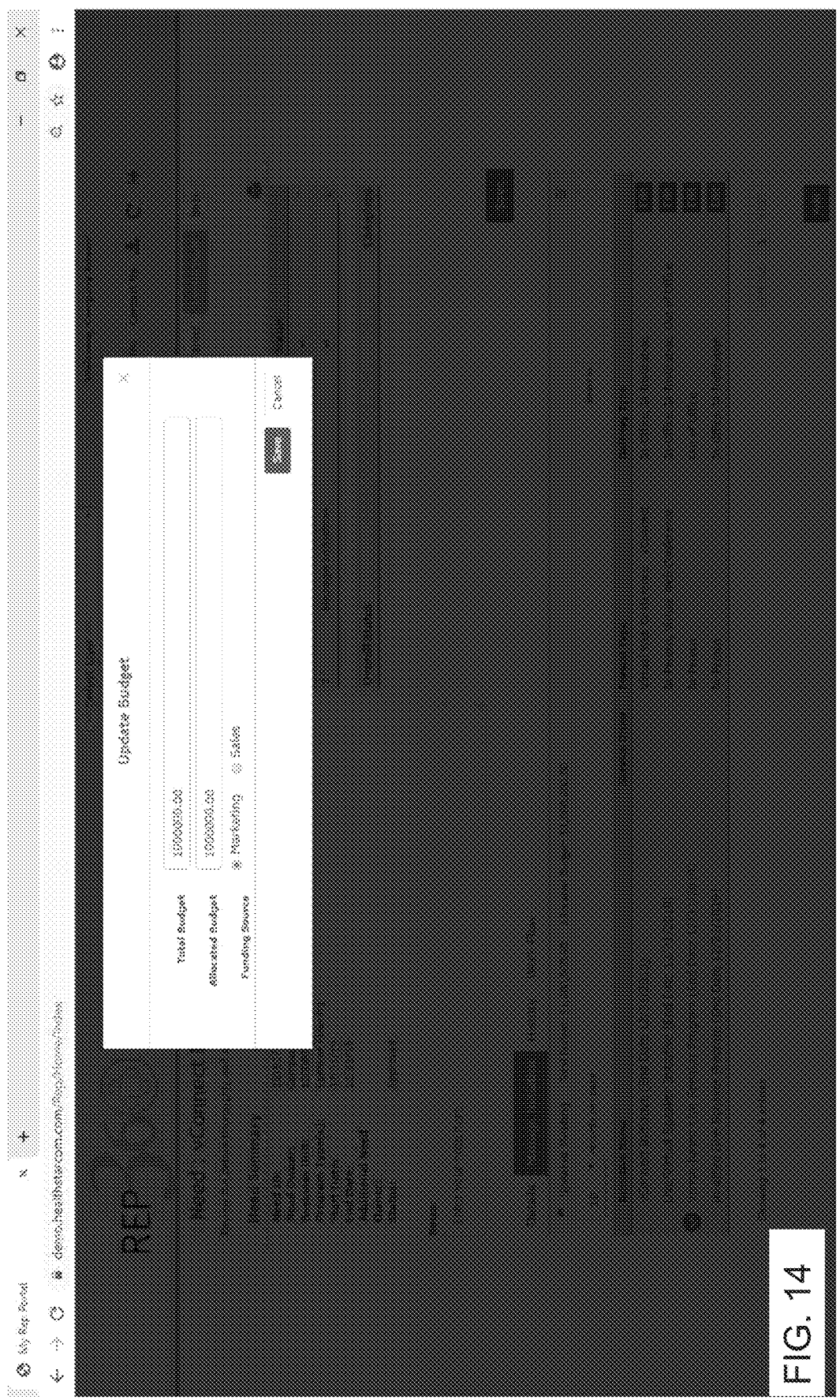
Figure 15:
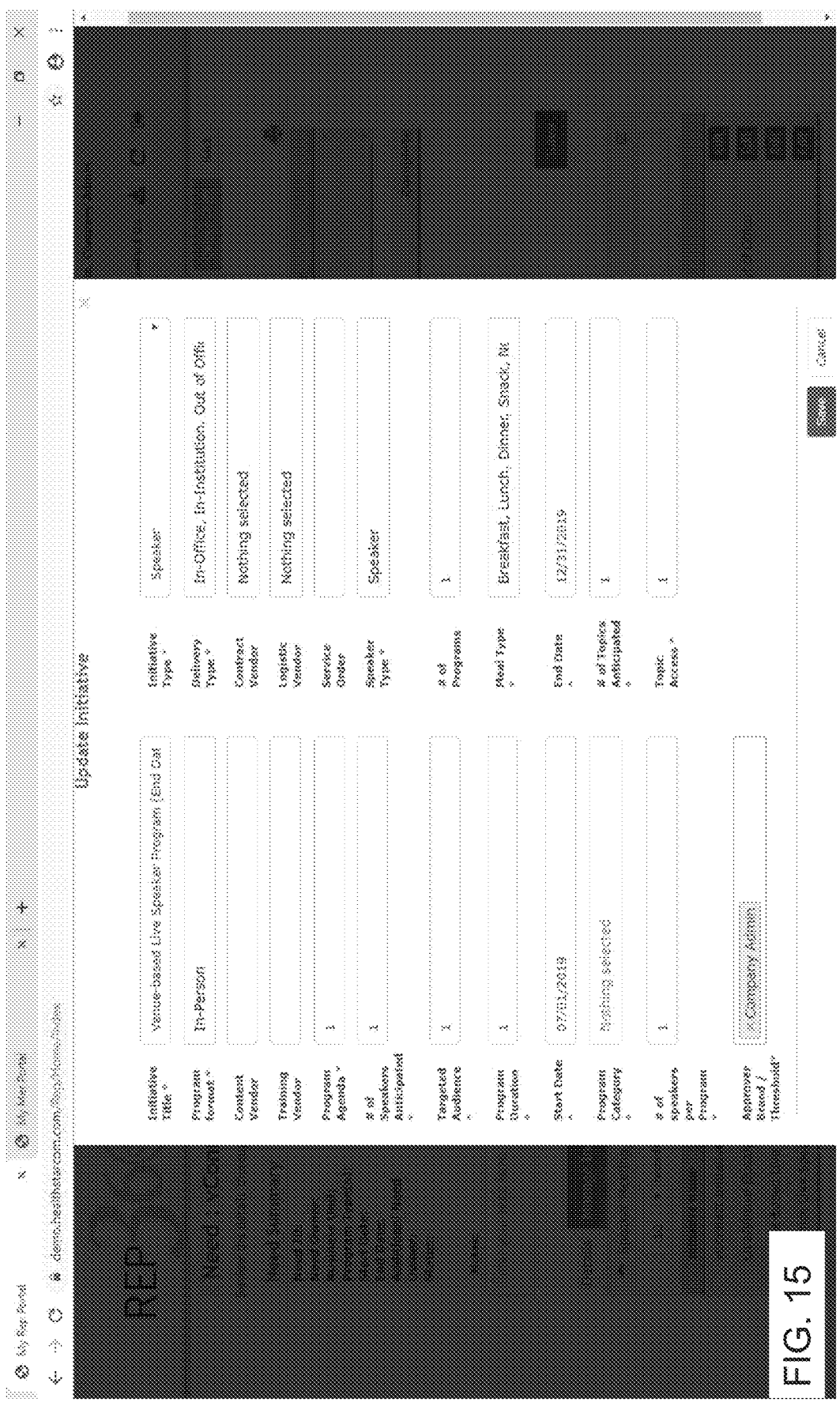
Figure 17:
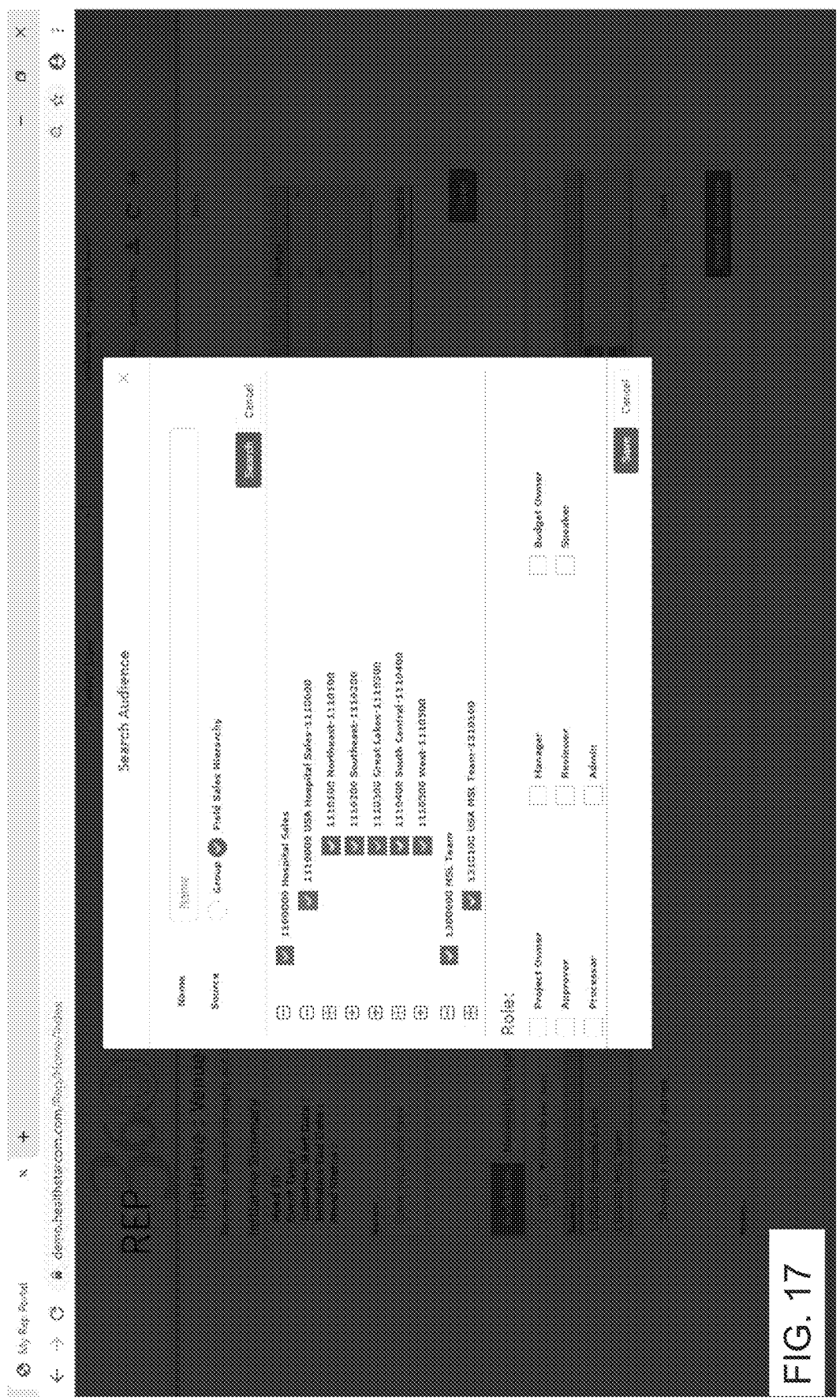
Figure 18:
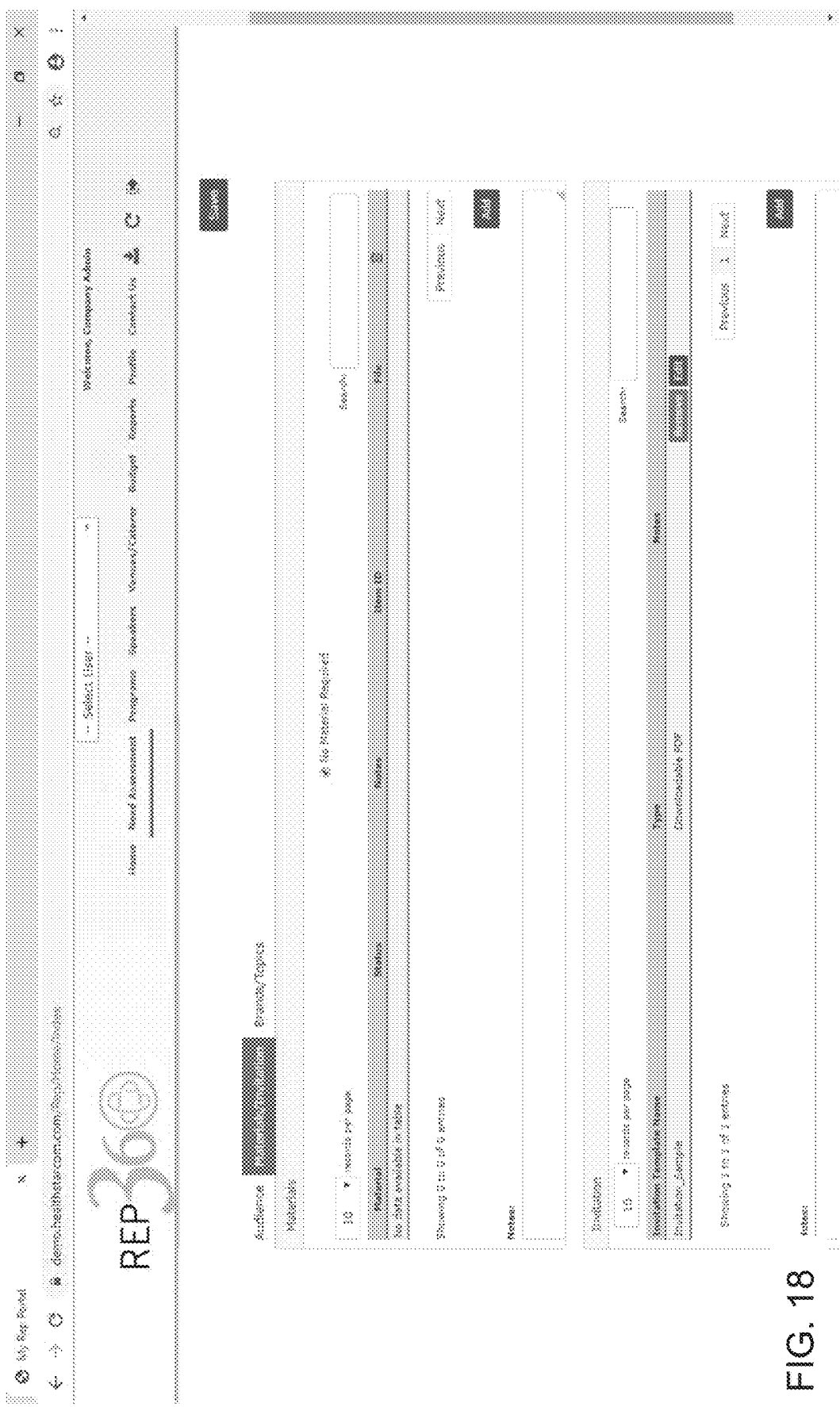
Figure 19:
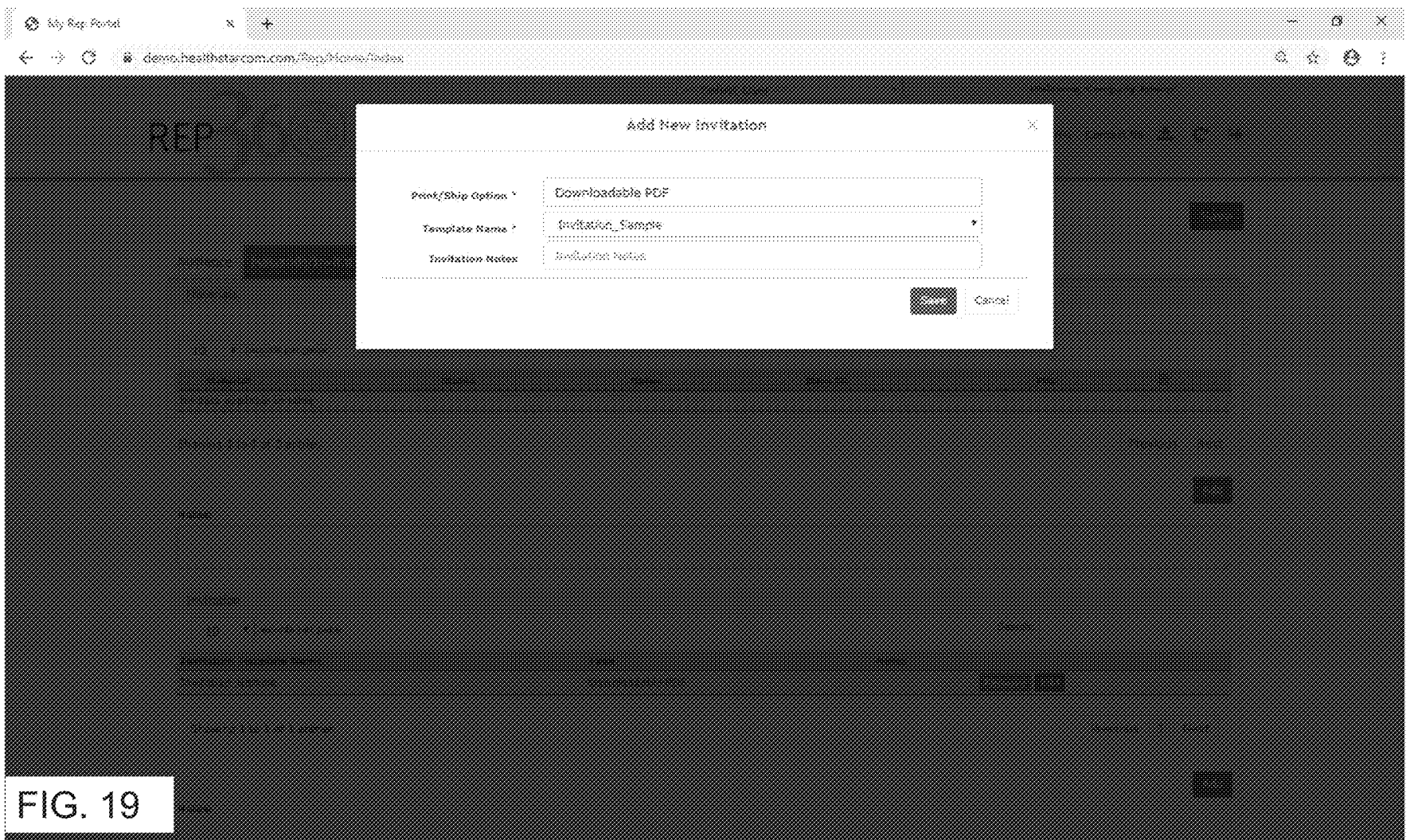
Figure 21:
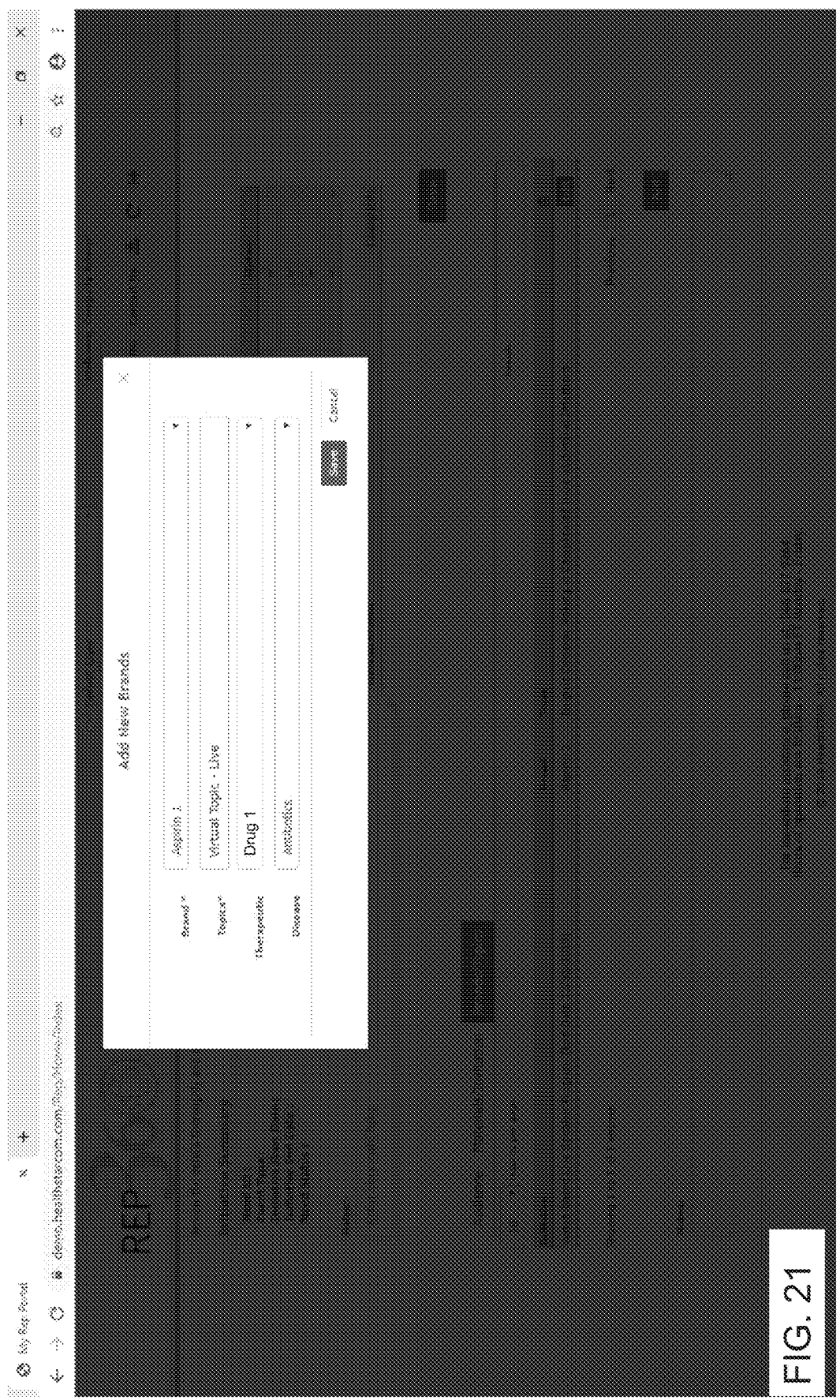
Figure 22:
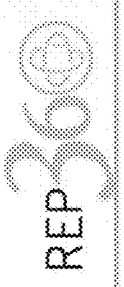
Figure 23:
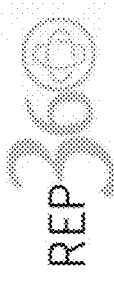
Figure 24:
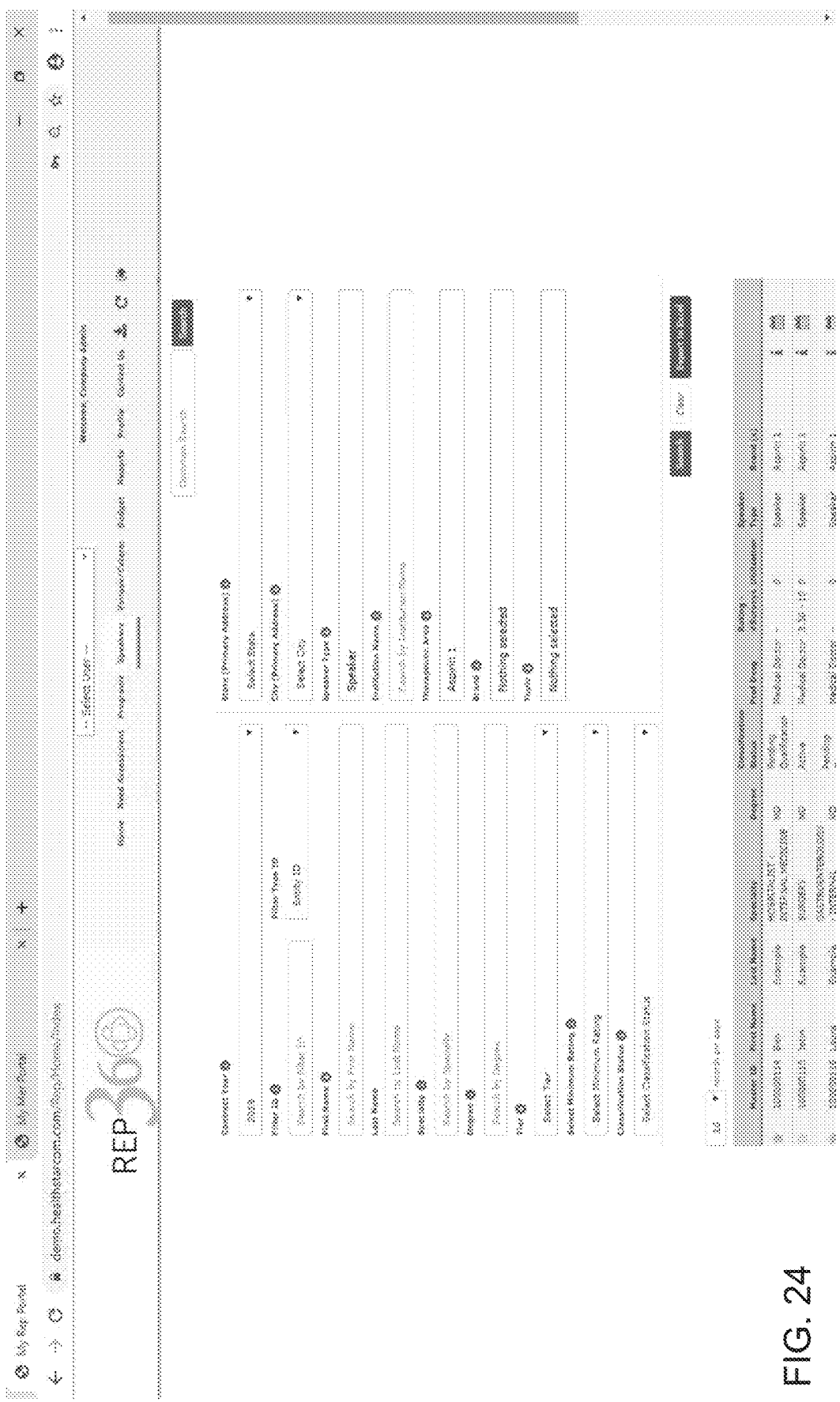
Figure 26:
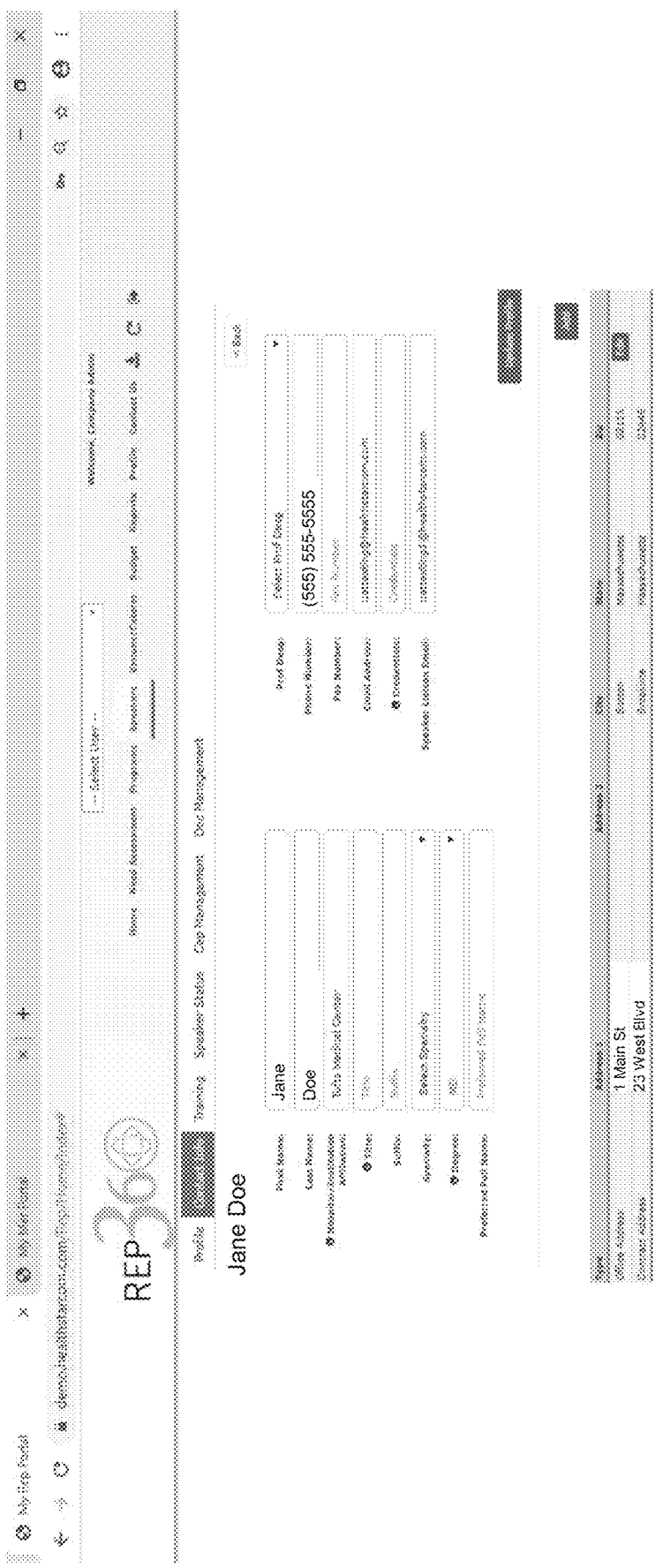
Figure 29:
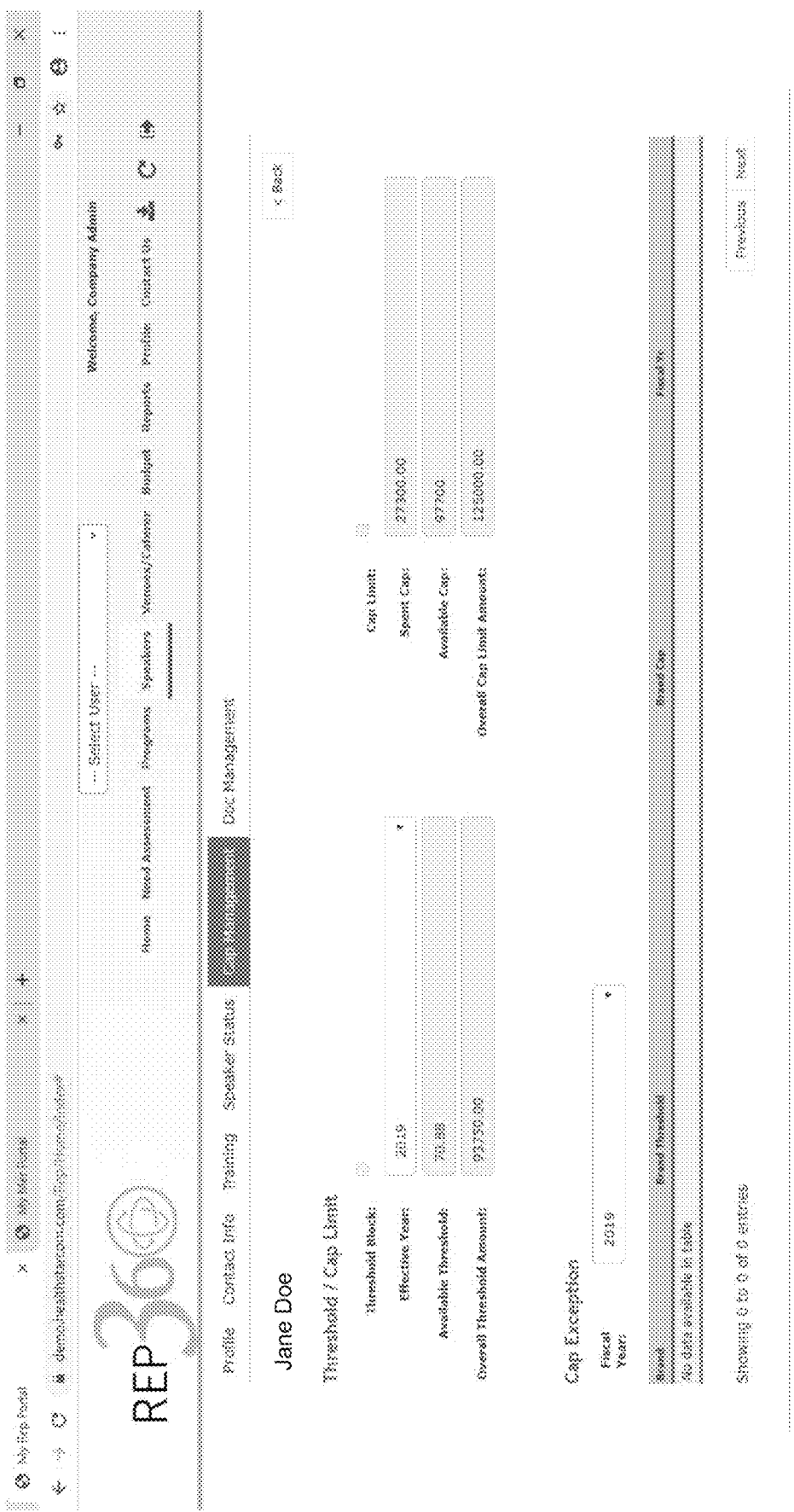
Figure 30:
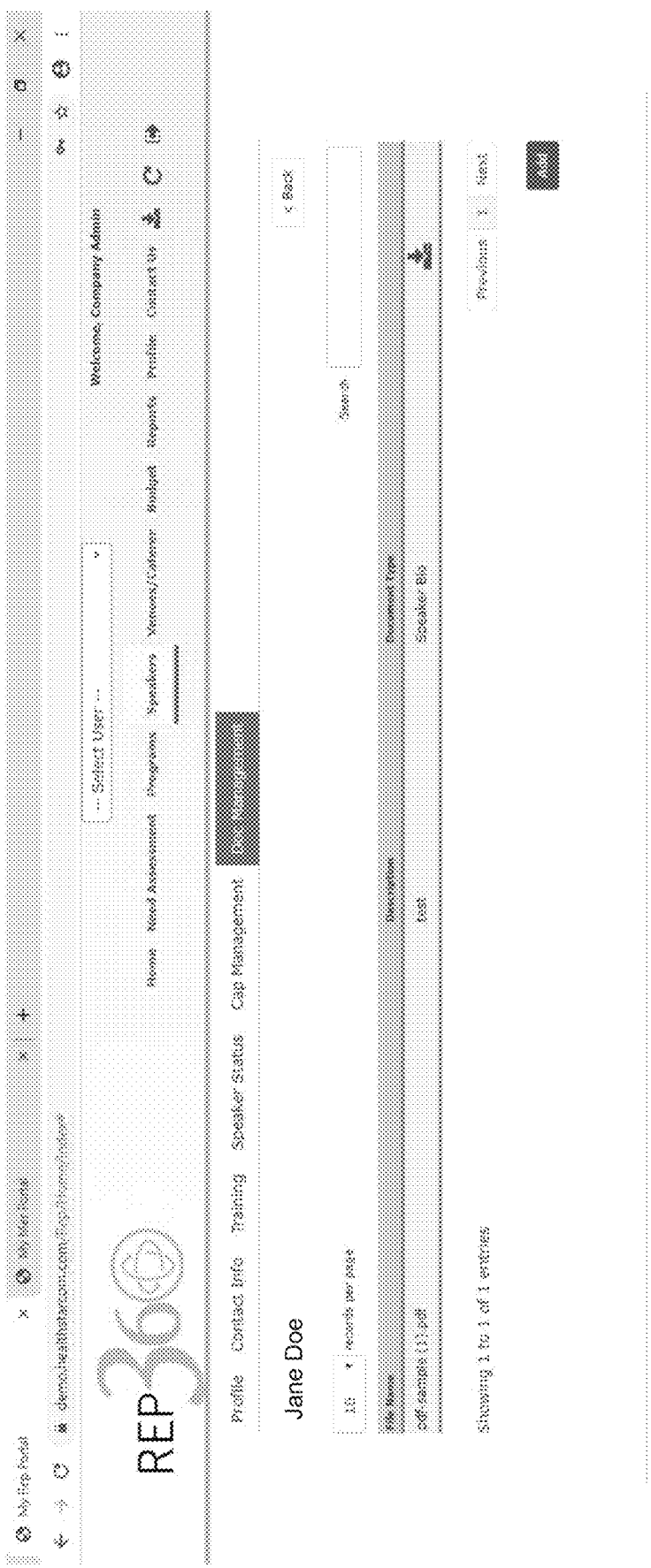

The needs assessment tab (FIGS. 10A-S and FIGS. 11-23) has search functionality, and a grid of all current needs is displayed. The grid has sub tabs to filter display based on status, and the grid can be exported to Excel or another data format. The user can create a new need from this tab via the 'Create a Need' button located at top right of the page (FIG. 11) or the 'Add' button at the bottom (FIG. 10A) depending on the particular embodiment. Need assessments are the highest level of control for program planning. In the creation of the Need, the user will define its 'Title', the Business Unit—only one per Need, the products associated with the need—multi-select, and the program type(s). The user will define the start and end dates of the need, and the communication points for the need if applicable. The user will also define the budget for the need. The user will define the types of initiatives available in the need. Initiatives are the next level of control for program planning and define the details of the programs available for that initiative. The initiatives will define the format, type, delivery options, meal types, speaker types, # of speakers per Program, # of topics per Program, and additional details for the initiatives. In the illustrative embodiment, there is no limit to the number of initiatives per need. FIGS. 10A-Q depict the initiation of a Need via the representative portal, and FIGS. 10R-V depict the approval of the Need via the representative portal and admin portal. It should be appreciated that, in some embodiments, the graphical user interface screens/pages may be completed in a sequential manner (e.g., in order to arrive at the next relevant interface page).

The program tab (FIGS. 49-82) displays for all users. The Program tab has search functionality, and a grid of all activities is displayed. The grid has sub tabs to filter display based on status, and the grid can be exported to Excel or another data format. The user can plan a new Program from this tab via the 'Plan a Program' button located at top right of the page. The user will be able to access a Program from grid by clicking on the Program ID or the Program Name hyperlink. The list of Programs that display are based on a combination of user alignment, level, and role.

Figure 70:
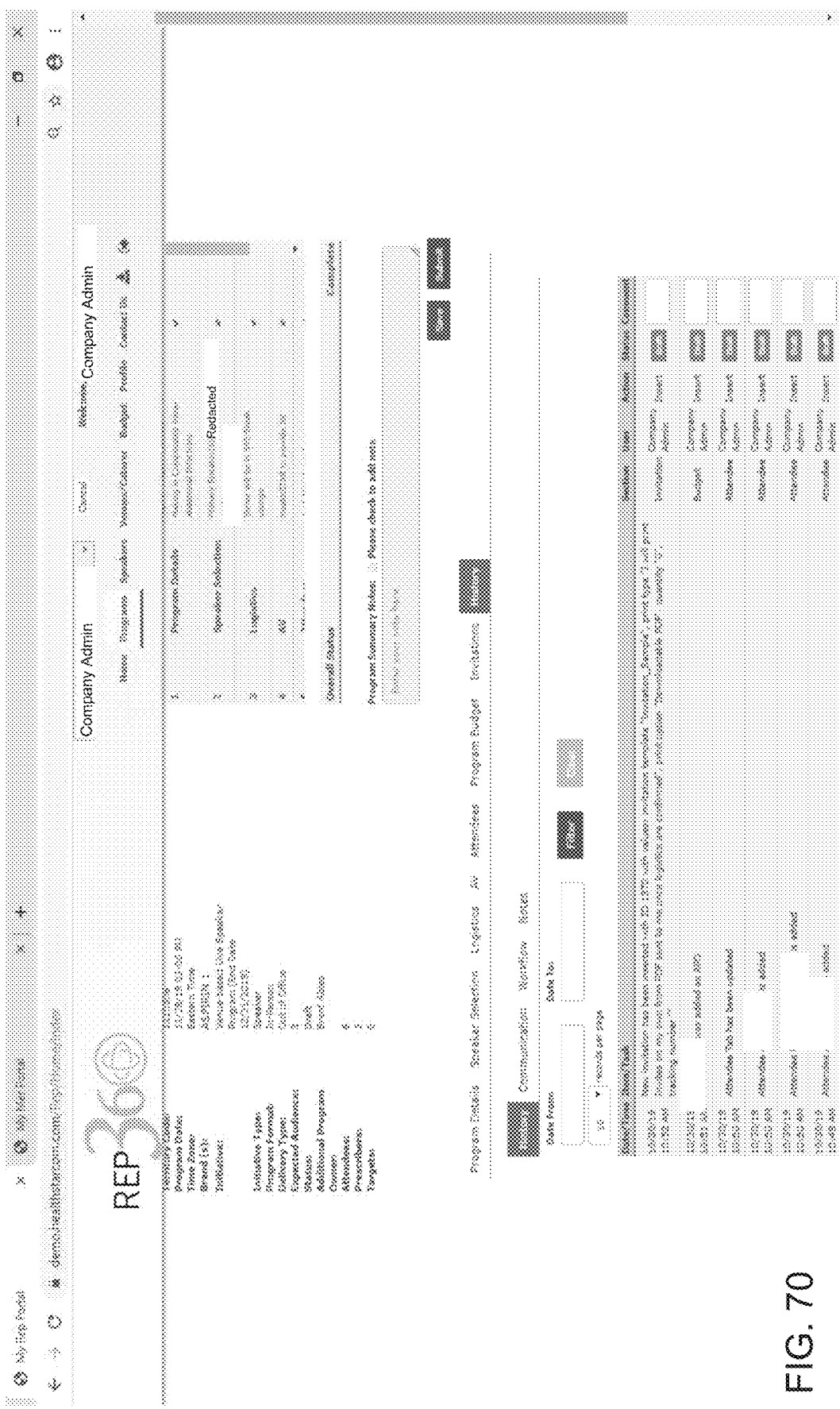
Figure 71:
Figure 72:
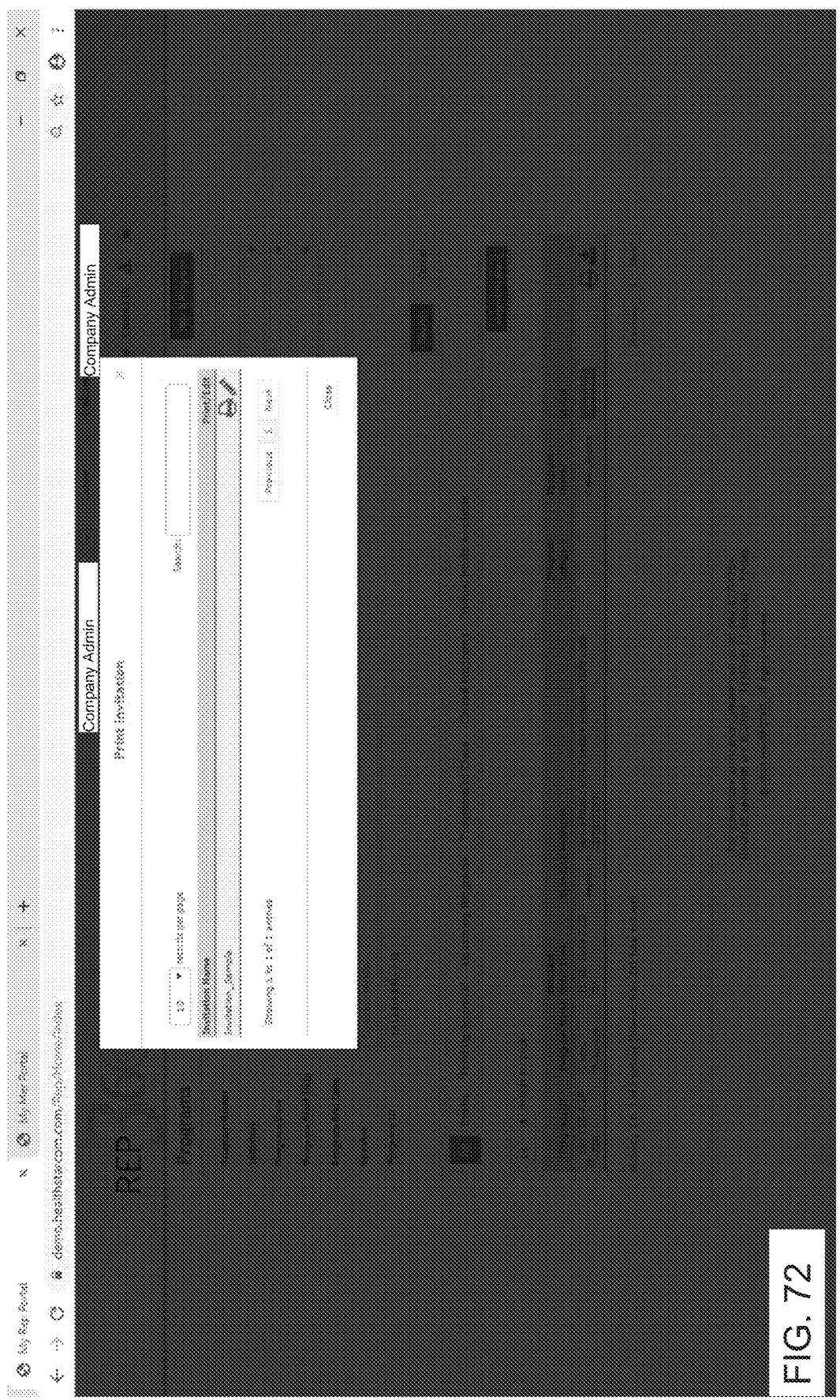
Figure 73:
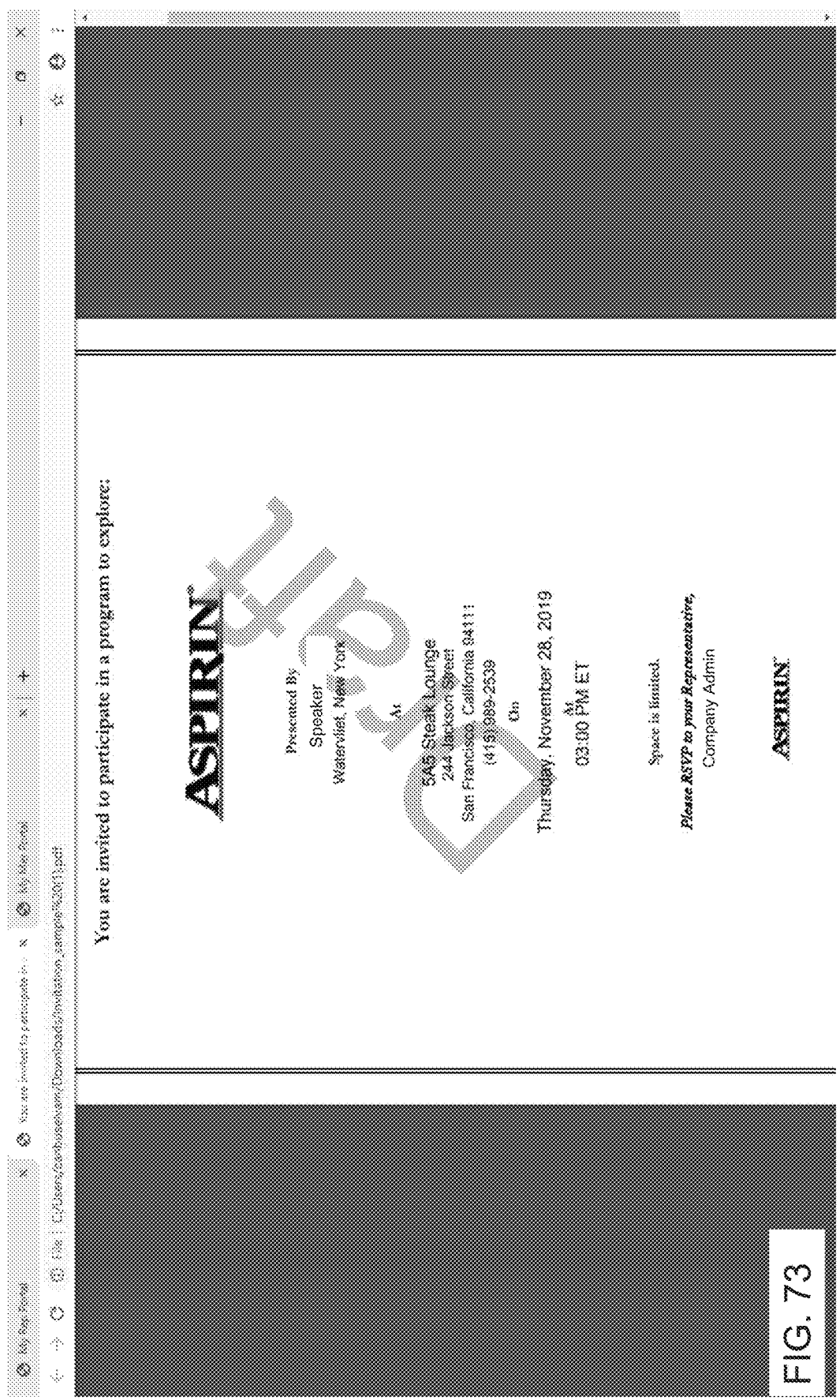
Figure 74:
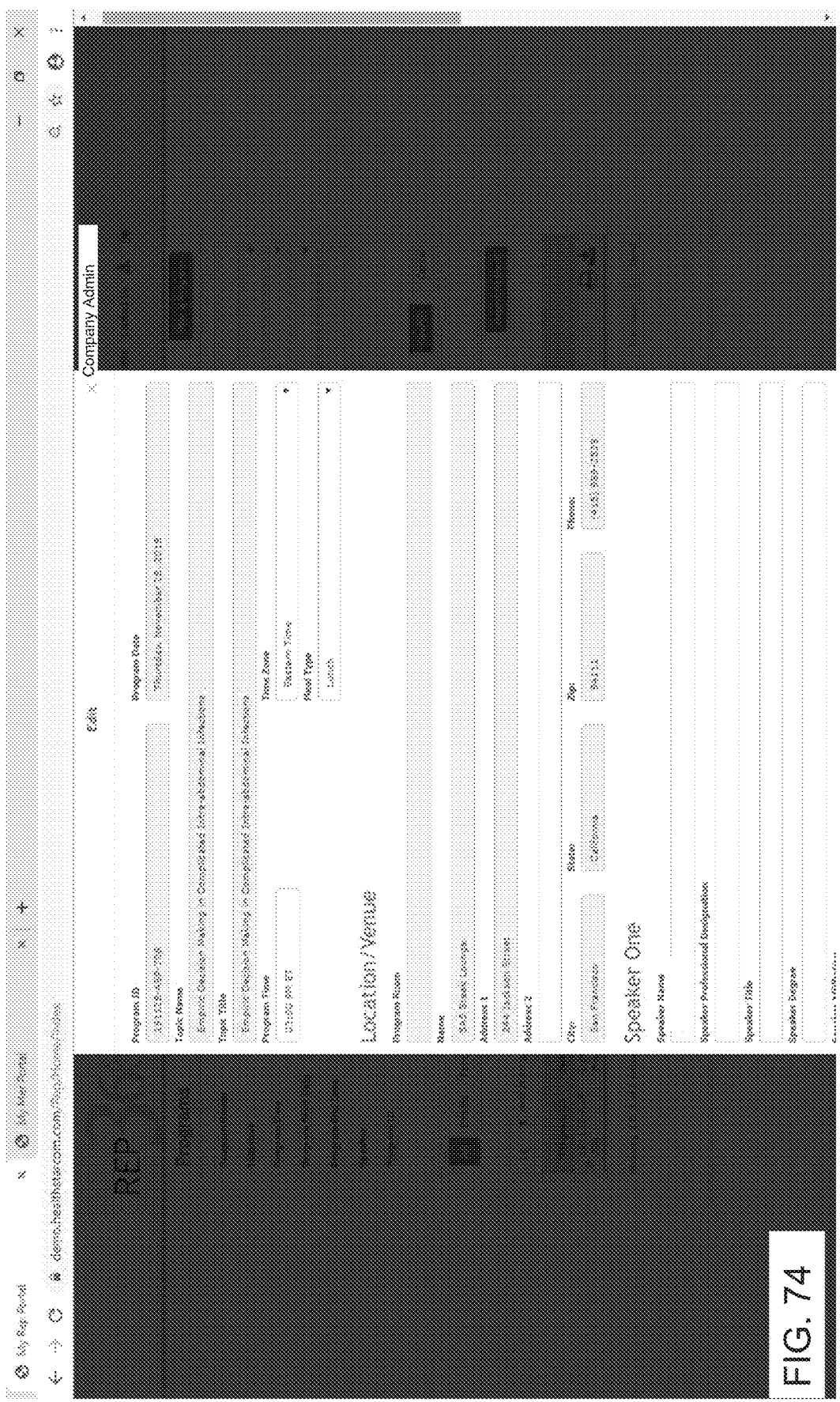
Figure 76:
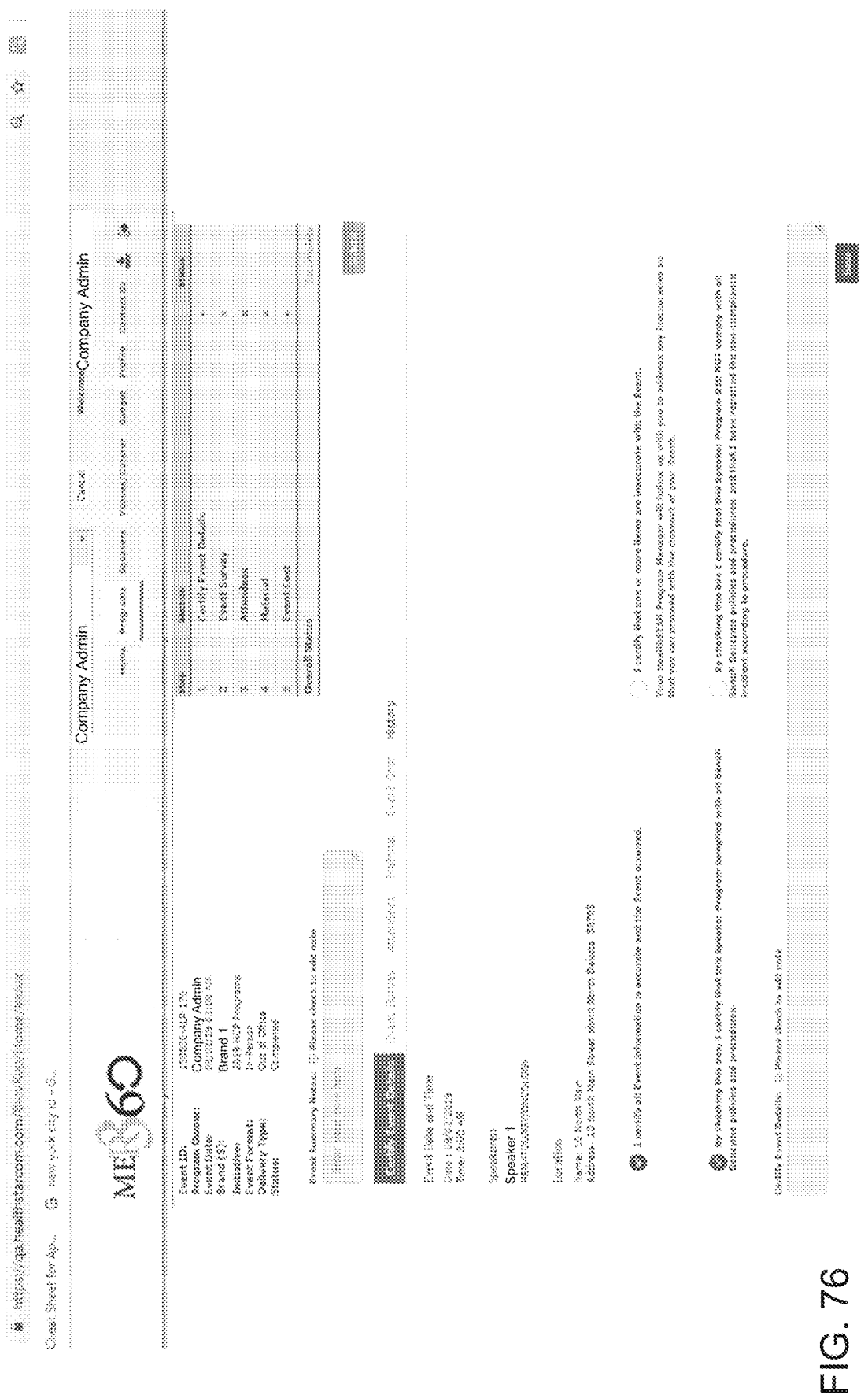
Figure 78:
Figure 80:
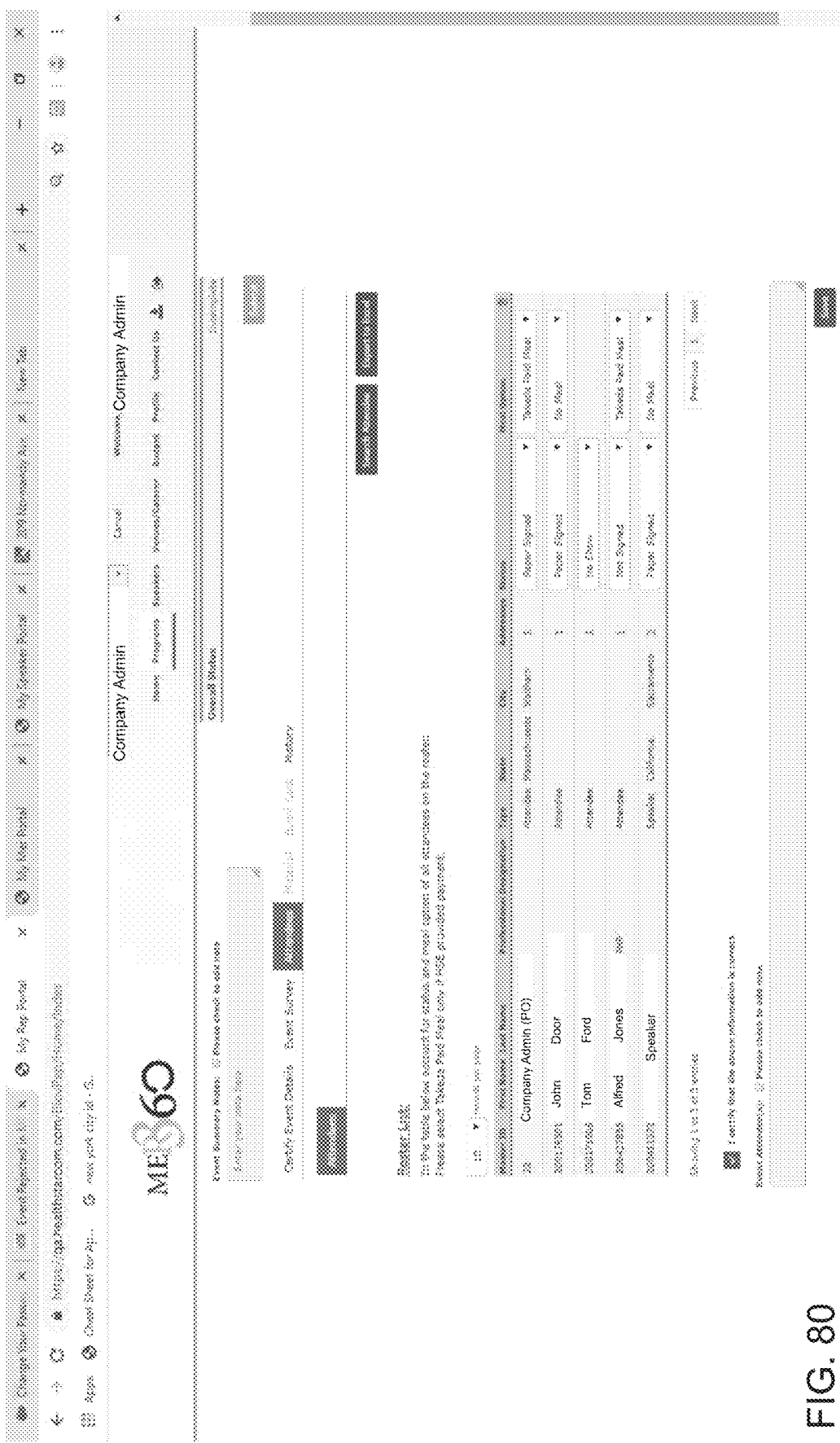
Figure 81:
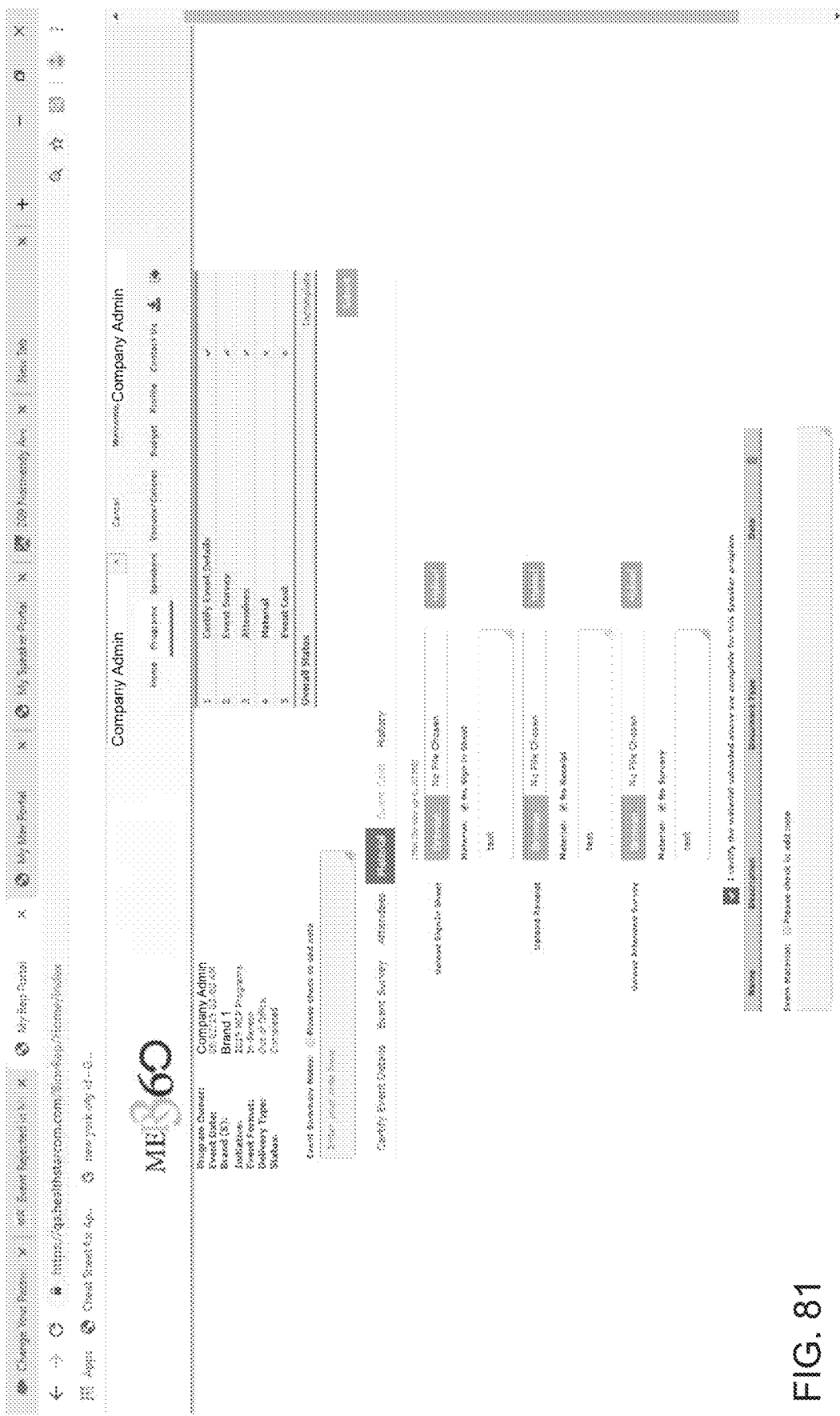

During the planning of a program, various subtabs of the program tab (FIGS. 49-82) are used. In particular, the representative may complete and/or view information regarding the program in the program details tab (FIG. 51), speaker selection tab (FIGS. 52-55), venue/logistics tab (FIGS. 56-58), AV tab (FIG. 59), attendees tab (FIGS. 60-65), the program budget tab (FIGS. 66-68), the invitations tab (FIG. 69), and the history tab (FIG. 70). Creation of an invitation and sign-in sheet are depicted in FIGS. 72-75. Further, the representative can certify the event details as depicted in FIGS. 76-82. As part of the attendee selection, the user may utilize the online attendee registration system (FIGS. 65A-E).

Additionally, in selecting the particular attendees, it should be appreciated that the representative may utilize the "heat map" (FIG. 64), which allows a representative to invite attendees that are on their "target". In particular, in some embodiments, the system provides a map with pins/indicia around the event location. Each of the pins/indicia represents a location (e.g., residential or business address) of an HCP that meets the criteria (e.g., correct subspecialty, etc.). Further, it should be appreciated that every HCP may be ranked by deciles into how marketable/approachable they are, and also how attractive they would be to a particular pharmaceutical company. In some embodiments, such data is retrieved from a third party database. For example, the top few tiers may be high profile doctors (for one reason or another), but the primary driver is that they are accessible, open to receiving marketing messages, etc. The bottom the deciles are often referred to as "no see" doctors, which means that they will not let the pharmaceutical company rep into the office (or will never see a doc, so the best they will do is drop samples). And then there are the HCPs between these two extremes. As such, the heat map (FIG. 64) may include various overlays/filters based on the relevant needs of the client. In other words, the heat map may be used to target a doctor that is part of a practice with 10-20 docs (or another suitable thresholds for number of HCPs in a medical practice) who see hundreds of thousands of patients a year (or another suitable threshold for patients seen per physician, per practice in over a period of time, or other patient volume threshold), is a specialist/subspecialist or particular type of specialist/subspecialist (e.g., endocrinologist with a diabetes practice, oncology, etc.), is attached to an academic/teaching hospital, and/or satisfies other relevant criteria.

The speakers tab (FIGS. 24-30) displays for all users. The Speaker tab has search functionality, and a grid of all speakers that match search criteria will be displayed. The grid can be exported to Excel or another data format. The grid contains the speaker's master ID number, first name, last name, specialty, degree, status, professional designation, current usage, speaker type, icon (additional information pop up), calendar icon (list of upcoming Programs pop up). The user is able to access the speaker's full profile by clicking on the speaker's first or last name in the grid.

The venue/caterers tab (FIGS. 31-32) displays for all users, and all users have the ability to search venue details.

A grid of all Venue/Caterers is displayed, and the grid can be exported to Excel or another data format. Each of the entries is classified in the type as: Venue, Caterer, or Both. Users may click on the Venue/Caterer name to access additional details. All users will have the ability to nominate a venue and/or caterer from the 'Nominate Venue/Caterer' button on top right of page. In the illustrative embodiment, it should be appreciated that the venue/caterers tab only lists those venues/caterers that have been approved (e.g., based on confirmation of compliance with various regulatory and/or other requirements). For example, in some circumstances, the venue must be able to seat a certain number of attendees, must have a private (e.g., sound proof) room, and/or satisfy other requirements. In some embodiments, venues/caterers not listed may be nominated for approval.

The budget tab (FIGS. 33-37) displays for all users. It contains 3 sub tabs—View Budget, Budget Allocation, and Budget History. The View Budget tab displays for all users and allows them to view the budget and program based on their level and role. The Budget Allocation tab does not display for rep level users. The Budget History Tab does not display for rep level users. The Budget Allocation tab will allow users to allocate, release, transfer, or pull up funds by org node. The Budget Allocation tab contains the Budget Allocation Tool, the Transfer Budget Tool, and the Needs Transfer tool, each allowing for particular budget management functionality. The Budget History tab records users' actions on the Budget Allocation tab.

The reports tab (FIG. 38) is displayed based on user role/group permissions. Reports may appear as embedded versions of reports hosted in the contractor's Reporting Services Server. Some reports will be distributed via email and off hours to avoid system performance issues.

The profile tab (FIGS. 39-44) displays for all users and contains 3 sub tabs: My Profile, My Favorites, and My Notifications. 'My Profile' will display the users profile information (First Name, Last Name, Territory Information, Contact information, etc.). It will also display the list of managers for the user-based on Org node hierarchy. 'My Favorites' contains additional subtabs, Favorite Speaker, Favorite Venue/Caterer, Favorite Attendees, Favorite Programs, and Favorite Needs—these will display when applicable. Each favorite subtab allows the user to manage their respective favorites. 'My Notifications' gives the users limited control over how they will be communicated with for certain notifications, alerts, and emails.

The contact us tab (FIG. 45) displays for all users, and it provides the user with a list contact points for support and questions. The download center (FIGS. 46-49) tab displays for all users and contains 2 subtabs: General Downloads and Content Management. The General Downloads subtab is a document repository for files that should be available to all users. The Content Management subtab displays all speaker program content available to the user based on the user and content's product alignment.

Figure 100:
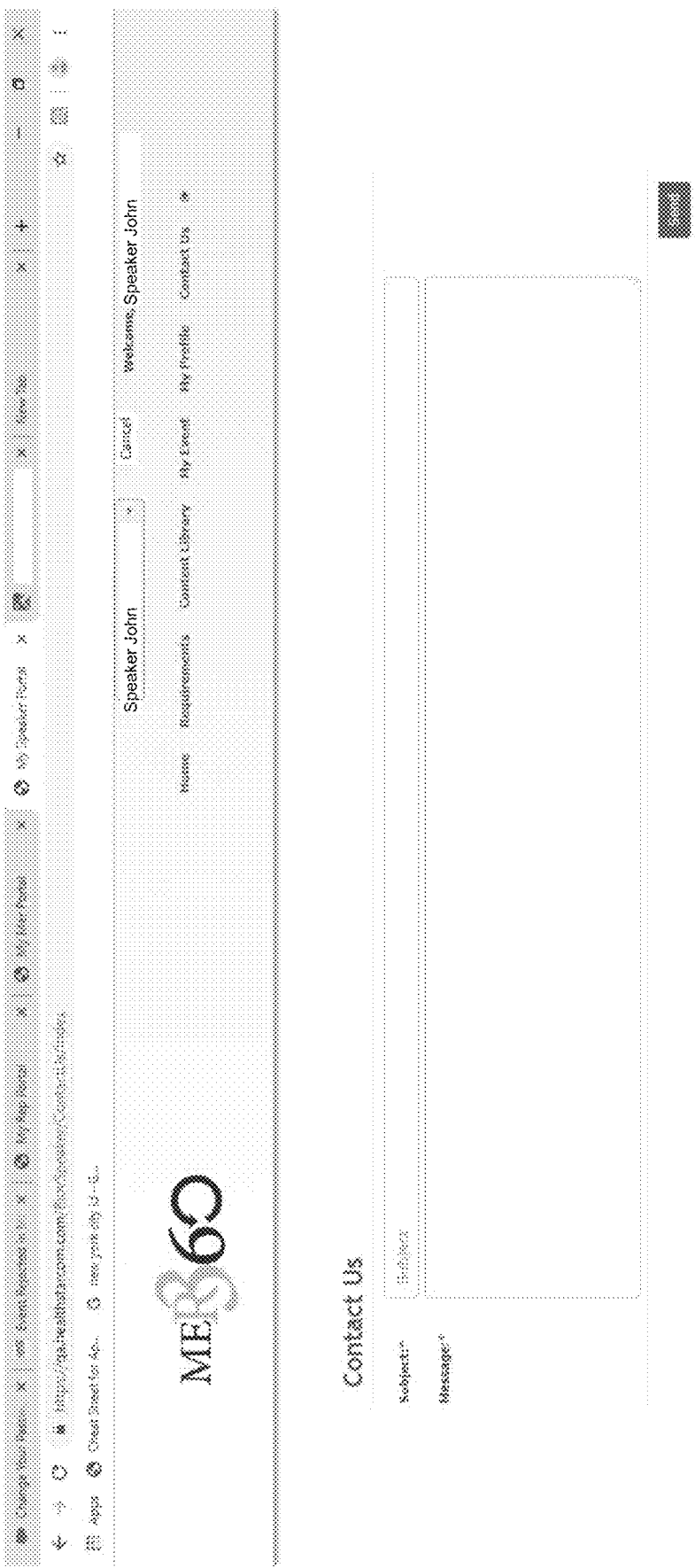
Figure 101:
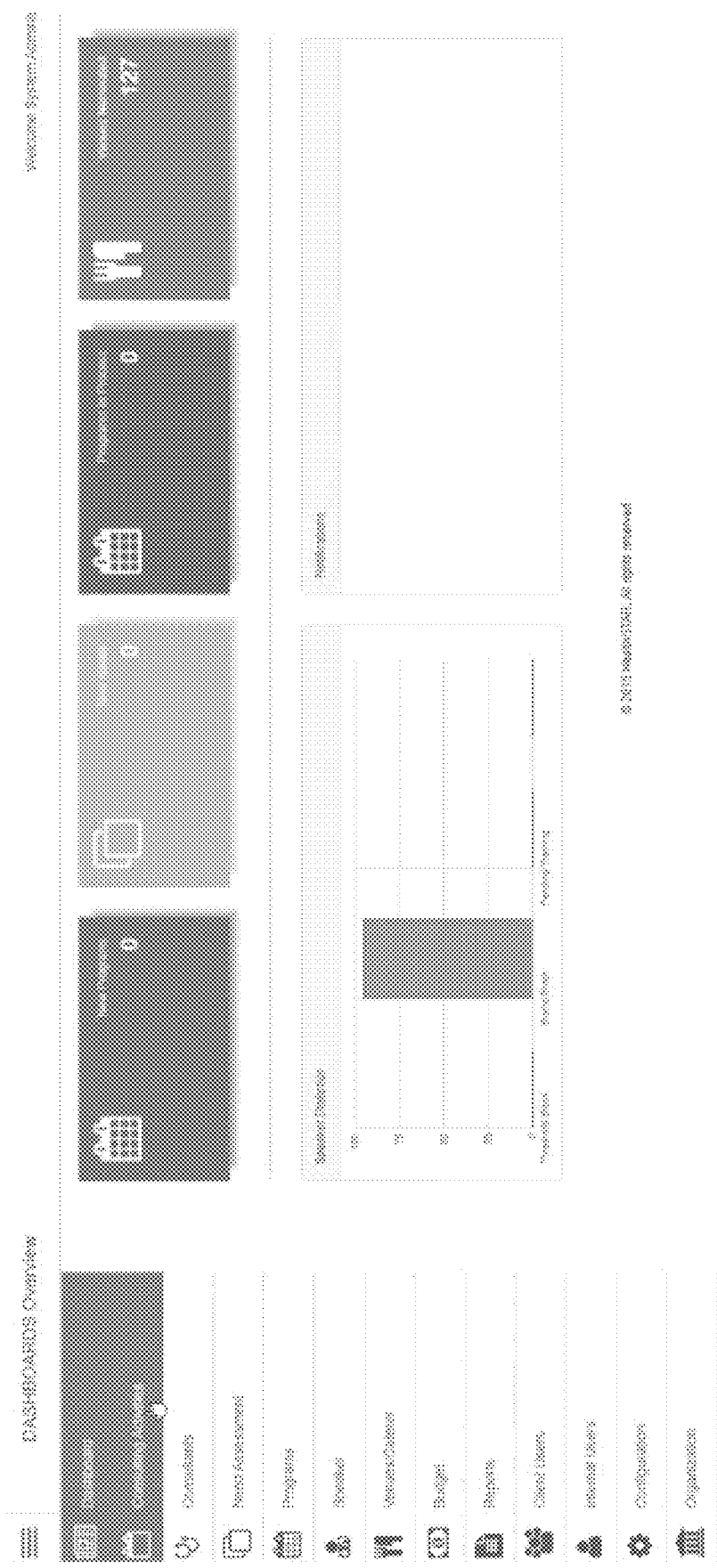
Figure 102:
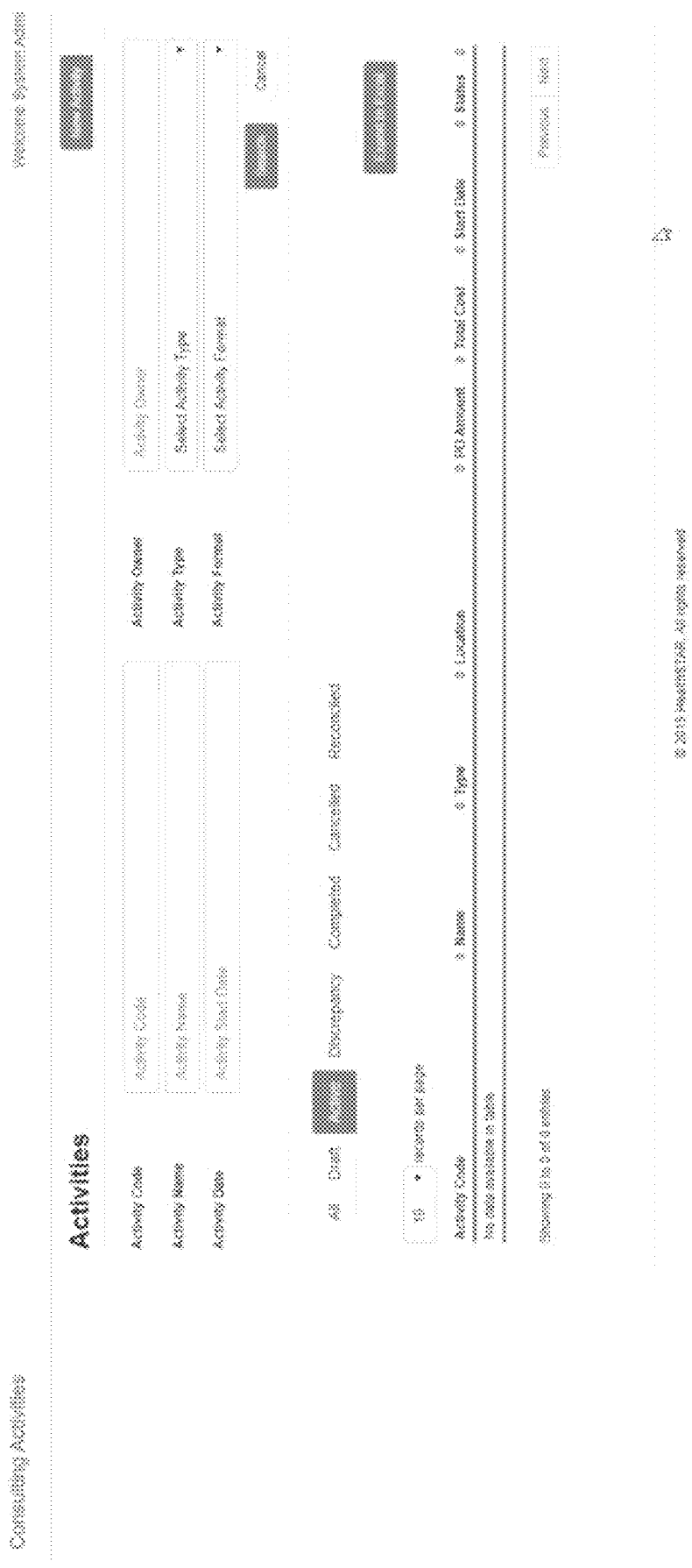
Figure 103:
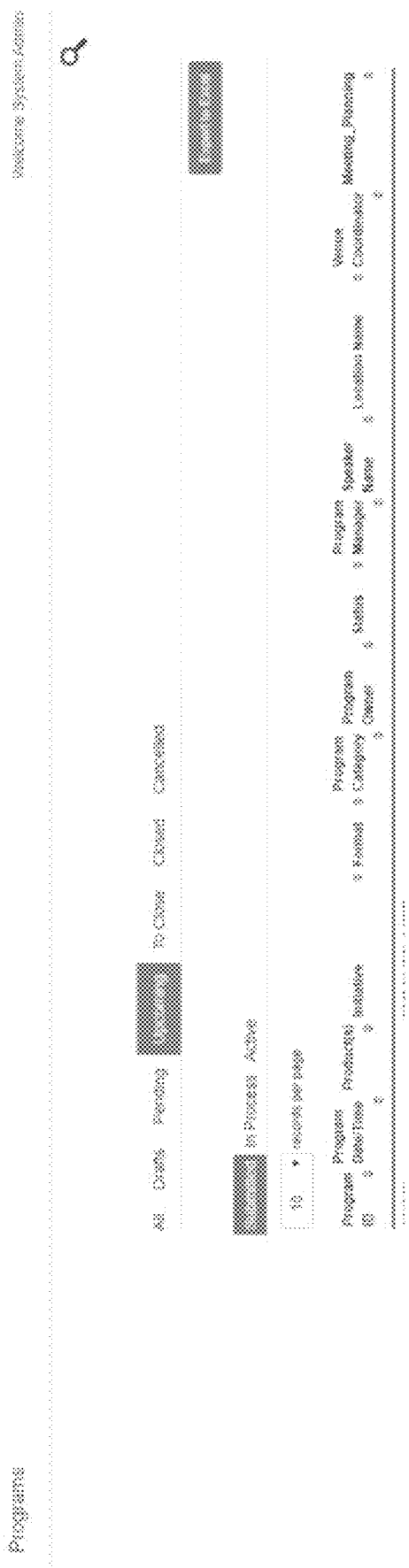
Figure 104:
Figure 105:

FIGS. 83-100 depict various configurations of the graphical user interface associated with the speaker portal. In the illustrative embodiment, the speaker portal includes the user home page (FIG. 84), a requirements tab (FIGS. 87-88), a content library tab (FIGS. 89-91), a 'My Event' or 'My Programs' tab (FIGS. 92-95), a 'My Profile' tab (FIGS. 96-99), and a contact us tab (FIG. 100). However, in some embodiments, it should be appreciated that the tabs visible may vary depending on various parameters within the system.

Figure 84:
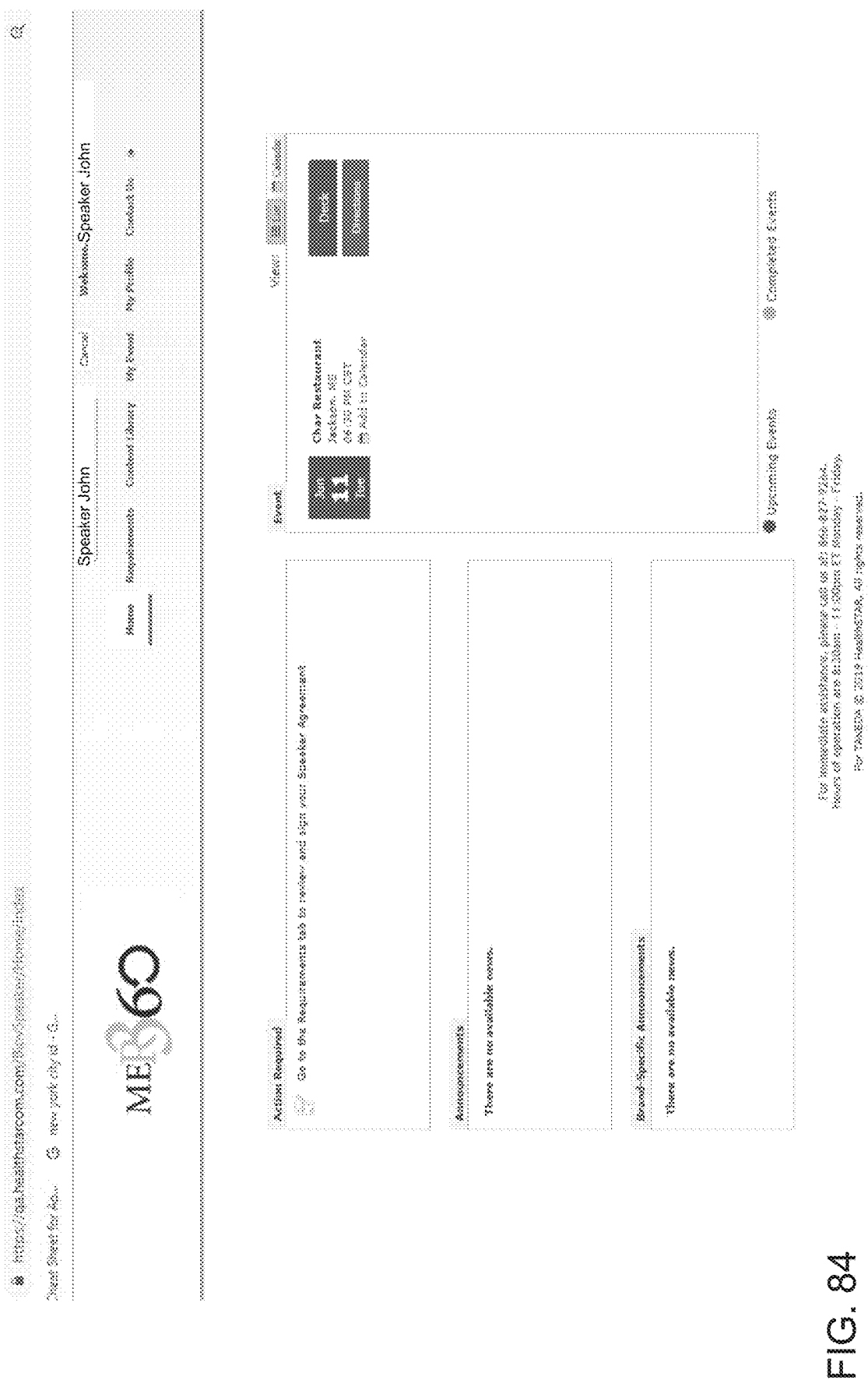
Figure 85:
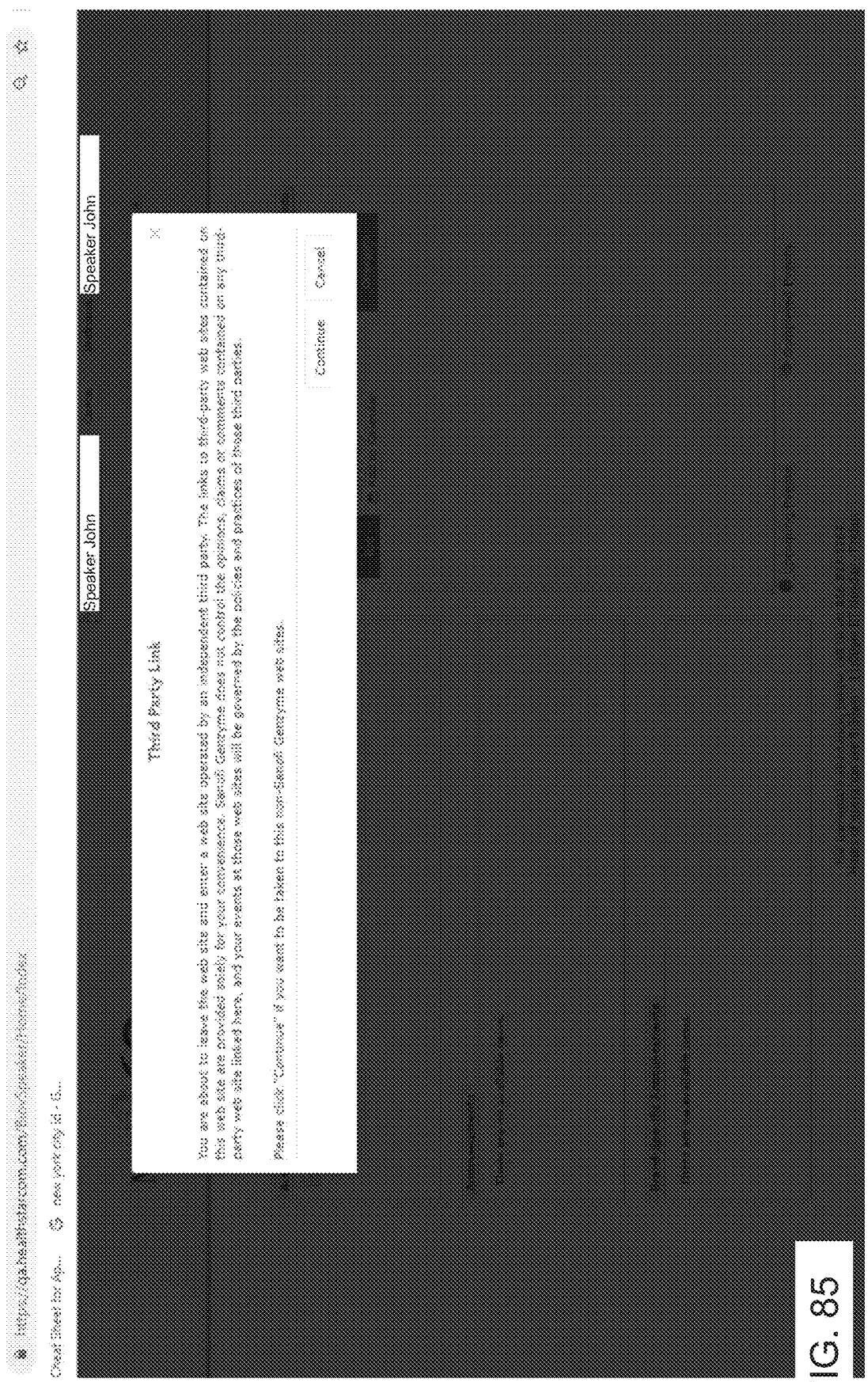
Figure 86:
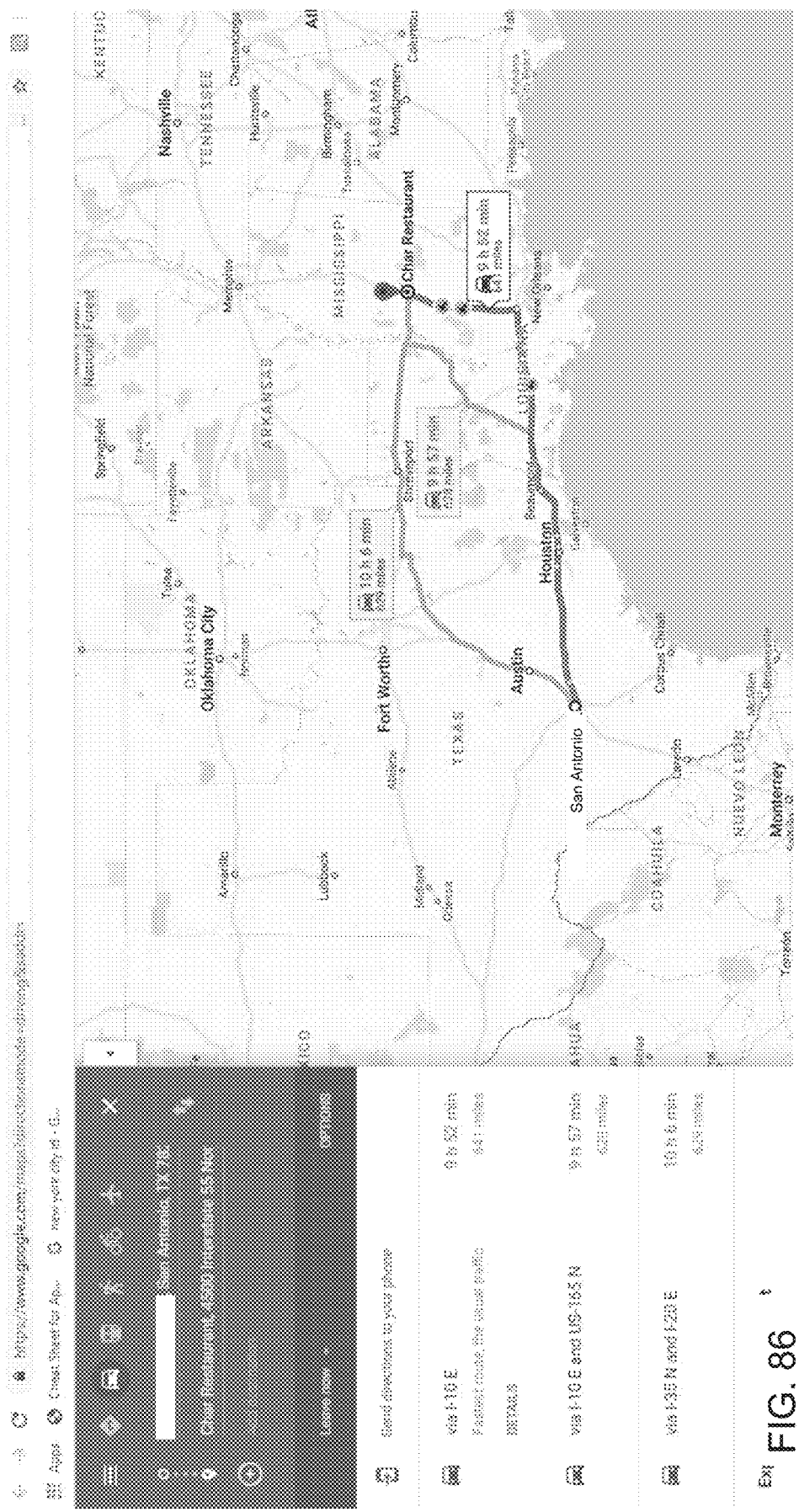

In general, upon logging in to the speaker portal, the user is brought to the speaker portal home page (FIG. 84). The user will see an Action Required Section and News on the left. The user will see a Program section on right that can be toggled between two views: calendar & list view. The user will be able to download presentation materials and a calendar file (e.g., .ics format) for each specific program from both the calendar and list views. The user will have a link to access event details including location and attendee information. The user will also have a link to access driving directions to the program from the user's default address via google maps (FIGS. 85-86).

Figure 88:
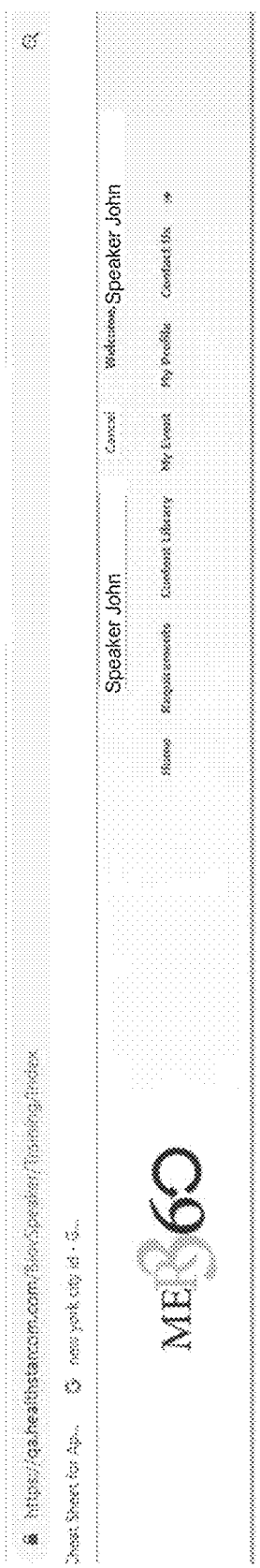
Figure 89:
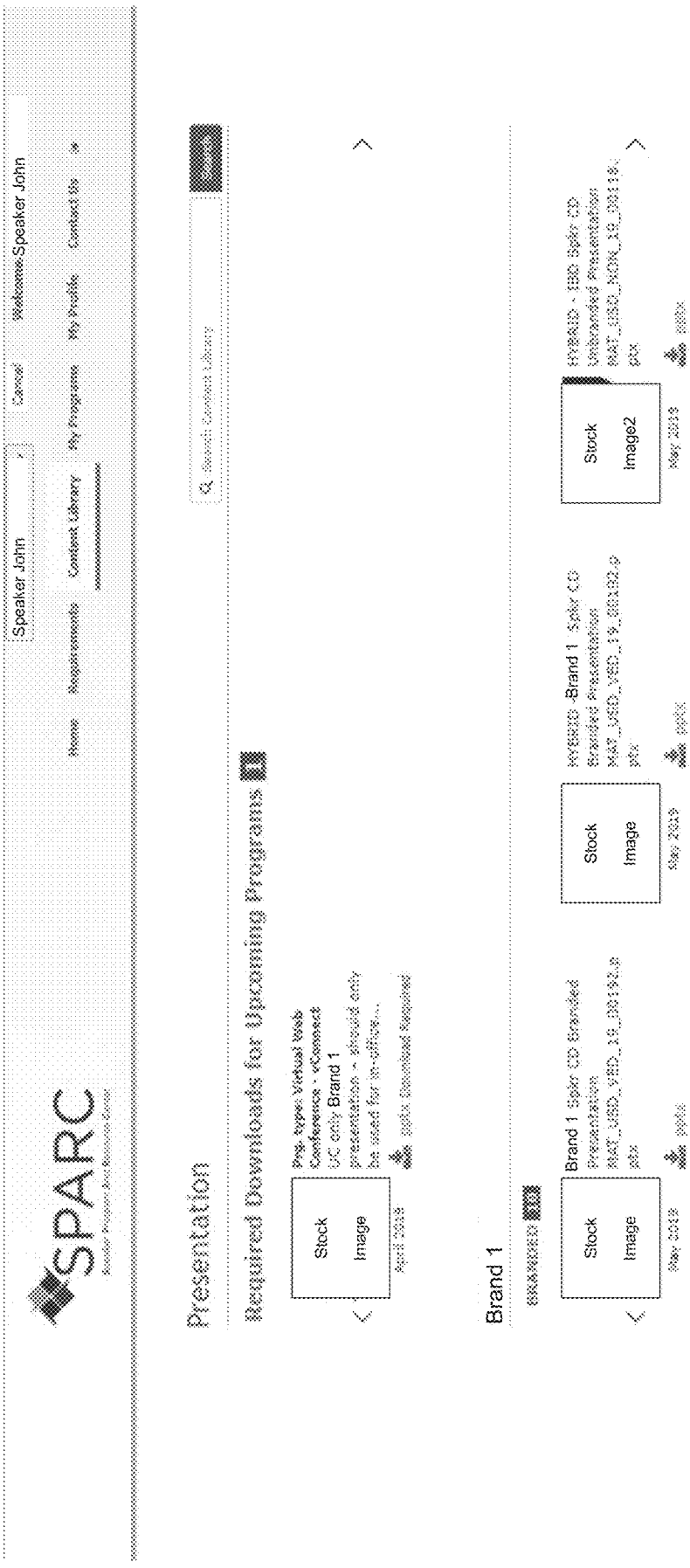

The requirements tab has 2 sub tabs: Contracts (FIG. 87), Training (FIG. 88). The Contracts tab will list all required, optional, and completed contracts and forms for the user. The user will be able to complete the contracts and forms directly in the portal. The Training tab will list all required, optional, and completed trainings. The user will be able to complete online training directly in portal when applicable.

Figure 90:
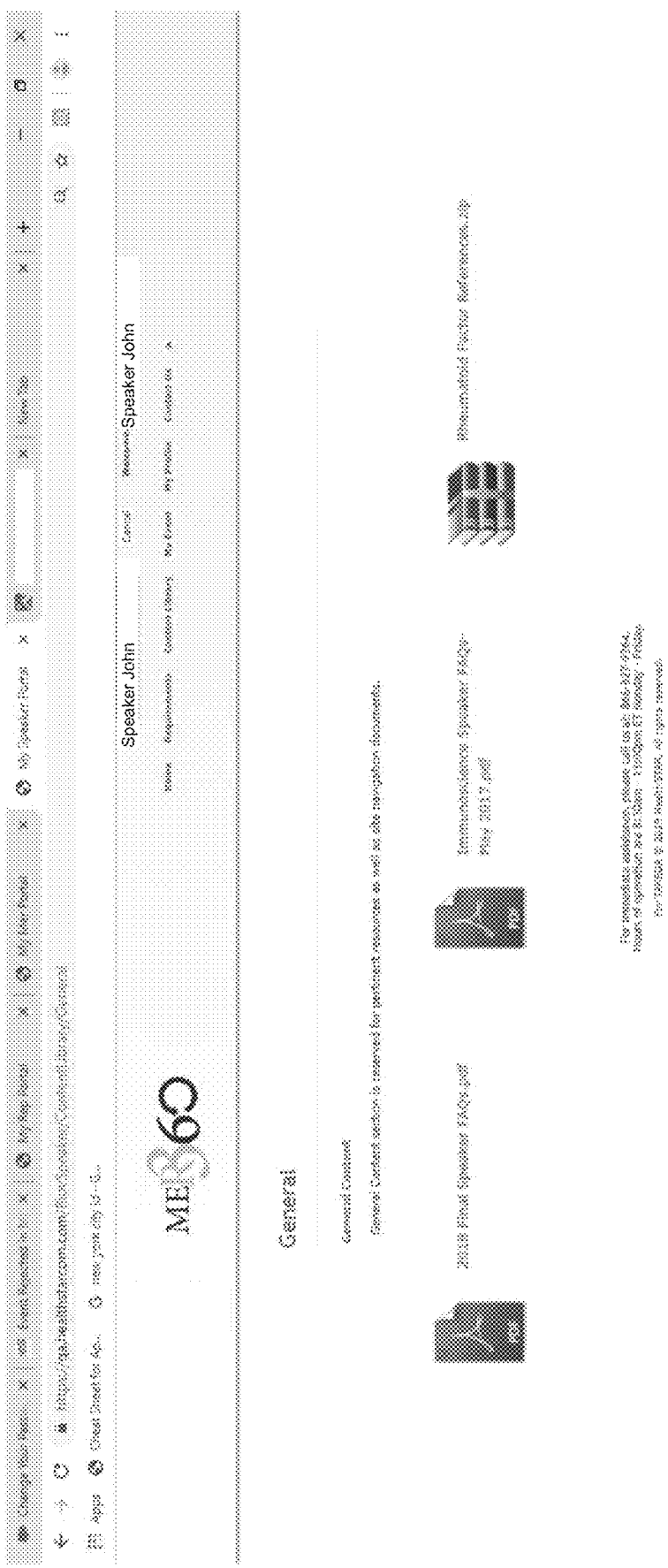
Figure 91:
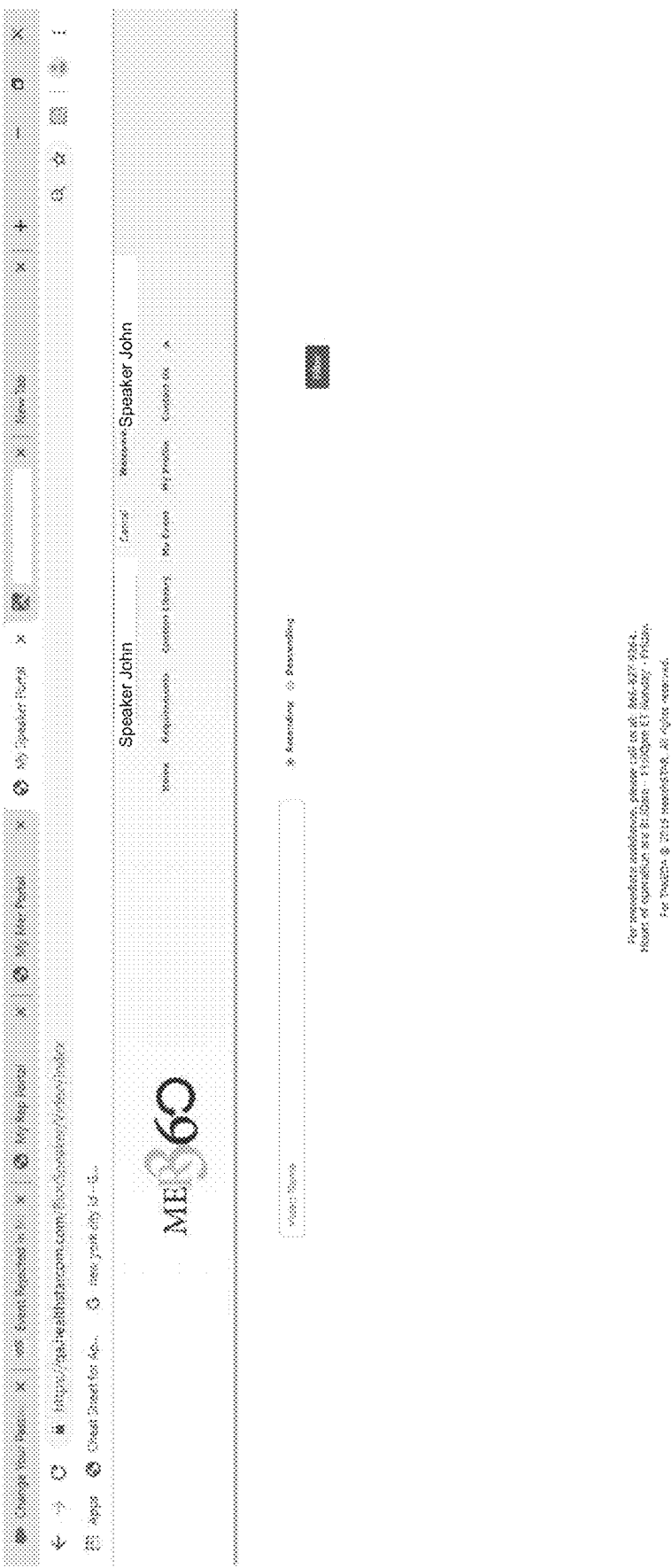
Figure 92:
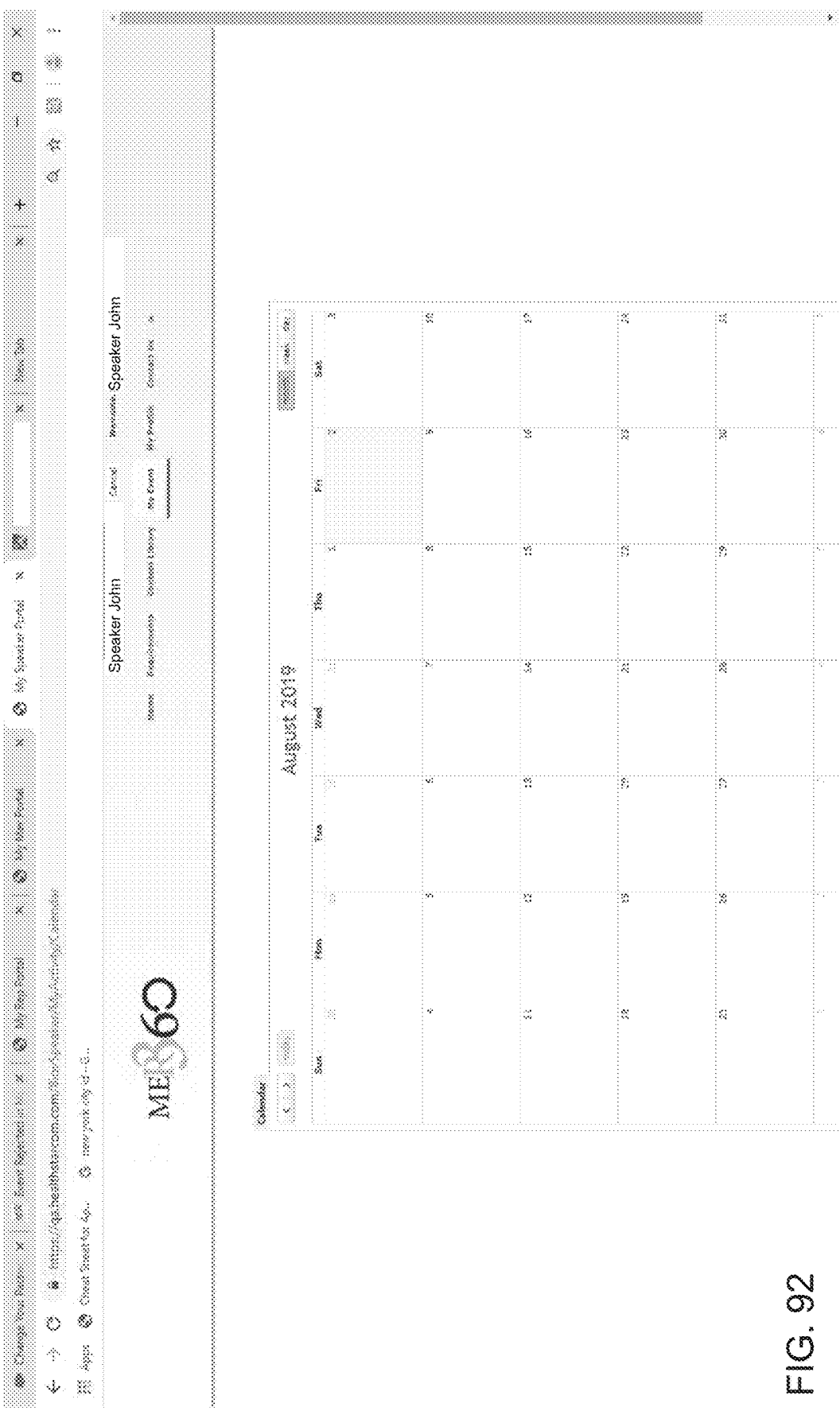
Figure 93:
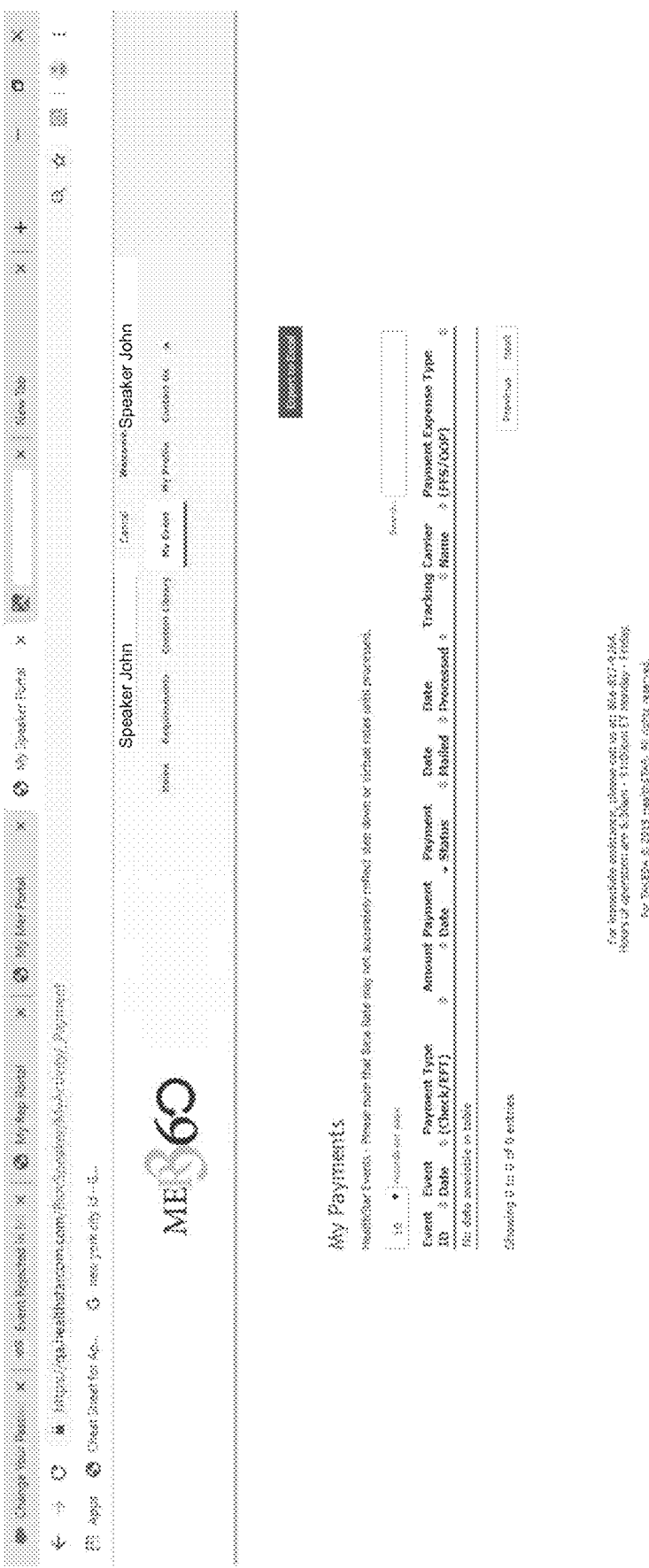

The Content Library tab has two sub tabs: Presentations (FIG. 89) and General (FIG. 90). The Presentations tab will give the user access to materials for upcoming programs in addition to a library of all content the user is permissioned for. The General tab will give the user access to materials that a client wants to make available to all users, such as policy documents, site navigation documents, etc.

Figure 94:
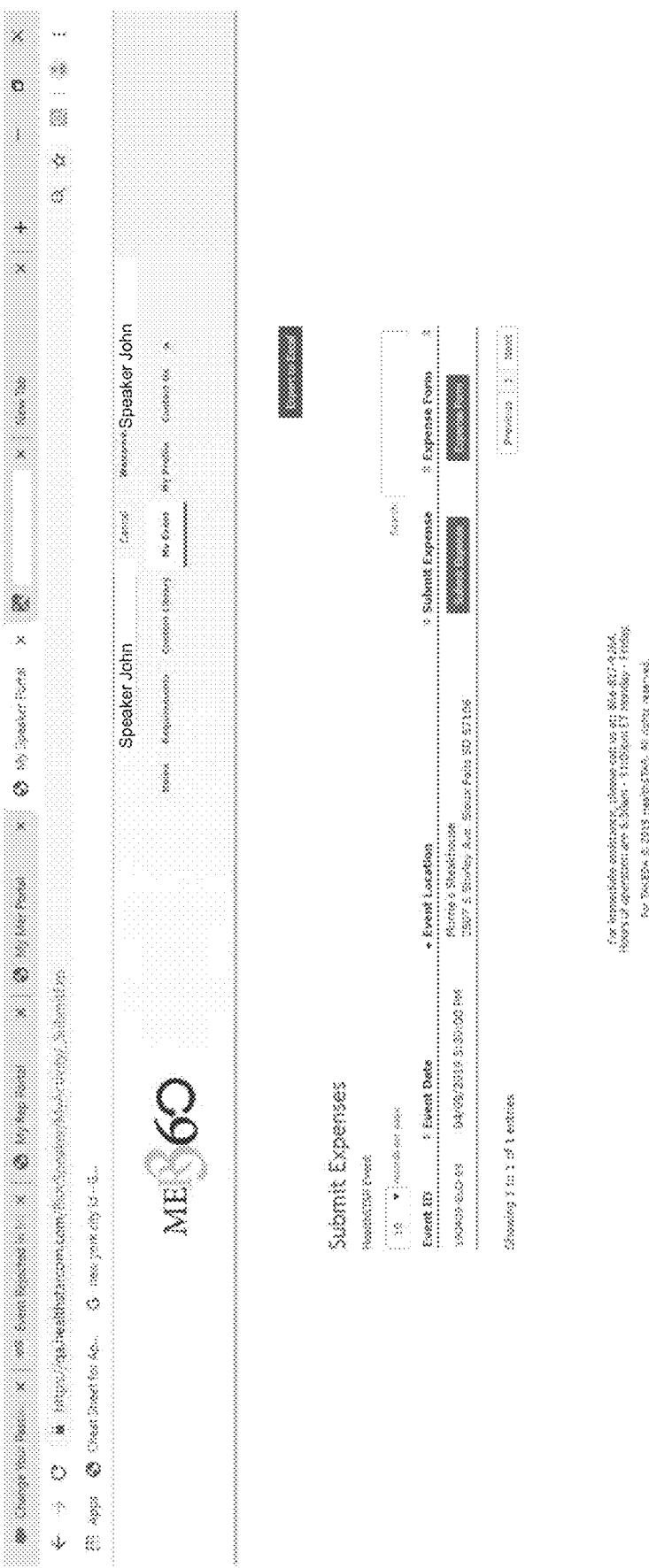
Figure 95:
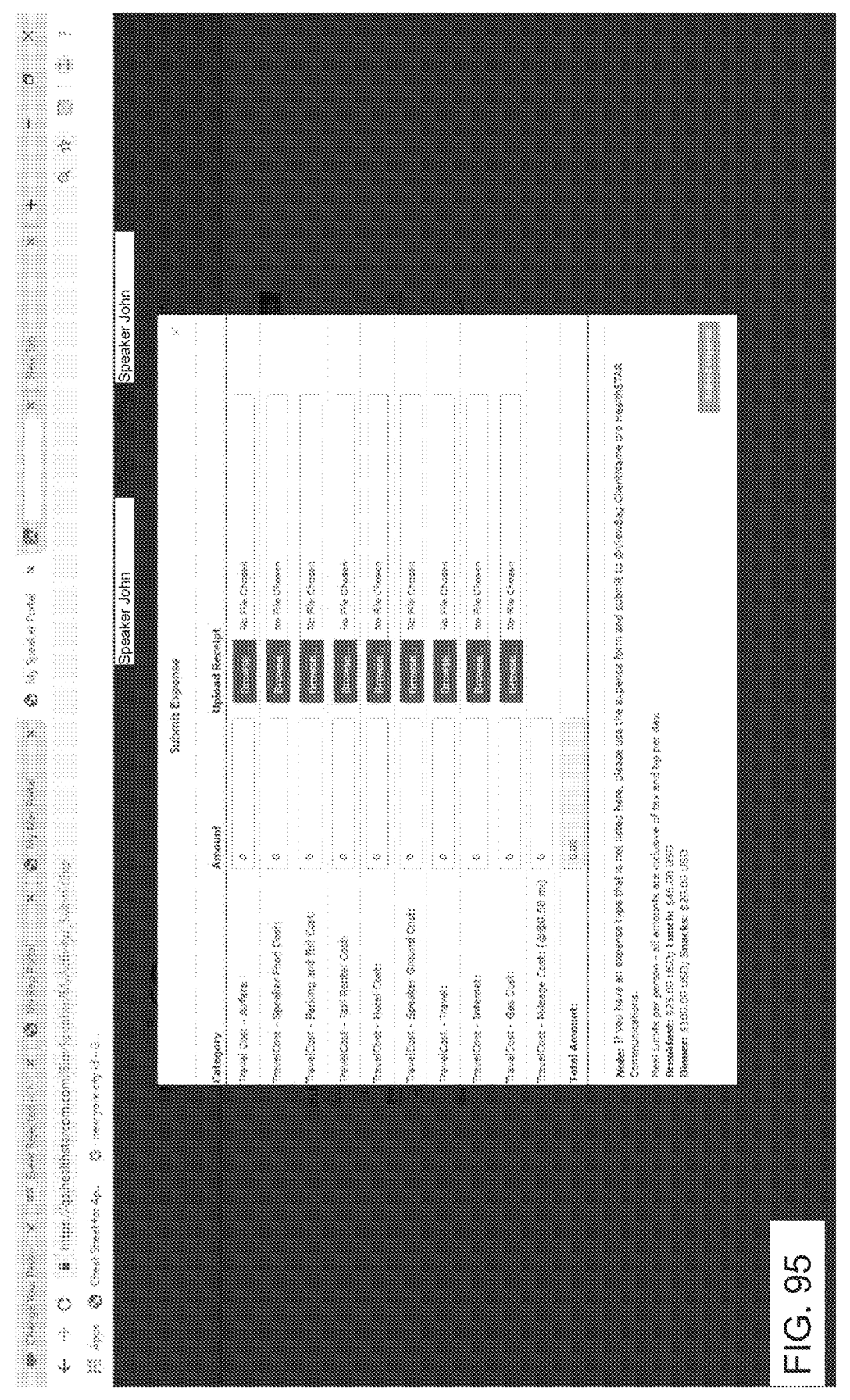
Figure 96:
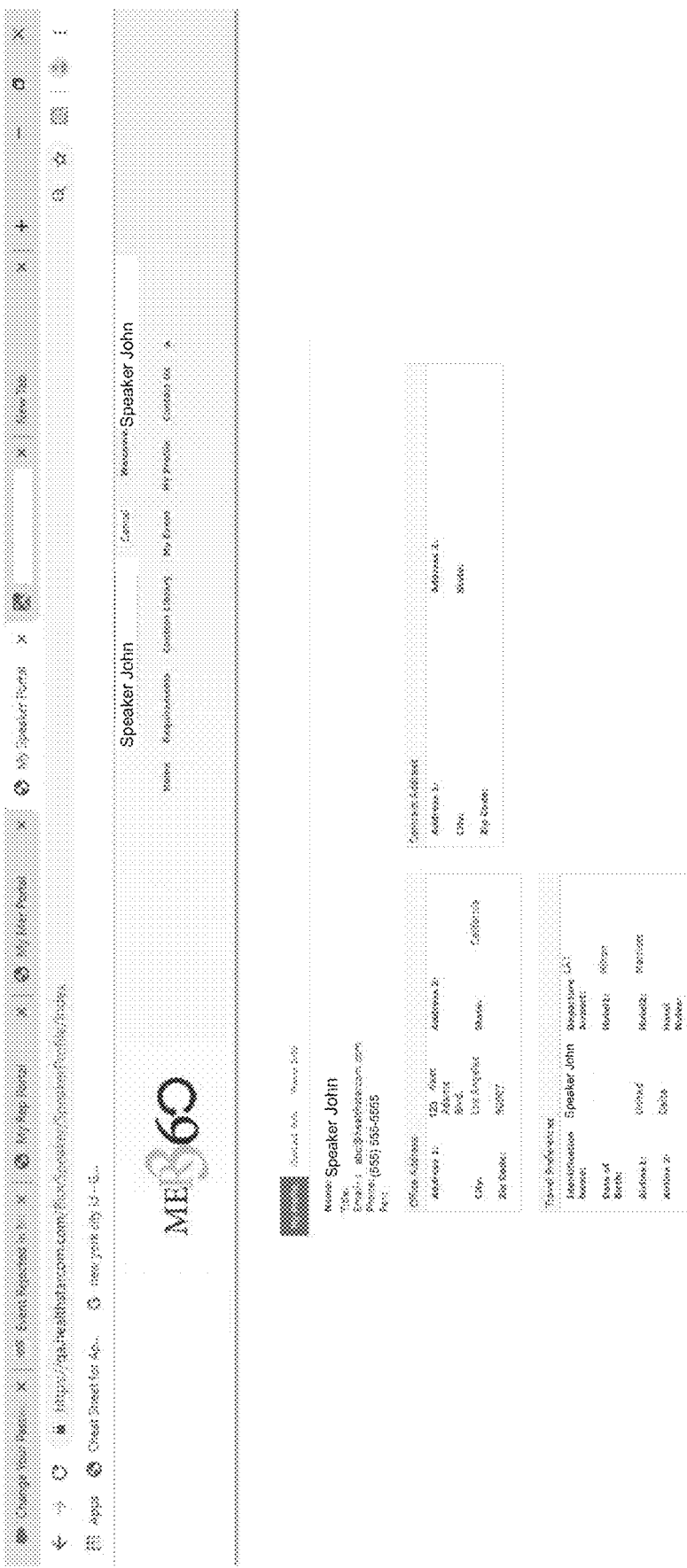
Figure 97:
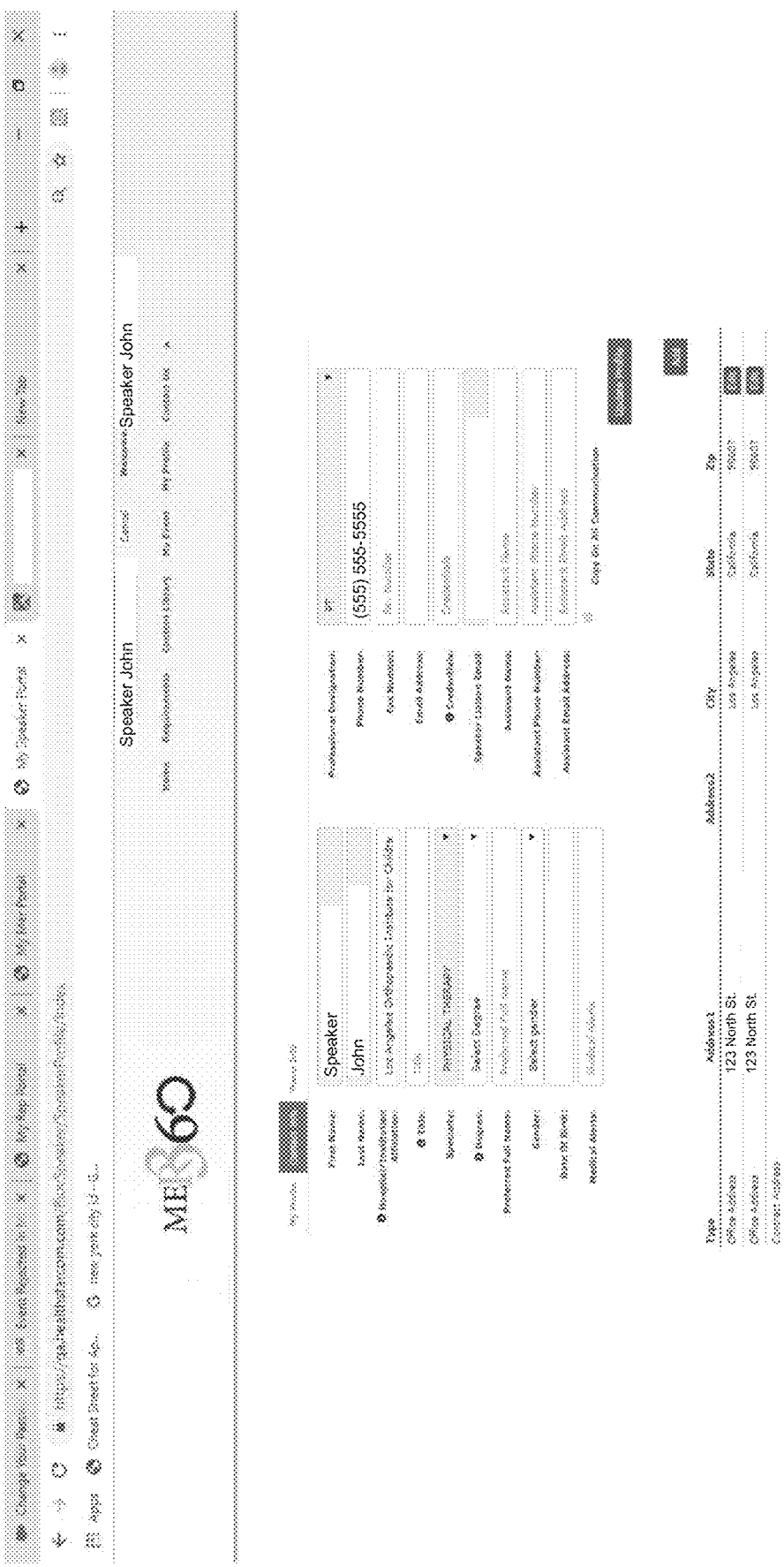
Figure 99:
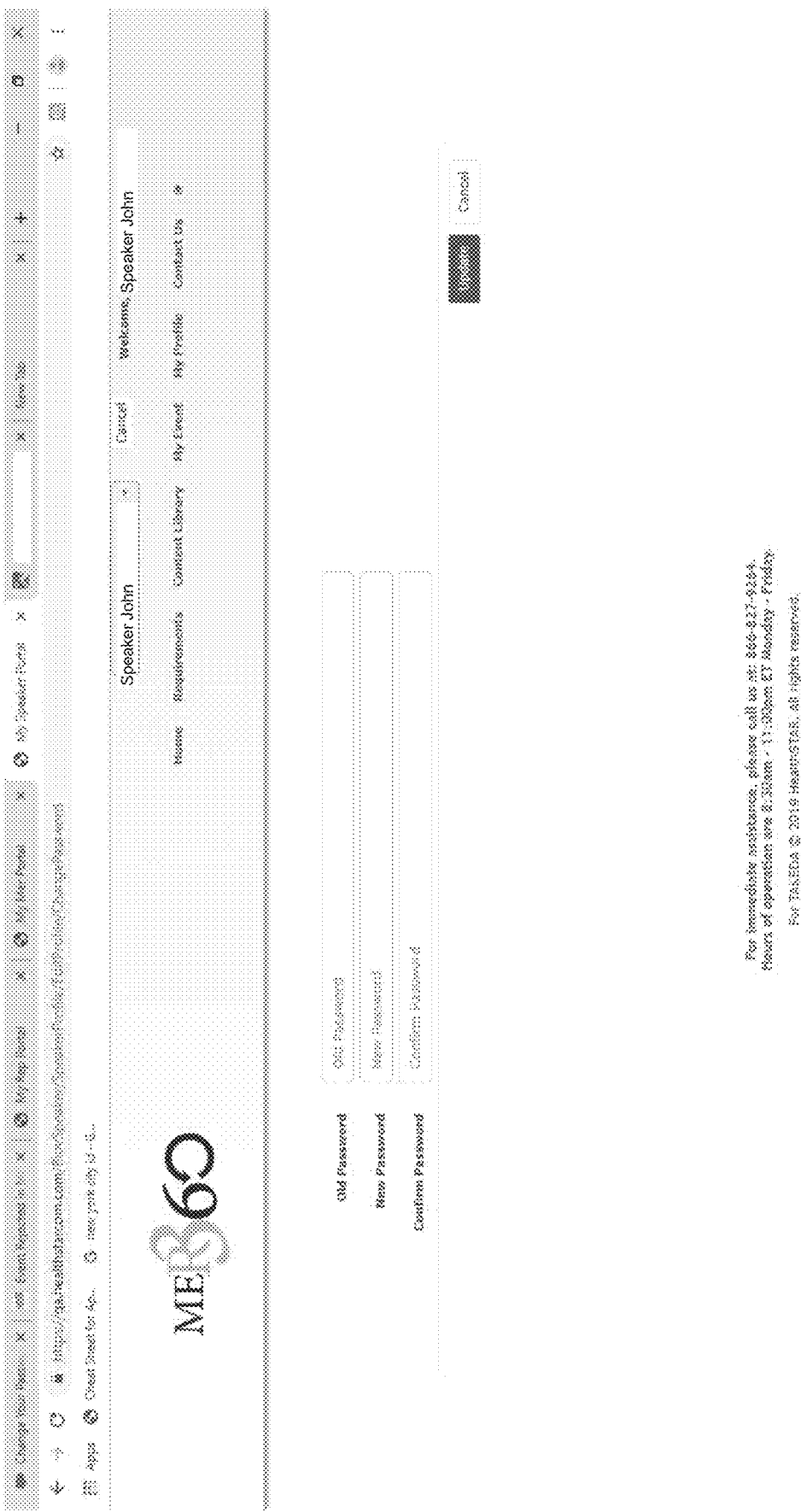

The My Event tab (FIGS. 92-95) contains the following sub-tabs: My Calendar (FIG. 92), My Payments (FIG. 93), and Submit Expenses (FIGS. 94-95). The My Calendar tab gives the user access to a calendar of upcoming and past events. The calendar can be toggled to display views for Month, Week, or Day. The user can access the event details from all views. The My Payments tab will list all payments requested and paid to the user with payment tracking links where applicable. The Submit Expenses sub tab will allow the user to submit their expenses and upload receipts directly in the portal. It should be appreciated that the "Submit Expense" button may merge fields based on the associated program and speaker in order to generate a partially filled digital form for completion by the speaker. Similarly, in some embodiments, the "Expense Form" button may merge fields to generate a partially completed document for completion and transmittal (e.g., via mail or email) by the speaker.

The 'My Profile' tab (FIGS. 96-99) allows the user to update limited profile settings, and the contact us tab (FIG. 100) allows the user to contact Speaker Bureau support from this page via message submission. The tab will also supply additional contact points for available support services.

It should be appreciated that the speaker portal is the system used by KOLs (HCPs contracted by pharma company). For example, a pharmaceutical company may provide a nomination file that says which speakers are being nominated and which brands they are being nominated for. Pharma co will also provide a tier file in which it will "tier" the speakers in conjunction with a ranking company. Each tier has a specific FMV that the speaker can be paid. The system takes that info, creates an XML file that allows the info to be sent to a $3^{rd}$ party company for background check, and XML file with the results of the background check is received back. If clear, speaker is eligible and ready to be on-boarded During speaker onboarding the user can click a button to generate a communication to the speaker's email saying they are welcome to login to speaker portal via provided URL with specific user name and pw (generated by HSC). After login, they can sign a contract and w-9. For execution online (e.g., e-signature), the fields are merged into the contract for electronic signature, and the system can provide EFT for payment transfer (or mail payment). After signing, the speaker is eligible for training. The system offers the training online. Also, the client can send info indicating that the speaker took outside training, which can be imported into the system. Training is for both topic/product training and compliance training. Once the training is completed, the speaker will be eligible to be selected as a speaker for an event. Adobe Connect integration may be used for online training. The system can also include Q&A at the end, or test, to confirm it was watched.

Figure 65E:
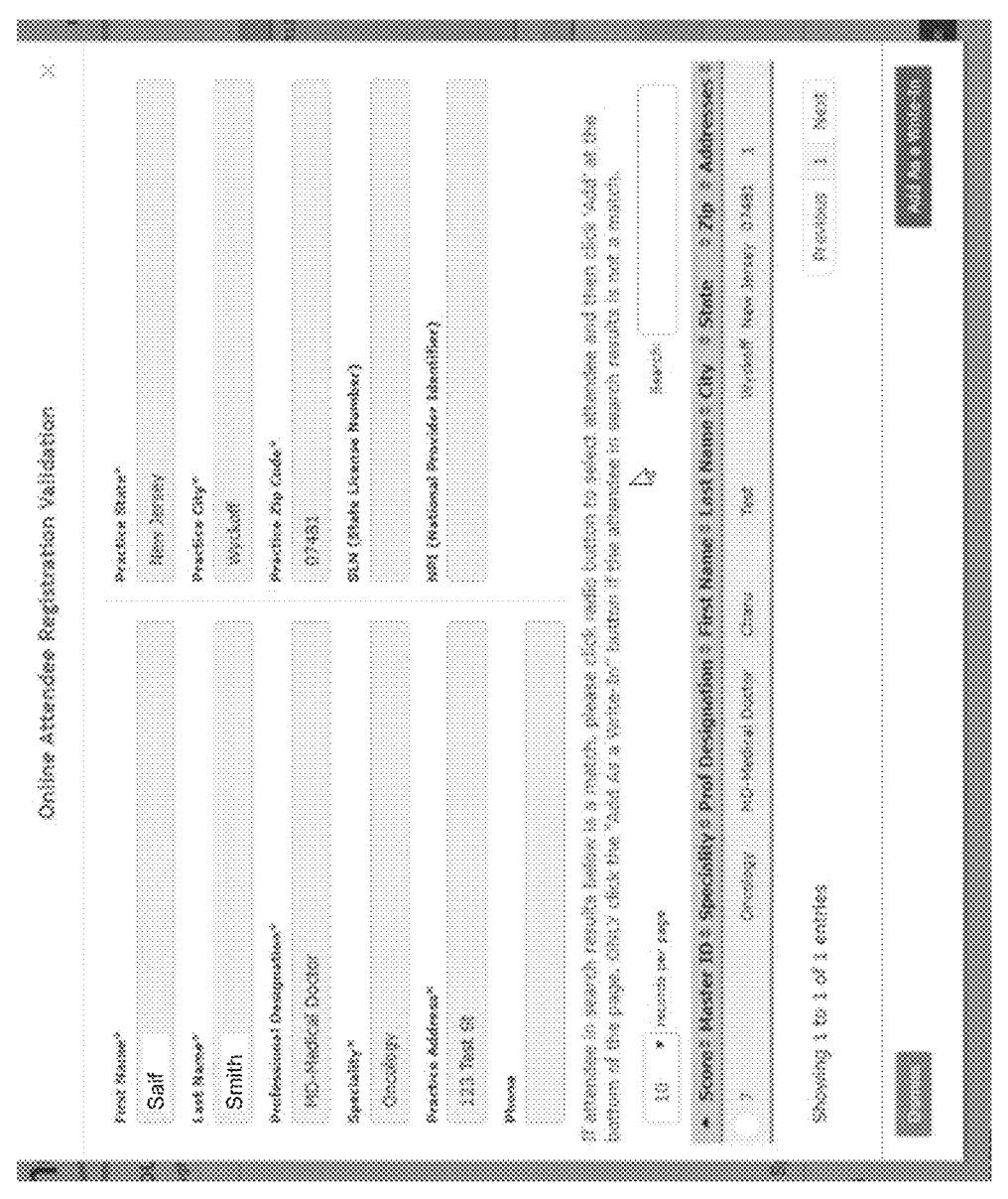

FIGS. 65A-E depict various configurations of the graphical user interface associated with the My Attendee Resource (MAR) (aka Online Attendee Registration) functionality of the enterprise platform. In some embodiments, the Online Registration module is an optional module and/or configurable module intended to be utilized by clients who desire to use it to support configurable/customizable Online Registration websites, which offer the ability for HCPs and other event Invitees to follow links in emailed or printed invitations to an event-specific Registration website where they are prompted to enter their name, address, contact, and credential information, in order to RSVP for an upcoming event or activity, and optionally receive confirmation, reminder, change, and (if the event is cancelled) cancelation emails.

The Online Registration module will include configuration tools which will utilize site templates for layout and presentation, content areas, and merge fields in order to generate the registration websites, and new source code and database components to extend the MER functionality for client end-users and operational staff in order to see and manage the RSVP data that has been collected.

Like the MER enterprise platform itself, this module is developed using Lean-Agile development methodology and new system updates are released to production in minor & major releases (Iterations/Sprints). This module will be optional and self-contained, so that it can either be used or not used by each individual client. Also like the MER platform itself, updates to this module are designed and built based on identifying customers' needs and performing an opportunity assessment to ensure that there is potential for value creation.

The new Registration Portal subsystem will house the configuration data used to generate the even specific "microsites" (one Registration page per event) that comprise this solution. The MER portal is the existing platform that serves as the main end-user web-based application for Client and employee users. This system has been updated in order to display and interact with the data being generated by the middle layer described in the next paragraph. The database layer is where all data is stored. This layer has been updated by database programmers to implement the new data schema as required to support Online Registration-specific functionality and data. The integration layer is where data are inserted and extracted from external sources, as well as extracting data for internal and client-facing reports as required to support Online Registration specific functionality.

In some embodiments, the MAR Online Registration system will have an app for mobile and tablet devices. The app will be available for Apple and Android devices running their respective operating systems. This app will allow a HCP user to Register/RSVP for an upcoming event or activity. The functionality of the app may allow a user to scan a QR-Code which is generated by the Online Registration platform and associated to an event or activity. A user can also type a specific client code and send the request to the Online Registration platform. A response from the platform will return a specific client registration template which will allow a user to Register/RSVP for an event or activity. This code can be generated via a text message OR the client specific code already generated for an event or activity.

A user may be able to login to the app by using a user name and password. Login to the application will allow a user to see only those events for which he/she registered for. The application will provide remainders, updates, or cancelations based on a number of days per global client configuration. The application may allow a user to get directions to the location where the event is going to take place, the directions will be provided by opening Google Maps and/or Apple Maps. The application will allow a HCP to register so that the system can generate a one-time password so they can login to the application and see the events or activities they registered for. The user may be able to reset their password in the event that they forget it.

Figure 106:
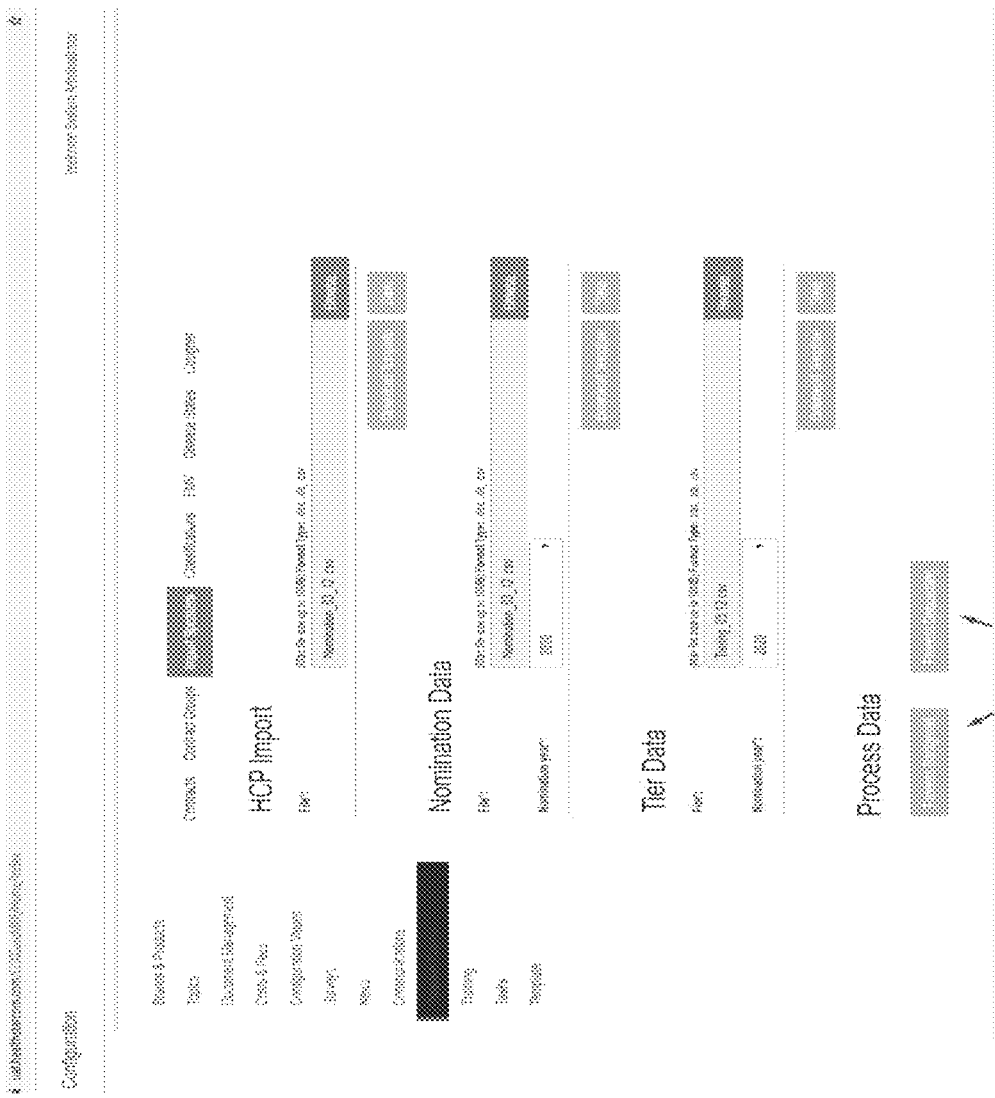
Figure 107:
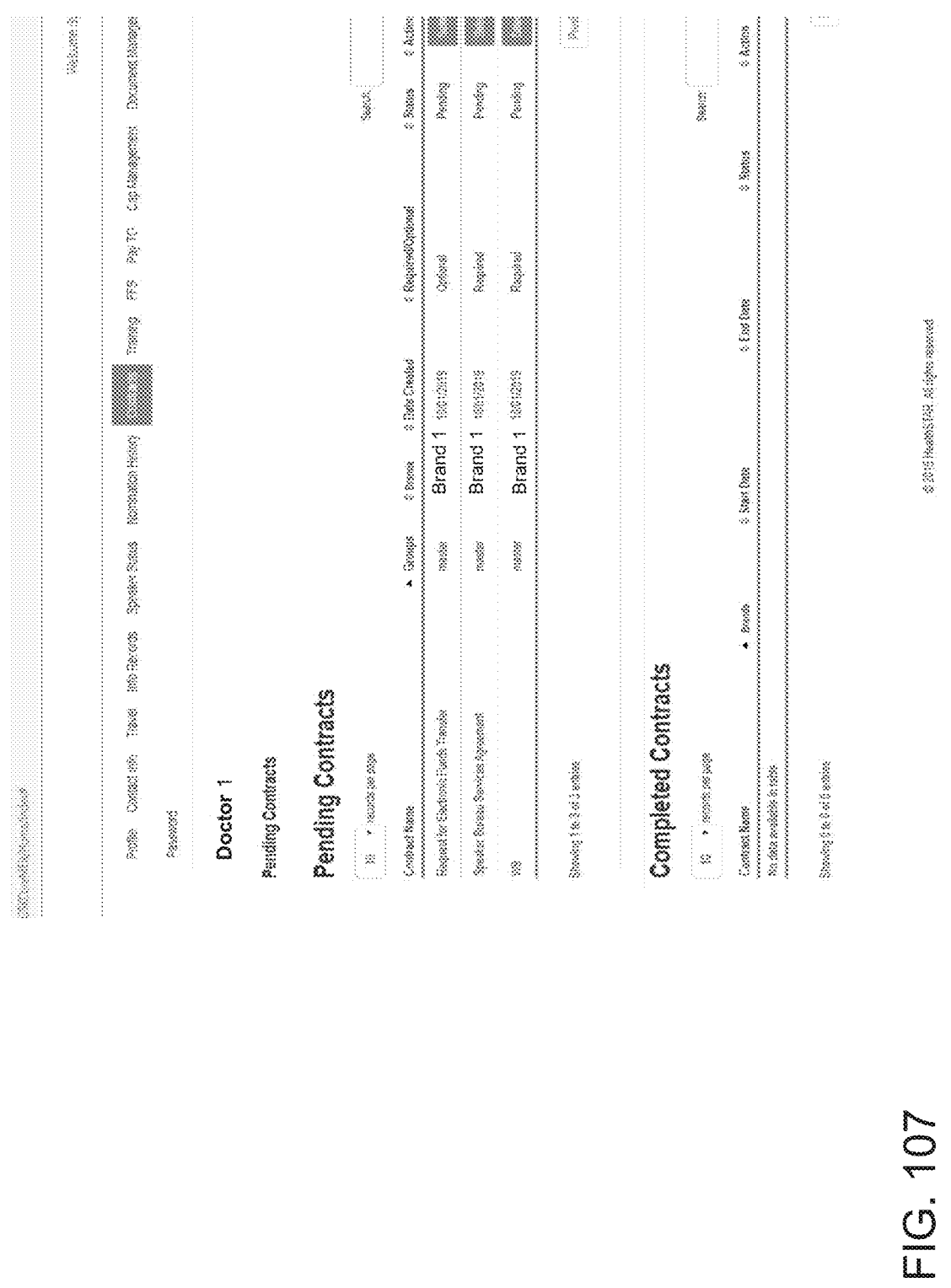
Figure 108:
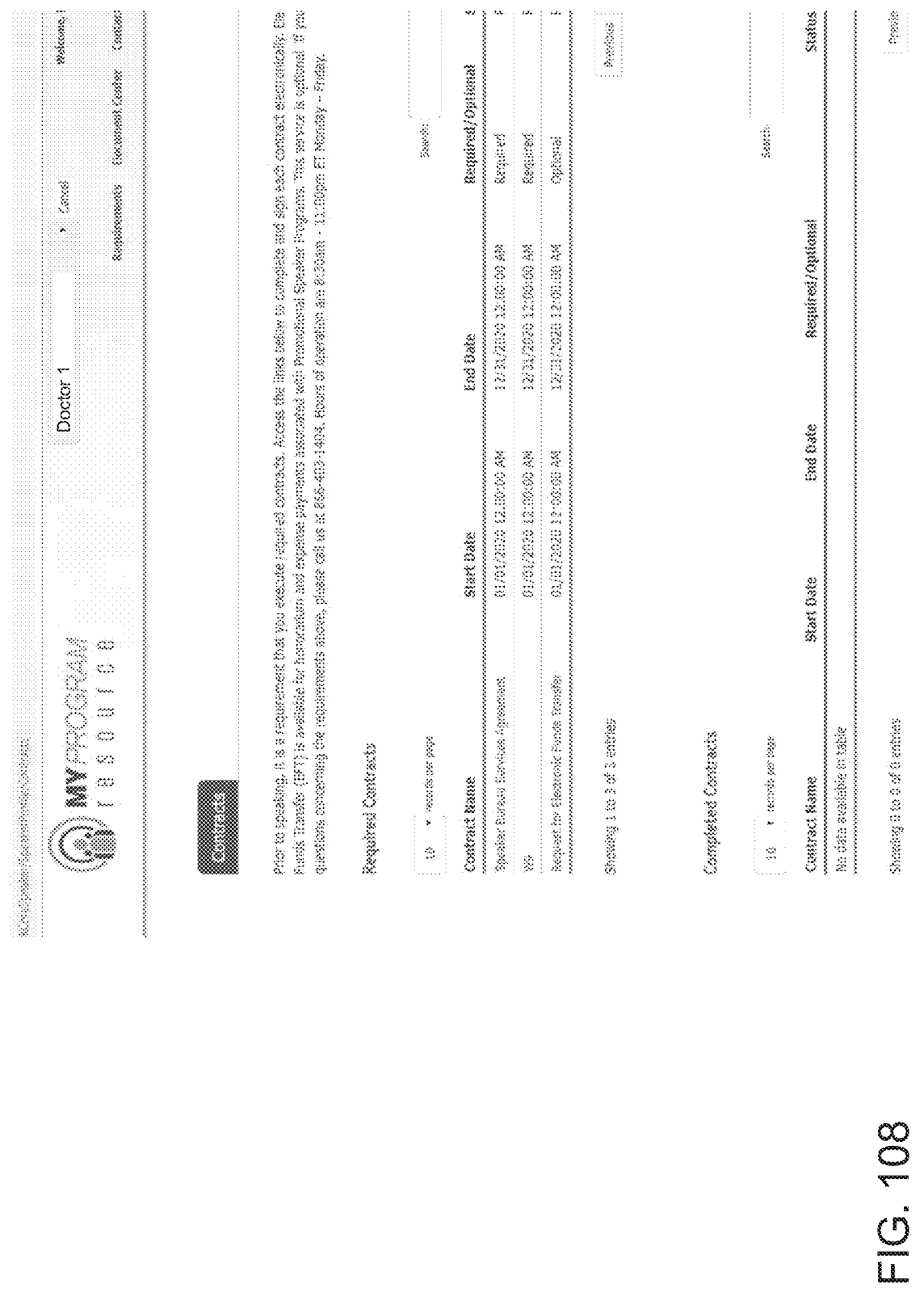
Figure 109:
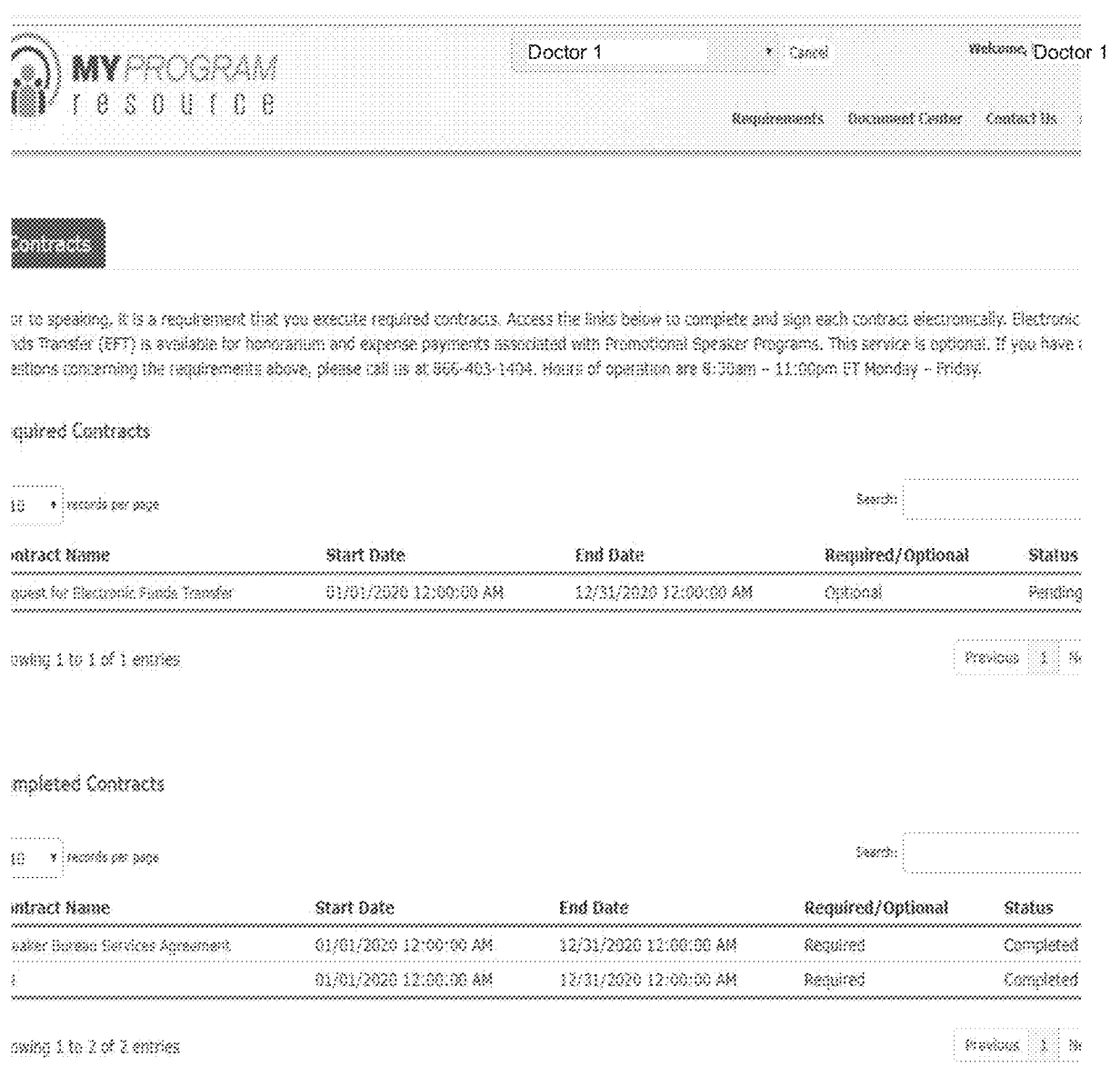
Figure 110:
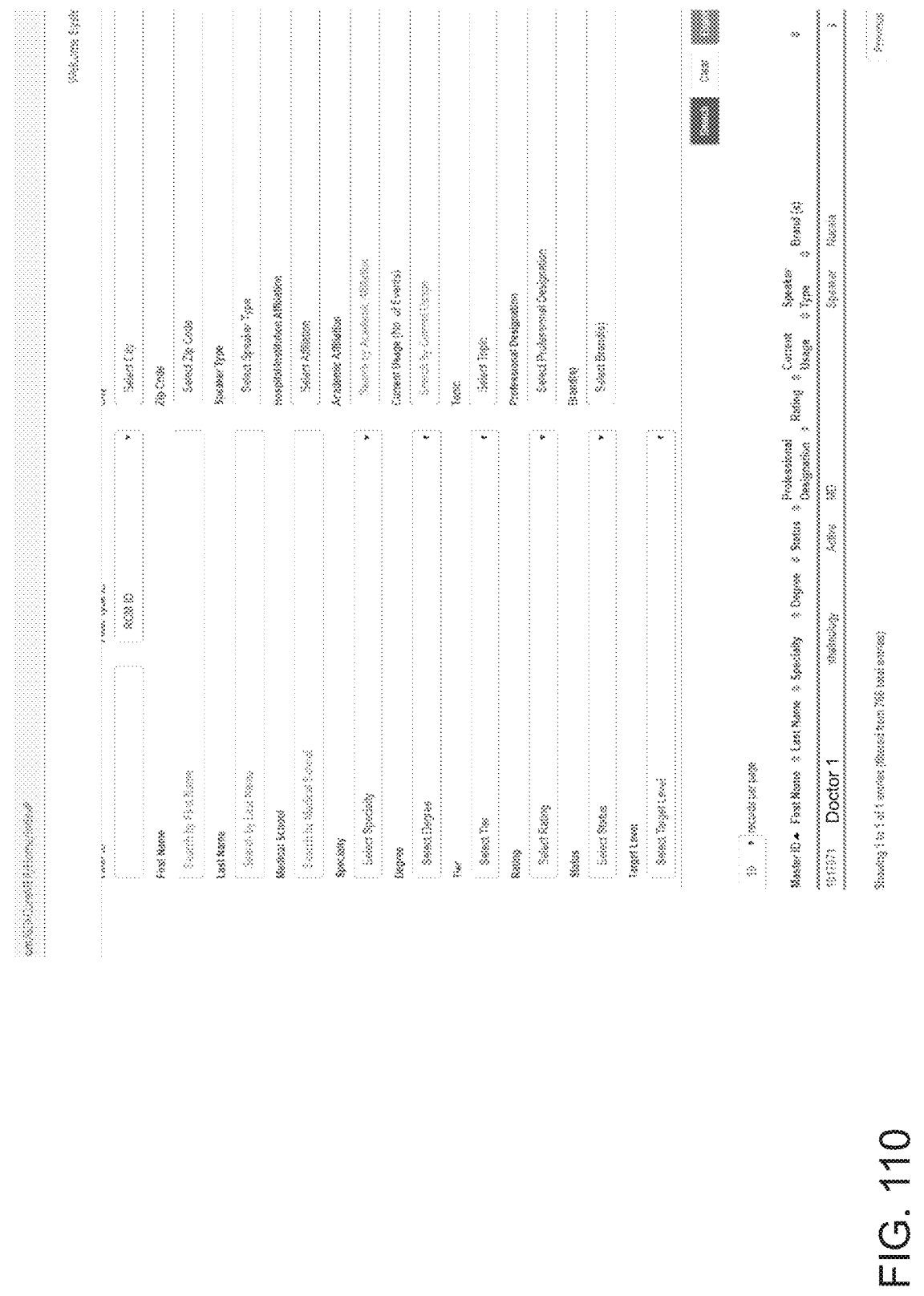
Figure 111:
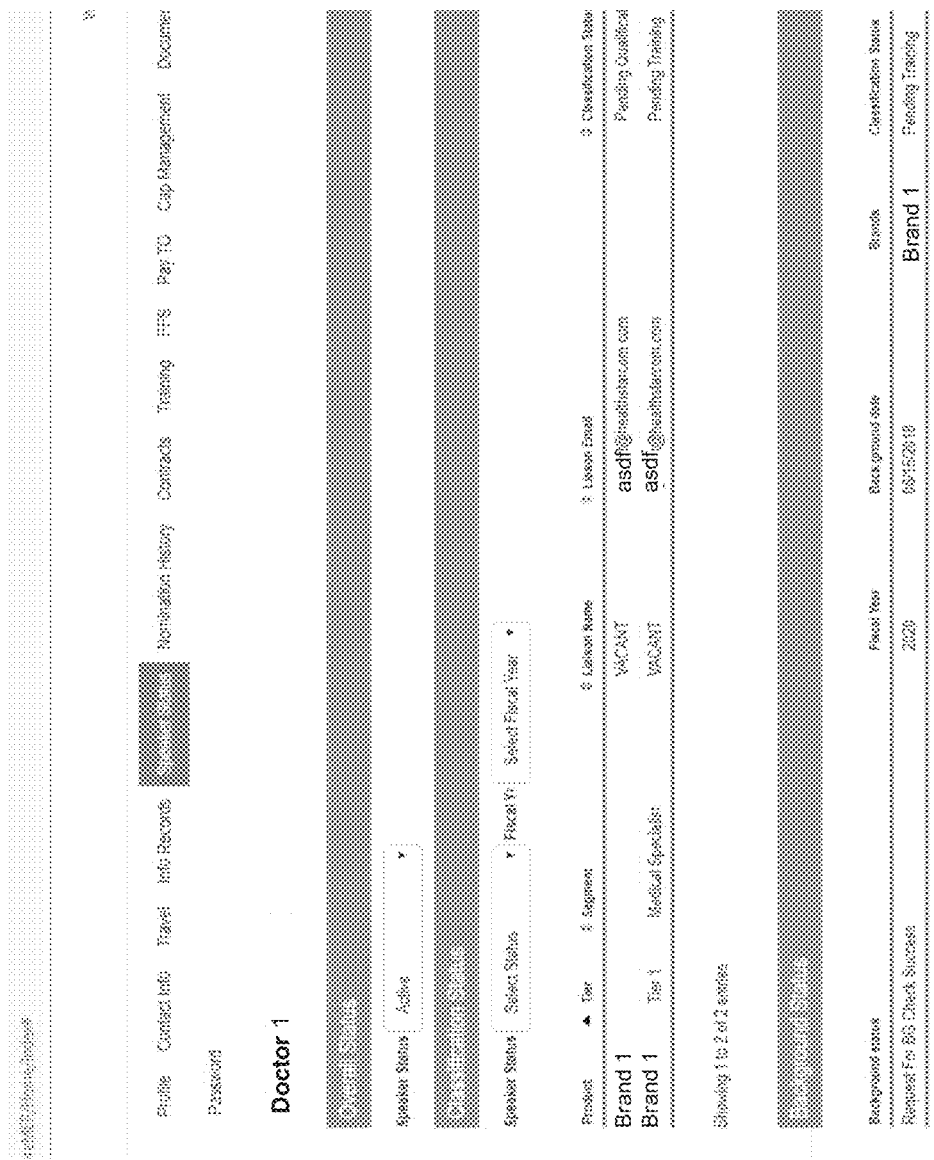

As depicted in FIGS. 106-111, the admin portal may be used by an administrator in order to nominate a particular speaker. As shown in FIG. 106, the HCP import may be a file with speaker information, the nomination data may include a nomination file, and the tier data may include information associated with the speaker's "tier" or credentials. The user may select Process Background in order to transmit the information to a third party vendor for a background check, or select Process Onboarding to trigger emails for new onboarding. As shown in FIGS. 107-108, once on-boarded, the speaker must complete a COI/SIF and W-9 form, and when completed, the speaker status moves to Pending Training. Once completed, the status is changed to Completed Contracts (FIG. 109), and the admin user will be able to view the speaker as active (FIG. 110). However, until training is completed, the speaker classification status is Pending Training (FIG. 111).

Figure 112:
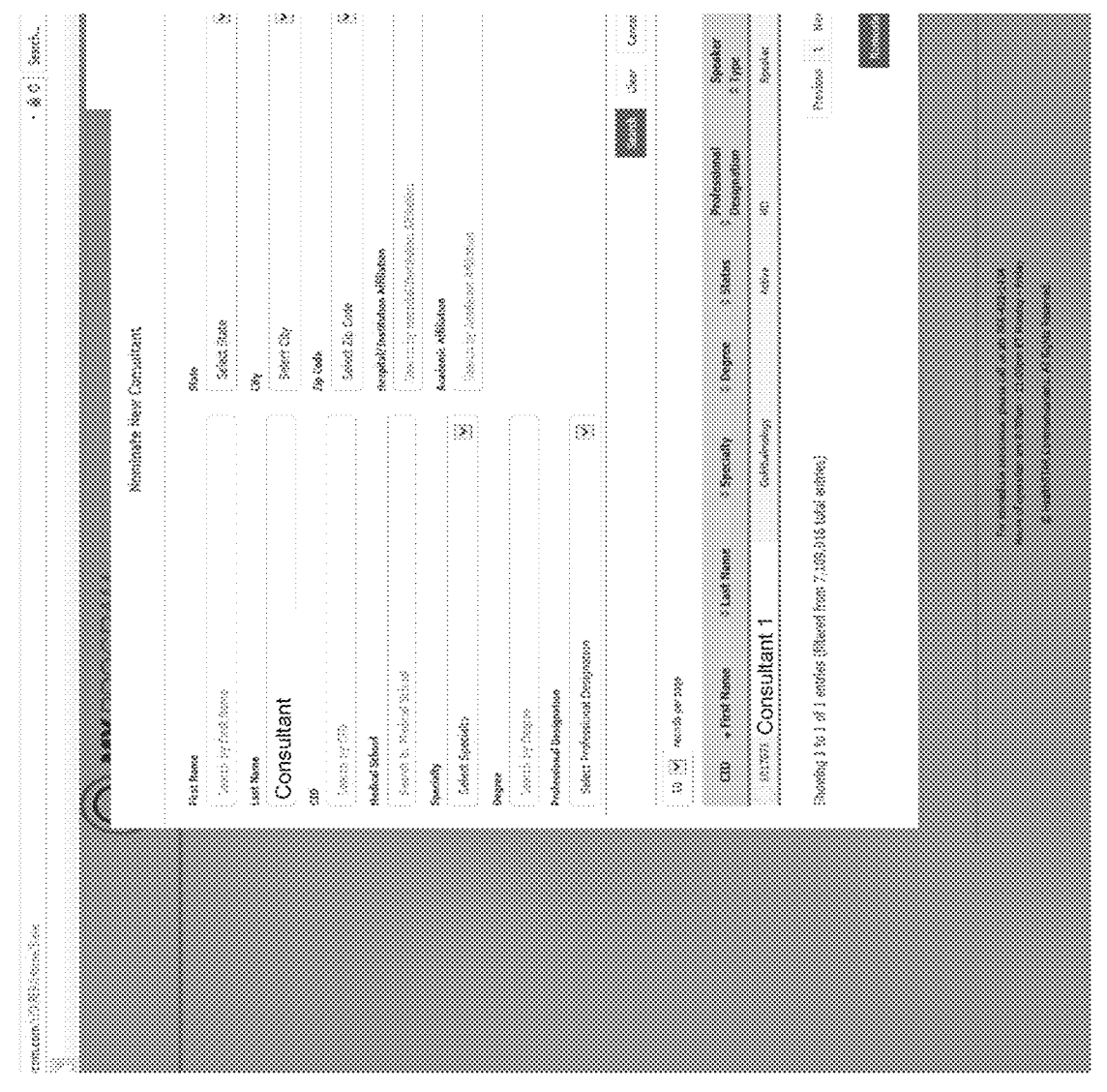
Figure 113:
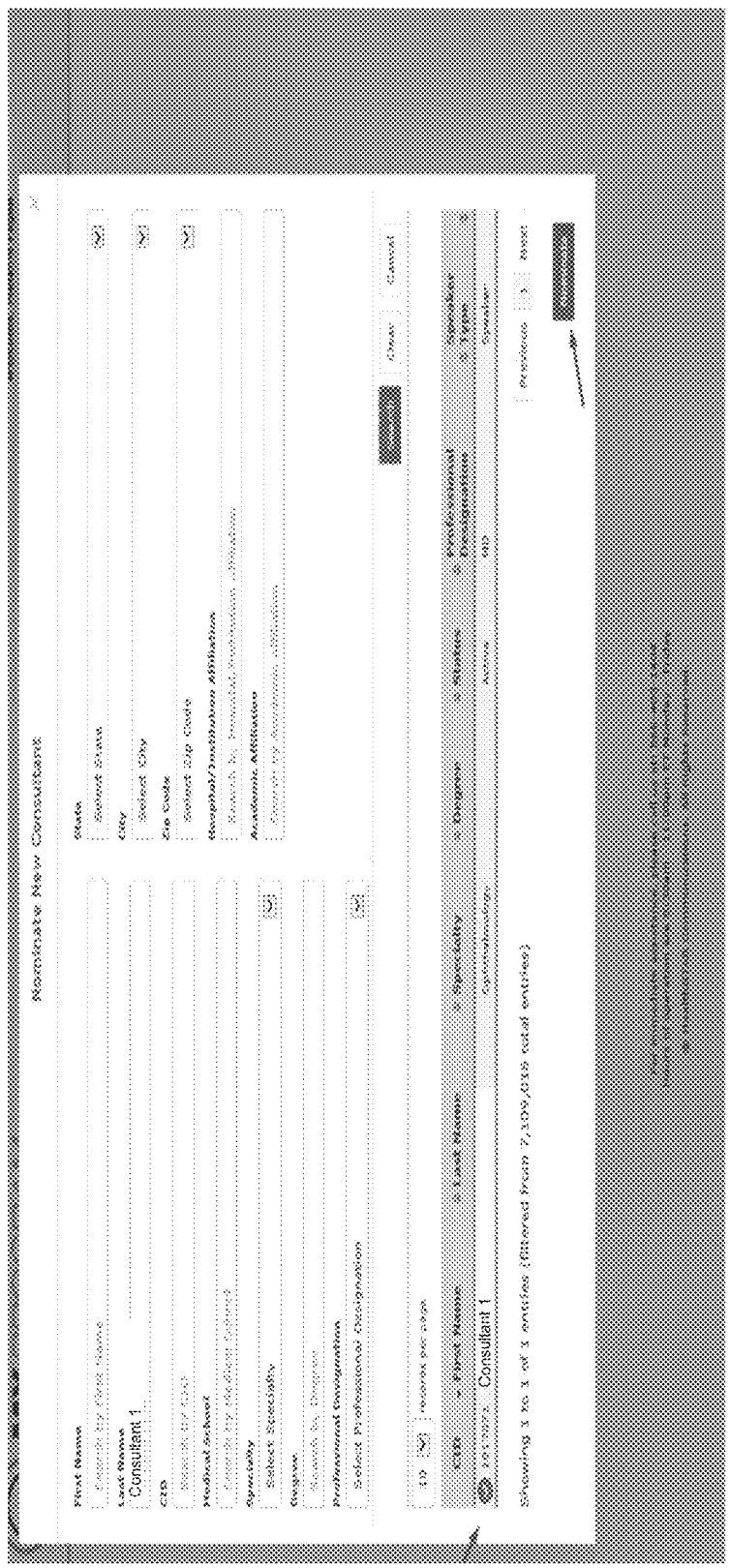
Figure 114:
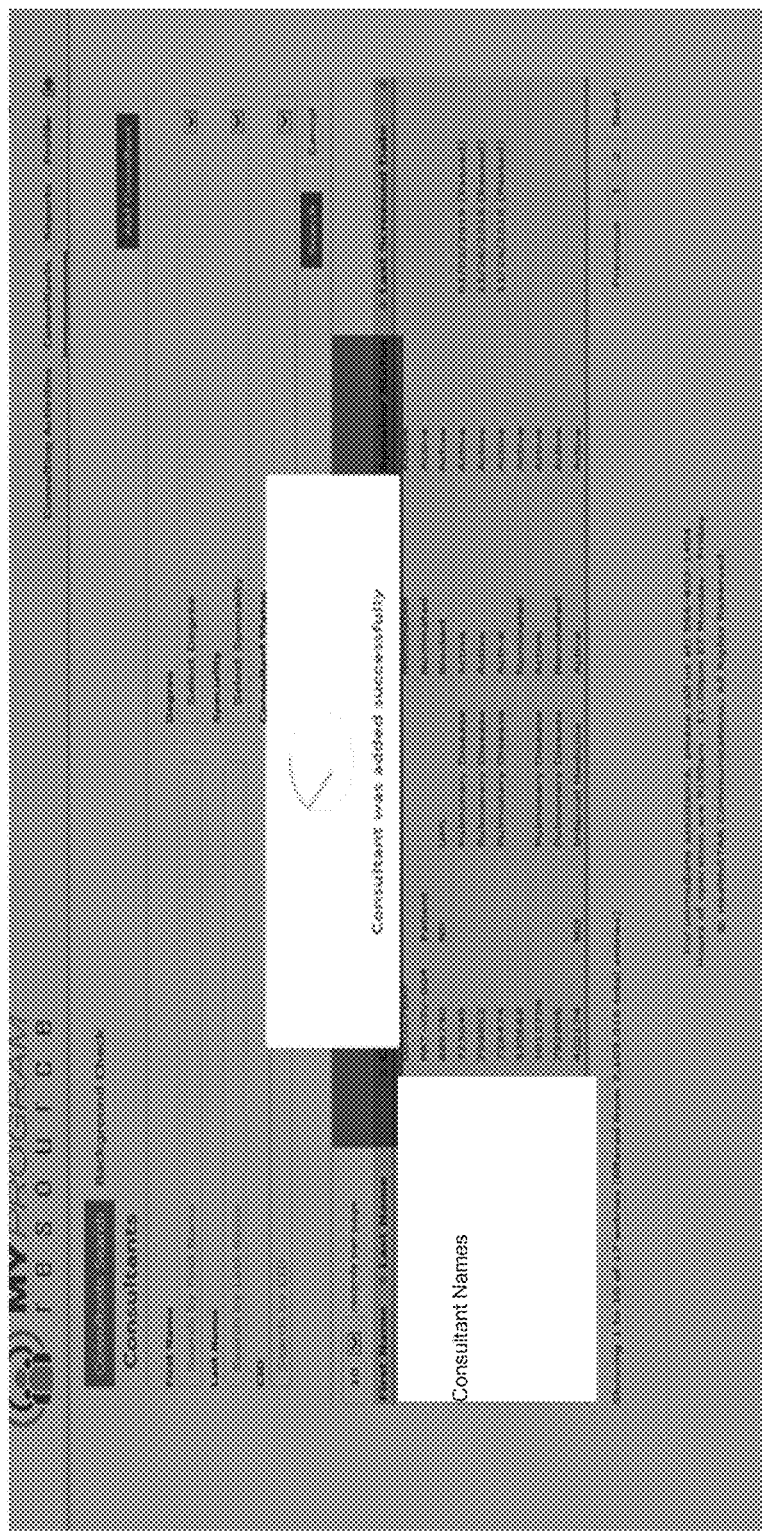
Figure 115:
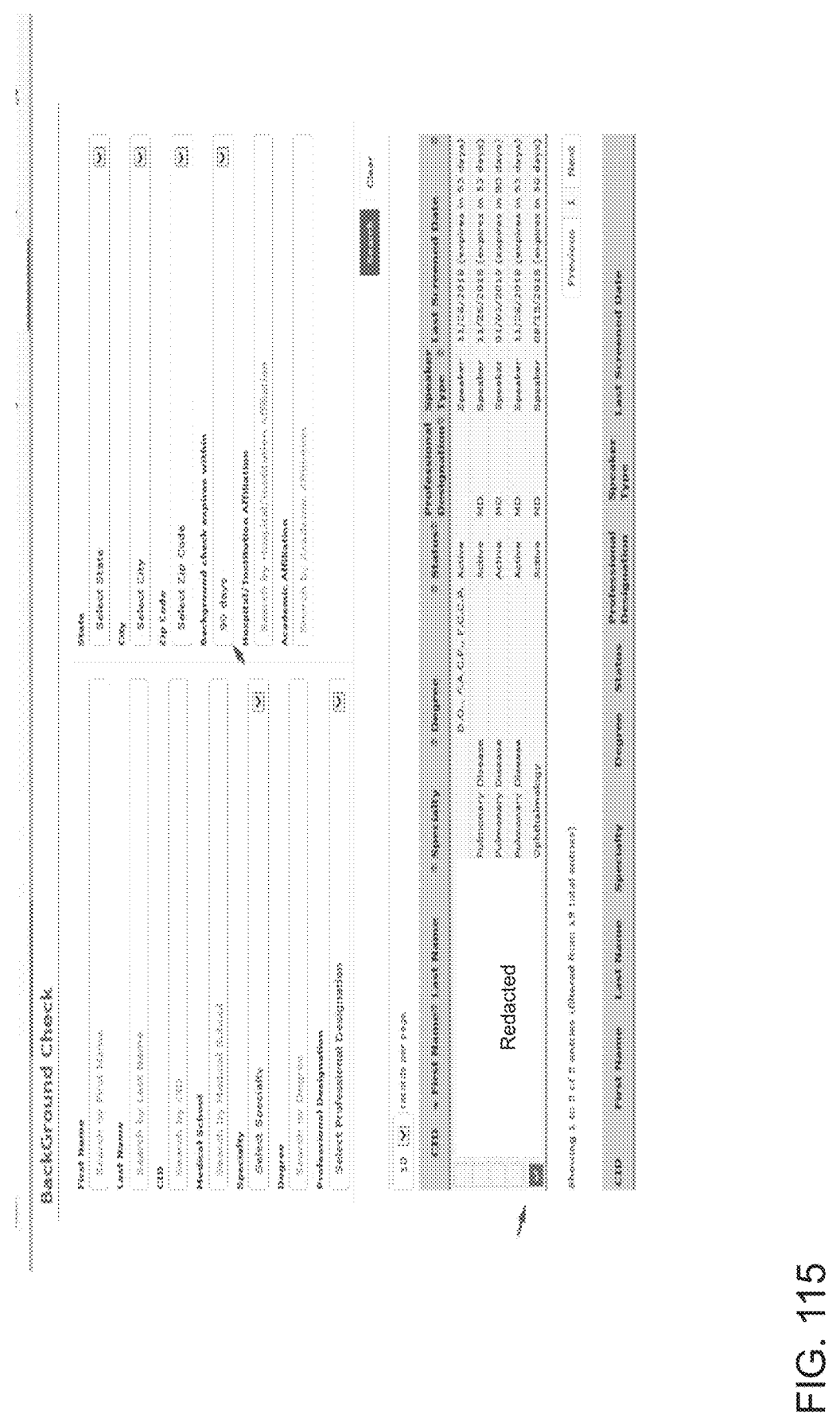

As shown in FIGS. 112-115, users with access to the My Program Resource (MPR) module may search for attendees and speakers and nominate someone to be a consultant (FIG. 112). As shown in FIG. 113, the user can select a speaker to nominate as a consultant, and the system processes and creates a consultant profile based on the information in the speaker/attendee profile (FIG. 114). Additionally, MPR users can search consultants using the background check tab, which allows users to determine which consultants require a background check and which consultants have a background check that is near expiration (FIG. 115).

Figure 118:
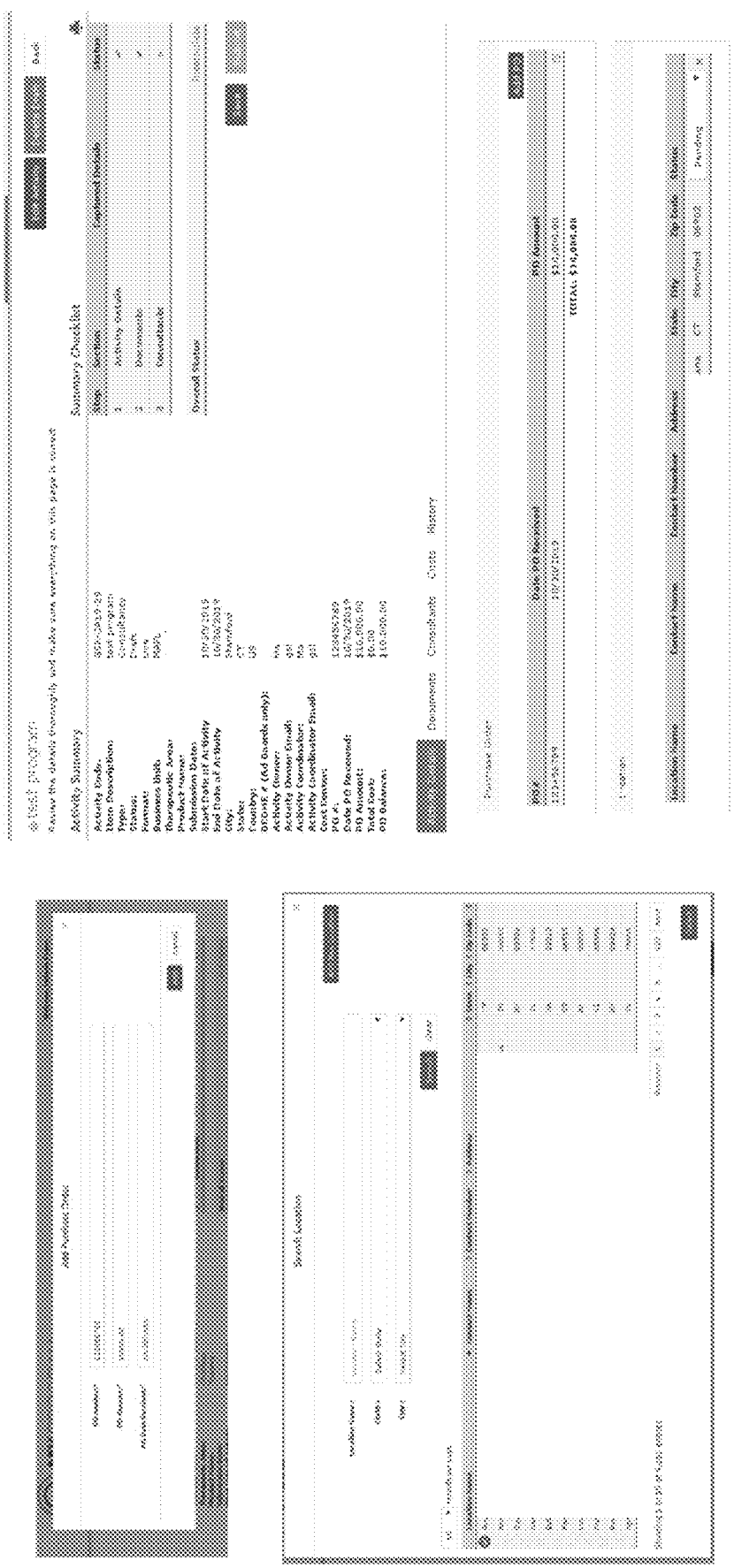
Figure 119:
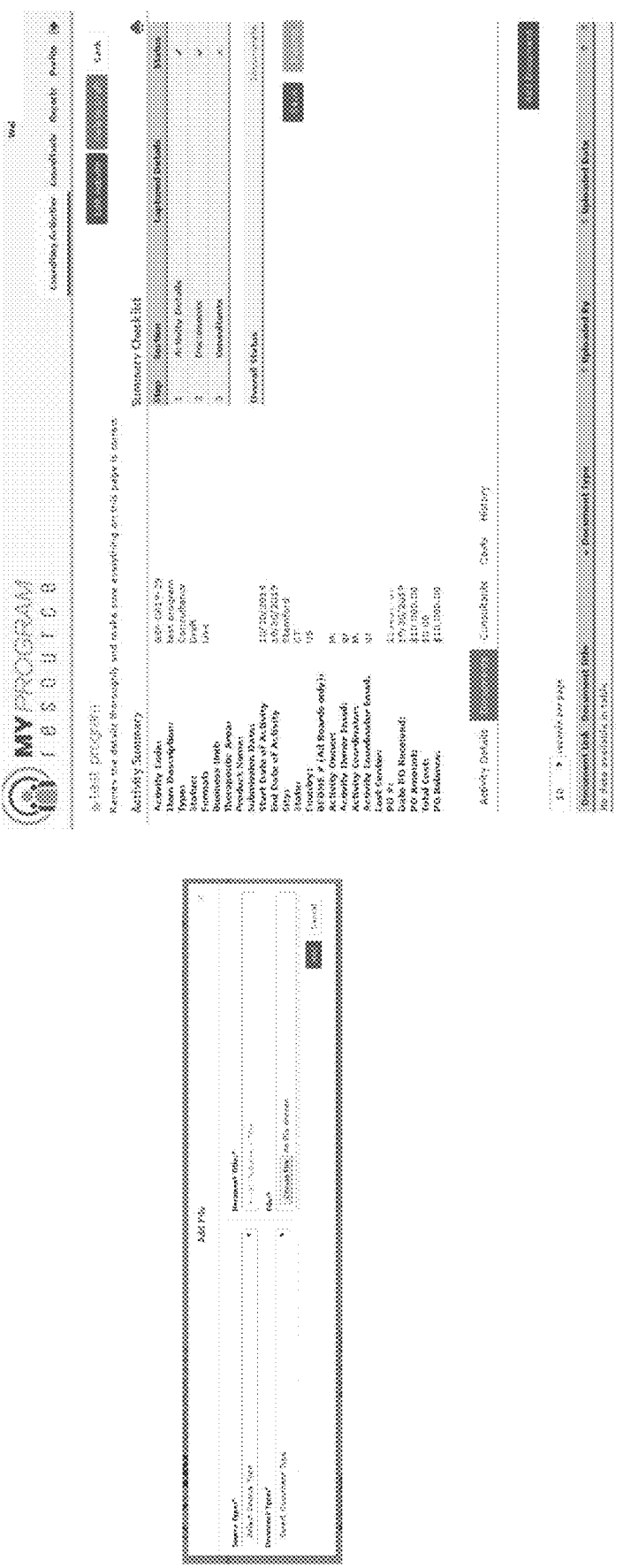
Figure 120:
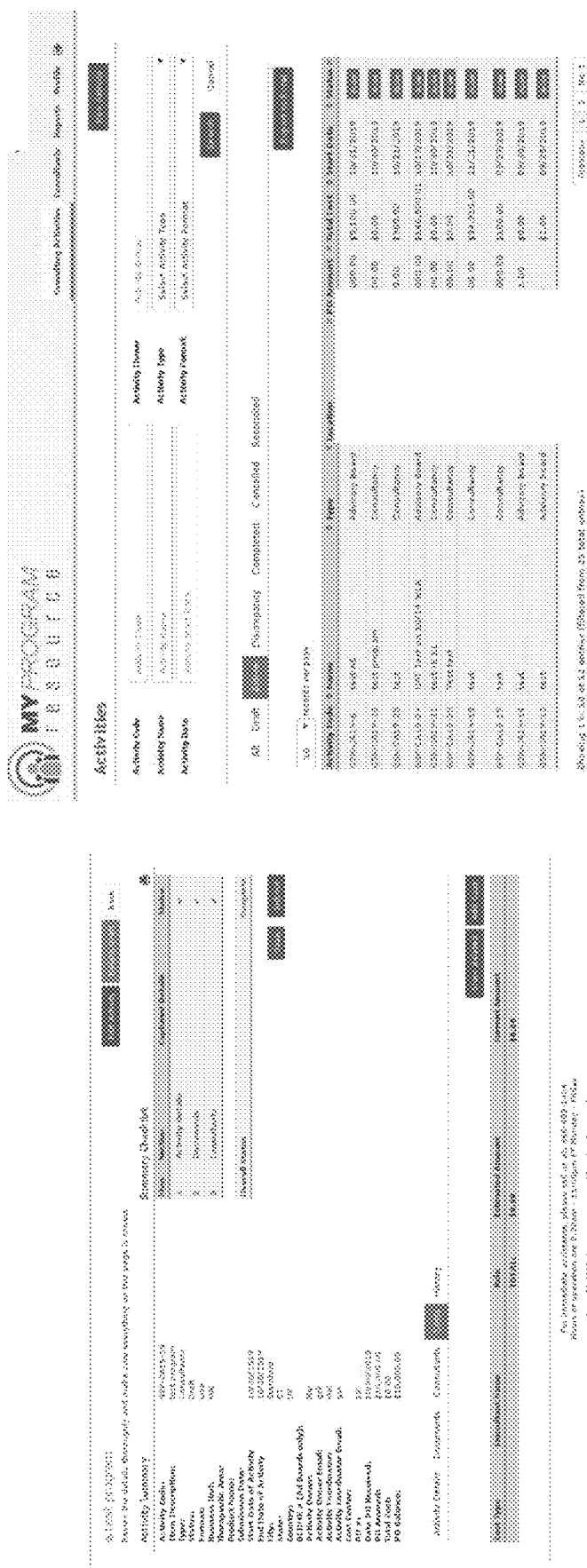
Figure 121:
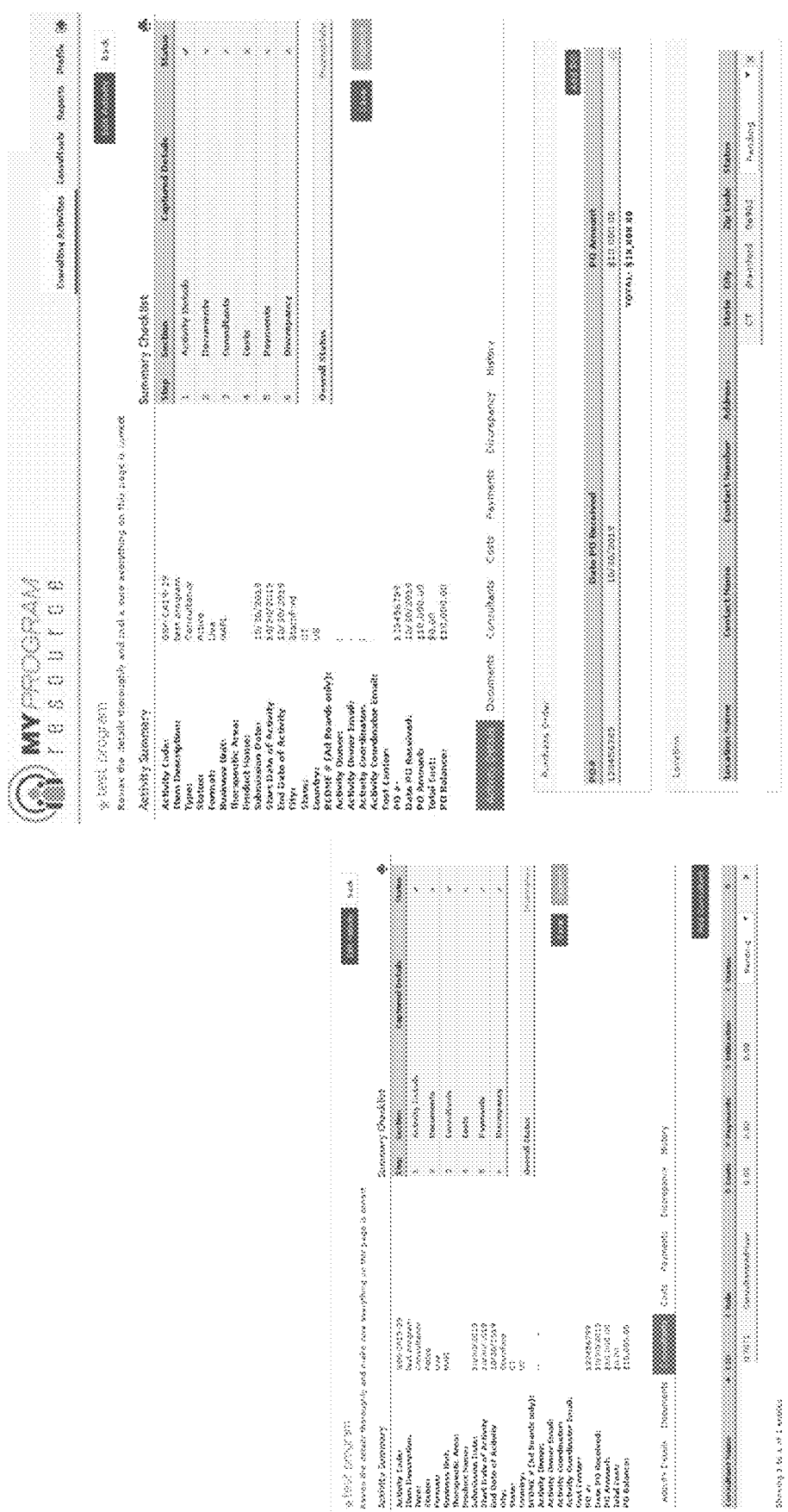
Figure 122:
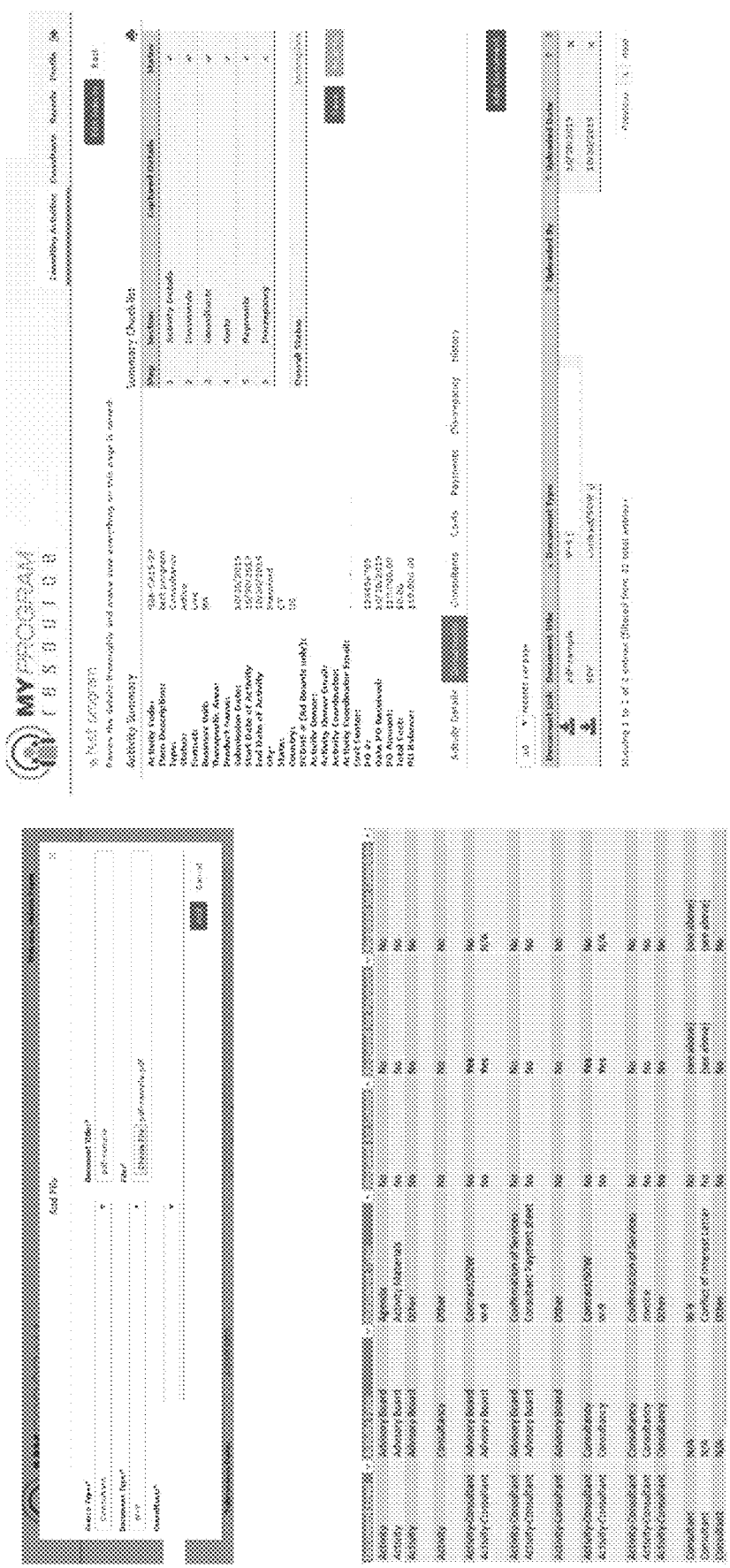
Figure 123:
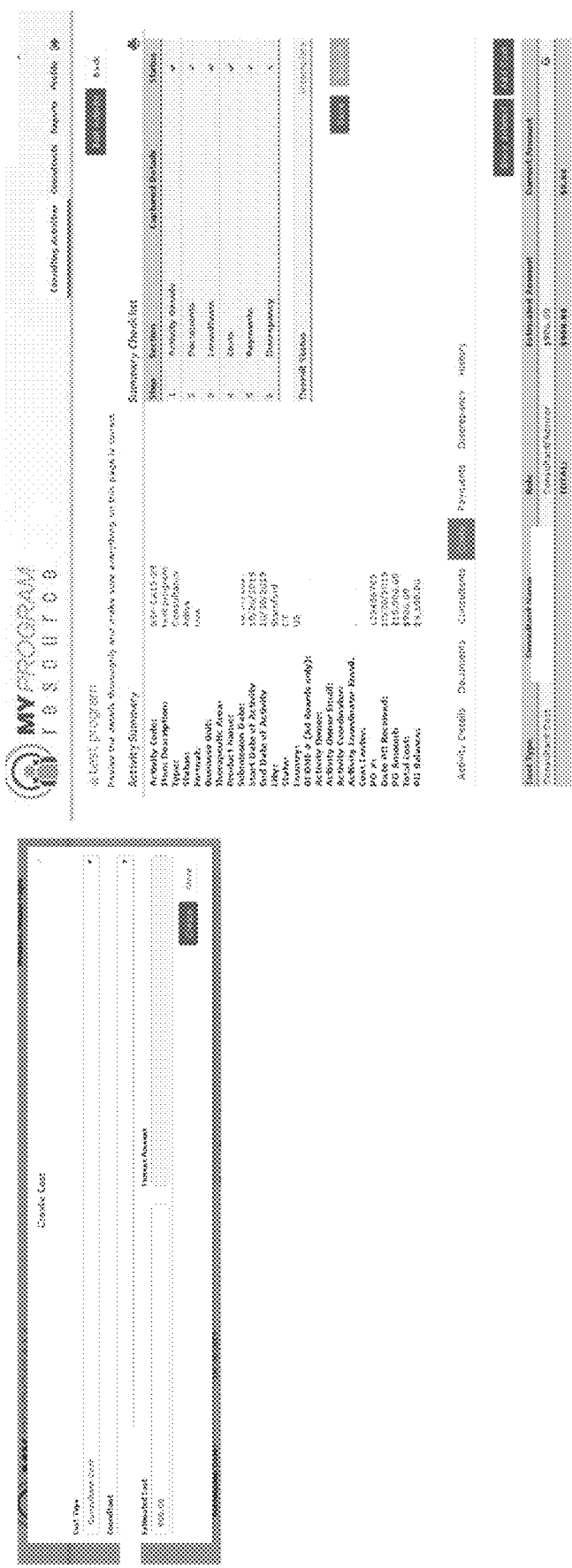
Figure 124:
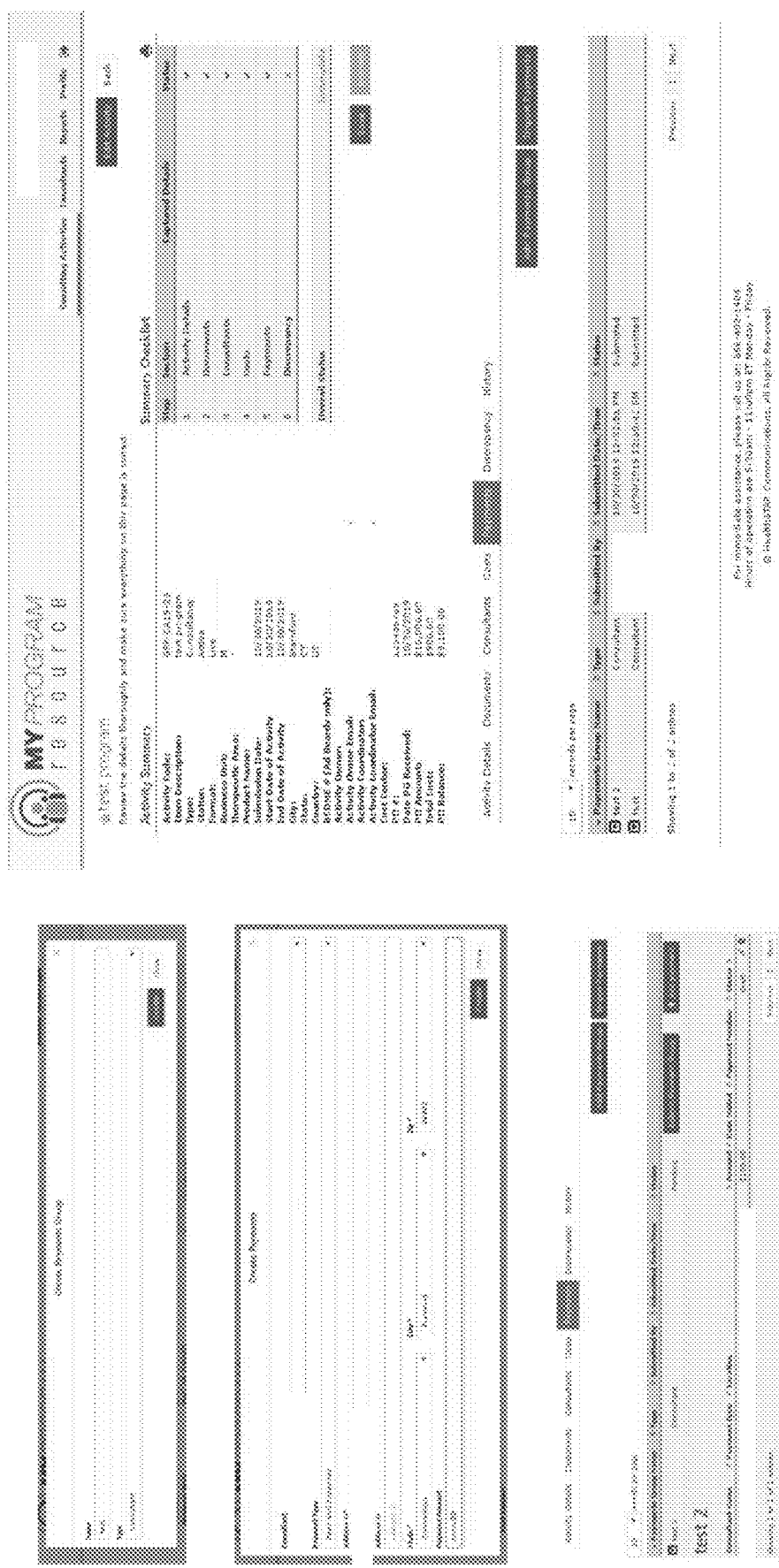
Figure 125:
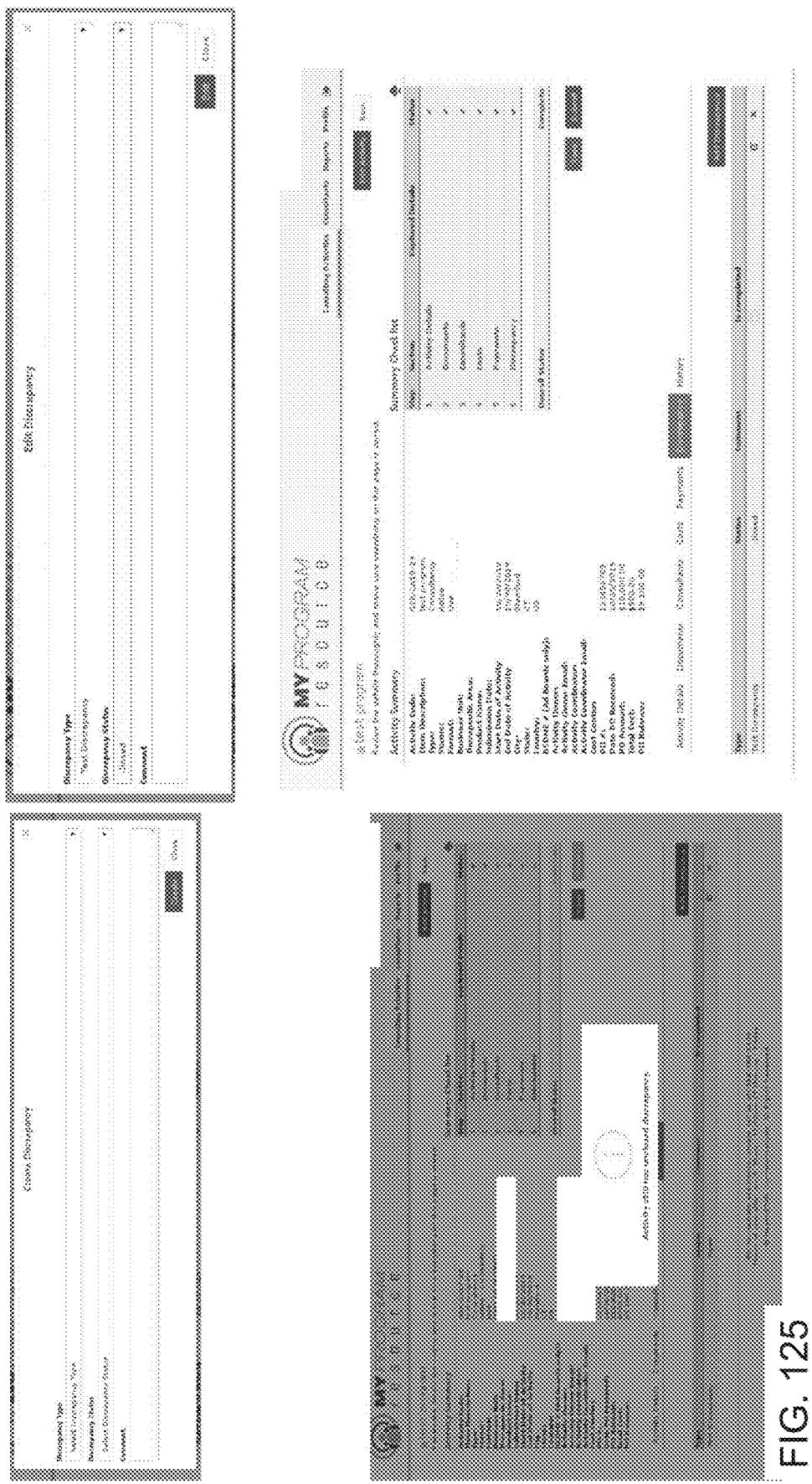
Figure 127:
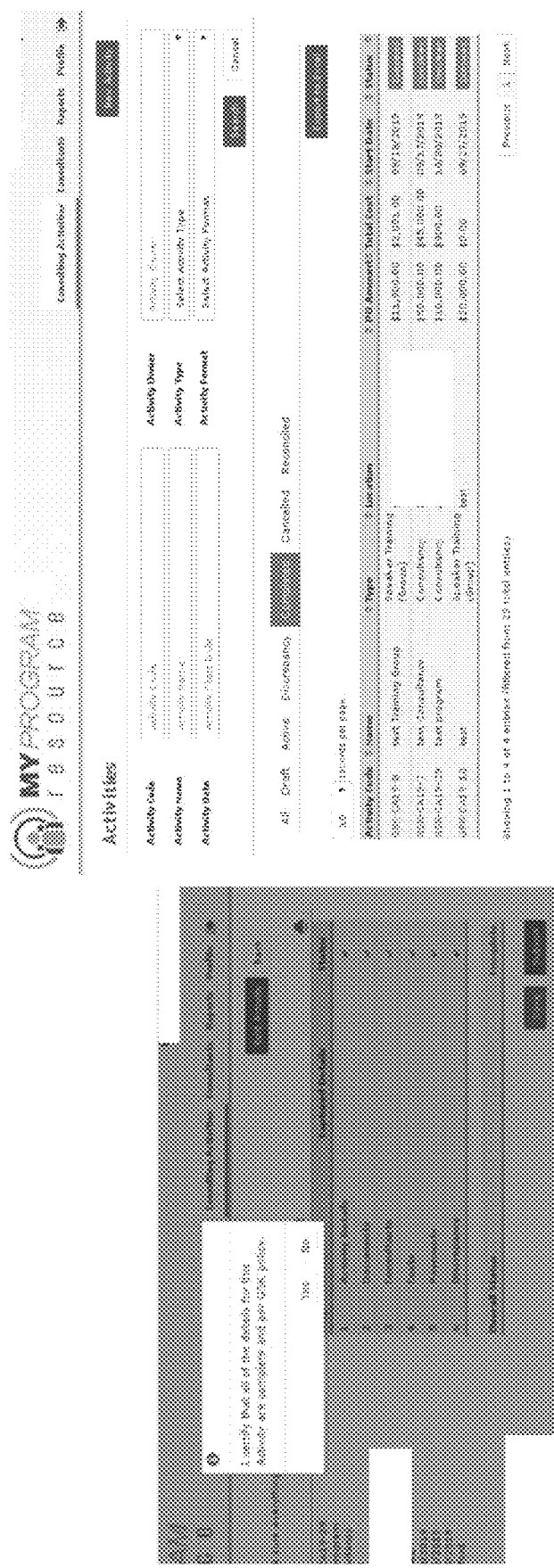

The consulting activities tab of MPR is depicted in FIGS. 116-127. As shown in FIG. 116, the consulting activities tab includes a button to create a new activity, fields to search the activities, and a grid showing all activities available. As shown in FIG. 117, a window for creating a new activity will be opened after the user clicks on the button 'New Activity' and all required fields should be populated. FIG. 118 depicts a view of the 'Activity Details' tab, which includes Purchase Order and Location data elements. FIG. 119 depicts a view of the 'Documents' tab. As shown in FIG. 120, when the user clicks 'Submit,' the program goes into Active status as shown in FIG. 121. The user may make changes to the data available at the 'Activity Details' and 'Consultants' tabs. FIG. 122 illustrates the 'Documents' tab, which provide the user with the ability to add documents (e.g., Contract, W-9, etc.). FIG. 123 illustrates the 'Cost' tab to add costs, and FIG. 124 illustrates the 'Payments' tab to add a Payments Group. FIG. 125 illustrates the 'Discrepancy' tab, and FIG. 126 illustrates the 'History' tab. As shown in FIG. 127, when the user selects the 'Submit' button and certifies the details are complete, the program will move to Completed status.

Figure 128:
Figure 129:
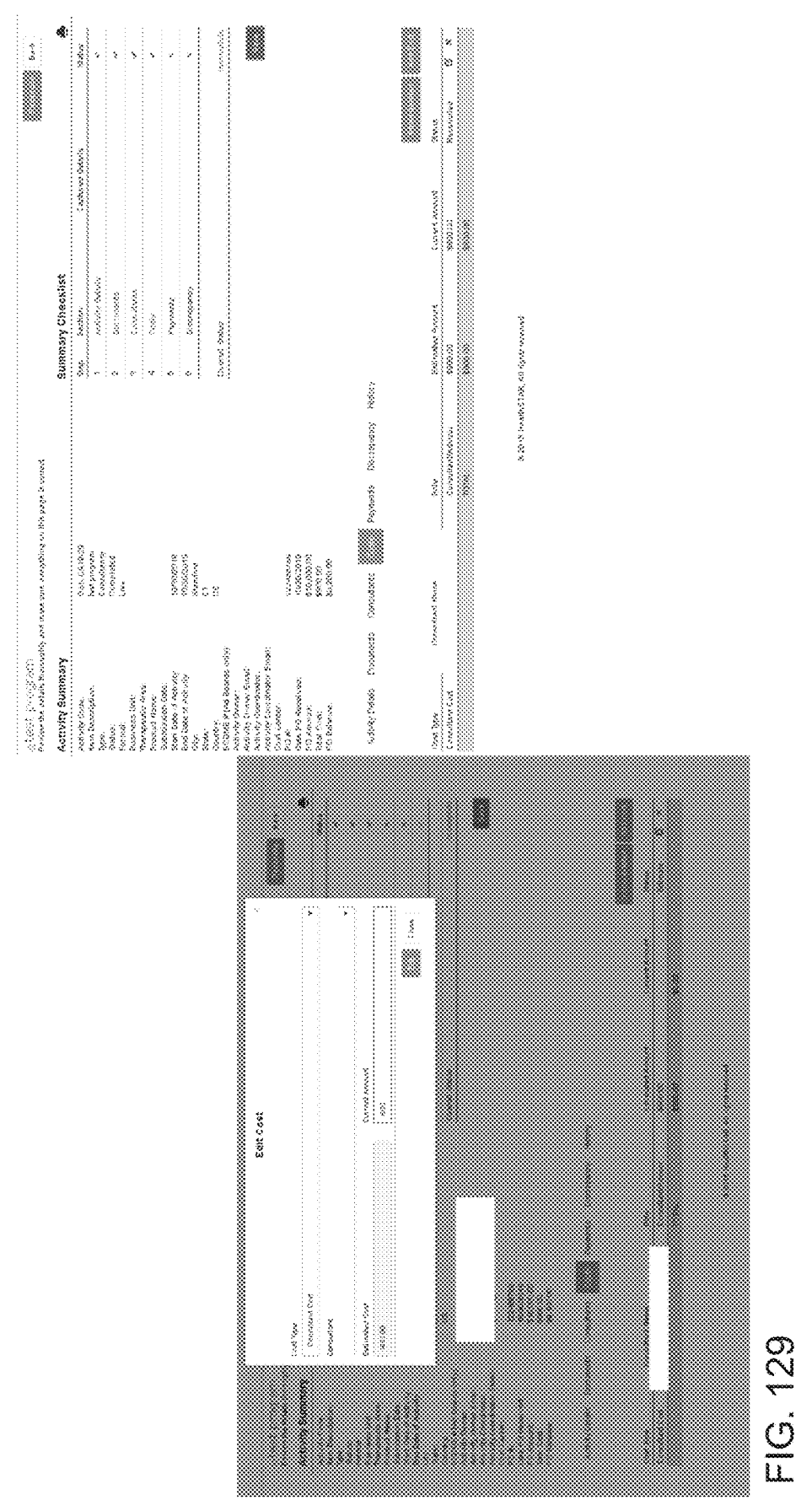
Figure 130:
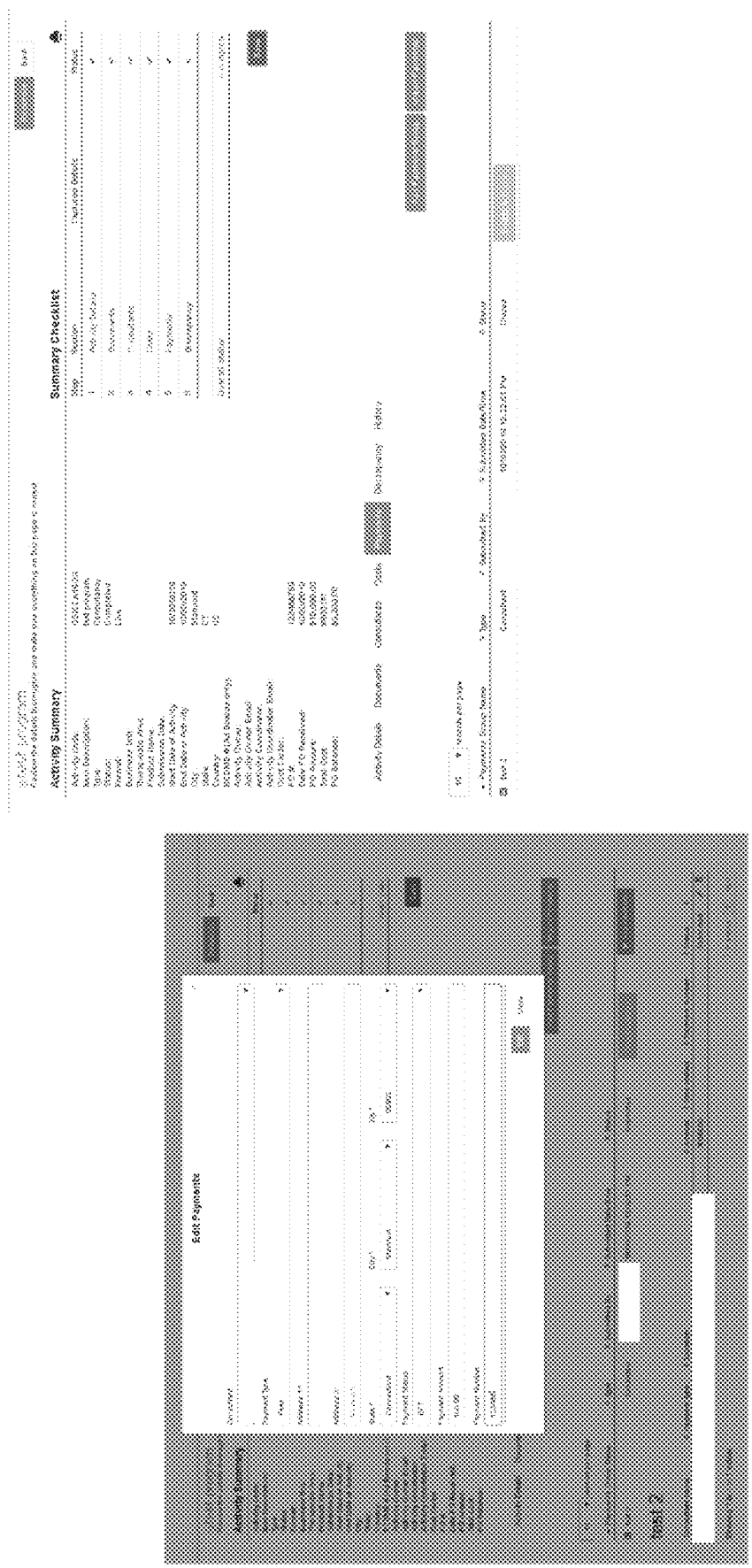
Figure 131:
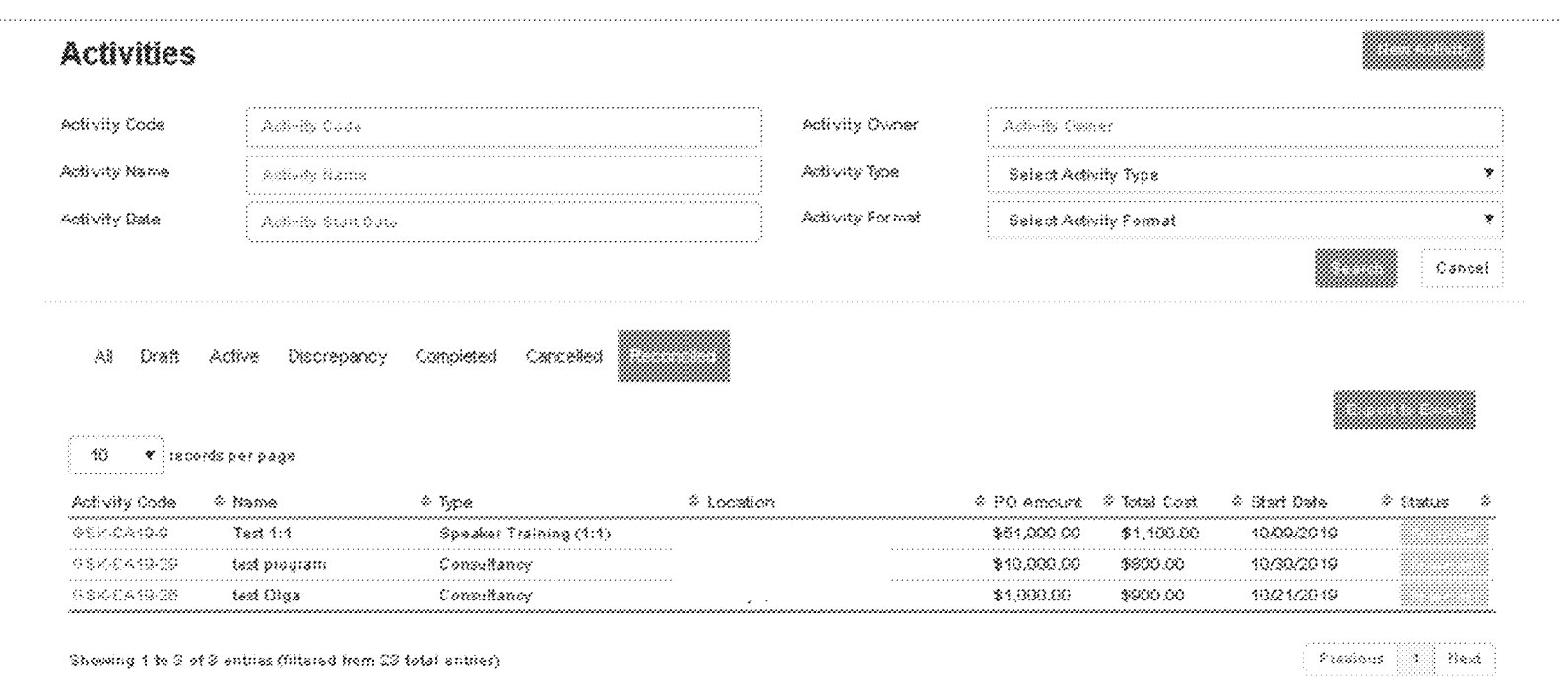

As shown in FIG. 128, the admin portal may be used to access the 'Consulting Activities' tab and reconcile the program (FIGS. 129-131).

Figure 132:
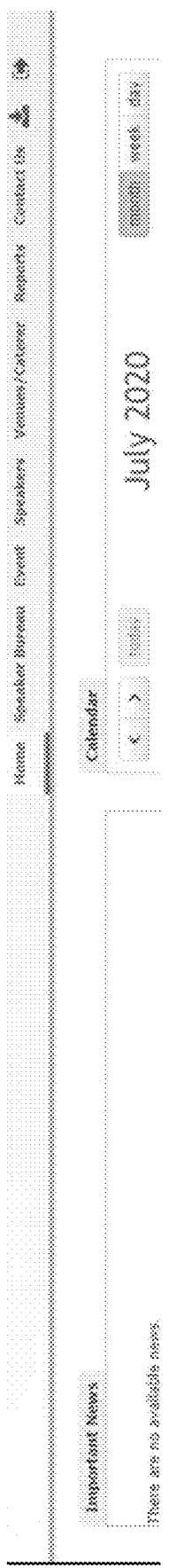
Figure 133:
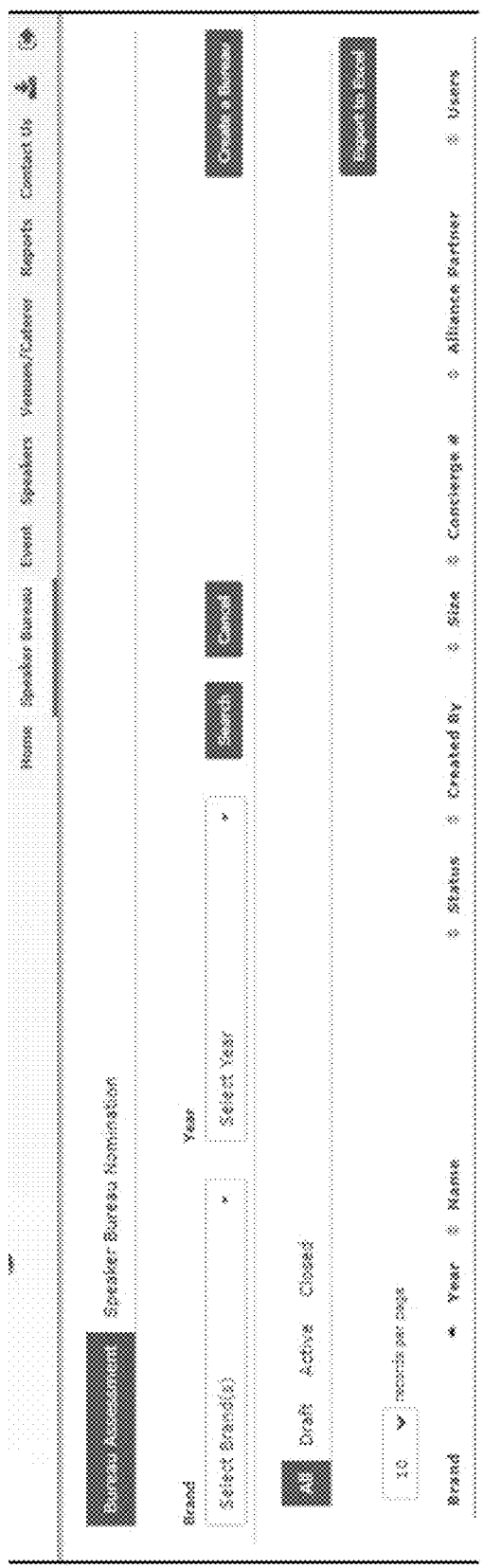

As described above, in some embodiments, the representative portal may include a speaker bureau tab as shown in FIG. 132 and described below in reference to FIGS. 133-160. The speaker bureau tab may allow for streamlining of the process of speaker bureau creation, management of nominations, and tracking the lifecycle of speaker contracting. The speaker bureau tab may allow users to nominate and approve potential speakers into the system while eliminating manual errors, providing real-time user access to view of the progress of the bureau and individual speakers, and to customize speaker profiles to show information parameters desired by the team. When creating the speaker bureau, the user may set up the bureau within a nomination tool of the speaker bureau tab including selecting the brand, number of speakers, and allowing others (e.g., TLLs) to nominate speakers. Those given permission to nominate speakers may nominate new speakers or nominate speakers based on prior year (or other prior period) bureaus. When ready to contract, the approvers can process the speakers and begin debarment. The speaker bureau tab may provide dashboard views to facilitate the tracking of the progress of the speaker bureau. In some embodiments, the speaker bureau may only be created within a predefined time period or interval (e.g., one time per year).

Figure 134:
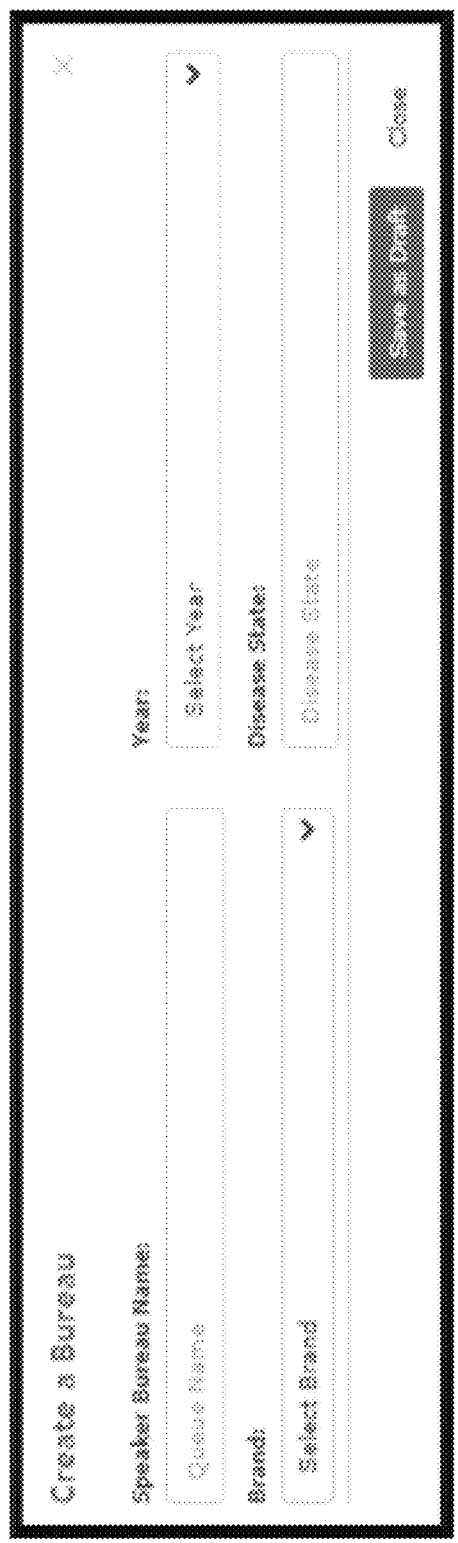
Figure 135:
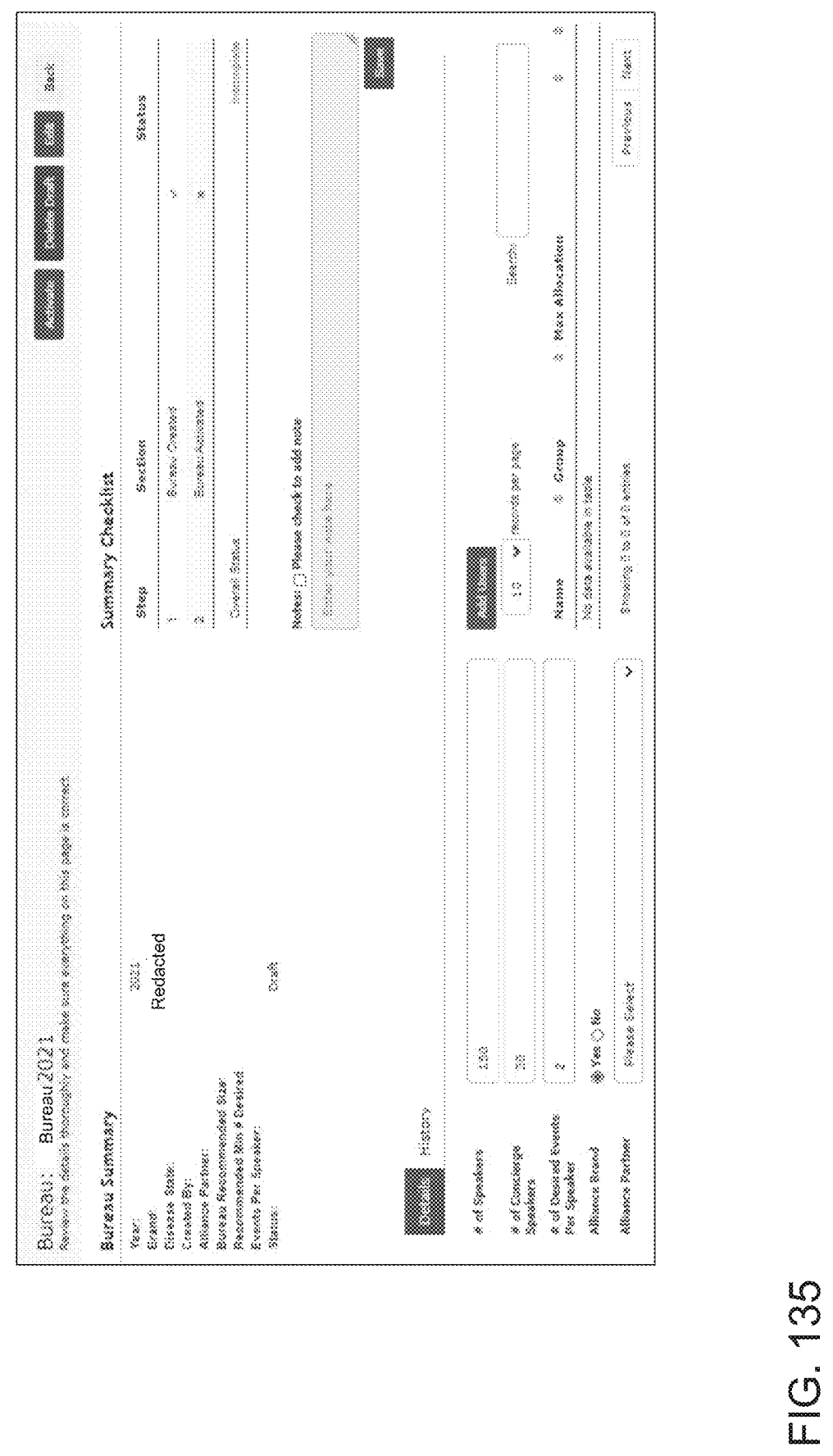
Figure 136:
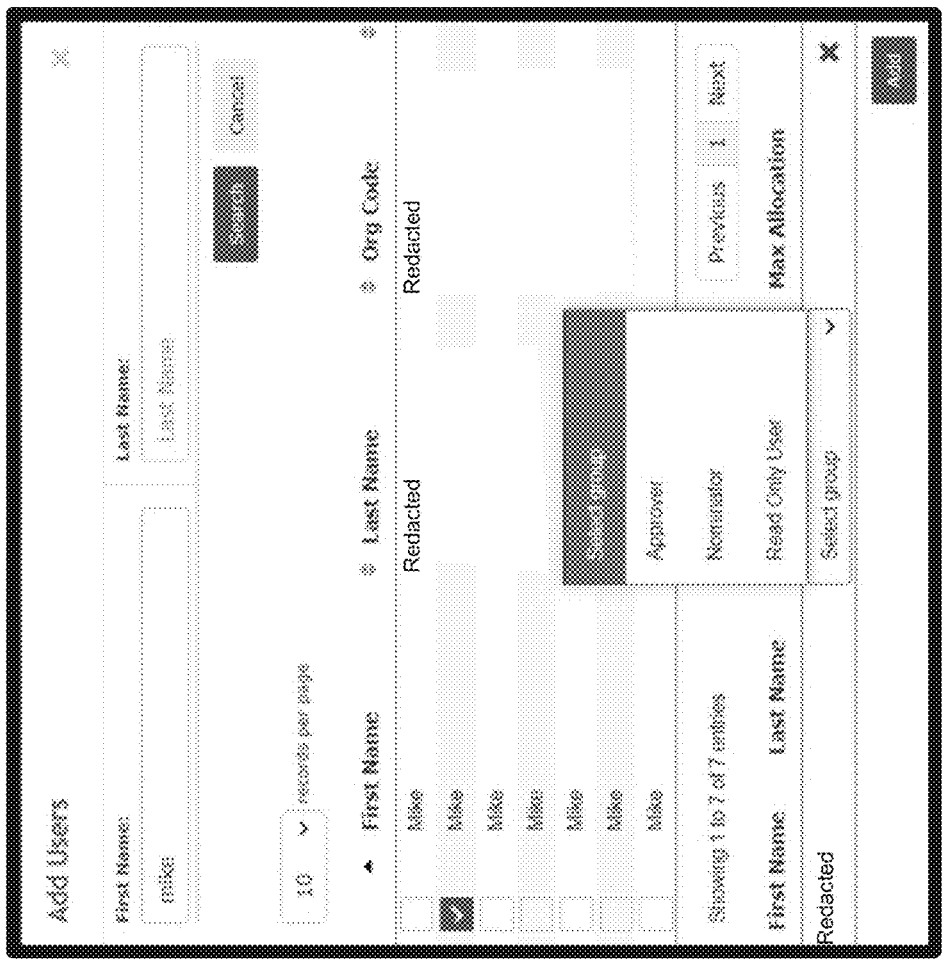
Figure 137:
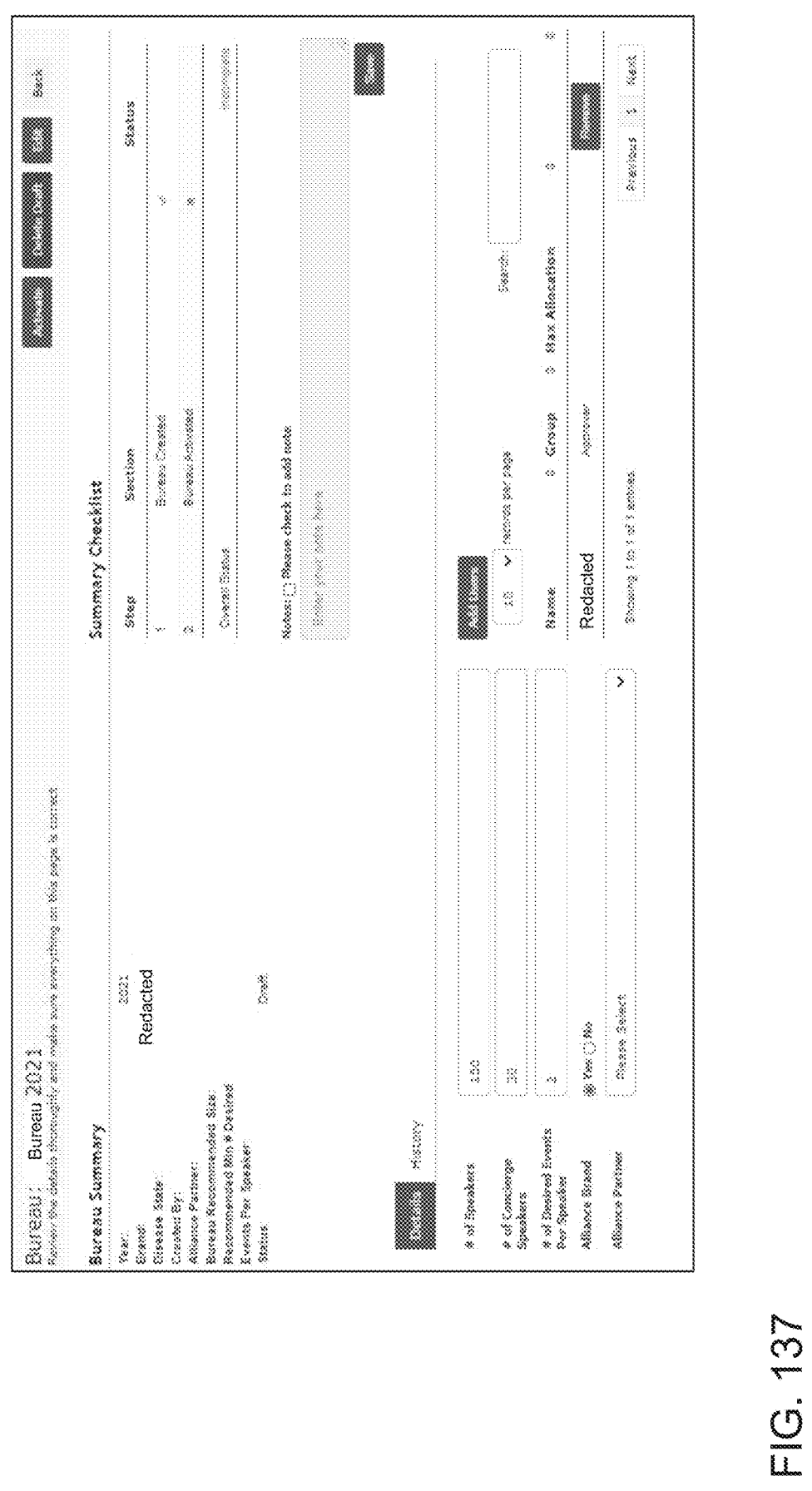

Upon selecting the speaker bureau tab (FIG. 132), the 'Bureau Assessment' tab is launched (FIG. 133), which enables the user to create/edit a new speaker bureau by selecting the 'Create a Bureau" button. For example, this section may be used to set up the administrative side of the speaker bureau, size, approves, etc. FIG. 134 allows the user to identify brand specifics (e.g., brand name, bureau name, etc.) for the creation of the speaker bureau, and FIG. 135 allows the user to review the details for accuracy. Upon selecting the 'Add Users' button, the user may add users who will nominate and approve the bureau (FIG. 136). It should be appreciated that the speaker bureau tab may recognize multiple user groups/roles. For example, in some embodiments, there may be a creator user group/role (e.g., having access to create/edit the bureau and add other users as approvers and/or nominators), approver user group/role (e.g., having the ability to nominate speakers and approval final speaker selection for the bureau), nominator user group/role (e.g., having the ability to nominate speakers to the bureau but not approve), and/or a read only user group/role (e.g., having the ability only to view the speaker bureau and utilize dashboards). As shown in FIG. 137, the user may select the 'Activate' button to start the bureau. Alternatively, the draft could be deleting or the speaker bureau information could be edited.

Figure 139:
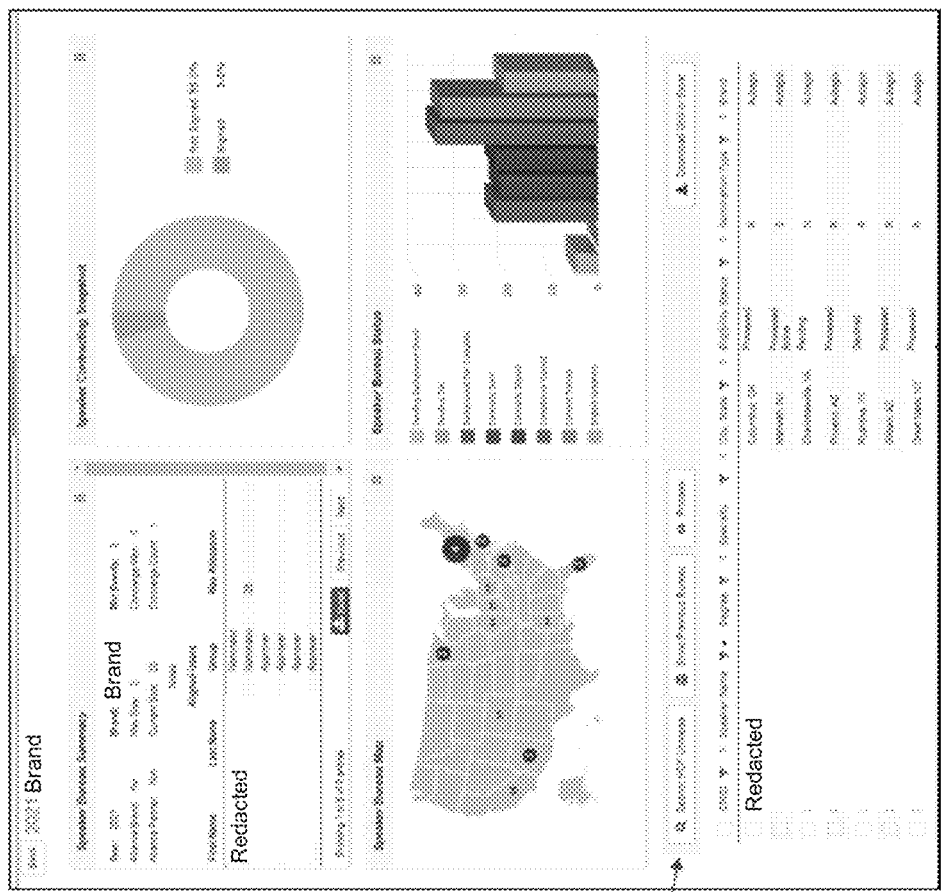
Figure 141:
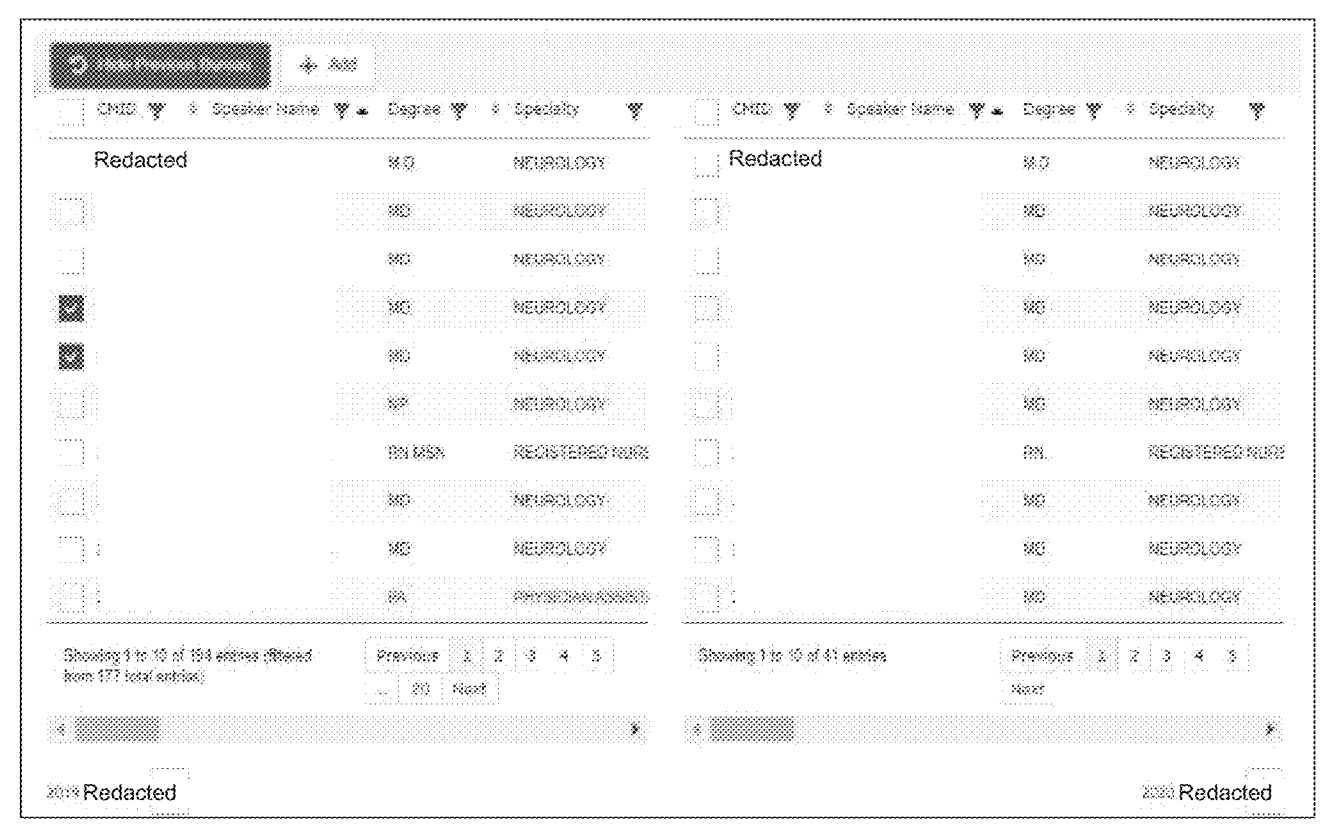
Figure 142:
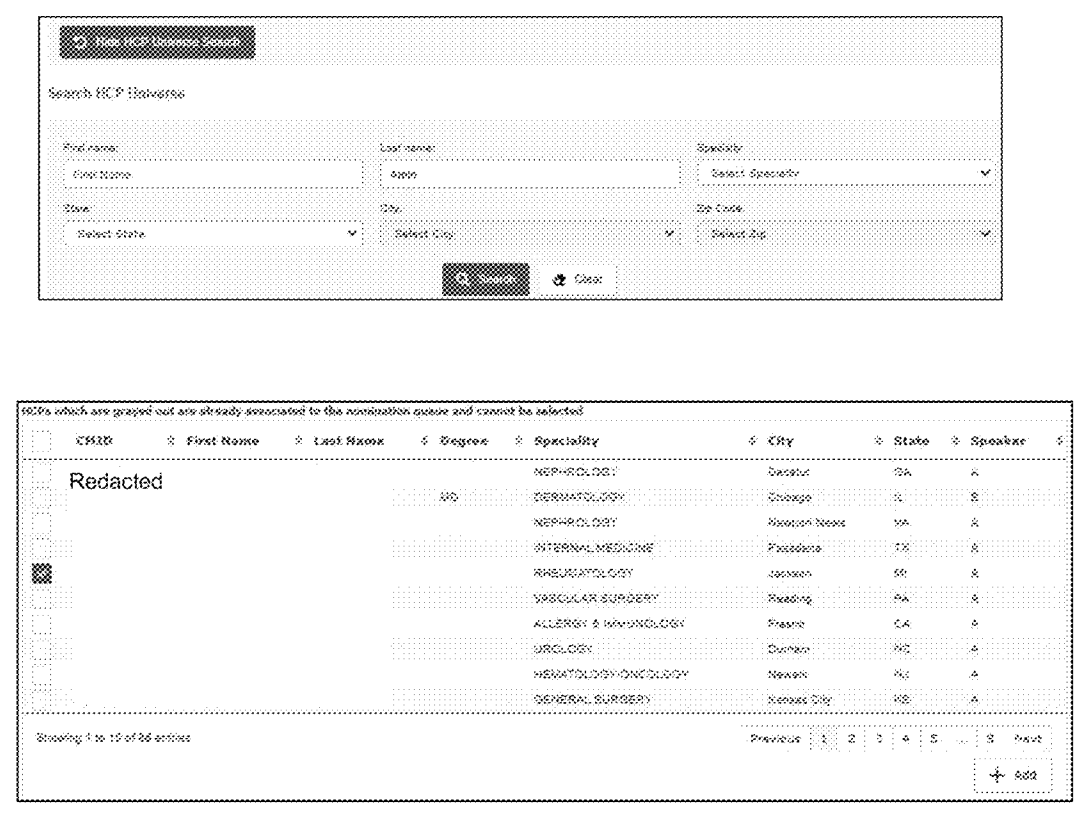

After the bureau has been created, the users who were given permission to nominate speakers can add speakers from a prior year's bureaus and/or nominate new speakers to the bureau. Accordingly, the 'Speaker Bureau Nomination' tab allows such nomination to occur and includes filters (e.g., by brand, nomination year, etc.) to identify the relevant speakers (FIG. 138). FIG. 139 provides a dashboard that educates the users on the nomination process and speakers included in the nomination list. For example, the user may 'Search HCP Universe." FIG. 140 allows the user to search for speakers that are not listed and/or show previous bureau results. In some embodiments, speakers may be automatically populated in the speaker bureau as a "safe harbor." The desired speakers may be selected to add to the new bureau. As shown in FIG. 141, the speakers may be highlighted via different colors (or otherwise) based on various criteria. FIG. 142 reflects that a speaker may be identified in the HCP universe by searching with various parameters (e.g., first name, last name, specialty, city, state, zip code, etc.).

As indicated above, approvers are responsible for approving the final speaker selection bureau and process the speakers after the nominations, including debarment. In some embodiments, debarment may include separate batches being created for debar only speakers, nominators adding all speakers to the speaker bureau, notifying approver of debar only speakers (e.g., if nominator is a different user), approver checking all speakers that will be debarred only and clicking approve, add "Debarment only for this batch" in notes, select "Process" speakers to the enterprise administrator, and transmitting a notification (e.g., via email) if a speaker is to be contracted (brand, speaker first name, speaker second name). In other embodiments, steps for debar and hold for manual contracts may include separate batches being created for manual contracts, nominators adding all speakers to the speaker bureau, notifying approver of "debar only manual contract" speakers (e.g., if nominator is a different user), approver checking all speakers that will be manually contracted and clicking approve, add "Debarment only manual contracts for this batch" in notes, select "Process" speakers to the enterprise administrator, providing PEM with a manual contract, sending the manual contract to the speaker for signature, sending the signed manual contract to the client, and obtaining the countersign for return to the enterprise administrator. In yet other embodiments, steps for fully contracting may include nominators adding all speakers to the speaker bureau, approver checking all speakers to be fully contracted and clicking approve, adding no notes, and processing speakers to the enterprise administrator.

Figure 143:
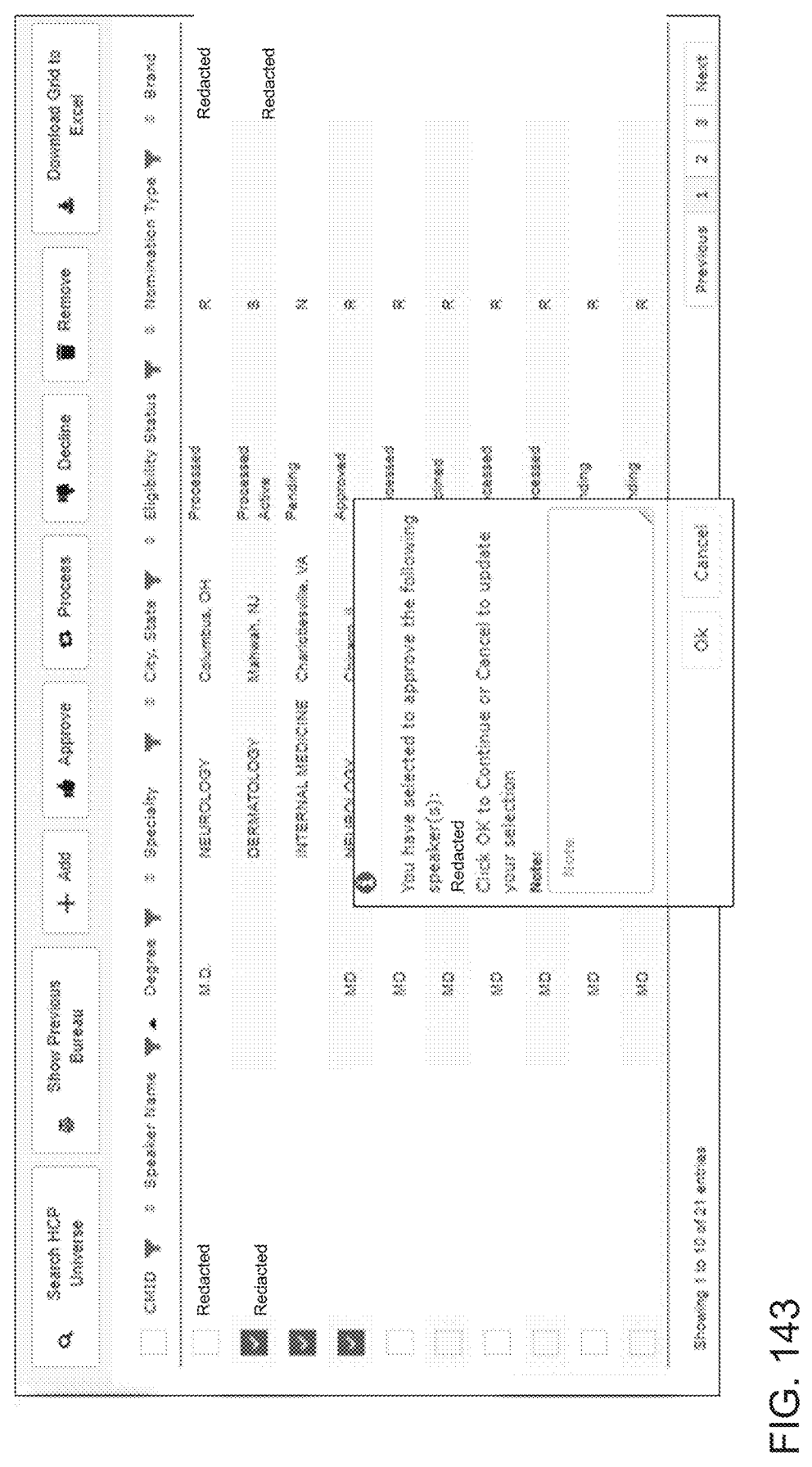
Figure 144:
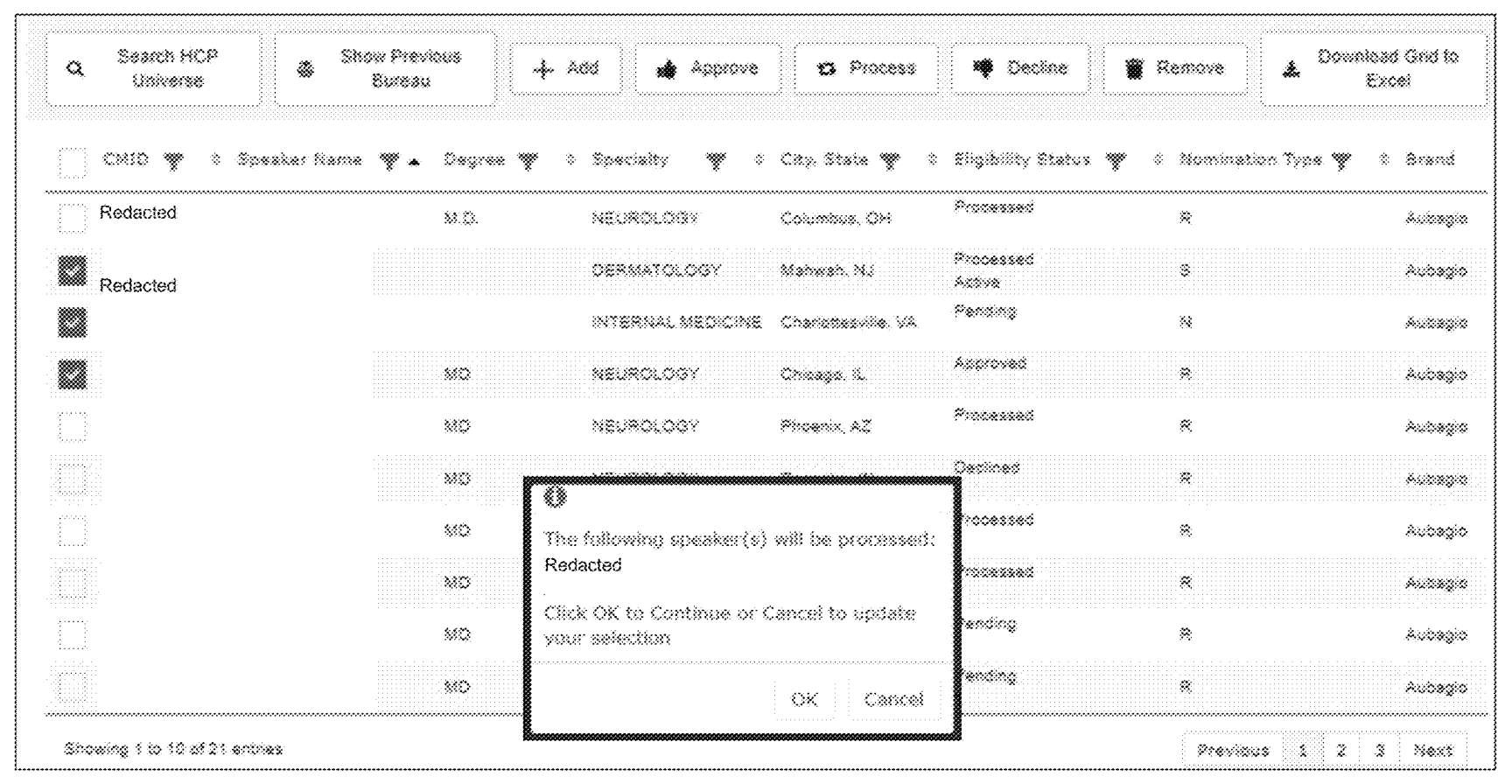
Figure 145:

FIG. 143 allows the user to approve or decline HCPs before contracting begins. A pop-up message may be generated after speakers have been selected for approval in order to confirm. Similarly, FIG. 144 allows the user to select the HCPs to begin debarment via the 'Process' button, and a pop-up message may be generated in order to confirm the selections. As shown in FIG. 145, when the approver processes one or more speakers for bureau nomination, the enterprise administrator may receive an internal message (e.g., email) immediately with the speaker(s) information to begin debarment. In some embodiments, the enterprise administrator will receive a separate internal message (e.g., email) every time one or more speakers are processed in the tool. In at least one embodiment of an eligibility status flow, a particular speaker may transition through various statuses including, for example, pending (speaker has been nominated in the bureau), approved (nomination has been approved but has not been sent to the enterprise administrator), processed pending qualification (nomination has been sent to the enterprise administrator for a background check), processed pending contract (contract has been sent to the speaker and awaiting speaker signature), processed pending training (contract signed but compliance and/or content training is still necessary), and/or processed active (speaker is eligible to conduct a program on one or more trained topics).

Figure 147:
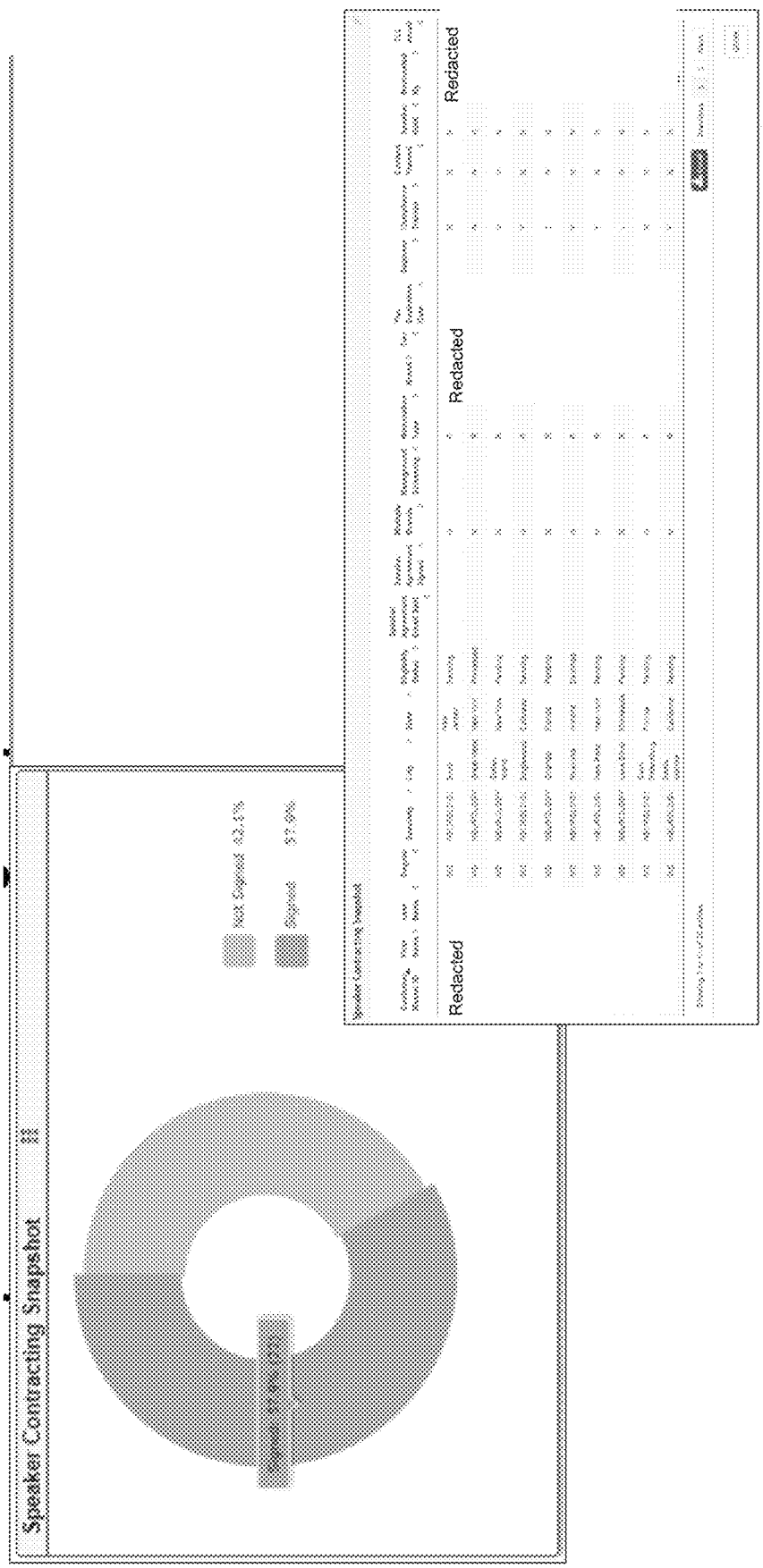
Figure 148:
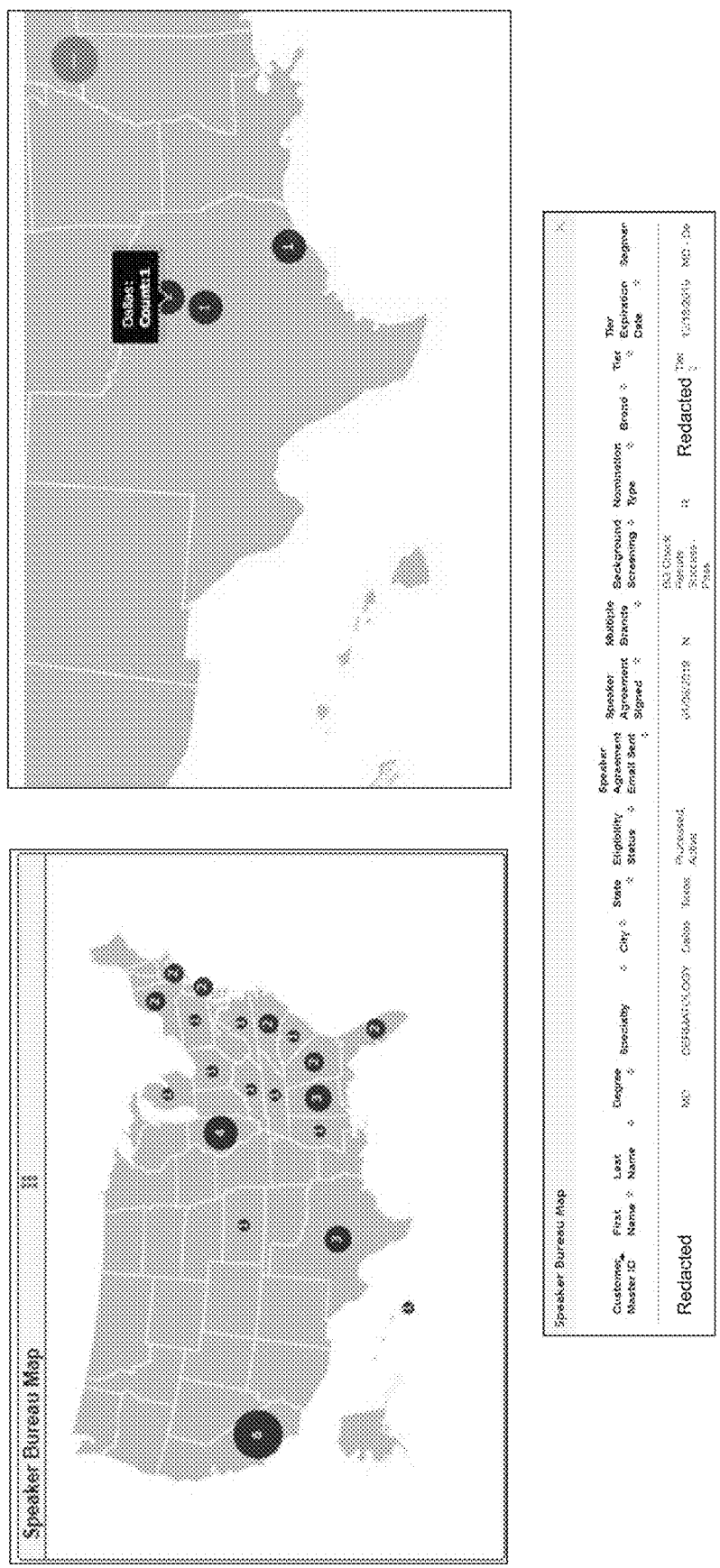
Figure 149:
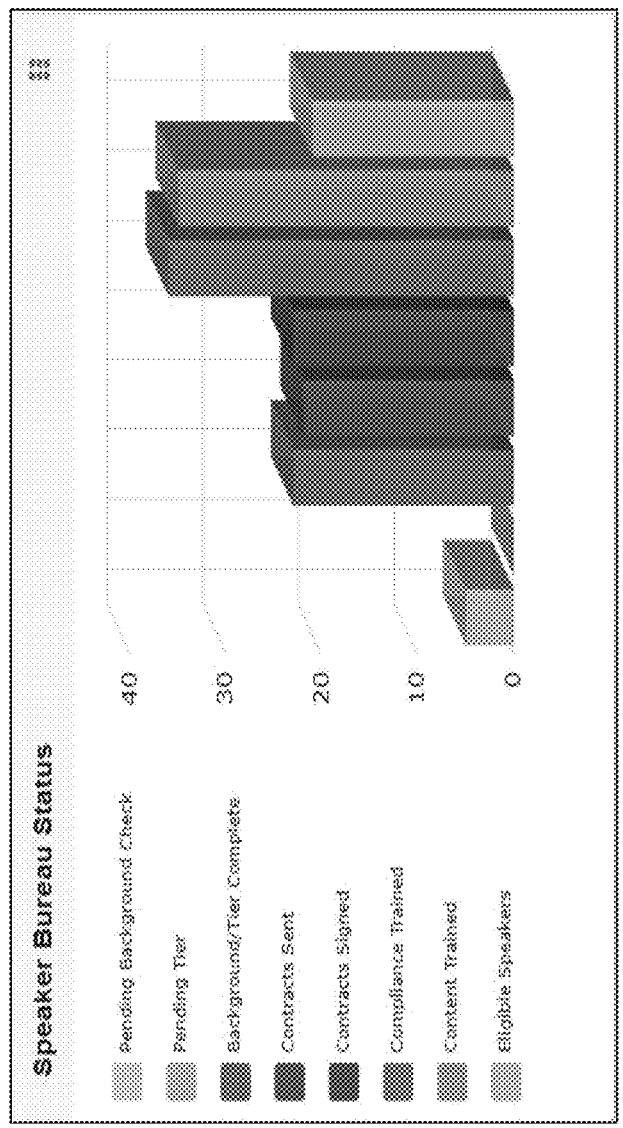

In some embodiments, various dashboard views may allow users to track the progress of the speaker bureau. FIG. 146 illustrates a speaker bureau summary that provides a snapshot summary of the bureau that was created, and FIGS. 147-149 provide further snapshot information. For example, the graph of FIG. 147 may allow a user to hover to show how many speakers signed or did not sign their contract out of the total, and the information may be drilled down on (e.g., populating a chart depending on the graphical selection). FIG. 148 includes a map with markers that indicate how many HCPs are in a particular state/region, with each marker being selectable to provide further details regarding the HCPs city, state, or region. For example, the image on the right shows the Texas marker from the left image being selected to drill into Texas HCP information. The bar graphs of FIG. 149 represent how many HCPs within the bureau have the corresponding status, which may be further drilled into and charted as depicted.

Figure 157:
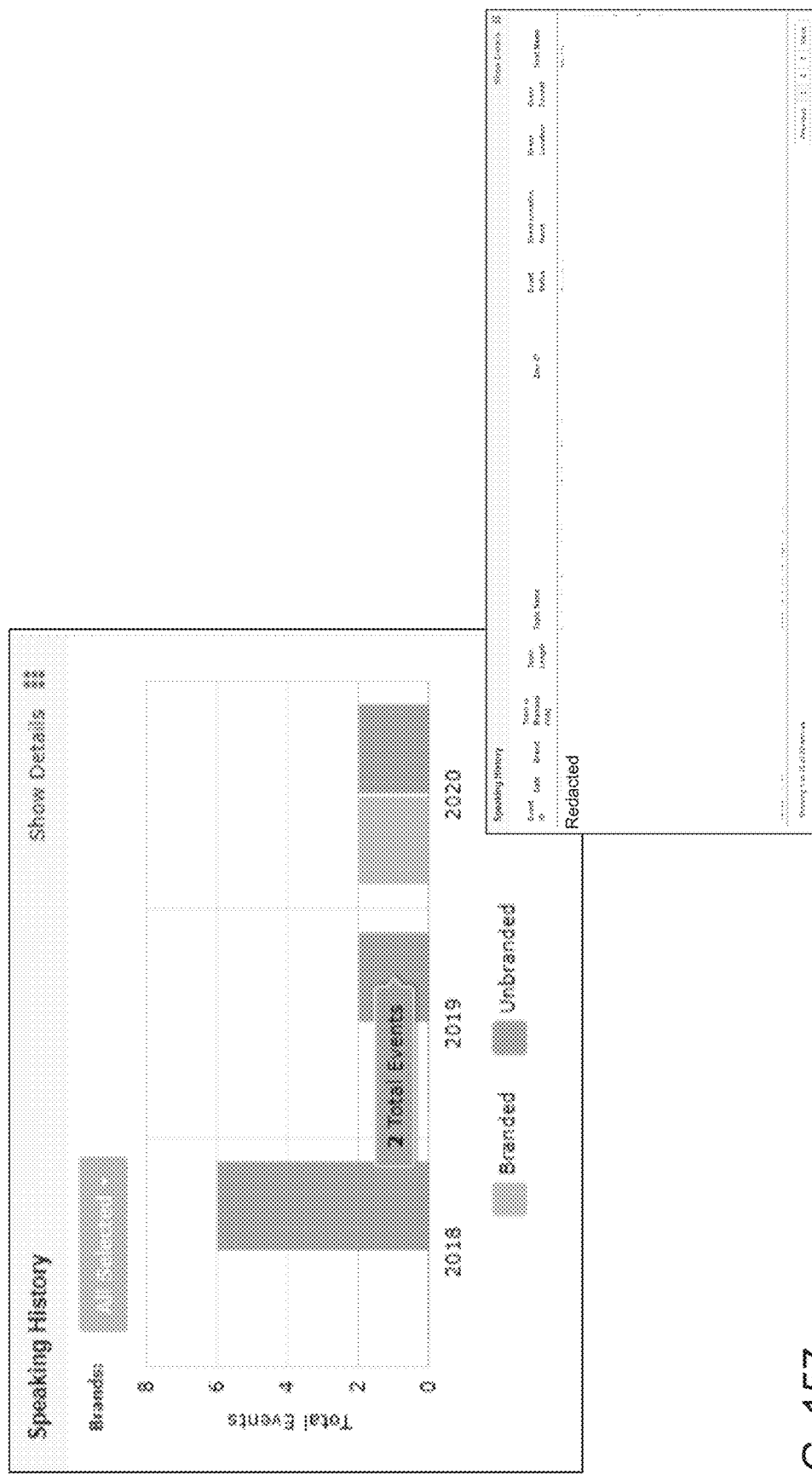

FIGS. 150-151 depict a speaker profile, which may be launched in response to a user's selection of a particular speaker's name during nomination, when searching through the speaker tab, or otherwise. After a speaker picture or CV has been uploaded, those documents are reflected on the speaker's profile (FIG. 152). The speaker's training status may be changed as depicted in FIG. 153, and the user may select a particular brand to access the speaker's training records for that particular brand (or all brands), which then populates a chart for the user to view. FIG. 154 depicts aligned TLLs by brand, FIG. 155 depicts the speaker's contracting history, FIG. 156 depicts the speaker's nomination history, and FIG. 157 depicts the user's event history. As shown in FIG. 158, an invitation sample may be generated for the speaker based on approved templates and merged fields (e.g., first name, last name, degree, affiliation(s), city, state, etc.). FIG. 159-160 reflect that information regarding the speaker FFS rates and cap may be viewed by the users.

What is claimed is:

1. A cloud-based enterprise platform for event handling, comprising:
    at least one processor; and
    at least one memory comprising a plurality of instructions stored thereon that, in response to execution by the at least one processor, causes the cloud-based enterprise platform to:
        communicate with a representative device of a pharmaceutical company representative to provide a representative portal to the representative device, wherein the representative portal includes at least a programs section that allows the representative to plan a program and a speakers section that allows the representative to view profiles of a plurality of healthcare providers identified as key opinion leaders, wherein the representative interacts with the representative portal via a graphical user interface corresponding with the representative portal displayed on the representative device; and
        communicate with a speaker device of a key opinion leader to provide a speaker portal to the speaker device, wherein the speaker portal allows the key opinion leader to interact with presentation materials and upcoming program data, wherein the key opinion leader interacts with the speaker portal via a graphical user interface corresponding with the speaker portal displayed on the speaker device;
    wherein the programs section allows the representative to target healthcare providers as prospective attendees to the program based on one or more criteria associated with the healthcare providers; and
    wherein a particular healthcare provider is identified as a prospective attendee based on a determination that the particular healthcare provider's medical practice includes at least a threshold number of healthcare providers.

2. The cloud-based enterprise platform of claim 1, wherein the particular healthcare provider is identified as a prospective attendee based further on a determination that the particular healthcare provider's medical practice has at least a threshold patient volume.

3. The cloud-based enterprise platform of claim 2, wherein the particular healthcare provider is identified as a prospective attendee based further on a determination that the particular healthcare provider's practice is of a particular specialty.

4. The cloud-based enterprise platform of claim 3, wherein the particular healthcare provider is identified as a prospective attendee based further on a determination that the particular healthcare provider is associated with an academic hospital.

5. The cloud-based enterprise platform of claim 1, wherein the targeted healthcare providers are identified on a geographical heat map that displays indicia corresponding with respective residential and/or business addresses of the targeted healthcare providers.

6. The cloud-based enterprise platform of claim 1, wherein the representative portal includes an online registration module configurable by the representative to support online customizable online event registration websites.

7. The cloud-based enterprise platform of claim 6, wherein the online registration module includes site templates for layout and presentation, content areas, and merged fields for customizable generation of online event registration websites.

8. The cloud-based enterprise platform of claim 1, wherein the programs section comprises a programs tab and the speakers section comprises a speakers tab of the graphical user interface corresponding with the representative portal.

9. The cloud-based enterprise platform of claim 1, wherein the threshold number is ten.

10. The cloud-based enterprise platform of claim 1, wherein the threshold number is a first threshold number; and
    wherein the particular healthcare provider is identified as a prospective attendee based on determinations that the particular healthcare provider's medical practice includes at least the first threshold number of healthcare providers and no more than a second threshold number of healthcare providers.

11. The cloud-based enterprise platform of claim 10, wherein the first threshold number is ten and the second threshold number is twenty.

12. A cloud-based enterprise platform for event handling, comprising:
    at least one processor; and
    at least one memory comprising a plurality of instructions stored thereon that, in response to execution by the at least one processor, causes the cloud-based enterprise platform to:
        communicate with a representative device of a pharmaceutical company representative to provide a representative portal to the representative device, wherein the representative portal includes at least a programs section that allows the representative to plan a program and a speakers section that allows the representative to view profiles of a plurality of healthcare providers identified as key opinion leaders, wherein the representative interacts with the representative portal via a graphical user interface corresponding with the representative portal displayed on the representative device; and communicate with a speaker device of a key opinion leader to provide a speaker portal to the speaker device, wherein the speaker portal allows the key opinion leader to interact with presentation materials and upcoming program data, wherein the key opinion leader interacts with the speaker portal via a graphical user interface corresponding with the speaker portal displayed on the speaker device; and wherein the plurality of instructions further causes the cloud-based enterprise platform to communicate with an administrative device of an administrator of the cloud-based enterprise platform to provide an admin portal to the administrative device.

\* \* \* \* \*